(12) United States Patent
Avniel et al.

(10) Patent No.: US 10,240,161 B2
(45) Date of Patent: *Mar. 26, 2019

(54) COMPOSITIONS AND METHODS FOR SILENCING GENE EXPRESSION

(71) Applicant: A.B. Seeds Ltd., Lod (IL)

(72) Inventors: Amir Avniel, Tel-Aviv (IL); Efrat Lidor-Nili, Nes Ziona (IL); Rudy Maor, Rechovot (IL); Ofir Meir, Doar-Na Emek Soreq (IL); Orly Noivirt-Brik, Givataim (IL); Osnat Yanai-Azulay, Rishon-LeZion (IL)

(73) Assignee: A.B. Seeds Ltd. (IL)

( * ) Notice: Subject to any disclaimer, the term of this patent is extended or adjusted under 35 U.S.C. 154(b) by 810 days.

This patent is subject to a terminal disclaimer.

(21) Appl. No.: 13/901,326

(22) Filed: May 23, 2013

(65) Prior Publication Data

US 2013/0318657 A1 Nov. 28, 2013

Related U.S. Application Data

(60) Provisional application No. 61/651,131, filed on May 24, 2012, provisional application No. 61/814,888, filed on Apr. 23, 2013, provisional application No. 61/814,890, filed on Apr. 23, 2013, provisional application No. 61/814,892, filed on Apr. 23, 2013, provisional application No. 61/814,899, filed on Apr. 23, 2013.

(51) Int. Cl.
*C12N 15/82* (2006.01)
*C12N 15/113* (2010.01)

(52) U.S. Cl.
CPC ........ *C12N 15/8218* (2013.01); *C12N 15/113* (2013.01); *C12N 15/8201* (2013.01); *C12N 15/825* (2013.01); *C12N 15/8206* (2013.01); *C12N 15/8216* (2013.01); *C12N 15/8261* (2013.01); *C12N 15/8266* (2013.01); *C12N 15/8267* (2013.01); *C12N 15/8271* (2013.01); *C12N 15/8279* (2013.01); *C12N 15/8282* (2013.01); *C12N 15/8283* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 6/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |

(Continued)

FOREIGN PATENT DOCUMENTS

| | | |
|---|---|---|
| AU | 2008258254 B2 | 7/2014 |
| CN | 101279950 A | 10/2008 |

(Continued)

OTHER PUBLICATIONS

Unnamalai et al, 2006, FEBS Letters, 566:307-310.*

(Continued)

*Primary Examiner* — Jason Deveau Rosen
(74) *Attorney, Agent, or Firm* — Amanda Carmany-Rampey; David Marsh; Arnold & Porter Kaye Scholer LLP

(57) ABSTRACT

A method of introducing naked dsRNA into a seed is provided. The method comprising contacting the seed with the naked dsRNA under conditions which allow penetration of the dsRNA into the seed, thereby introducing the dsRNA into the seed.

22 Claims, 104 Drawing Sheets
(3 of 104 Drawing Sheet(s) Filed in Color)
Specification includes a Sequence Listing.

(56) References Cited

U.S. PATENT DOCUMENTS

| | | |
|---|---|---|
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 7/2002 | McElroy et al. |
| 6,437,217 B1 | 8/2002 | McElroy et al. |
| 6,453,609 B1 | 9/2002 | Soli et al. |
| 6,479,291 B2 | 11/2002 | Kumagai et al. |
| 6,506,559 B1 | 1/2003 | Fire et al. |
| 6,642,435 B1 | 11/2003 | Antoni et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |

(56) References Cited

U.S. PATENT DOCUMENTS

| | | |
|---|---|---|
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,445,603 B2 | 9/2016 | Baum et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cal et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1* | 7/2010 | Ren .............. C12N 15/8209 800/13 |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1* | 2/2011 | Trias Vila ............ A01C 1/02 47/58.1 SE |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1* | 12/2011 | Sammons ............ A01N 63/02 800/298 |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0164205 A1 | 6/2012 | Baum et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |

(56) References Cited

U.S. PATENT DOCUMENTS

| | | |
|---|---|---|
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1* | 8/2014 | Avniel ............... C12N 15/1137 800/279 |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2015/0096079 A1* | 4/2015 | Avniel ................ C12N 15/113 800/286 |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |

FOREIGN PATENT DOCUMENTS

| | | |
|---|---|---|
| CN | 101279951 A | 10/2008 |
| CN | 101914540 A | 12/2010 |
| CN | 102822350 A | 12/2012 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 157 991 A2 | 11/2001 |
| EP | 1 238 586 A1 | 9/2002 |
| EP | 1 416 049 A1 | 5/2004 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009067739 A | 4/2009 |
| JP | 2009114128 A | 5/2009 |
| JP | 2009126792 A | 6/2009 |
| JP | 2009137851 A | 6/2009 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/024585 A1 | 5/1999 |
| WO | WO 99/26467 | 6/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 02/14472 | 2/2002 |
| WO | WO 02/14472 A2 | 2/2002 |
| WO | WO 02/066660 A2 | 8/2002 |
| WO | WO 03/000679 A2 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A1 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005007860 A1 * | 1/2005 ......... C12N 15/8206 |
| WO | WO 2005/040152 A1 | 5/2005 |
| WO | WO 2005/047233 A1 | 5/2005 |
| WO | WO 2005/047281 A1 | 5/2005 |

(56) References Cited

FOREIGN PATENT DOCUMENTS

| | | |
|---|---|---|
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/039454 | 4/2007 |
| WO | WO 2007/039454 A1 | 4/2007 |
| WO | WO 2007/050715 A2 | 5/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/051462 A2 | 10/2007 |
| WO | WO 2007/051462 A3 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/035150 A2 | 3/2009 |
| WO | WO 2009/046384 A1 | 4/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 | 10/2009 |
| WO | WO 2009/125401 A2 | 10/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 | 1/2011 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 | 6/2011 |
| WO | WO 2011/067745 A2 | 6/2011 |
| WO | WO 2011/080674 A2 | 7/2011 |
| WO | WO 2011/112570 | 9/2011 |
| WO | WO 2011/112570 A1 | 9/2011 |
| WO | WO 2011/132127 | 10/2011 |
| WO | WO 2011/132127 A1 | 10/2011 |
| WO | WO 2012/001626 | 1/2012 |
| WO | WO 2012/001626 A1 | 1/2012 |
| WO | WO 2012/056401 | 5/2012 |
| WO | WO 2012/056401 A1 | 5/2012 |
| WO | WO 2012/092580 A2 | 7/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A1 | 10/2014 |
| WO | WO 2014/164797 A2 | 10/2014 |
| WO | WO 2015/010026 A2 | 1/2015 |

OTHER PUBLICATIONS

Salanenka et al, 2011, HortScience, 46:622-626.*
Hagio, 2009, Electroporation and Sonoporation in Developmental Biology, p. 285-293.*
Li et al, 2009, Agricultural Science in China, 8:658-663.*
Alarcón-Reverte et al., "Resistance to ACCase-inhibiting herbicides in the weed *Lolium multiflorum,*" *Comm. Appl. Biol. Sci.*, 73(4):899-902 (2008).
Amarzguioui et al., "An algorithm for selection of functional siRNA sequences," *Biochemical and Biophysical Research Communications*, 316:1050-1058 (2004).
An et al., "Transient RNAi Induction against Endogenous Genes in *Arabidopsis* Protoplasts Using in Vitro-Prepared Double-Stranded RNA," *Biosci Biotechnol Biochem*, 69(2):415-418 (2005).
Andersson et al., "A novel selection system for potato transformation using a mutated AHAS gene," *Plant Cell Reports*, 22(4):261-267 (2003).
Anonymous, "A handbook for high-level expression and purification of 6xHis-tagged proteins," *The QUIexpressionist*, (2003).
Anonymous, "Agronomy Facts 37: Adjuvants for enhancing herbicide performance," n.p. 1-8, (Jan. 26, 2000), *Web*, (Jan. 21, 2014).
Anonymous, "Devgen, The mini-Monsanto," KBC Securities (2006).

(56) References Cited

OTHER PUBLICATIONS

Anonymous, "Do Monsanto have the next big thing?," *Austalian Herbicide Resistance Initiative (AHRI)*, (Apr. 23, 2013) *Web.* (Jan. 19, 2015).
Aoki et al., "In Vivo Transfer Efficiency of Antisense Oligonucleotides into the Myocardium Using HVJ-Liposome Method," *Biochem Biophys Res Commun*, 231:540-545 (1997).
Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).
Artmymovich, "Using RNA interference to increase crop yield and decrease pest damage," *MMG 445 Basic Biotech.*, 5(1):7-12 (2009).
Australian Patent Examination report No. 1 dated Nov. 11, 2013, in Australian Application No. 2011224570.
Axtell et al., "A Two-Hit Trigger for siRNA Biogenesis in Plants," *Cell*, 127:565-577 (2006).
Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).
Bannerjee et al., "Efficient production of transgenic potato (*S. tuberosum* L. ssp. *andigena*) plants via *Agrobacterium tumefaciens*-mediated transformation," *Plant Sci.*, 170:732 738 (2006).
Baulcombe, "RNA silencing and heritable epigenetic effects in tomato and *Arabidopsis*," Abstract 13$^{th}$ Annual Fall Symposium, Plant Genomes to Phenomes, Donald Danforth Plant Science Center, 28-30 (2011).
Bayer et al., "Programmable ligand-controlled riboregulators of eukaryotic gene expression," *Nature Biotechnol.*, 23(3):337-343 (2005).
Beal, et al., "Second Structural Motif for Recognition of DNA by Oligonucleotide-Directed Triple-Helix Formation," *Science*, 251:1360-1363 (1992).
Becker et al., "Fertile transgenic wheat from microprojectile bombardment of scutellar tissue," *The Plant Journal*, 5(2):299-307 (1994).
Bhargava et al., "Long double-stranded RNA-mediated RNA interference as a tool to achieve site-specific silencing of hypothalamic neuropeptides," *Brain Research Protocols*, 13:115-125 (2004).
Boletta et al., "High Efficient Non-Viral Gene Delivery to the Rat Kidney by Novel Polycationic Vectors," *J. Am Soc. Nephrol.*, 7:1728 (1996).
Bolognesi et al., "Characterizing the Mechanism of Action of Double-Stranded RNA Activity against Western Corn Rootworm(*Diabrotica virgifera virgifera* LeConte)," *PLoS ONE* 7(10):e47534 (2012).
Bolter et al., "A chloroplastic inner envelope membrane protease is essential for plant development," *FEBS Letters*, 580:789-794 (2006).
Breaker et al. "A DNA enzyme with Mg2$^+$-dependent RNA phosphoesterase activity," *Chemistry and Biology*, 2:655-660 (1995).
Brodersen et al., "The diversity of RNA silencing pathways in plants," *Trends in Genetics*, 22(5):268-280 (2006).
Busi et al., "Gene flow increases the initial frequency of herbicide resistance alleles in unselectedpopulations," *Agriculture, Ecosystems and Environments*, Elsevier, Amsterdam, NL, 142(3):403-409 (2011).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Chakravarty et al., "Genetic Transformation in Potato: Approaches and Strategies," *Amer J Potato Res*, 84:301 311 (2007).
Chen et al., "In Vivo Analysis of the Role of atTic20 in Protein Import into Chloroplasts," *The Plant Cell*, 14:641-654 (2002).
Cheng et al., "Production of fertile transgenic peanut (*Arachis hypogaea* L.) plants using *Agrobacterium tumefaciens*," *Plant Cell Reports*, 15:653-657 (1996).
Chinese Office Action dated Aug. 28, 2013 in Chinese Application No. 201180012795.2.
Clough et al., "Floral dip: a simplified method for Agrobacterium-mediated transformation of *Arabidopsis thaliana*," *The Plant Journal*, 16(6):735-743 (1998).

CN101914540 Patent Diclosure, "Introduction of RNA into plant by interference," (2010).
Colbourne et al., "The Ecoresponsive Genome of Daphnia pulex," *Science*, 331(6017):555-561 (2011).
Colombian Office Action dated Aug. 2, 2013 in Application No. 12 152898.
Colombian Office Action dated Feb. 21, 2014 in Application No. 12 152898.
Cooney et al., "Site-Specific Oligonucleotide Binding Represses Transcription of the Human c-myc Gene in Vitro," *Science* ,241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," *Breast Cancer Res. Treat*, 115:545-560 (2009).
Dalmay et al., "An RNA-Depenedent RNA Polymerase Gene in *Arabidopsis* Is Required for Posttranscriptional Gene Silencing Mediated by a Transgene but Not by a Virus," *Cell*, 101:543-553 (2000).
Database EMBL CBIB Daphnia—XP-002732239 (2011).
Davidson et al., "Engineering regulatory RNAs," *TRENDS in Biotechnology*, 23(3):109-112 (2005).
De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
della-Cioppa et al., "Import of a precursor protein into chloroplasts is inhibited by the herbicide glyphosate," *The EMBO Journal*, 7(5):1299-1305 (1988).
Diallo et al., "Long Endogenous dsRNAs Can Induce Complete Gene Silencing in Mammalian Cells and Primary Cultures," *Oligonucleotides*, 13:381-392 (2003).
Dietemann et al.,"*Varroa destructor*: research avenues towards sustainable control," *Journal of Apicultural Research*, 51(1):125-132 (2012).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Eurasian Office Action dated Feb. 24, 2014, in Application No. 201201264.
European Cooperation in the field of Scientific and Technical Research—Memorandum of Understanding for COST Action FA0806 (2008).
European Supplemental Search Report dated Oct. 8, 2013 in Application No. 11753916.3.
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Mar. 17, 2015, in European Patent Application No. 12 831 684.1.
Extended European Search Report dated Mar. 3, 2015, in European Patent Application No. 12 831 166.9.
Fukuhara et al., "The Unusual Structure of a Novel RNA Replicon in Rice," *The Journal of Biological Chemistry*, 270(30):18147-18149 (1995).
Further Examination Report issued in New Zealand Patent Application No. 601784 dated May 16, 2014.
GenBank Accession No. AY545657.1, published 2004.
GenBank Accession No. DY640489, PU2_plate27_F03 PU2 Prunus persica cDNA similar to expressed mRNA inferred from Prunus

(56) References Cited

OTHER PUBLICATIONS persica hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank Accession No. GI:186478573, published Jan. 22, 2014.
GenEmbl FJ861243, published Feb. 3, 2010.
Gong et al., "Silencing of Rieske iron-sulfur protein using chemically synthesised siRNA as a potential biopesticide against Plutella xylostella," *Pest Manag Sci*, 67:514-520 (2011).
Gressel et al., "A strategy to provide long-term control of weedy rice while mitigating herbicide resistance transgene flow, and its potential use for other crops with related weeds," *Pest Manag Sci*, 65(7):723-731 (2009).
Gutensohn et al., "Functional analysis of the two *Arabidopsis* homologues of Toc34, a component of the chloroplast protein import apparatus," *The Plant Journal*, 23(6):771-783 (2000).
Hamilton et al., "Two classes of short interfering RNA in RNA silencing," *EMBO J.*, 21(17):4671-4679 (2002).
Hannon, "RNA interference," *Nature*,481:244-251 (2002).
Harrison et al., "Does Lowering Glutamine Synthetase Activity in Nodules Modigy Nitrogen Metabolism and Growth of *Lotus japonicus?,*" *Plant Physiology*, 133:253-262 (2003).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).
Himber et al., "Transitivity-dependant and -independent cell-to-cell movement of RNA silencing," *The EMBO Journal*, 22(17):4523-4533 (2003).
Hirschberg et al., "Molecular Basis of Herbicide Resistance in *Amaranthus hybridus,*" *Science*, 222:1346-1349 (1983).
Hoekema et al., "A binary plant vector strategy based on separation of vir- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Search Report and the Written Opinion dated Feb. 25, 2013, in International Application No. PCT/US12/054883.
International Search Report and the Written Opinion dated Feb. 27, 2013, in International Application No. PCT/US12/054814.
International Search Report and the Written Opinion dated Feb. 27, 2013, in International Application No. PCT/US12/054842.
International Search Report and the Written Opinion dated Feb. 27, 2013, in International Application No. PCT/US12/054862.
International Search Report and the Written Opinion dated Feb. 27, 2013, in International Application No. PCT/US12/054894.
International Search Report and the Written Opinion dated Feb. 27, 2013, in International Application No. PCT/US12/054974.
International Search Report and the Written Opinion dated Feb. 27, 2013, in International Application No. PCT/US12/054980.
International Search Report and the Written Opinion dated May 10, 2011, in International Application No. PCT/US11/027528.
International Search Report dated Mar. 12, 2013, in International Application No. PCT/US 12/54789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Isaacs et al., "Engineered riboregulators enable post-transcriptional control of gene expression," *Nature Biotechnology*, 22(7):841-847 (2004).
Jones-Rhoades et al., "MicroRNAs and Their Regulatory Roles in Plants," *Annu. Rev. Plant Biol.*, 57:19-53 (2006).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana,*" *Proc. Natl. Acad. Sci. U S A.*, 88:5212-5216 (1991).
Khachigian, "DNAzymes: Cutting a path to a new class of therapeutics," *Curr Opin Mol Ther* 4(2):119-121 (2002).
Kirkwood, "Use and Mode of Action of Adjuvants for Herbicides: A Review of some Current Work," *Pestic Sci.*, 38:93-102 (1993).
Klahre et al., "High molecular weight RNAs and small interfering RNAs induce systemic posttranscriptional gene silencing in plants," *Proc. Natl. Acad. Sci. USA*, PNAS, 99(18):11981-11986 (2002).
Kronenwett et al., "Oligodeoxyribonucleotide Uptake in Primary Human Hematopoietic Cells Is Enhanced by Cationic Lipids and Depends on the Hematopoietic Cell Subset," *Blood*, 91(3):852-862 (1998).
Kumar et al., "Sequencing, De Novo Assembly and Annotation of the Colorado Potato Beetle, *Leptinotarsa decemlineata*,Transcriptome," *PLoS One*, 9(1):e86012 (2014).
Kusaba et al., "Low glutelin content1: A Dominant Mutation That Suppresses the Glutelin Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lee et al., "Aptamer Database," *Nucleic Acids Research*, 32:D95-D100 (2004).
Lermontova et al., "Reduced activity of plastid protoporphyrinogen oxidase causes attenuated photodynamic damage during high-light compared to low-light exposure," *The Plant Journal*, 48(4):499-510 (2006).
Lesnik et al., "Prediction of rho-independent transcriptional terminators in *Escherichia coli,*" *Nucleic Acids Research*, 29(17):3583-3594 (2001).
Li et al., "Establishment of a highly efficient transformation system for pepper (*Capsicum annuum* L.)," *Plant Cell Reports*, 21: 785-788 (2003).
Li et al., "The FAST technique: A simplified Agrobacterium-based transformation method for transient gene expression analysis in seedlings of *Arabidopsis* and other plant species," *Plant Methods*, 5(6):1-15 (2009).
Liu et al., "Comparative study on the interaction of DNA with three different kinds of surfactants and the formation of multilayer films," *Bioelectrochemistry*, 70:301-307 (2007).

(56) References Cited

OTHER PUBLICATIONS

Liu et al., "DNAzyme-mediated recovery of small recombinant RNAs from a 5S rRNA-derived chimera expressed in *Escherichia coli,*" *BMC Biotechnology*, 10:85 (2010).
Llave et al., "Endogenous and Silencing-Associated Small RNAs in Plants," *The Plant Cell*, 14:1605-1619 (2002).
Lu et al., "OligoWalk: an online siRNA design tool utilizing hybridization thermodynamics," *Nucleic Acids Research*, 36:W104-W108 (2008).
Lu et al., "RNA silencing in plants by the expression of siRNA duplexes," *Nucleic Acids Res.*, 32(21):e171 (2004).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
Maher III et al., "Inhibition of DNA binding proteins by oligonucleotide-directed triple helix formation," *Science*, 245(4919):725-730 (1989).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana,*" *Trends Plant Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Misawa et al., "Functional expression of the *Erwinia uredovora* carotenoid biosynthesis gene crtI in transgenic plants showing an increase of β-carotene biosynthesis activity and resistance to the bleaching herbicide norflurazon," *The Plant Journal*, 4(5):833-840 (1993).
Miura et al., "The Balance between Protein Synthesis and Degradation in Chloroplasts Determines Leaf Variegation in *Arabidopsis* yellow variegated Mutants," *The Plant Cell*, 19:1313-1328 (2007).
Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants Are Mobile and Direct Epigenetic Modification in Recipient Cells," *Science*, 328:872-875 (2010).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Nowak et al., "A new and efficient method for inhibition of RNA viruses by DNA interference," *The FEBS Journal*, 276:4372-4380.
Office Action dated Feb. 17, 2014, in Mexican Patent Application No. MX/a/2012/010479.
Office Action dated Jan. 6, 2015, in Japanese Patent Application No. 2012-557165.
Office Action dated Nov. 19, 2014, in Eurasian Patent Application No. 201201264/28.
Ongvarrasopone et al., "A Simple and Cost Effective Method to Generate dsRNA for RNAi Studies in Invertebrates," *Science Asia*, 33:35-39 (2007).
Ouellet et al., "Members of the Acetohydroxyacid Synthase Muligene Family of Brassica napus Have Divergent Patterns of Expression," *The Plant Journal*, Blackwell Scientific Publications, Oxford, GB, 2(3):321-330 (1992).
Paddison et al., "Stable suppression of gene expression by RNAi in mammalian cells," *Proc. Natl Acad. Sci. USA*, 99(3):1443-1448 (2002).
Palauqui et al., "Activation of systemic acquired silencing by localised introduction of DNA," *Current Biology*, 9:59-66 (1999).
Partial Supplementary European Search Report dated Mar. 2, 2015, in European Patent Application No. 12 831 494.5.
Paungfoo-Lonhienne et al., "DNA is Taken up by Root Hairs and Pollen, and Stimulates Root and Pollen Tube Growth," *Plant Physiology*, 153:799-805 (2010).
Pei et al., "On the art of identifying effective and specific siRNAs," *Nature Methods*, 3(9):670-676 (2006).
Pornprom et al., "Glutamine synthetase mutation conferring target-site-based resistance to glufosinate in soybean cell selections," *Pest Manag Sci*, 2009; 65(2):216-222 (2009).
Preston et al., "Multiple effects of a naturally occurring proline to threonine substitution within acetolactate synthase in two herbicide-resistant populations of *Lactuca serriola,*" *Pesticide Biochem. Physiol.*, 84(3):227-235 (2006).
Qiwei," Advance in DNA interference," *Progress in Veterinary Medicine*, 30(1):71-75 (2009).
Rajur et al., "Covalent Protein—Oligonucleotide Conjugates for Efficient Delivery of Antisense Molecules," *Bioconjug Chem.*, 8:935-940 (1997).
Reddy et al "Organosilicone Adjuvants Increased the Efficacy of Glyphosate for Control of Weeds in Citrus (*Citrus* spp.)" *HortScience* 27(9):1003-1005 (1992).
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Reynolds et al., "Rational siRNA design for RNA interference," *Nature Biotechnology*, 22:326-330 (2004).
Ryabov et al., "Cell-to-Cell, but Not Long-Distance, Spread of RNA Silencing That Is Induced in Individual Epidermal Cells," *Journal of Virology*, 78(6):3149-3154 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Sharma et al., "A simple and efficient *Agrobacterium*-mediated procedure for transformation of tomato," *J. Biosci.*, 34(3):423 433 (2009).
Silwet L-77 Spray Adjuvant for agricultural applications, product description from Momentive Performance Materials, Inc. (2003).
Singh et al., "Absorption and translocation of glyphosate with conventional and organosilicone adjuvants," *Weed Biology and Management*, 8:104-111 (2008).
Steeves et al., "Transgenic soybeans expressing siRNAs specific to a major sperm protein gene suppress *Heterodera glycines* reproduction," *Funct. Plant Biol.*, 33:991-999 (2006).
Stock et al., "Possible Mechanisms for Surfactant-Induced Foliar Uptake of Agrochemicals," *Pestic. Sci.*, 38:165-177 (1993).
Strat et al., "Specific and nontoxic silencing in mammalian cells with expressed long dsRNAs," *Nucleic Acids Research*, 34(13):3803-3810 (2006).
Sudarsan et al., "Metabolite-binding RNA domains are present in the genes of eukaryotes," *RNA*, 9:644-647 (2003).

(56) References Cited

OTHER PUBLICATIONS

Sun et al., "A Highly efficient Transformation Protocol for Micro-Tom, a Model Cultivar for Tomato Functional Genomics," *Plant Cell Physiol.*, 47(3):426-431 (2006).
Sun et al., "Antisense oligodeoxynucleotide inhibition as a potent strategy in plant biology: identification of SUSIBA2 as a transcriptional activator in plant sugar signalling," *The Plant Journal*, 44:128-138 (2005).
Sun et al., "Sweet delivery—sugar translocators as ports of entry for antisense oligodeoxynucleotides in plant cells," *The Plant Journal*, 52:1192-1198 (2007).
Takasaki et al., "An Effective Method for Selecting siRNA Target Sequences in Mammalian Cells," *Cell Cycle*, 3:790-795 (2004).
Temple et al., "Can glutamine synthetase activity levels be modulated in transgenic plants by the use of recombinant DNA technology?" *Transgenic Plants and Plant Biochemistry*, 22:915-920 (1994).
Temple et al., "Down-regulation of specific members of the glutamine synthetase gene family in Alfalfa by antisense RNA technology," *Plant Molecular Biology*, 37:535-547 (1998).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus diseases in plants," *Virus Research*, 102:85-96 (2004).
Third Party Submission filed on Nov. 29, 2012 in U.S. Appl. No. 13/042,856.
Thompson, et al., "Clustal W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Toriyama et al., "Transgenic Rice Plants After Direct Gene Transfer Into Protoplasts," *Bio/Technology*, 6:1072-1074 (1988).
Tran et al., "Control of specific gene expression in mammalian cells by co-expression of long complementary RNAs," *FEBS Lett*.;573(1-3):127-134 (2004).
Tuschl, "Expanding small RNA interference," *Nature Biotechnol.*, 20: 446-448 (2002).
Tuschl, "RNA Interference and Small Interfering RNAs," *ChemBiochem.* 2(4):239-245 (2001).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Unniraman et al., "Alternate Paradigm for Intrinsic Transcription Termination in Eubacteria," *The Journal of Biological Chemistry*, 276(45)(9):41850-41855 (2001).
van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vert et al., "An accurate and interpretable model for siRNA efficacy prediction," *BMC Bioinformatics*, 7:520 (2006).

Vionnet et al., "Systemic Spread of Sequence-Specific Transgene RNA Degradation in Plants Is Initiated by Localized Introduction of Ectopic Promoterless DNA," *Cell*, 95:177-187 (1998).
Wakelin et al., "A target-site mutation is present in a glyphosate-resistant *Lolium rigidum* population," *Weed Res.* (Oxford), 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Numbers of Independently Transformed Fertile Barley Plants," *Plant Physiol.*, 104:37-48 (1994).
Wardell, "Floral Induction of Vegetative Plants Supplied a Purified Fraction of Deoxyribonucleic Acid from Stems of Flowering Plants," *Plant Physiol*, 60:885-891 (1977).
Wardell,"Floral Activity in Solutions of Deoxyribonucleic Acid Extracted from Tobacco Stems," *Plant Physiol*, 57:855-861 (1976).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated May 8, 2014, in International Application No. PCT/IL2013/050447.
Written Opinion dated Sep. 1, 2014, in Singapore Patent Application No. 201206152-9.
Xu et al., Characterization and Functional Analysis of the Calmodulin-Binding Domain of Rac1 GTPase, *Plos One*, 7(8)1-12:e42975 (2012).
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "*Agrobacterium*-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "DEG: a database of essential genes," *Nucleic Acids Res.*, 32:D271-D272 (2004).
Zhang et al., "Transgenic rice plants produced by electroporation-mediated plasmid uptake into protoplasts," *The Plant Cell Rep.*, 7:379-384 (1988).
Zhao et al.,"*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata,*" *Pest Manag Sci*, 67:175-182 (2010).
Agrios, G., *Plant Pathology* (Second Edition) 2:466-470 (1978).
Arnbms et al., "The Diverse Roles of RNA Helicases in RNAi," *Cell Cycle*, 8(21):3500-3505 (2009).
Bai, Y., et al. "Naturally Occurring Broad-Spectrum Powdery Mildew Resistance in a Central American Tomato Accession Is Caused by Loss of Mlo Function," *MPMI* 21:30-39 (2007).
Butler et al., "Priming and re-drying improve the survival of mature seeds of *Digitalis purpurea* during storage," *Annals of Botany*, 103:1261-1270 (2009).

(56) References Cited

OTHER PUBLICATIONS

Chabbouh et al., "Cucumber mosaic virus in artichoke," *FAO Plant Prot. Bull.*, 38:52-53 (1990).
Chi et al., "The Function of RH22, a DEAD RNA Helicase, in the Biogenesis of the 50S Ribosomal Subunits of *Arabidopsis* Chloroplasts," *Plant Physiology*, 158:693-707 (2012).
Chupp et al., "Vegetable diseases and their control," pp. 267-269. The Ronald Press Company. New York. 693 pp. (1960).
Farooq et al., "Rice seed priming," *IPRN*, 30(2):45-48 (2005).
Fire et al., "Potent and specific genetic interference by double-stranded RNA in *Caenorhabditis elegans*," *Nature*, 391:806-811 (1998).
Fukuhara et al., "Enigmatic double-stranded RNA in Japonica rice," *Plant Molecular Biology*, 21:1121-1130 (1993).
Fukuhara et al., "The wide distribution of endornaviruses, large double-stranded RNA replicons with plasmid-like properties," *Archives of Virology*, 151:995-1002 (2006).
Ilaigh, "The Priming of Seeds: Investigation into a method of priming large quantities of seeds using salt solutions," Thesis submitted to Macquarie University (1983).
Hamilton et al., "Guidelines for the Identification and Characterization of Plant Viruses," *J. gen. Virol.*, 54:223-241 (1981).
Han et al., "Molecular Basis for the Recognition of Primary microRNAs by the Drosha-DGCR8 Complex," *Cell*, 125(5):887-901 (2006).
Hardegree, "Drying and storage effects on germination of primed grass seeds," *Journal of Range Management*, 47(3):196-199 (1994).
Ji et al., "Regulation of small RNA stability: methylation and beyond," *Cell Research*, 22:624-636 (2012).
Kam et al., "Nanotube Molecular Transporters: Internalization of Carbon Nanotube—Protein Conjugates into Mammalian Cells," *J. Am. Chem. Soc.*, 126(22):6850-6851 (2004).
Khan, et al., "Matriconditioning of Vegetable Seeds to Improve Stand Establishment in Early Field Plantings," *J. American Soc. Hort. Sci.* 117(1):41-47 (1992).
Khodakovskaya et al., "Carbon Nanotubes Are Able to Penetrate Plant Seed Coat and Dramatically Affect Seed Germination and Plant Growth," *ACS Nano*, 3(10):3221-3227 (2009).
Leopold, el al., "Moisture as a Regulator of Physiological Reaction in Seeds," *Seed Moisture ,CSSA Special Publication No. 14*, pp. 51-67 (1989).
Liu et al., "Carbon Nanotubes as Molecular Transporters for Walled Plant Cells," *Nano Letters*, 9(3):1007-1010 (2009).
Makkouk et al., "Virus diseases of peas, beans, and faba bean in the Mediterranean region," *Adv Virus Res*, 84:367-402 (2012).
Moriyama et al., "Double-stranded RNA in rice: a novel RNA replicon in plants," *Mol Gen Genet*, 248:364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Peretz et al., "A Universal Expression/Silencing Vector in Plants," *Plant Physiology*, 145:1251-1263 (2007).
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Ryan, "Human endogenous retroviruses in health and disease: a symbiotic perspective," *Journal of the Royal Society of Medicine*, 97:560-565 (2004).
Schwab et al., "RNA silencing amplification in plants: Size matters," *PNAS*, 107(34):14945-14946(2010).
Schwember et al., "Drying Rates following Priming Affect Temperature Sensitivity of Germination and Longevity of Lettuce Seeds," *HortScience*, 40(3):778-781 (2005).
Selvarani et al., "Evaluation of seed priming methods to improve seed vigour of onion (*Allium cepa* cv. *Aggregatum*) and carrot (*Daucus carota*)," *Journal of Agricultural Technology*, 7(3):857-867 (2011).
Sijen et al., "On the Role of RNA Amplification in dsRNA-Triggered Gene Silencing," *Cell*, 107:465-476 (2001).
Taylor, A., "Seed Storage, Germination and Quality," *The Physiology of Vegetable Crops*, 1-36 (1997).
Tepfer, "Risk assessment of virus resistant transgenic plants," *Annu. Rev. Phytopathol.*, 40:467-491 (2002).
The Seed Biology Place, Website Gerhard Leubner Lab Royal Holloway, University of London, <http://www.seedbiology.de/seedtechnology.asp>, 6 pages, 2000.
Turina et al., "Tospoviruses in the Mediterranean Area," *Advances in Virus Research*, 84:403-437 (2012).
Töpfer et al., "Uptake and Transient Expression of Chimeric Genes in Seed-Derived Embryos," *Plant Cell*, 1:133-139 (1989).
Urayama et al., "Knock-down of OsDCL2 in Rice Negatively Affects Maintenance of the Endogenous dsRNA Virus, *Oryza sativa* Endornavirus," *Plant and Cell Physiology*, 51(1):58-67 (2010).
Zhang el al., "A novel rice gene, NRR responds to macronutrient deficiency and regulates root growth," *Mol Plant*, 5(1):63-72 (2012).
Bourgeois et al., "Field and producer survey of ACCase resistant wild oat in Manitoba," *Canadian Journal of Plant Science*, 709-715 (1997).
Brugière et al., "Glutamine Synthetase in the Phloem Plays a Major Role in Controlling Proline Production," *The Plant Cell*, 11:1995-2011 (1999).
Campbell et al., "Gene-knockdown in the honey bee mite *Varroa destructor* by a non-invasive approach: studies on a glutathione S-transferase," *Parasites & Vectors*, 3(1):73, pp. 1-10 (2010).
Chang et al., "Cellular Internalization of Fluorescent Proteins via Arginine-rich Intracellular Delivery Peptide in Plant Cells," *Plant Cell Physiol.*, 46(3):482-488 (2005).
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Mar. 18, 2016, in European Patent Application No. 12 832 160.1.
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Oct. 23, 2015, in European Patent Application No. 12 831 945.6.
Database Accession No. HD315444, "Sequence 192160 from Patent EP2213738," (2010).
Desai et al., "Reduction in deformed wing virus infection in larval and adult honey bees (*Apis mellifera* L.) by double-stranded RNA ingestion," *Insect Molecular Biology*, 21(4):446-455 (2012).
Emery et al., "Radial Patterning of *Arabidopsis* Shoots by Class III HD-ZIP and Kanadi Genes," *Current Biology*, 13:1768-1774 (2003).
Extended European Search Report dated Jan. 20, 2016, in European Patent Application No. 13 794 339.5.
Extended European Search Report dated Jun. 29, 2015, in European Patent Application No. 12 831 494.5.
Final Office Action dated Nov. 10, 2015, in U.S. Appl. No. 13/612,985.
Final Office Action dated Nov. 30, 2015, in U.S. Appl. No. 13/612,948.
Final Office Action dated Nov. 7, 2013, in U.S. Appl. No. 13/042,856.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.
First Office Action dated May 27, 2015, in Chinese Patent Application No. 201280054179.8.
First Office Action dated Sep. 9, 2015, in Chinese Patent Application No. 201280055409.2.
Fukunaga et al., "dsRNA with 5' overhangs contributes to endogenous and antiviral RNA silencing pathways in plants," *The EMBO Journal*, 28(5):545-555 (2009).

(56) References Cited

OTHER PUBLICATIONS

Further Examination Report dated May 16, 2014, in New Zealand Patent Application No. 601784.
Gaines et al., "Gene amplification confers glyphosate resistance in *Amaranthus palmeri*," *Proc. Natl. Acad. Sci. USA*, 107(3):1029-1034 (2010).
Gallie et al., "Identification of the motifs within the tobacco mosaic virus 5'-leader responsible for enhancing translation," *Nucleic Acids Res.*, 20(17):4631-4638 (1992).
Gan et al., "Bacterially expressed dsRNA protects maize against SCMV infection," *Plant Cell Rep*, 11:1261-1268 (2010).
Gao et al., "Down-regulation of acetolactate synthase compromises 01-1-mediated resistance to powdery mildew in tomato," *BMC Plant Biology*, 14 (2014).
Garbian et al., "Bidirectional Transfer of RNAi between Honey Bee and *Varroa destructor*: *Varroa* Gene Silencing Reduces *Varroa* Population," 8(12):1-9:e1003035 (2012).
Ge et al., "Rapid vacuolar sequestration: the horseweed glyphosate resistance mechanism," *Pest Management Sci.*, 66:345-348 (2010).
International Preliminary Report on Patentability (Chapter II) dated Jul. 24, 2015, in International Application No. PCT/US2014/047204.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated Nov. 24, 2015, in International Application No. PCT/US2015/037522.
International Search Report and Written Opinion dated Nov. 27, 2015, in International Application No. PCT/US2015/037015.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Jofre-Garfias et al., "*Agrobacterium*-mediated transformation of Amaranthus *hypochondriacus*: light- and tissue-specific expression of a pea chlorophyll a/b-binding protein promoter," *Plant Cell Reports*, 16:847-852 (1997).
Kim et al., "Synthetic dsRNA Dicer substrates enhance RNAi potency and efficacy," *Nature Biotechnology*, 23(2):222-226 (2005).
Lein et al., "Target-based discovery of novel herbicides," *Current Opinion in Plant Biology*, 7:219-225 (2004).
MacKenzie et al., "Transgenic *Nicotiana debneyii* expressing viral coat protein are resistant to potato virus S infection," *Journal of General Virology*, 71:2167-2170 (1990).
Maori et al., "IAPV, a bee-affecting virus associated with Colony Collapse Disorder can be silenced by dsRNA ingestion," *Insect Molecular Biology*, 18(1):55-60 (2009).
Molina et al., "Inhibition of protoporphyrinogen oxidase expression in *Arabidopsis* causes a lesion-mimic phenotype that induces systemic acquired resistance," *The Plant Journal*, 17(6):667-678 (1999).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Nord-Larsen et al., "Cloning, characterization and expression analysis of tonoplast intrinsic proteins and glutamine synthetase in ryegrass (*Lolium perenne* L.)," *Plant Cell Reports*, 28(10):1549-1562 (2009).
Notice of Allowance dated Oct. 5, 2015, in U.S. Appl. No. 13/583,302.
Nowak et al., "A new and efficient method for inhibition of RNA viruses by DNA interference," *The FEBS Journal*, 276:4372-4380 (2009).
Office Action dated Aug. 2, 2013, in Colombian Patent Application No. 12 152898.
Office Action dated Aug. 28, 2013, in Chinese Patent Application No. 201180012795.2.
Office Action dated Feb. 21, 2014, in Colombian Patent Application No. 12 152898.
Office Action dated Feb. 24, 2014, in Eurasian Patent Application No. 201201264.
Office Action dated Jul. 23, 2015, in Ukrainian Patent Application No. 201211548.
Office Action dated Oct. 5, 2015, in Eurasian Patent Application No. 201201264/28.
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Patent Examination Report No. 1 dated Feb. 8, 2016, in Australian Patent Application No. 2014262189.
Patent Examination Report No. 1 dated Nov. 11, 2013, in Australian Patent Application No. 2011224570.
Paungfoo-Lonhienne et al., "DNA uptake by *Arabidopsis* induces changes in the expression of CLE peptides which control root morphology," *Plant Signaling & Behavior*, 5(9):1112-1114 (2010).
Pratt et al., "*Annaranthus rudis* and *A. tuberculatus*, One Species or Two?," *Journal of the Torrey Botanical Society*, 128(3):282-296 (2001).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 21, 2014, in U.S. Appl. No. 13/583,302.
Riggins et al., "Characterization of de novo transcriptome for waterhemp (*Amaranthus tuberculatus*) using GS-FLX 454 pyrosequencing and its application for studies of herbicide target-site genes," *Pest Manag. Sci.*, 66:1042-1052 (2010).
Rose et al., "Functional polarity is introduced by Dicer processing of short substrate RNAs," *Nucleic Acids Research*, 33(13):4140-4156 (2005).
Schweizer et al., "Double-stranded RNA interferes with gene function at the single-cell level in cereals," *The Plant Journal*, 24(6):895-903 (2000).
Second Office Action dated Mar. 4, 2016, in Chinese Patent Application No. 201280054820.8.
Second Office Action dated Feb. 25, 2016, in Chinese Patent Application No. 201280054179.8.
Senthil-Kumar et al., "A systematic study to determine the extent of gene silencing in *Nicotiana benthamiana* and other Solanaceae species when heterologous gene sequences are used for virus-induced gene silencing," *New Phytologist*, 176:782-791 (2007).

(56) References Cited

OTHER PUBLICATIONS

Shintani et al., "Antisense Expression and Overexpression of Biotin Carboxylase in Tobacco Leaves," *Plant Physiol.*, 114:881-886 (1997).
Snead et al., "Molecular basis for improved gene silencing by Dicer substrate interfering RNA compared with other siRNA variants," *Nucleic Acids Research*, 41(12):6209-6221 (2013).
Stevens et al., "New Formulation Technology—Silwet® Organosilicone Surfactants Have Physical and Physiological Properties Which Enhance the Performance of Sprays," *Proceedings of the 9th Australian Weeds Conference*, pp. 327-331 (1990).
Street, "Why is DNA (and not RNA) a stable storage form for genetic information?," *Biochemistry Revisited*, pp. 1-4 (2008).
Sutton et al., "Activity of mesotrione on resistant weeds in maize," *Pest Manag. Sci.*, 58:981-984 (2002).
Tank Mixing Chemicals Applied to Peanut Crops: Are the Chemicals Compatible?, College of Agriculture & Life Sciences, NC State University, AGW-653, pp. 1-11 (2004).
Tranel et al., "Resistance of weeds to ALS-inhibiting herbicides: what have we learned?," *Weed Science*, 50:700-712 (2002).
Tsugawa et al., "Efficient transformation of rice protoplasts mediated by a synthetic polycationic amino polymer," *Theor Appl Genet*, 97:1019-1026 (1998).
Vermeulen et al., "The contributions of dsRNA structure to Dicer specificity and efficiency," *RNA*, 11(5):674-682 (2005).
Wang et al., "Foliar uptake of pesticides—Present status and future challenge," ScienceDirect, 87:1-8 (2007).
Hilson et al., "Versatile Gene-Specific Sequence Tags for *Arabidopsis* Functional Genomics: Transcript Profiling and Reverse Genetics Applications," *Genome Research*, 14:2176-2189 (2004).
Lee et al., "A systematic RNAi screen identifies a critical role for mitochondria in *C. elegans* longevity," *Nature Genetics*, 33:40-48 (2003).
Agricultural Chemical Usage 2006 Vegetables Summary, Agricultural Statistics Board, NASS, USDA, pp. 1-372 (2007).
Agrios, Plant Pathology (Second Edition), 2:466-470 (1978).
Al-Kaff et al., "Plants rendered herbicide-susceptible by cauliflower mosaic virus—elicited suppression of a 35S promoter-regulated transgene," Nature Biotechnology, 18:995-999 (2000).
Andersen et al., "Delivery of siRNA from lyophilized polymeric surfaces,"Biomaterials, 29:506-512 (2008).
Anonymous, "A handbook for high-level expression and purification of 6xHis-tagged proteins," The QiaExpressionist, (2003).
Artymovich, "Using RNA interference to increase crop yield and decrease pest damage," MMG 445 Basic Biotech., 5(1):7-12 (2009).
Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Bai et al., "Naturally Occurring Broad-Spectrum Powdery Mildew Resistance in a Central American Tomato Accession Is Caused by Loss of Mlo Function," MPMI, 21(1):30-39 (2008).
Balibrea et al., "Extracellular Invertase is an Essential Component of Cytokinin-Mediated. Delay of Senescence," The Plant Cell, 16(5):1276-1287 (2004).
Bart et al., "A novel system for gene silencing using siRNAs in rice leaf and stem-derived protoplasts," Plant Methods, 2(13):1-9 (2006).
Basu et al., "Weed genomics: new tools to understand weed biology," Trends in Plant Science, 9(8):391-398 (2004).
Busch et al., "RNAi for discovery of novel crop protection products," Pflanzenschutz-Nachrichten Bayer, 58(1):34-50 (2005).
Chabannes et al., "In situ analysis of lignins in transgenic tobacco reveals a differential impact of individual transformations on the spatial patterns of lignin deposition at the cellular and subcellular levels," The Plant Journal, 28(3):271-282 (2001).
Chabbouh et al., "Cucumber mosaic virus in artichoke," FAO Plant Protection Bulletin, 38:52-53 (1990).
Chee et al., "Transformation of Soybean (*Glycine max*) by Infecting Germinating Seeds with Agrobacterium tumefaciens," Plant Physiol., 91:1212-1218 (1989).

Chen et al., "Transfection and Expression of Plasmid DNA in Plant Cells by an Arginine-Rich Intracellular Delivery Peptide without Protoplast Preparation," FEBS Letters 581, pp. 1891-1897 (2007).
Chupp et al., "Chapter 8: White Rust," Vegetable Diseases and Their Control, The Ronald Press Company, New York, pp. 267-269 (1960).
Colliver et al., "Differential modification of flavonoid and isoflavonoid biosynthesis with an antisense chalcone synthase construct in transgenic Lotus corniculatus," Plant Molecular Biology, 35:509-522 (1997).
Concise Descriptions of Relevance filed by a third party on Nov. 29, 2012, in U.S. Appl. No. 13/042,856.
Dalakouras et al., "Induction of Silencing in Plants by High-Pressure Spraying of In vitro-Synthesized Small RNAs," Frontiers in Plant Science, 7(1327):1-5 (2016).
Dawson et al., "cDNA cloning of the complete genome of tobacco mosaic virus and production of infectious transcripts," Proc. Natl. Acad. Sci. USA, 83:1832-1836 (1986).
Extended European Search Report dated Oct. 8, 2013, in European Patent Application No. 11753916.3.
Extended European Search Report dated Sep. 29, 2016, in European Patent Application No. 14778840.0.
Feuillet et al., "Crop genome sequencing: lessons and rationales," Trends Plant Sci., 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Nov. 10, 2016, in U.S. Appl. No. 13/583,302.
Final Office Action dated Nov. 19, 2015, in U.S. Appl. No. 13/612,941.
Final Office Action dated Oct. 20, 2016, in U.S. Appl. No. 14/480,199.
Final Office Action dated Oct. 22, 2015, in U.S. Appl. No. 14/608,951.
Final Office Action dated Sep. 9, 2016, in U.S. Appl. No. 13/612,954.
Final Office Action dated Sep. 9, 2016, in U.S. Appl. No. 14/608,951.
Final Office Action dated Sep. 9, 2016, in U.S. Appl. No. 14/603,347.
First Examination Report dated Apr. 23, 2013, in New Zealand Patent Application No. 601784.
First Examination Report dated Jul. 28, 2014, in New Zealand Patent Application No. 627060.
Fraley et al., "Liposome-mediated delivery of tobacco mosaic virus RNA into tobacco protoplasts: A sensitive assay for monitoring liposome-protoplast interactions," Proc Natl Acad Sci U S A., 79(6):1859-1863 (1982).
Fukunaga et al., "dsRNA with 5' overhangs v contributes to endogenous and antiviral RNA silencing pathways in plants," The EMBO Journal, 28(5):545-555 (2009).
Gan et al., "Inhibition of Leaf Senescence by Autoregulated Production of Cytokinin," Science, 270:1986-1988 (1995).
Gao et al., "Nonviral Methods for siRNA Delivery," Molecular Pharmaceutics, 6(3):651-658 (2008).
GenBank Accession No. AY545657.1 (2004).
GenBank Accession No. CB377464, "CmaE1_37_J02_J3 Cowpea weevil larvae Lambda Zap Express Library Callosobruchus maculatus cDNA, mRNA sequence," (2007).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolactate synthase (ALS) gene" (2007).
GenBank Accession No. EW765249, "ST020010B10C12 Normalized and subtracted western corn rootworm female head cDNA library *Diabrotica virgifera virgifera* cDNA clone STO20010B10C12 5-, mRNA sequence," (2007).
GenBank Accession No. EW771198, "ST020010BI0C12 Normalized and subtracted western corn rootworm female head cDNA library *Diabrotica virgifera virgifera* cDNA clone STO20010BI0C12 5-, mRNA sequence," (2007).

(56) References Cited

OTHER PUBLICATIONS

GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenBank Accession No. U87257.1, "Daucus carota 4-hydroxyphenylpyruvate dioxygenase mRNA, complete cds" (1997).
GenBank Accession. No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
GenEmbl Accession No. FJ861243 (2010).
Gossamer Threads, Compendium of Herbicide Adjuvants: Organo-Silicone Surfactant, p. 1-4 (1998).
Gudkov, "Minireview: The L7/L12 ribosomal domain of the ribosome: structural and functional studies," FEBS Letters, 407:253-256 (1997).
Hajirezaei et al., "Impact of elevated cytosolic and apoplastic invertase activity on carbon metabolism during potato tuber development," Journal of Experimental Botany, 51:439-445 (2000).
Heffer et al., "Rapid isolation of gene homologs across taxa: Efficient identification and isolation of gene orthologs from non-model organism genomes, a technical report," EvoDevo Journal, 2(7):1-5 (2011).
Holtra et al., "Assessment of the Physiological Condition of Salvinia Natans L. Exposed to Copper(II) Ions," Environ. Protect. Eng., 41:147-158 (2015).
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, Nature, 436(10:793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15 2014, in International Application No. PCT/US2014/025305.
International Search Report and the Written Opinion dated Jul. 22 2014, in International Application No. PCT/IL2013/051083.
International Search Report and the Written Opinion dated Jul. 22 2014, in International Application No. PCT/IL2013/051085.
International Search Report and the Written Opinion dated Jul. 24 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated May 26, 2016, in International Application No. PCT/US2016/014344.
International Search Report dated Mar. 12, 2013, in International Application No. PCT/US2012/054789.
Jin et al., "Posttranslational Elevation of Cell Wall Invertase Activity by Silencing its Inhibitor in Tomato Delays Leaf Senescence and Increases Seed Weight and Fruit Hexose Level," The Plant Cell, 21:2072-2089 (2009).
Josse et al., "A DELLA in Disguise: SPATULA Restrains the Growth of the Developing Arabidopsis Seedling," Plant Cell, 23:1337-1351 (2011).
Kaloumenos et al., "Identification of a Johnsongrass (Sorghum halepense) Biotype Resistant to ACCase-Inhibiting Herbicides in Northern Greece," Weed Technol, 23:470-476 (2009).
Kambiranda et al., "Relationship Between Acid Invertase Activity and Sugar Content in Grape Species," Journal of Food Biochemistry, 35:1646-1652 (2011).
Khan et al., "Matriconditioning of Vegetable Seeds to Improve Stand Establishment in Early Field Plantings," J. Amer. Soc. Hort. Sci., 117(1):41-47 (1992).
Kim et al., "Optimization of Conditions for Transient Agrobacterium-Mediated Gene Expression Assays in Arabidopsis," Plant Cell Reports, 28:1159-1167 (2009).
Kirkwood, "Herbicides and Plants," Botanical Journal of Scotland, 46(3):447-462 (1993).
Knudsen, "Promoter2.0: for the recognition of PolI promoter sequences," Bioniformatics, 15(5):356-361 (1999).
Leopold et al., "Chapter 4: Moisture as a Regulator of Physiological Reaction in Seeds," Seed Moisture, CSSA Special Publication No. 14, pp. 51-69 (1989).
Liu et al., "Identification and Application of a Rice Senescence-Associated Promoter," Plant Physiology, 153:1239-1249 (2010).
Liu, "Influence of Sugars on the Foliar Uptake of Bentazone and Glyphosate," New Zealand Plant Protection, 55:159-162 (2002).
Luque et al., "Water Permeability of Isolated Cuticular Membranes: A Structural Analysis," Archives of Biochemistry and Biophysics, 317(2):417-422 (1995).
Migge et al., "Greenhouse-grown conditionally lethal tobacco plants obtained by expression of plastidic glutamine synthetase antisense RNA may contribute to biological safety," Plant Science 153:107-112 (2000).
Mora et al., "How Many Species Are There on Earth and in the Ocean?," PLOS Biol., 9(8):e100127, p. 1-8 (2011).
Moriyama et al., "Double-stranded RNA in rice: a novel RNA replicon in plants," Molecular & General Genetics, 248(3):364-369 (1995).
Mount et al., "Gene and Metabolite Regulatory Network Analysis of Early Developing Fruit Tissues Highlights New Candidate Genes for the Control of Tomato Fruit Composition and Development," Plant Physiology, 149:1505-1528 (2009).
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.

(56) References Cited

OTHER PUBLICATIONS

Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Mar. 1, 2016, in U.S. Appl. No. 13/612,954.
Non-Final Office Action dated Nov. 9, 2016, in U.S. Appl. No. 14/901,003.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Non-Final Office Action dated Sep. 6, 2016, in U.S. Appl. No. 14/335,135.
Nookaraju et al., "Molecular approaches for enhancing sweetness in fruits and vegetables," Scientia Horticulture, 127:1-15 (2010).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Office Action dated Apr. 13, 2016, in Chinese Patent Application No. 201280053985.3.
Office Action dated Aug. 25, 2016, in Eurasian Patent Application No. 201201264.
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. a 2014 03849.
Office Action dated Dec. 27, 2016, in Ukrainian Patent Application No. a 2012 11548.
Office Action dated Jul. 18, 2016, in Indonesian Patent Application No. W00201203610.
Office Action dated Jun. 20, 2016, in Chinese Patent Application No. 201280054819.5.
Office Action dated Jun. 24, 2016, in Chinese Patent Application No. 201280053984.9.
Office Action dated Mar. 16, 2017, in Chinese Patent Application No. 201280054819.5.
Office Action dated Nov. 15, 2016, in Mexican Patent Application. No. MX/a/2014/003068.
Office Action dated Sep. 5, 2016, in Ukrainian Patent Application No. a 2014 03846.
Office Action dated Nov. 3, 2014, in Chinese Patent Application No. 201180012795.2.
Parera et al., "Dehydration Rate after Solid Matrix Priming Alters Seed Performance of Shrunken-2 Corn," J. Amer. Soc. Hort. Sci., 119(3):629-635 (1994).
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Promoter Prediction for Seq ID No. 1702 from 13/612929/MK/, Promoter 2.0 Prediction Results, pp. 1-4 (2016).
Promoter Prediction for Seq ID No. 4 from 13/612995/MK/, Promoter 2.0 Prediction Results, pp. 1-3 (2016).
Promoter Prediction for Seq ID No. 7 from 13/612936/MK/, Promoter 2.0 Prediction Results, pp. 1-2 (2016).
Promoter Prediction for Seq ID No. 8 from 13/612,925/MK/, Promoter 2.0 Prediction Results, pp. 1-6 (2016).
Regalado, "The Next Great GMO Debate," MIT Technology Review,pp. 1-19 (2015) <https://www.technologyreview.com/s/540136/the-next-great-gmo-debate/>.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Oct. 13, 2016, in U.S. Appl. No. 14/206,707.
Restriction Requirement dated Oct. 28, 2015, in U.S. Appl. No. 14/603,347.
Restriction Requirement dated Sep. 2, 2015, in U.S. Appl. No. 14/532,596.
Roberts, "Fast-track applications: The potential for direct delivery of proteins and nucleic acids to plant cells for the discovery of gene function," Plant Methods, 1(12):1-3 (2005).
Robson et al., "Leaf senescence is delayed in maize expressing the Agrobacterium IPT gene under the control of a novel maize senescence-enhanced promoter," Plant Biotechnology Journal, 2:101-112 (2004).
Roitsch et al., "Extracellular invertase: key metabolic enzyme and PR protein," Journal of Experimental Botany, 54(382):513-524 (2003).
Roitsch et al., "Function and regulation of plant invertases: sweet sensations," Trades in Plant Science, 9(12):606-613 (2004).
Rothnie et al., Pararetroviruses and Retroviruses: A Comparative Review of Viral Structure and Gene Expression Strategies, Advances in Virus Research, 44:1-67 (1994).
Ruan et al., "Suppression of Sucrose Synthase Gene Expression Represses Cotton Fiber Cell Initiation, Elongation, and Seed Development," The Plant Cell, 15:952-964 (2003).
Salanenka et al., "Seedcoat Permeability: Uptake and Post-germination Transport of Applied Model Tracer Compounds," HortScience, 46(4):622-626 (2011).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Scott et al., Botanical Insecticides for Controlling Agricultural Pests: Piperamides and the Colorado Potato Beetle *Leptinotarsa decemlineata* Say (Coleoptera: Chrysomelidae), Archives of Insect Biochemistry and Physiology, 54:212-225 (2003).
Second Chinese Office Action dated Jun. 10, 2014, in Chinese Patent Application No. 201180012795.2.
Shaoquan, "The action target of herbicide and the innovation of a new variety," Chemical Industry Press, pp. 23-24 (2001).
Showalter, "Structure and Function of Plant Cell Wall Proteins," The Plant Cell, 5:9-23 (1993).
Song et al., "Herbicide," New Heterocyclic Pesticide, Chemical Industry Press, 354-356 (2011).
Stevens, "Organosilicone Surfactants as Adjuvants for Agrochemicals," Journal of Pesticide Science, 38:103-122 (1993).
Tang et al., "Efficient delivery of small interfering RNA to plant cells by a nanosecond pulsed laser-induced stress wave for post-transcriptional gene silencing," Plant Science, 171:375-381 (2006).
Taylor, "Seed Storage, Germination and Quality," The Physiology of Vegetable Crops, pp. 1-36 (1997).
Temple et al., "Can glutamine synthetase activity levels be modulated in transgenic plants by the use of recombinant DNA technology?" Transgenic Plants and Plant Biochemistry, 22(4):915-920 (1994).
Tenllado et al., "Double-Stranded RNA-Mediated Interference with Plant Virus Infection," Journal of Virology, 75(24):12288-12297 (2001).
Tepfer, "Risk assessment of virus resistant transgenic plants," Annual Review of Phytopathology, 40:467-491 (2002).

(56) References Cited

OTHER PUBLICATIONS

Thomas et al., "Size constraints for targeting post-transcriptional gene silencing and for RNA-directed methylation in Nicotiana benthamiana using a potato virus X vector," The Plant Journal, 25(4):417-425 (2001).
Tomlinson et al., "Evidence that the hexose-to-sucrose ratio does not control the switch to storage product accumulation in oilseeds: analysis of tobacco seed development and effects of overexpressing apoplastic invertase," Journal of Experimental Botany, 2004, 55:2291-2303.
Unniraman et al., "Conserved Economics of Transcription Termination in Eubacteria," Nucleic Acids Research, 30(3):675-684 (2002).
Voinnet et al., "Systemic Spread of Sequence-Specific Transgene RNA Degradation in Plants Is Initiated by Localized Introduction of Ectopic Promoterless DNA," Cell, 95:177-187 (1998).
Widholm et al., "Glyphosate selection of gene amplification in suspension cultures of 3 plant species," Phyisologia Plantarum, 112:540-545 (2001).
Wiesman et al., "Novel cationic vesicle platform derived from vernonia oil for efficient delivery of DNA through plant cuticle membranes," Journal of Biotechnology, 130:85-94 (2007).
Wild Carrot, Noxious Weed Control Board (NWCB) of Washington State (2010) <www.nwcb.wa.gov/detailasp?weed=46>.
Written Opinion dated Apr. 7, 2016, in Singapore Patent Application No. 201206152-9.
Written Opinion dated Mar. 6, 2017, in Singaporean Patent Application No. 2012061529.
Zhang et al., "Chapter 10: New Characteristics of Pesticide Research & Development," New Progress of the world agriculture chemicals, p. 209 (2010).
Ascencio-Ibanez et al., "DNA abrasion onto plants is an effective method for geminivirus infection and virus-induced gene silencing," Journal of Virological Methods, 142:198-203 (2007).
Bedell et al., "Sorghum Genome Sequencing by Methylation Filtration," PLOS Biology, 3(1):E13/104-115 (2005).
Burgos et al., "Review: Confirmation of Resistance to Herbicides and Evaluation of Resistance Levels," Weed Science, 61 (1):4-20 (2013).
Chen et al., "Exploring MicroRNA-Like Small RNAs in the Filamentous Fungus *Fusarium oxysporum*," PLOS One, 9(8):e104956:1-10 (2014).
Constan et al., "An outer envelope membrane component of the plastid protein import apparatus plays an essential role in *Arabidopsis*," The Plant Journal, 38:93-106 (2004).
Di Stilio et al., "Virus-Induced Gene Silencing as a Tool for Comparative Functional Studies in Thalictrum," PLoS One, 5(8):e12064 (2010).
Eamens et al., "RNA Silencing in Plants: Yesterday, Today, and Tomorrow," Plant Physiology, 147(2):456-468 (2008).
Fassler, BLAST Glossary, National Center for Biotechnology Information (2011).
Fernandez et al., "Uptake of Hydrophilic Solutes Through Plant Leaves: Current State of Knowledge and Perspectives of Foliar Fertilization," Critical Reviews in Plant Sciences, 28:36-38 (2009).
Friedberg, "Automated protein function prediction—the genomic challenge," Briefings in Bioinformatics, 7(3):225-242 (2006).
Funke et al., "Molecular basis for herbicide resistance in Roundup Ready crops," PNAS, 103:13010-13015 (2006).
Gan et al., "Bacterially expressed dsRNA protects maize against SCMV infection," Plant Cell Rep, 29(11):1261-1268 (2010).
Gaskin et al., "Novel organosillicone adjuvants to reduce agrochemical spray volumes on row crops," New Zealand Plant Protection, 53:350-354 (2000).
GenBank Accession No. EF143582 (2007).
Hagio, "Chapter 25: Direct Gene Transfer into Plant Mature Seeds via Electroporation After Vacuum Treatment," Electroporation and Sonoporation in Developmental Biology, p. 285-293 (2009).
Hess, "Surfactants and Additives," 1999 Proceedings of the California Weed Science Society, 51:156-172 (1999).
Huang et al., "In Vivo Analyses of the Roles of Essential Omp85-Related Proteins in the Chloroplast Outer Envelope Membrane," Plant Physiol., 157:147-159 (2011).
Ivanova et al., "Members of the Toc159 Import Receptor Family Represent Distinct Pathways for Protein Targeting to Plastids," Molecular Biology of the Cell, 15:3379-3392 (2004).
Jacque et al., "Modulation of HIV-1 replication by RNA interference," Nature, 418, 435-438 (2002).
Jang et al., "Resistance to herbicides caused by single amino acid mutations in acetyl-CoA carboxylase in resistant populations of grassy weeds," New Phytologist, 197(4):1110-1116 (2013).
Kikkert et al., "Stable Transformation of Plant Cells by Particle Bombardment/Biolistics," Methods in Molecular Biology, 286:61-78 (2005).
Li et al., "A Simplified Seed Transformation Method for Obtaining Transgenic *Brassica napus* Plants," Agricultural Sciences in China, 8(6):658-663 (2009).
Liu et al, "The Helicase and RNaseIIIa Domains of *Arabidopsis* Dicer-Like1 Modulate Catalytic Parameters during MicroRNA Biogenesis," Plant Physiology, 159:748-758 (2012).
McGinnis, "RNAi for functional genomics in plants," Brief Funct Genomics, 9(2):111-7 (2010).
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Jul. 11, 2017, in Mexican Patent Application No. MX/a/2015/013118 (with English translation).
Office Action dated Jul. 3, 2017, in Mexican Patent Application No. MX/a/2015/012632 (with English translation).
Office Action dated Jul. 6, 2017, in Mexican Patent Application No. MX/a/2015/013103 (with English translation).
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 6, 2017, in Chinese Patent Application No. 2014800154012 (with English translation).
Patent Examination Report No. 1 dated Jun. 8, 2017, in Australian Patent Application No. 2012308686.
Powles el al., "Evolution in Action: Plants Resistant to Herbicides," Annual Review of Plant Biology, 61(1):317-347 (2010).
Rakoczy-Trojanowska, "Alternative Methods of Plant Transformation—a short review," Cellular & Molecular Biology Letters, 7:849-858 (2002).
Richardson et al., "Targeting and assembly of components of the TOC protein import complex at the chloroplast outer envelope membrane," Frontiers in Plant Science, 5:1-14 (2014).
Search Report dated Jul. 24, 2017, in Chinese Patent Application No. 201480014392.5 (with English translation).
Small, "RNAi for revealing and engineering plant gene functions," Current Opinion in Biotechnology, 18:148-153 (2007).
Statement of Grounds and Particulars dated Sep. 1, 2017, in Australian U.S. Patent No. 2014262189.
Stevens, "Formulation of Sprays to Improve the Efficacy of Foliar Fertilisers," New Zealand Journal of Forestry Science, 24(1):27-34 (1994).
Stevens, "Organosilicone Surfactants as Adjuvants for Agrochemicals," New Zealand Journal of Forestry Science, 24:27-34 (1994).
Trucco et al., "Amaranthus hybridus can be pollinated frequently by A. tuberculatus under filed conditions," Heredity, 94:64-70 (2005).
Voinnet, "Origin, Biogenesis, and Activity of Plant MicroRNAs," Cell, 136:669-687 (2009).
Wool et al., "Structure and evolution of mammalian ribosomal proteins," Biochem. Cell Biol., 73:933-947 (1995).

(56) References Cited

OTHER PUBLICATIONS

Xu et al., "Characterization and Functional Analysis of the Calmodulin-Binding Domain of Rac1 GTPase," PLoS One, 7(8):e42975 (2012).
Zhang et al., "Development and Validation of Endogenous Reference Genes for Expression Profiling of Medaka (*Oryzias latipes*) Exposed to Endocrine Disrupting Chemicals by Quantitative Real-Time RT-PCR," Toxicological Sciences, 95(2):356-368 (2007).
Zhang, "Artificial trans-acting small interfering RNA: a tool for plant biology study and crop improvements," Planta, 239:1139-1146 (2014).
Zhang, Chapter 10: New Characteristics of Pesticide Research & Development, p. 209 (2010).
Zhong et al., "A forward genetic screen to explore chloroplast protein import in vivo identifies Moco sulfurase, pivotal for ABA and IAA biosynthesis and purine turnover," The Plant Journal, 63:44-59 (2010).
Baulcombe, RNA silencing in plants, Nature, 431:356-363 (2004).
Declaration of Jerzy Zabkiewicz executed Nov. 28, 2017, as filed by Opponent in Australian Patent Application No. 2014262189, pp. 1-73.
Declaration of Jerzy Zabkiewicz executed Nov. 28, 2017, as filed by Opponent in Australian Patent Application No. 2014262189, pp. 1-4.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
Dietzgen et al., "Transgenic gene silencing strategies for virus control," Australasian Plant Pathology, 35:605-618 (2006).
Kirkwood, "Recent developments in our understanding of the plant cuticle as a barrier to the foliar uptake of pesticides," *Pestic Sci*, 55:69-77 (1999).
Lucas et al., "Plasmodesmata—bridging the gap between neighboring plant cells," Trends in Cell Biology, 19:495-503 (2009).
Qichuan et al., Seed Science, China Agriculture Press, pp. 101-103, Table 2-37 (2001).
Wang et al., "Principle and technology of genetic engineering in plants," in Plant genetic engineering principles and techniques, Beijing: Science Press, pp. 313-315 (1998).
Zabkiewicz, "Adjuvants and herbicidal efficacy—present status and future prospects," Weed Research, 40:139-149 (2000).
Zaimin et al., Botany, Chapter III—Seeds and Seedlings, Northwest A&F University Press, p. 87-92 (2009).
Chang et al., "Dual-target gene silencing by using long, sythetic siRNA duplexes without triggering antiviral responses," Molecules and Cells, 27(6)"689-695 (2009).
Cheng et al., "Transient Expression of Minimum Linear Gene Cassettes in Onion Epidermal Cells Via Direct Transformation," Appl Biochem Biotechnol, 159:739-749 (2009).
Examination Report dated Mar. 1, 2018, in Australian Patent Application No. 2013264742.
Extended European Search Report dated Apr. 13, 2018, in European Patent Application No. 15812530.0.
Extended European Search Report dated Mar. 15, 2018, in European Patent Application No. 17181861.0.
Hu et al., "High efficiency transport of quantum dots into plant roots with the aid of silwet L-77," Plant Physiology and Biochemistry, 48:703-709 (2010).
Jiang et al., Chapter III Seeds and Seedlings, Botany, Northwest A&F University Press, pp. 87-92 (2009).
Liu Gengling, "The Transformation of Nucleic Acid Degradants in Plants," China Organic Fertilizers, Agriculture Press, pp. 216-217 (1991) (English translation only).
Non-Final Office Action dated Mar. 21, 2018, in U.S. Appl. No. 13/619,980.
Office Action dated Feb. 21, 2018, in Mexican Patent Application No. MX/a/2015/012632 (with English translation).
Office Action dated Mar. 8, 2018 (with English translation), in Chilean Patent Application No. 201403192.
Partial Supplementary European Search Report dated Jan. 11, 2018, in European Patent Application No. 15812530.0.
Sun, "Characterization of Organosilicone Surfactants and Their Effects on Sulfonylurea Herbicide Activity," Thesis Submitted to the Faculty of the Virginia Polytechnic Institute and State University dated Apr. 5, 1996.
Yan et al., Seed Science, China Agriculture Press, pp. 101-103, Tables 2-37 (2001).
Zhao et al. *Vegetable Standardized Production Technologies*, Zhejiang Science and Technology Press, pp. 18-20 (2008).

* cited by examiner

CGMMV STABILITY IN RICE SEEDS

L 1 2 3 4 5 6 7 8 9 10 11 12 13 14 15 16 17 18

CGMMV 250 bp

TUBULIN 550 bp

*FIG. 1A*

CGMMV STABILITY IN RICE SEEDS

L 1 2 3 4 5 6 7 8 9 10 11 12 13 14 15

CGMMV 250 bp

L 1 2 3 4 5 6 7 8 9 10 11 12 13 14 15

TUBULIN 550 bp

*FIG. 1B*

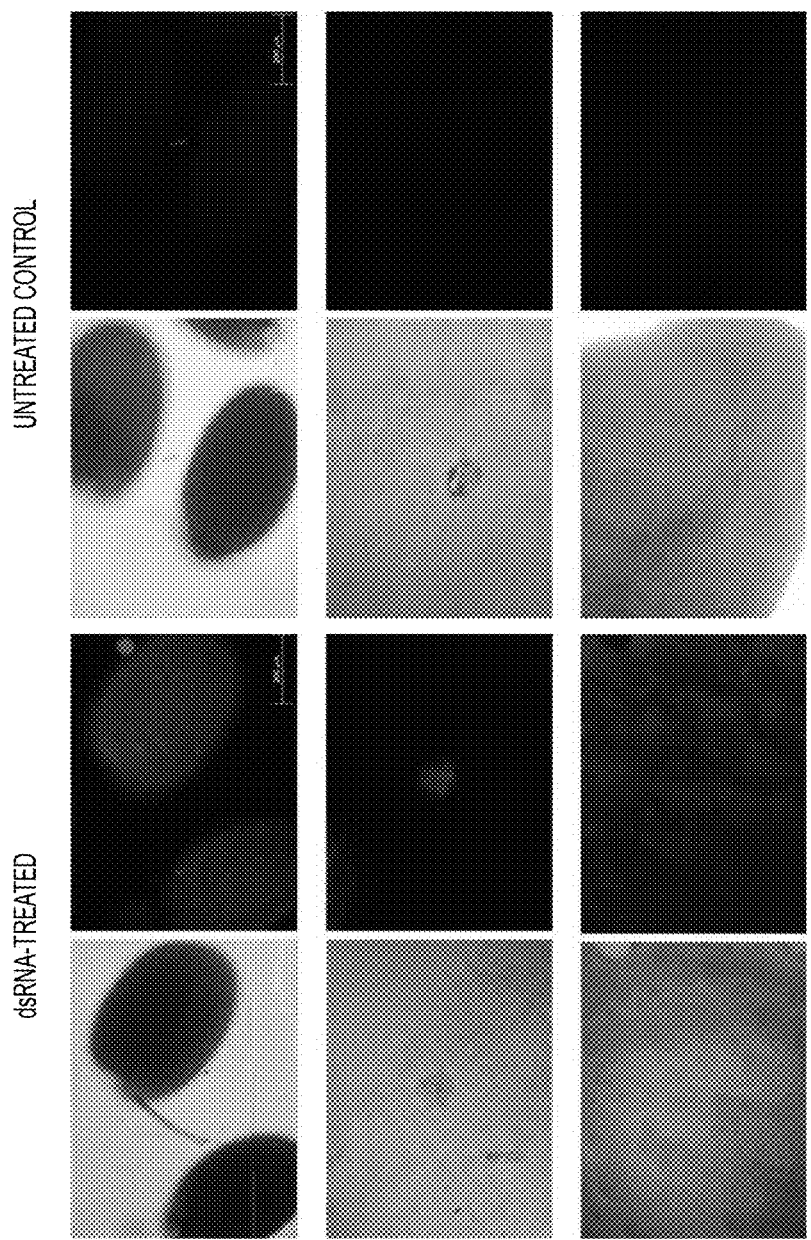

48 h RICE (ORYZA SATIVA) SLICES 48 h RICE (ORYZA SATIVA) SLICES 48 h RICE (ORYZA SATIVA) SLICES

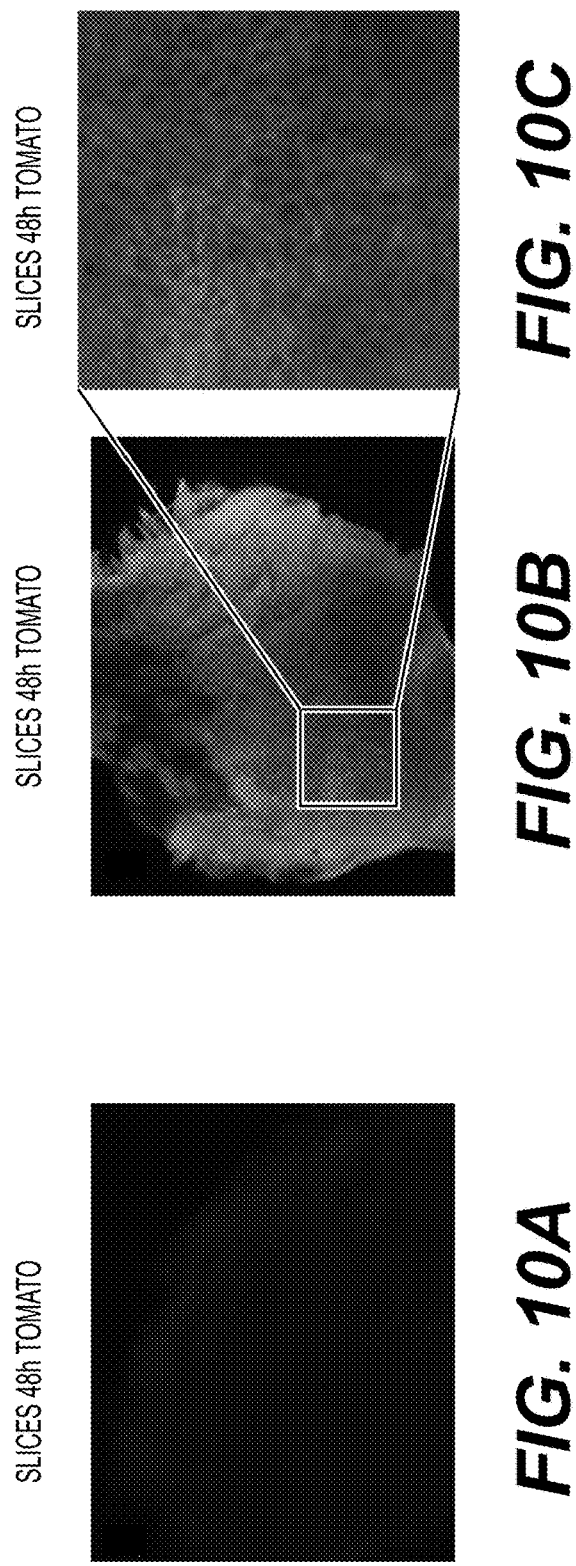

SLICES 48h TOMATO

SLICES 48h TOMATO

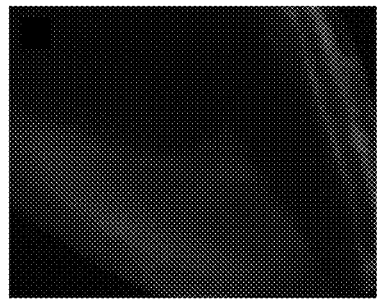
FIG. 11D
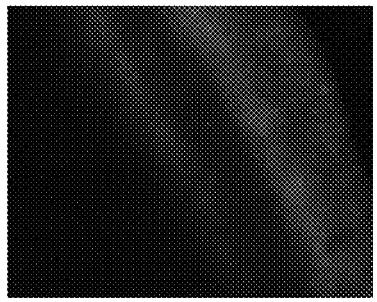  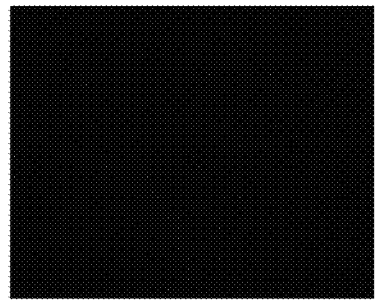
FIG. 11E  FIG. 11F

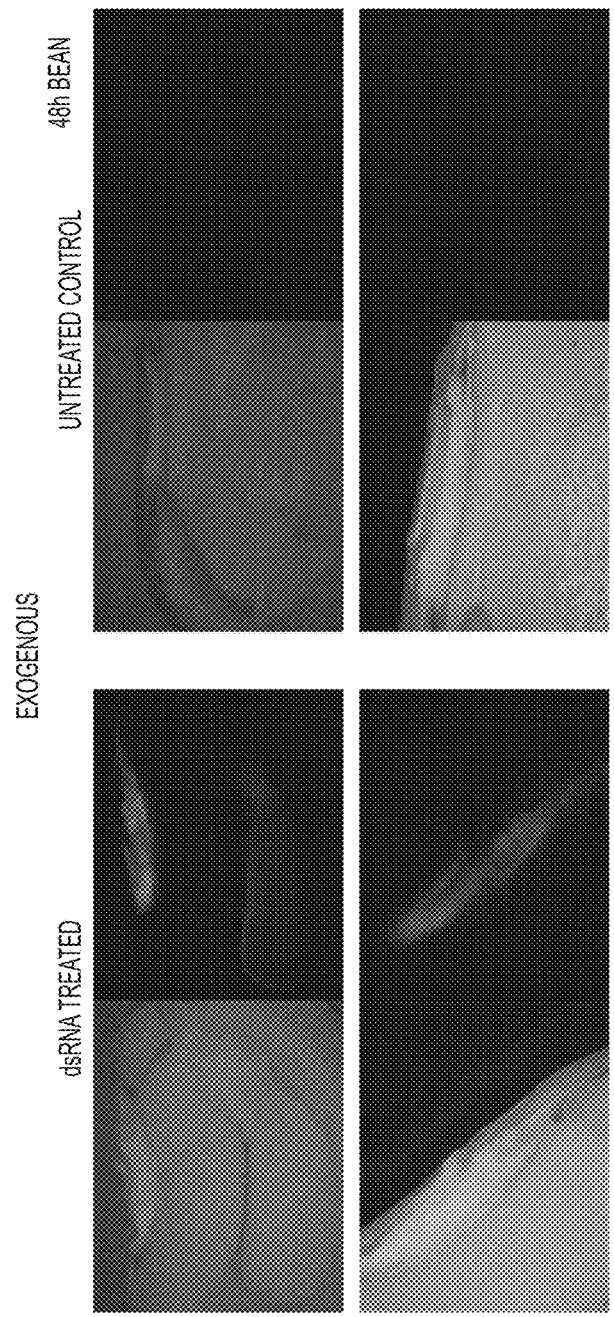

TREATMENT OF ARF8 dsRNA TO TOMATO SEEDS
(TARGET OF mir167):
VISUAL PHENOTYPES

TREATMENT OF ARF8 dsRNA TO TOMATO SEEDS
(TARGET OF mir167):
VISUAL PHENOTYPES

TREATMENT OF FW2.2 dsRNA TO TOMATO SEEDS
FIG. 34

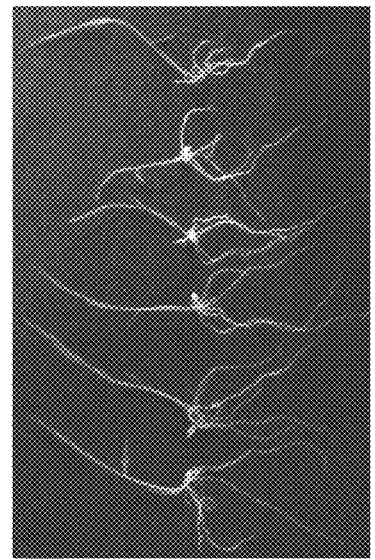
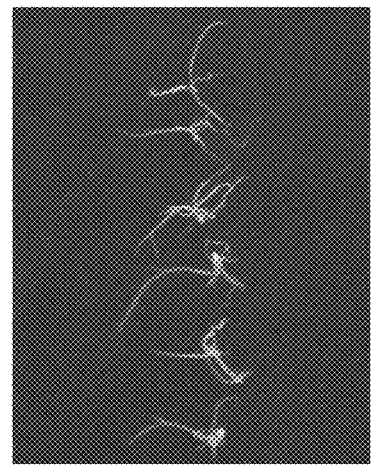
TREATMENT OF NRR dsRNA TO RICE SEEDS
FIG. 36A
FIG. 36B

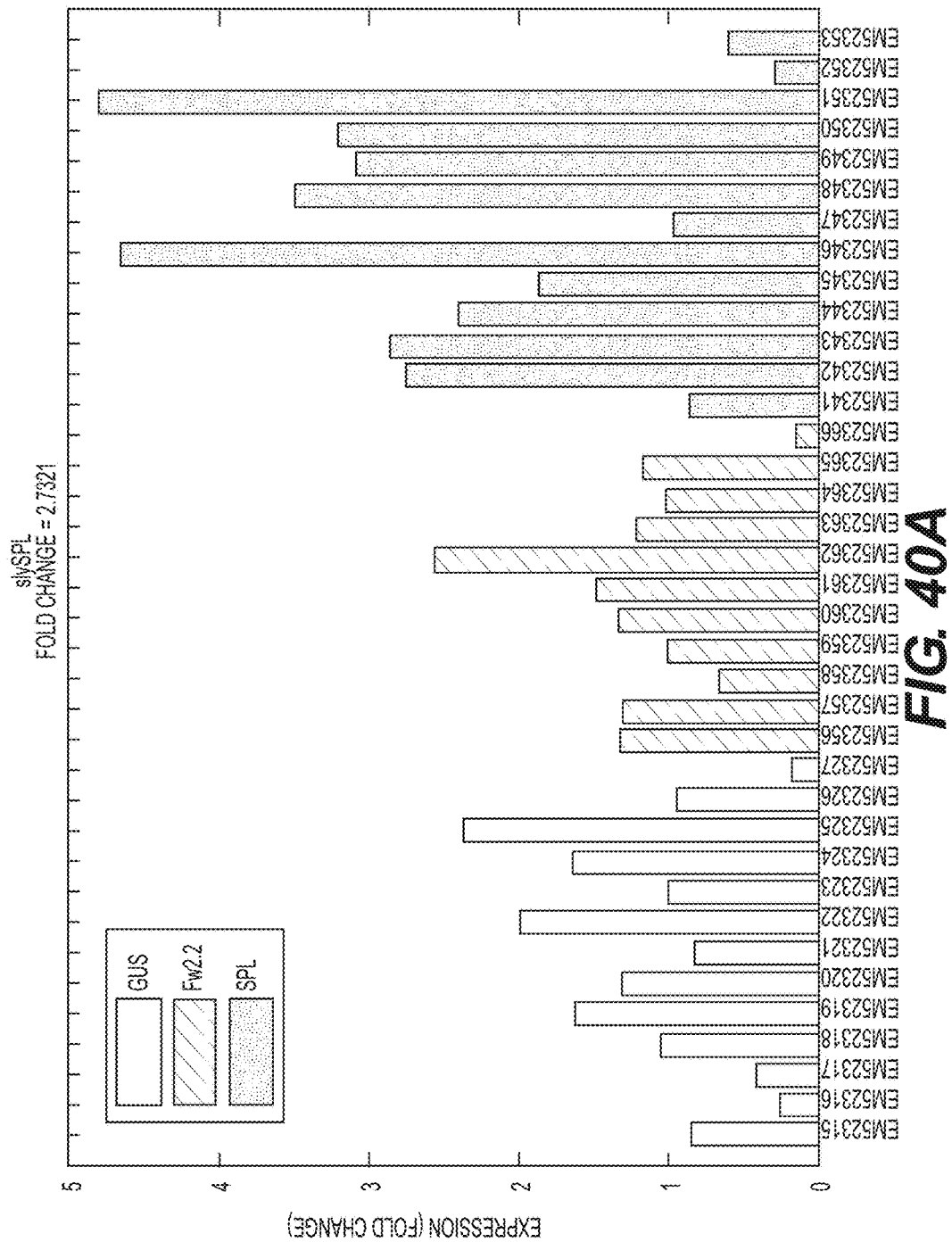

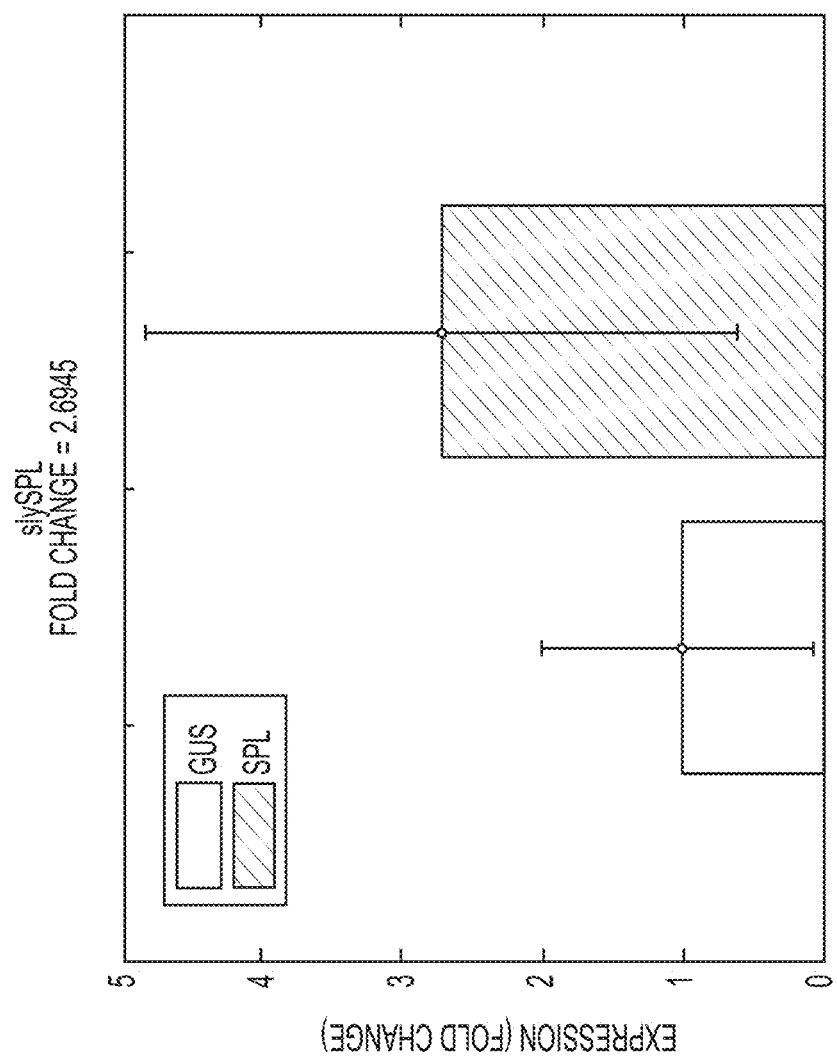

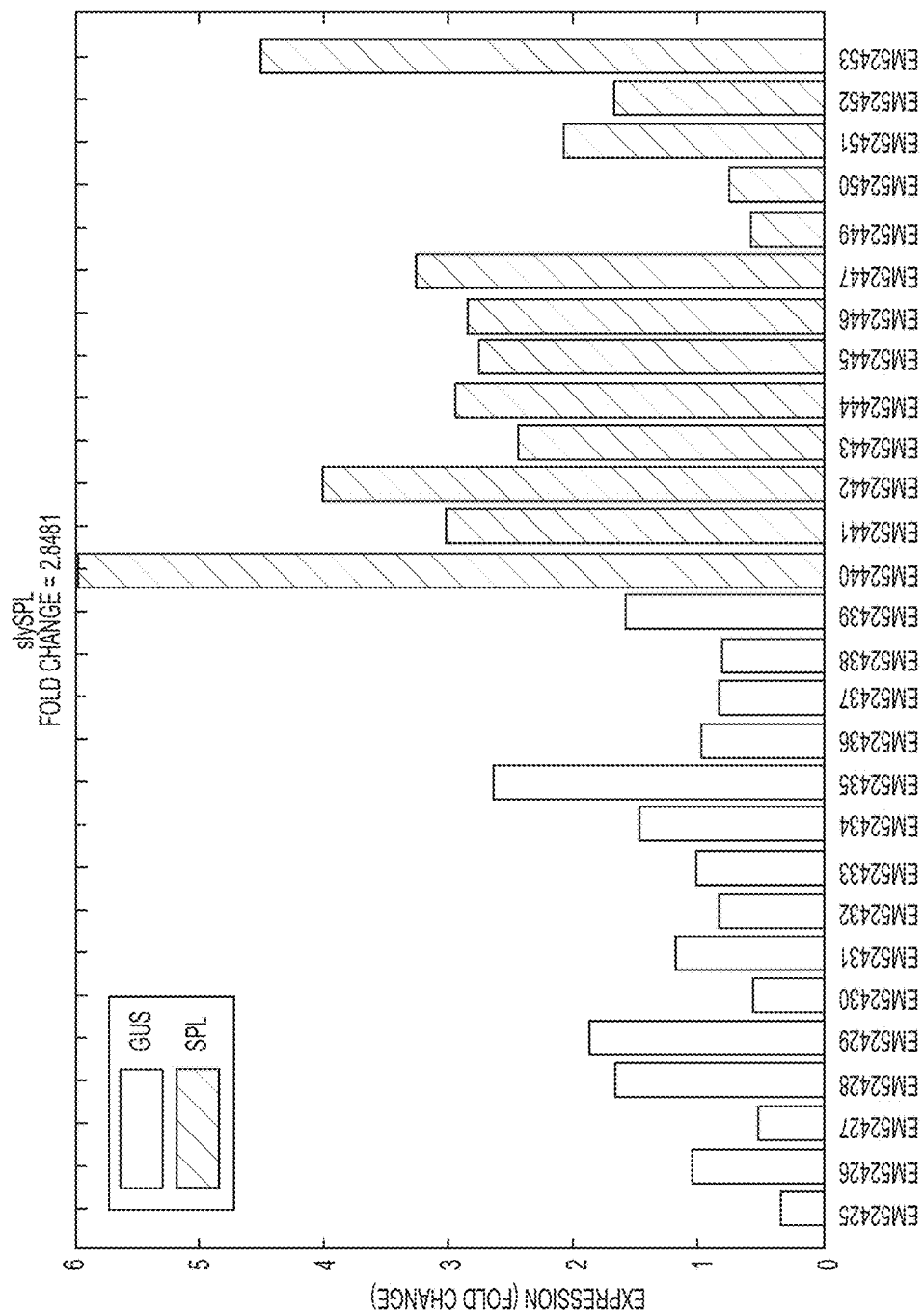

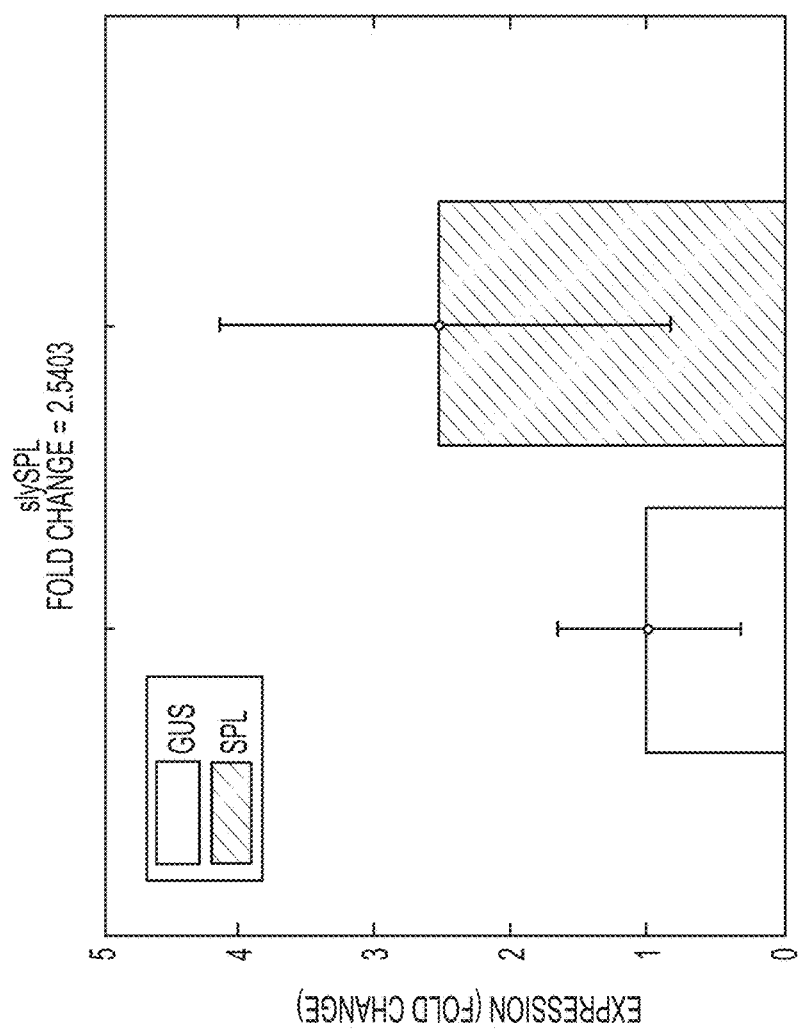

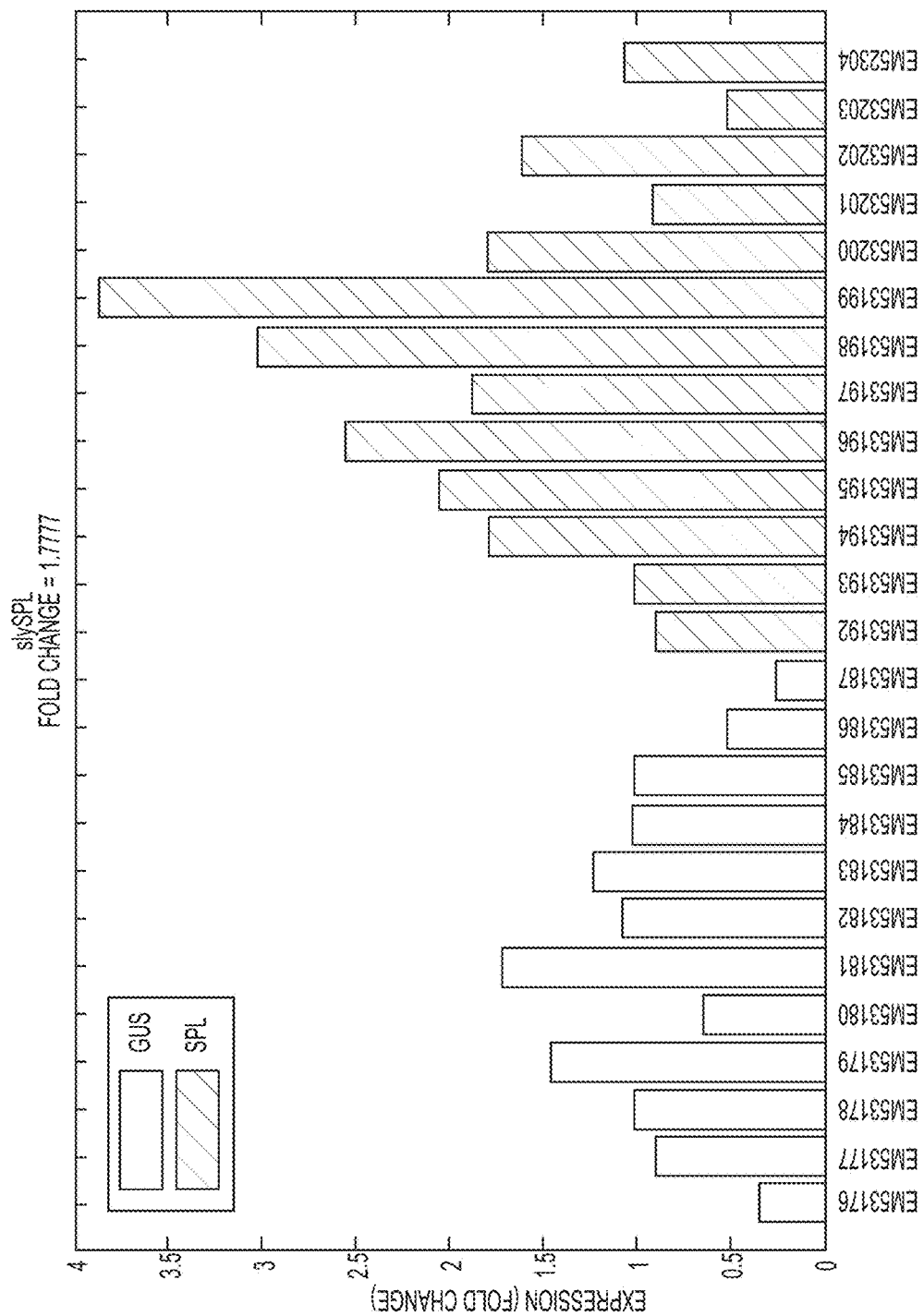

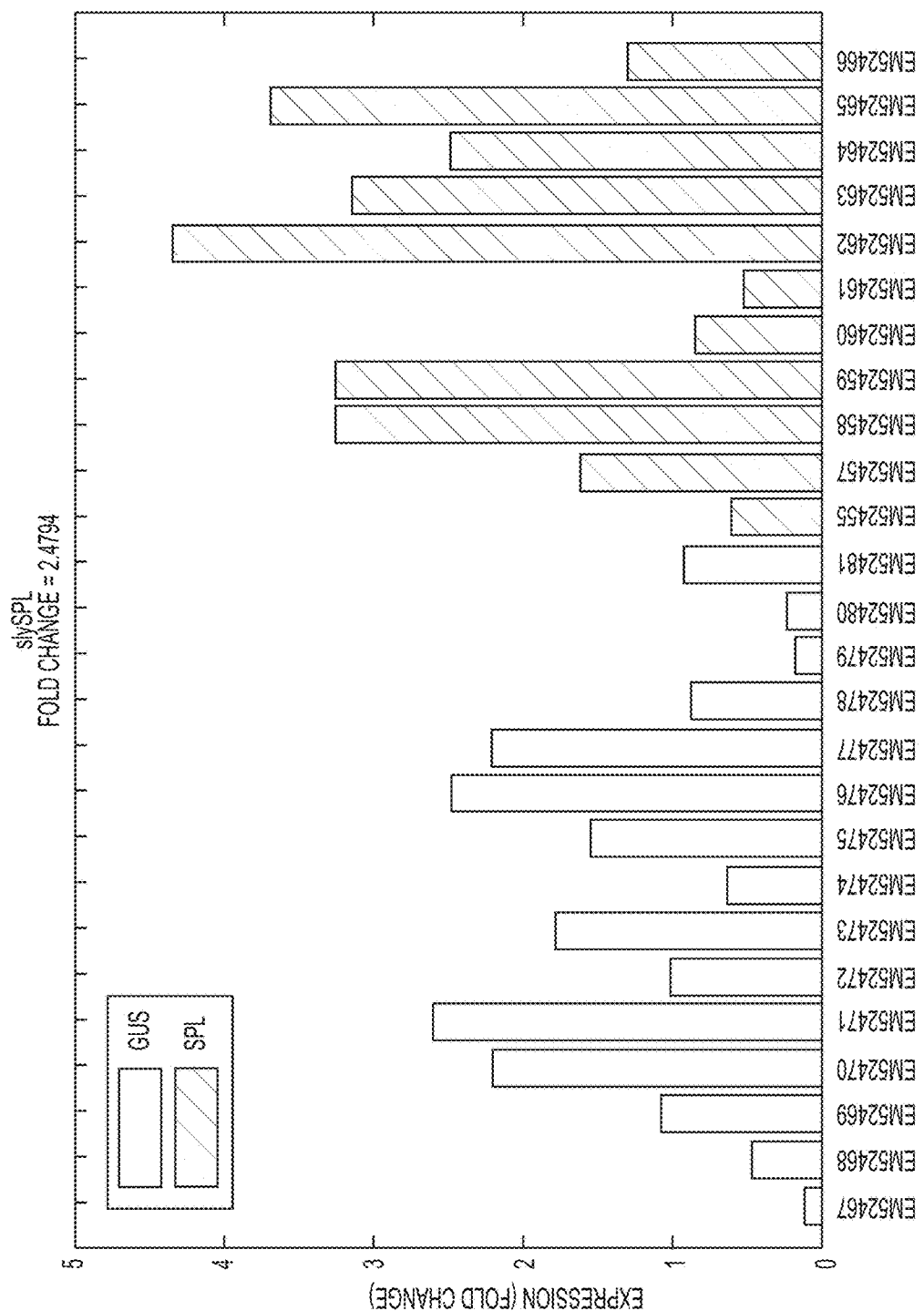

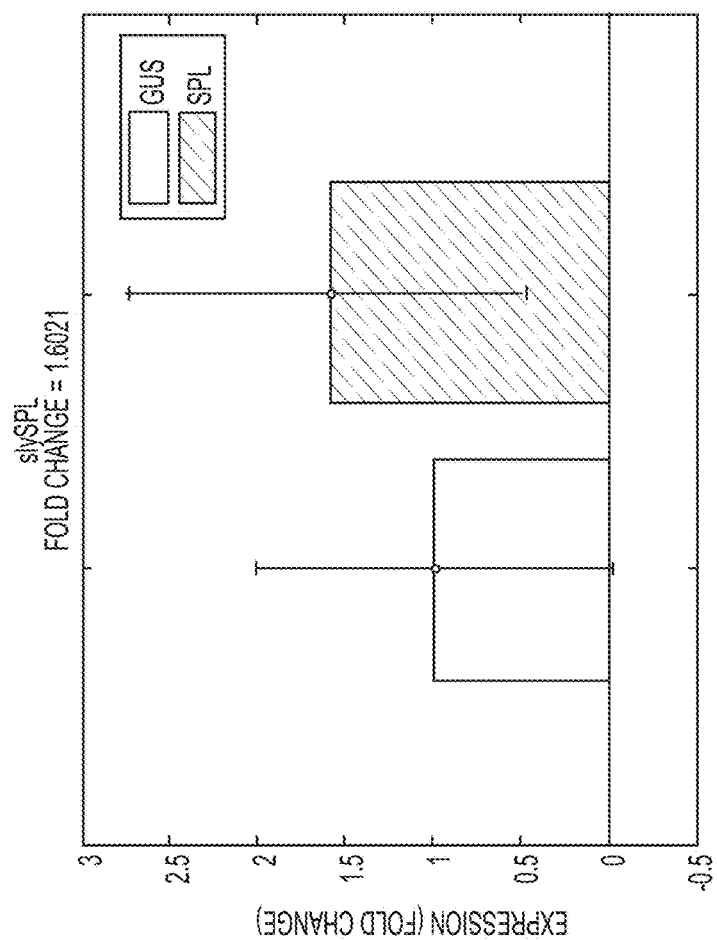

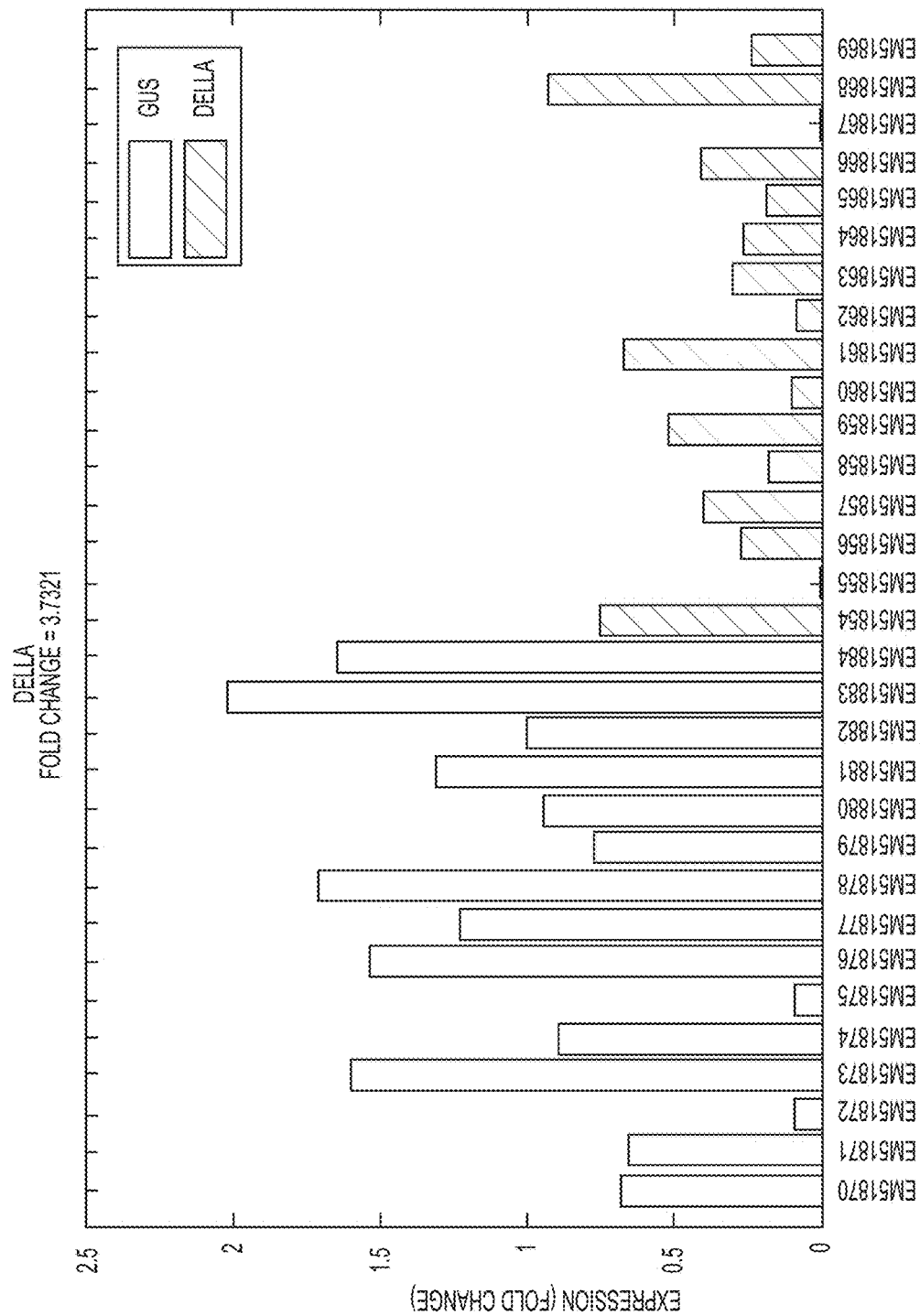

COMPOSITIONS AND METHODS FOR SILENCING GENE EXPRESSION

CROSS REFERENCE TO RELATED APPLICATIONS

This application claims the benefit under 35 U.S.C. § 119 of U.S. Provisional Application Nos. 61/651,131 filed May 24, 2012, 61/814,888 filed Apr. 23, 2013, 61/814,890 filed Apr. 23, 2013, 61/814,892 filed Apr. 23, 2013, 61/814,899 filed Apr. 23, 2013. Each of the foregoing applications is herein incorporated by reference in their entirety.

INCORPORATION OF THE SEQUENCE LISTING

This application contains a sequence listing including a file named P34078US00_SequenceListing.txt, which is 73,728 bytes in size (measured in MS-DOS) and was created on May 23, 2013, which is herein incorporated by reference in its entirety.

FIELD AND BACKGROUND OF THE INVENTION

The present invention, in some embodiments thereof, relates to methods of introducing dsRNA to plant seeds for modulating gene expression.

With a growing world population, increasing demand for food, fuel and fiber, and a changing climate, agriculture faces unprecedented challenges. Development of plants with improved traits is highly desirable, with some of the major traits that are of major interest to farmers and seed companies include improved abiotic stress tolerance, fertilizer use efficiency, disease resistance, yield and more.

Plant trait improvement is typically performed by either genetic engineering or classical breeding. New methods for trait improvement through specific gene alteration are highly desirable. These include methods for over-expression of genes or gene silencing. A powerful technique for sequence-specific gene silencing is through RNA interference (RNAi). First discovered in the nematode *C. elegans* (Fire et al 1998, *Nature*, 391:806-811), RNAi is a mechanism in which expression of an individual gene can be specifically silenced by introducing a double-stranded RNA (dsRNA) that is homologous to the selected gene, into cells. Inside the cell, dsRNA molecules are cut into shorter fragments of 21-27 nucleotides by an RNase III-related enzyme (Dicer). These fragments, called small interfering RNAs (siRNAs), get incorporated into the RNA-induced silencing complex (RISC). After additional processing, the siRNAs are transformed into single-stranded RNAs that act as guide sequences to eventually cleave target messenger RNAs. By using RNAi to specifically silence relevant target genes, one can alter basic traits of an organism. Specifically for plants, it holds incredible potential for modifications that may lead to increased stress resistance and better crop yield.

In plants, RNAi is typically performed by producing transgenic plants that over-express a DNA fragment that is transcribed to produce a dsRNA. This dsRNA is then processed into siRNAs that mediate the cleavage and silencing of target genes.

The major technical limitation for this technology is that many important plant crop species are difficult or impossible to transform, precluding the constitutive expression of constructs directing production of dsRNA. Moreover, questions concerning the potential ecological impact of virus-resistant transgenic plants have so far significantly limited their use [Tepfer, 2002, Annu. Rev. Phytopathol. 40, 467-491].

An additional hurdle for obtaining transgenic plants is attributed to the difficulty of having the transformation and regeneration events occur in the same cell types.

Therefore the development of a method for obtaining transformed seeds which is independent of the methods inherent to tissue culture procedures is at the cutting edge of plant molecular biology research.

Additional Background Art Includes:

U.S. 20040055041 teach seed transformation by making use of the sonication system followed by infection by *Agrobacterium*.

Chee et al. 1989 Plant Physiol. 91:1212-1218 teach soybean transformation by inoculating the plumule, cotyledonary node and adjacent cotyledon tissues of germinating soybean using an *Agrobacterium* that contained a binary vector expressing a transgene.

Additional related background art: WO2011/001434, U.S. 20080022423, WO 2011112570, WO 2007/080127 WO 2007/080126, U.S. 20060272049, U.S. 2010068172, U.S. 20070250947, WO9926467, U.S. 20030154508, WO 02/14472, U.S. 20030150017, U.S. 201000154083.

SUMMARY OF THE INVENTION

According to an aspect of some embodiments of the present invention there is provided a method of introducing naked dsRNA into a seed, the method comprising contacting the seed with the naked dsRNA under conditions which allow penetration of the dsRNA into the seed, thereby introducing the dsRNA into the seed.

According to an aspect of some embodiments of the present invention there is provided an isolated seed comprising an exogenous naked dsRNA, wherein the seed is devoid of a heterologous promoter for driving expression of the dsRNA in a plant.

According to an aspect of some embodiments of the present invention there is provided an isolated seed comprising an exogenous naked dsRNA.

According to an aspect of some embodiments of the present invention there is provided an isolated seed comprising an exogenous dsRNA being present at a similar concentration in an embryo and an endosperm of the seed.

According to an aspect of some embodiments of the present invention there is provided an isolated seed comprising an exogenous dsRNA being spatially distributed in an embryo and an endosperm of the plant seed in a spatial distribution that differs from a spatial distribution of the exogenous dsRNA in a seed derived from a transgenic plant that recombinantly expresses the exogenous dsRNA.

According to an aspect of some embodiments of the present invention there is provided an isolated seed comprising an exogenous dsRNA, wherein a concentration ratio of the exogenous dsRNA to siRNA maturing therefrom is higher in the seed as compared to a transgenic seed recombinantly expressing the exogenous dsRNA.

According to an aspect of some embodiments of the present invention there is provided an isolated seed comprising an exogenous dsRNA, wherein the plant seed is devoid of a heterologous promoter for driving expression of the exogenous dsRNA, wherein a spatial distribution of the exogenous dsRNA and/or siRNA maturing therefrom is altered in the seed as compared to same in a transgenic seed recombinantly expressing the exogenous dsRNA.

According to an aspect of some embodiments of the present invention there is provided a plant or plant part comprising an exogenous naked dsRNA and being devoid of a heterologous promoter for driving expression of the dsRNA in the plant.

According to an aspect of some embodiments of the present invention there is provided a seed containing device comprising a plurality of the seeds.

According to an aspect of some embodiments of the present invention there is provided a sown field comprising a plurality of any of the seeds.

According to some embodiments of the invention, the method further comprises drying said seed following said contacting.

According to some embodiments of the invention, the method further comprises growing said plant under abiotic or biotic stress following said generating.

According to some embodiments of the invention, the naked dsRNA is designed for down regulating expression of a gene of the plant.

According to an aspect of some embodiments of the present invention there is provided a method of producing a plant, the method comprising:
(a) providing any of the seeds; and
(b) germinating the seed so as to produce the plant.

According to an aspect of some embodiments of the present invention there is provided a method of modulating gene expression, the method comprising:
(a) contacting a seed of a plant with a naked dsRNA, under conditions which allow penetration of the dsRNA into the seed, thereby introducing the dsRNA into the seed; and optionally
(b) generating a plant of the seed.

According to some embodiments of the invention, the naked dsRNA is designed for down regulating expression of a gene of the plant.

According to some embodiments of the invention, the naked dsRNA is designed for down regulating expression of an edogenous gene of the plant.

According to some embodiments of the invention, the naked dsRNA is designed for down regulating expression of a gene of a viral pathogen.

According to some embodiments of the invention, the penetration is to an endosperm and alternatively or additionally an embryo of the seed.

According to some embodiments of the invention, the naked dsRNA does not integrate into the genome of the seeds.

According to some embodiments of the invention, the conditions result in presence of the dsRNA in the plant for at least 10 days following germination.

According to an aspect of some embodiments of the present invention there is provided a method of inhibiting expression of a target gene in a plant virus, the method comprising providing to the plant virus the plant or plant part, thereby inhibiting expression of a target gene in the plant virus.

According to some embodiments of the invention, the method further comprises observing reduced infectability or replicability of the viral pathogen following the providing.

According to an aspect of some embodiments of the present invention there is provided a kit for introducing naked dsRNA to seeds comprising;
(i) naked dsRNA; and
(ii) a priming solution.

According to some embodiments of the invention, the naked dsRNA and the priming solutions are comprised in separate containers.

According to some embodiments of the invention, the dsRNA comprises siRNA.

According to some embodiments of the invention, the dsRNA comprises siRNA and dsRNA.

According to some embodiments of the invention, the contacting is effected by inoculating the seed with the dsRNA.

According to some embodiments of the invention, the method further comprises priming the seed prior to the contacting.

According to some embodiments of the invention, the priming is effected by:
(i) washing the seed prior to the contacting; and
(ii) drying the seed following step (i).

According to some embodiments of the invention, the washing is effected in the presence of double deionized water.

According to some embodiments of the invention, the washing is effected for 2-6 hours.

According to some embodiments of the invention, the washing is effected at 4-28° C.

According to some embodiments of the invention, the drying is effected at 25-30° C. for 10-16 hours.

According to some embodiments of the invention, the contacting is effected in a presence of the naked dsRNA at a final concentration of 0.001-100 µg/µl.

According to some embodiments of the invention, the contacting is effected in a presence of the naked dsRNA at a final concentration of 0.001-0.5 µg/µl.

According to some embodiments of the invention, the method further comprises treating the seed with an agent selected from the group consisting of a pesticide, a fungicide, an insecticide, a fertilizer, a coating agent and a coloring agent following the contacting.

According to some embodiments of the invention, the treating comprises coating the seed with the agent.

According to some embodiments of the invention, the seed is free of an agent selected from the group consisting of a pesticide, a fungicide, an insecticide, a fertilizer, a coating agent and a coloring agent.

According to some embodiments of the invention, the dsRNA is for downregulating expression of a coding gene.

According to some embodiments of the invention, the dsRNA is for downregulating expression of a non-coding gene.

According to some embodiments of the invention, the seed is of the Viridiplantae super-family.

According to some embodiments of the invention, the conditions allow accumulation of the dsRNA in the endosperm and alternatively or additionally embryo of the seed.

According to some embodiments of the invention, a concentration of the naked dsRNA is adjusted according to a parameter selected from the group consisting of, seed size, seed weight, seed volume, seed surface area, seed density and seed permeability.

According to some embodiments of the invention, the contacting is effected prior to breaking of seed dormancy and embryo emergence.

According to some embodiments of the invention, the seed is a primed seed.

According to some embodiments of the invention, the seed or the plant comprises RNA dependent RNA polymerase activity for amplifying expression of the dsRNA.

According to some embodiments of the invention, the seed is a hybrid seed.

According to an aspect of some embodiments of the present invention there is provided a seed obtainable according to the methods described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C show the stability of dsRNA for CGMMV in rice seedlings up to 3 weeks post germination. FIG. 1A: Identification of dsRNA by RT-PCR, 1 week post germination. Top panel: L—100 bp DNA ladder, lanes 1-6: untreated control seeds, 7-16: treated seeds, lane 17: negative control (mix) and lane 18: positive control (plasmid). Bottom panel serves as a positive control for the cDNA quality, PCR for the housekeeping gene—tubulin. FIG. 1B: Identification of dsRNA by PCR, 2 weeks post germination. Top panel: L—DNA ladder, 1-2 control seeds, 3-12 dsRNA-treated seeds, 13—positive control (plasmid), 14-15 negative controls (DDW). Bottom panel shows results for tubulin housekeeping gene. FIG. 1C: stability of dsRNA 3 weeks post germination. Top panel: L—DNA ladder, 1-4 control seeds, 5-9 dsRNA-treated seeds, 11—positive control (plasmid) and 12 is negative control (mix). Bottom panel shows results for tubulin housekeeping gene.

FIG. 2A: CGMMV dsRNA is stable in tomato seedlings 10 days after germination. L—DNA ladder, 1-4: control seeds, 5-17: dsRNA-treated seeds, 18-19: negative controls (DDW), 20—PCR positive control (plasmid). FIG. 2B: CGMMV dsRNA is stable in sorghum seedlings 4 weeks after germination. 1-2: control seeds, 3-6: treated seeds, 7—negative control (DDW).

FIG. 4A: GUS dsRNA is stable in shoots of corn seedlings 1 week after germination. L is DNA ladder, 1-5 are control plants, 6-8 and 11-18 are dsRNA treated plants, 9 is a negative control (ddW) and 10 is a positive control (plasmid). FIG. 4B: GUS dsRNA is stable in corn seedlings' roots 1 week post germination. 1-5 are control plants, 6-10 are dsRNA treated plants, 11 is a negative control (ddW), and 12 is a positive control (plasmid). FIG. 4C: GUS dsRNA is stable in corn seedlings' roots 15 days post germination. L—DNA ladder, 1 is a positive control (plasmid), 2 is a control plant, 3 is a negative control (ddW) and 4 is a dsRNA-treated plant.

FIGS. 7A-C are images showing penetration of fluorescent siRNA molecules to various plant seeds. Seeds treated with fluorescent siRNA are shown on the two left images, and the untreated control seeds are shown on the two right images. Fluorescent images were taken 24 hours after seed treatment with siRNA at 2 µM final concentration. FIG. 7A—Arabidopsis seeds seen under 10× objective magnification, FIG. 7B—rice seeds seen under 5× objective magnification, FIG. 7C—tomato seeds seen under 5× objective magnification.

FIG. 9A—Light modality of 4 rice seeds: 2 siGLO-treated seeds at the bottom and 2 untreated seeds at the top. FIG. 9B—Fluorescence image of seeds seen in FIG. 9A. FIG. 9C—Zoomed in fluorescence image of a siGLO-treated rice seed (seen on bottom left of FIGS. 9A and B). FIG. 9D—Zoomed in fluorescence image of an untreated rice seed. FIG. 9E—Zoomed in fluorescence image of a siGLO-treated seed exhibiting a more absolute staining pattern compared to the seed seen in FIG. 9C. FIG. 9F—Zoomed in fluorescence image of an untreated seed for comparison to FIG. 9E.

FIGS. 10A-E are fluorescent images of sliced tomato seeds 48 hours following treatment with siGLO dsRNA. siGLO-treated and control tomato seeds are sliced to view the interior distribution of the fluorescent dsRNA using a fluorescent binocular. FIG. 10A—Fluorescence image of the outside surface of an untreated tomato seed. FIG. 10B—Fluorescence image of the outside surface of a siGLO-treated tomato seed. FIG. 10C—Zoomed in image of a section (see box on image of FIG. 10B) of the outside surface of a siGLO-treated tomato seed. FIG. 10D—Fluorescence image of the inside surface of a sliced untreated tomato seed. FIG. 10E—Fluorescence image of the inside surface of a sliced siGLO-treated tomato seed, the outline of the embryo is clearly seen.

FIGS. 11A-H are fluorescent images of sliced cucumber seeds 48 hours following treatment with siGLO dsRNA. siGLO-treated and control cucumber seeds are sliced to view the interior distribution of the fluorescent dsRNA using a fluorescent binocular. FIG. 11A—Fluorescence image of the inside surface of a siGLO-treated cucumber seed. FIG. 11B—Fluorescence image of the inside surface of an untreated cucumber seed. FIGS. 11C-E—Zoomed in images of the anterior, middle and posterior (respectively) sections of the inside surface of a siGLO-treated cucumber seed. The embryonic outline can be seen in the middle section (FIG. 11D). FIGS. 11F-H—Zoomed in images of the anterior, middle and posterior (respectively) sections of the inside surface of an untreated cucumber seed.

FIGS. 12A-D are fluorescent images of sliced seeds of various plant species, including bean, tomato, sorghum and wheat, 48 hours following treatment with siGLO dsRNA. siGLO-treated and control seeds are sliced to view the interior distribution of the fluorescent dsRNA using a fluorescent binocular. Light images are shown alongside the fluorescent image of the seed for reference. dsRNA-treated seeds are shown in the two left images and untreated control seeds are shown in the two right images. FIG. 12A shows two examples of dsRNA-treated and control bean seeds. FIG. 12B shows dsRNA-treated and control tomato seeds. FIG. 12C shows dsRNA-treated and control sorghum seeds. FIG. 12D shows dsRNA-treated and control wheat seeds.

FIG. 14A—Analysis of the PDS-1 dsRNA on 2% agarose gel. From left to right: 100 bp, dsDNA and dsRNA product 1, dsDNA and dsRNA after DNase turbo, dsDNA and dsRNA after DNase turbo and RNaseIII, space and the same for product 2. FIG. 14B—A picture of germinated rice seeds 5 days after treatment, control on the left. FIG. 14C—A picture of germinated rice seeds 7 days after treatment, control on the bottom. FIG. 14D—A Picture of planted rice seeds 14 days after treatment, the red x represents dead seedling, control on the left.

FIG. 16A is a picture of germinated rice seeds 7 days after treatment, control on the bottom. FIG. 16B—A picture of planted rice seeds 5 weeks after treatment, the control plant is on the left and has a darker green color compared to PDS-1 silenced plant. FIG. 16C—RNA was extracted from control and PDS-1 silenced plants and PDS-1 expression levels were checked by Real Time PCR. UBQ5 expression levels were served as normalizers and the PDS-1 expression levels in the control plants served as calibrators and got a value of 1.

FIG. 18A—RT-PCR using a first primer set where both primers are located inside the dsRNA molecule itself. FIG. 18B—Second primer set where the 5' part of the forward primer is in the dsRNA and the 3' part is in the mRNA, the reverse primer is located outside the dsRNA. FIG. 18C—Third primer set where primers are located outside of dsRNA molecule on the Hap2e gene. Results with all primer sets are consistent and give similar qualitative data. The average fold change of Hap2e expression of 5 control plants is used as a reference and is plotted as having a value of 1. Treated samples are plotted separately and their respective fold change of Hap2e target gene is calculated relative to expression in control plants. Five out of nine dsRNA-treated plants exhibit Hap2e down-regulation compared to control (5/9 of treated plants, efficiency of 55.5%).

FIG. 23A presents the height distribution of control plants (blue bars) and FIG. 23B shows the height distribution of treated plants (yellow bars).

In FIG. 26A, four plants show an ARF-8 gene down-regulation of over 26%, and in FIG. 26B, seven plants show an ARF-8 gene down-regulation of over 50%.

FIG. 28A—RT-PCR using first primer set where both primers are located inside the dsRNA molecule itself. FIG. 28B—Second primer set where primers are located on the SPL17 ORF, outside of the dsRNA molecule. The average fold change of SPL17 expression of 5 control plants is used as a threshold reference and is plotted as having a value of 1. Treated samples are plotted separately and their respective fold change of SPL17 target gene is calculated relative to expression in control plants. It is suggested the primer set #1 amplifies both the endogenous sequence and the dsRNA molecules introduced into the plant, whereas primer set #2 only amplifies the endogenous sequence.

FIG. 31D shows the average height of control plants compared with that of treated plants 62 days following treatment.

In FIG. 32A, top picture is a side view and bottom picture is a top view of the same plants. Treated plants are shorter and more branched compared to same-age control plants.

FIG. 33A shows the fold change of FW2.2 expression in control (shown in red bars) and dsRNA-treated (shown in blue bars) plants, which is plotted for each individual plant to demonstrate the variation in expression level of FW2.2 gene in the two plant groups. FIG. 33B shows the average expression of FW2.2 in control (red bar) compared to treated plants (blue bar). Down-regulation in expression level of FW2.2 gene is evident in treated plants compared to control plants.

FIG. 34 shows no phenotypic differences between control and FW2.2 dsRNA-treated plants 72 days after treatment. Both control plants (on the left) and dsRNA treated plants (on the right) have the same height on average and exhibit similar physical properties.

FIGS. 36A-B show longer and more developed root and shoot systems in rice seedlings grown from rice seeds treated against the NRR gene (FIG. 36B) compared to control plants (FIG. 36A) when the seedlings were grown on nitrogen free growth medium.

FIG. 37A—RT-PCR expression results for Hap2e gene, FIG. 37B—RT-PCR expression results for Della gene, FIG. 37C—RT-PCR expression results for SQS gene. Down-regulation of all genes is apparent in the dsRNA treated plants, ranging from 30% to 100% (complete silencing) expression reduction.

FIGS. 38A-B are fluorescent images while FIGS. 38C-D show transmitted light images. Images are taken 24 hours following seed treatment with siRNA at 1 µM final concentration.

FIGS. 40A-B are bar graphs showing real-time PCR analyses of SPL mRNA expression in 17-days old tomato plants germinated from seeds treated with 50 µg/ml dsRNA for 24 hours. FIG. 40A shows fold change in SPL mRNA expression following treatment with SPL (blue bars, SEQ ID NO: 126), GUS (red bars, SEQ ID NO: 21) and FW2.2 (green bars, SEQ ID NO: 114) dsRNAs. Each bar represents one plant. Expression values per individual plants are normalized to the median expression of all plants treated with GUS dsRNA. FIG. 40B shows that Median values of the data shown in FIG. 40A. p-value=0.02 for difference in SPL expression level relative to GUS control and p-value=0.07 for difference in SPL expression level relative to FW2.2 control. Error bars represent one standard deviation of the data.

FIGS. 41A-B are bar graphs showing real-time PCR analyses of SPL mRNA expression in 18-days old tomato plants germinated from seeds treated with 50 µg/ml dsRNA for 6 hours (the dsRNAs are as in FIGS. 40A-B). FIG. 41A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 41B shows Median values of the data shown in FIG. 41A. The change in expression relative to control group is significant (p-value=0.012). Error bars represent one standard deviation of the data.

FIGS. 42A-B are bar graphs showing real-time PCR analyses of SPL mRNA expression in 18-days old tomato plants germinated from seeds treated with 50 µg/ml dsRNA for 2 hours (the dsRNAs are as in FIGS. 40A-B). FIG. 42A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 42B shows Median values of the data shown in FIG. 42A. The change in expression relative to control group is significant (p-value=0.0015). Error bars represent one standard deviation of the data.

FIGS. 43A-B are bar graphs showing real-time PCR analysis of SPL mRNA expression in 18-days old tomato plants germinated from seeds treated with 50 µg/ml dsRNA for 10 minutes (the dsRNAs are as in FIGS. 40A-B). FIG. 43A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 43B shows Median values of the data shown in FIG. 43A. The change in expression relative to control group is significant (p-value=0.0035). Error bars represent one standard deviation of the data.

FIGS. 44A-B are bar graphs showing real-time PCR analysis of SPL mRNA expression in 13-days old tomato plants germinated from seeds dipped in 50 µg/ml dsRNA solution (the dsRNAs are as in FIGS. 40A-B). FIG. 44A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 44B shows Median values of the data shown in FIG. 44A. The change in expression relative to control group is significant (p-value=0.017). Error bars represent one standard deviation of the data.

FIGS. 45A-B are bar graphs showing real-time PCR analyses of SPL mRNA expression in 17-days old tomato plants germinated from seeds treated with 25 µg/ml dsRNA for 24 hours (the dsRNAs are as in FIGS. 40A-B). FIG. 45A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 45B shows Median values of the data shown in FIG. 45A. The change in expression relative to control group is significant (p-value=0.049). Error bars represent one standard deviation of the data.

FIG. 46A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 46B shows Median values of the data shown in FIG. 46A. The change in expression relative to control group is significant (p-value=0.0062). Error bars represent one standard deviation of the data.

FIG. 47A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 47B shows Median values of the data shown in FIG. 47A. Error bars represent one standard deviation of the data.

FIG. 48A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 48B shows Median values of the data shown in FIG. 48A. Error bars represent one standard deviation of the data.

FIG. 49A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 49B shows Median values of the data shown in FIG. 49A. Error bars represent one standard deviation of the data.

FIGS. 50A-B are bar graphs showing real-time PCR analyses of SPL mRNA expression in 18-days old tomato plants germinated from seeds treated with 1 µg/ml dsRNA for 10 minutes (the dsRNAs are as in FIGS. 40A-B). FIG. 50A shows fold change in SPL mRNA expression following treatment with SPL dsRNA, for which GUS dsRNA treatment is used as control baseline. Each bar represents one plant. Expression values per individual plants are normalized to the median expression of all plants treated with GUS dsRNA. FIG. 50B shows Median values of the data shown in FIG. 50A. Error bars represent one standard deviation of the data.

FIG. 51A shows fold change in SPL mRNA expression following treatment with SPL siRNA for which GUS siRNA treatment is used as control baseline. Expression values per individual plants are normalized to the median expression of all plants treated with GUS siRNA. FIG. 51B shows Median values of the data shown in FIG. 51A. The change in expression relative to control group has a p-value of 0.12. Error bars represent one standard deviation of the data.

FIG. 53A shows fold change in FW2.2 mRNA expression following treatment with FW2.2 dsRNA (SEQ ID NO: 114), for which GUS dsRNA (SEQ ID NO: 21) treatment is used as control baseline. Each bar represents one plant. Expression values per individual plants are normalized to the median expression of all plants treated with GUS dsRNA. FIG. 53B shows Median values of the data shown in FIG. 53A. The change in FW2.2 expression relative to control group is significant (p-value=0.024). Error bars represent one standard deviation of the data.

FIG. 54A shows fold change in FW2.2 mRNA expression following treatment with FW2.2 dsRNA, for which GUS dsRNA treatment is used as control baseline. Each bar represents one plant. Expression values per individual plants are normalized to the median expression of all plants treated with GUS dsRNA. FIG. 54B shows Median values of the data shown in FIG. 54A. The change in FW2.2 expression relative to control group has a p-value of 0.1. Error bars represent one standard deviation of the data.

FIG. 55A shows fold change in FW2.2 mRNA expression following treatment with FW2.2 dsRNA, for which GUS dsRNA treatment is used as control baseline. Each bar represents one plant. Expression values per individual plants are normalized to the median expression of all plants treated with GUS dsRNA. FIG. 55B shows Median values of the data shown in FIG. 55A. The change in FW2.2 expression relative to control group is significant (p-value=0.049). Error bars represent one standard deviation of the data.

FIGS. 56A-B are bar graphs showing real-time PCR analyses of DELLA mRNA expression in 13-days old rice plants germinated from seeds treated with 142 µg/ml dsRNA for 24 hours. FIG. 56A shows fold change in DELLA mRNA expression following treatment with DELLA dsRNA (SEQ ID NO: 123), for which GUS dsRNA (SEQ ID NO: 21) treatment is used as control baseline. Each bar represents one plant. Expression values per individual plants are normalized to the median expression of all plants treated with GUS dsRNA. FIG. 56B shows Median values of the data shown in FIG. 56A. The change in DELLA expression relative to control group is significant (p-value=$6.28 \times 10^{-4}$). Error bars represent one standard deviation of the data.

FIG. 58A shows fold change in TB1 mRNA expression following treatment with TB1 dsRNA (SEQ ID NO: 145) and CGMMV dsRNA (SEQ ID NOs: 8 and 11) as control. Each bar represents one plant. Expression values per individual plants are normalized to the median expression of all plants treated with CGMMV dsRNA. FIG. 58B shows Median values of the data shown in FIG. 58A. The change in TB1 expression relative to CGMMV control has a p-value of 0.065. Error bars represent one standard deviation of the data.

FIG. 59A—Seeds put in germination boxes after treatment with dsRNAs (SEQ ID NOs; 83 and 21 for NAC and GUS, respectively). FIG. 59B—Seeds washed and dried after treatment with dsRNAs. GUS dsRNA served as control. Each dot represents one plant. FIG. 59C—Real-time PCR analysis of NAC mRNA expression in 12-days old corn leaves germinated from seeds treated in the same way as in FIGS. 59A and 59B, and planted in soil. Note the upregulation in NAC mRNA 5 days following germination and down regulation thereafter.

FIG. 60A shows the expression levels of HY5.5 mRNA in one-week old plants following treatment with HY5.5 dsRNA (SEQ ID NO: 156), HY5.6 dsRNA (SEQ ID NO: 160) or a mix of the two (1:1, altogether 50 µg/ml). GUS dsRNA (SEQ ID NO: 21) or 0.1 mM EDTA (buffer) served as controls. Each dot represents one plant. FIG. 60B shows the expression levels of HY5.6 mRNA in one-week old plants following treatment with HY5.5 dsRNA, HY5.6 dsRNA or a mix of the two. GUS dsRNA or 0.1 mM EDTA (buffer) served as controls. Each dot represents one plant. FIG. 60C shows the expression levels of HY5.5 mRNA in two-week old plants following treatment with HY5.5 dsRNA (SEQ ID NO: 156), HY5.6 dsRNA (SEQ ID NO: 160) or a mix of the two (1:1, altogether 50 µg/ml). GUS dsRNA (SEQ ID NO: 21), DHFR dsRNA (SEQ ID NO: 167) or 0.1 mM EDTA (buffer) served as controls. Each dot represents one plant. FIG. 60D shows the expression levels of HY5.6 mRNA in two-week old plants following treatment with HY5.5 dsRNA (SEQ ID NO: 156), HY5.6 dsRNA (SEQ ID NO: 160) or a mix of the two (1:1, altogether 50 µg/ml). GUS dsRNA (SEQ ID NO: 21), DHFR dsRNA (SEQ ID NO: 167) or 0.1 mM EDTA (buffer) served as controls. Each dot represents one plant.

FIG. 62A is a graph showing real-time PCR analysis of DND1 mRNA expression in 15-days old cucumber plants germinated from seeds treated with 100 µg/ml dsRNA (SEQ ID NOs: 171 and 172) for 24 hours. GUS dsRNA (SEQ ID NO: 21) or 0.1 mM EDTA (formulation) served as controls. Each dot represents one plant. FIG. 62B shows percent gall rating of cucumber roots 11 days after seed treatment with DND1 dsRNA. GFP dsRNA and 0.1 mM EDTA (formulation) are control treatments.

DESCRIPTION OF SPECIFIC EMBODIMENTS OF THE INVENTION

Figure 1C:
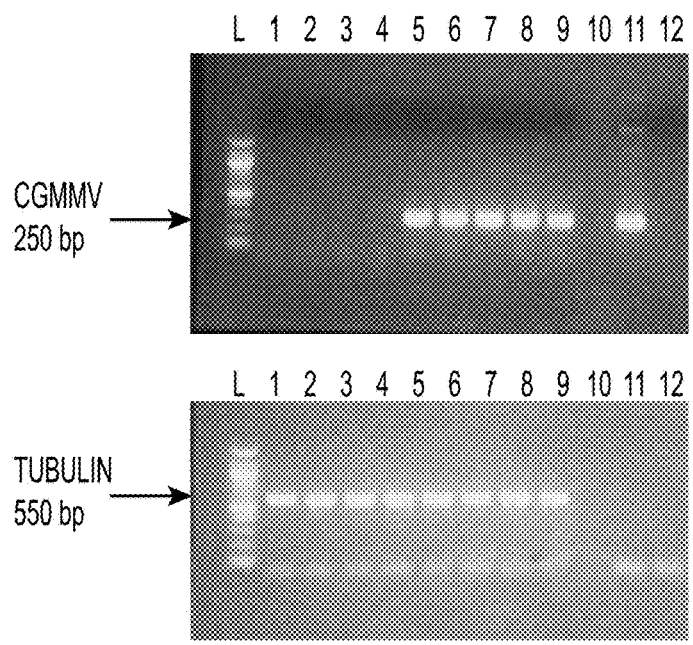

The present invention, in some embodiments thereof, relates to methods of introducing dsRNA to plant seeds for modulating gene expression.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

With the extensive growth of the world-population and the limited habitats for plant growth and cultivation, there is an urging need to improve plant yields under these changing conditions.

RNAi has emerged as a powerful tool for modulating gene expression which can be used for generating plants with improved stress tolerance.

In plants, RNAi is typically performed by producing transgenic plants that express a DNA fragment that is transcribed to produce a dsRNA. This dsRNA is then processed into siRNAs that mediate the silencing of target genes, typically by targeting cleavage of the target gene by an RNA Induced Silencing Complex (RISC) or by translational repression.

The major technical limitation for this technology is that many important plant crop species are difficult or impossible to transform, precluding the constitutive expression of constructs directing production of dsRNA. Moreover, questions concerning the potential ecological impact of virus-resistant transgenic plants have so far significantly limited their use [Tepfer, 2002, Annu. Rev. Phytopathol. 40, 467-491].

The present inventors have now devised a novel technology for introducing dsRNA molecules directly to the plant seed. These dsRNA molecules enter seeds and start a silencing process, which is continued during the life cycle of the plant, resulting in a plant with an improved trait of interest. The introduced dsRNA is naked and as such no exogenous transcription regulatory elements are introduced into the plant thus lowering the environmental concerns associated with transgenic plants. In addition, the modified seed can be germinated to generate a plant without the need of going through the laborious and cumbersome steps of tissue culture regeneration.

As is illustrated herein below and in the Examples section, which follows, embodiments of the present invention includes configuring the conditions necessary to introduce naked dsRNA into the seeds (see e.g., Example 1). The naked dsRNA doesn't integrate into the genome and is highly stable in the plant and in solution (Examples 2-4). The naked dsRNA penetrates through the seed coat (i.e., testa) of both monocot and dicot plants and distributes in the endosperm and seed embryo (Examples 5-6). In one aspect, embodiments of the present invention include altering expression of endogenous genes (Examples 7-14). In another aspect, embodiments of the present invention include introducing into seeds dsRNA directed to viral genes (Example 2). These results were reproduced over a number of plants of both monocot and dicot groups. In a further aspect, embodiments of the present invention include providing a wide range of doses and kinetics which resulted in a significant alteration of gene expression (see e.g., Examples 23-29). These results are further established in wheat and substantiated by a biological effect showing delayed germination ((Example 30). Further, as shown in Examples 31 and 32, gene expression is altered in Corn following introduction of dsRNA for various targets. Examples 33-37 show dsRNA treatment of other vegetables, including cucumber and lettuce ( ). In a further aspect, embodiments of the present invention include altering gene expression in another commercial crop i.e., soy (see, e.g., Example 42). Thus, the present results are sufficient to show that the present teachings provide a cost-effective treatment of plant seeds to achieve a desired agricultural and horticultural phenotype. Without being bound by theory, it is suggested that the newly suggested transformation modality and modulation of gene expression is dependent on and associated with:

(i) Introduction of naked dsRNA into the interior of seeds (as opposed to mere seed coating). The introduction is effected by soaking the seeds in a solution which comprises the dsRNA such that the dsRNA penetrates through the seed coat or by dipping such that the dsRNA coats the seed and penetrates through the coat after sowing;

(ii) Amplification of the dsRNA signal; and (iii) Spreading of the dsRNA signal throughout the plant.

The first step occurs only once, during and shortly after the initial seed treatment, while the second and third steps occur in a repetitive loop for as long as the silencing signal remains active in the plant.

A suggested unbinding mode of action for the described invention is based on each step:

Introduction of dsRNA into Seeds

A typical mature seed consists of an embryo encapsulated within a maternal seed coat (testa) and an abundant layer of endosperm tissue between the embryo and seed coat. The endosperm serves as a nutrient source for the embryo during seed development, germination and seedling establishment.

Seed germination typically begins with exposure of the seeds to water, which is absorbed by the embryo and endosperm. The endosperm then expands in volume, with the endosperm of some plant species being able to grow several-fold from their original volume. The embryo, which was dormant until this stage, is now released from dormancy and cell division, expansion and differentiation begin. The endosperm feeds the developing embryo until it is developed enough to begin photosynthesis and autotrophic growth.

Based on these known mechanisms of seed germination, two possible modes of action for the initial step of "Introduction of dsRNA into seeds" are suggested:

The dsRNA molecules enter the embryo directly, carried by the water-based solution which is used for the seed treatment.

The dsRNA molecules enter the endosperm as part of the endosperm's water-absorption process. These molecules then feed the embryo as it develops as part of the nutrient flow from the endosperm during germination and seed development.

Based on the results described in FIGS. 7-13, it is estimated that a combination of the two options takes place. That is, some of the dsRNA enters the embryo directly and some is retained in the endosperm and feeds the developing embryo during seed germination.

Amplification of the dsRNA Signal

Once the dsRNA molecules enter the embryo, they are recognized and processed by RNase III-like enzymes such as Dicer or Dicer-like (DCL) enzymes. DCL enzymes process the long dsRNA molecules into short, double strand RNAs (known as siRNAs or shRNAs), which are typically 21-24 nucleotides (nt) long. One of the siRNA strands is typically rapidly degraded and the second one can be incorporated in RISC (RNA Induced Silencing Complex) protein complexes, which contain an Argonaute (AGO) protein. AGO proteins contain a PIWI domain to bind siRNAs and a PAZ domain with RNase activity. Subsequently, the siRNA/AGO complex identifies an mRNA molecule, which is complementary to the siRNA and results in its silencing by cleavage or translational repression.

The siRNA is then released from the RISC complex and can now act as a primer for an RNA-Dependant RNA Polymerase (RDRP), this is an enzyme which is unique to the plant kingdom and can generate amplification of the silencing signal by generating new dsRNA molecules (secondary siRNA). These newly-synthesized dsRNAs can be processed again as described above, therefore maintaining and amplifying the silencing signal.

Spreading of the Silencing Signal

Silencing spreading is a known and well-understood phenomenon in plants. It is believed that short distance, cell-to-cell spreading occurs through plasmodesmata. This process is thought to be mediated by a 21nt-long siRNA, which is the product of a DCL enzyme. Additionally, systemic spreading is achieved through the phloem across the entire plant from source to sink.

It is assumed that in the described methodology, spreading of the silencing signal occurs once the silencing signal begins and is amplified as described above. This may include both short-distance and systematic spreading by various siRNA signal molecules.

Thus according to an aspect of the invention, there is provided a method of introducing naked double-stranded RNA (dsRNA) into a seed, the method comprising contacting the seed with the naked dsRNA under conditions which allow penetration of the dsRNA into the seed, thereby introducing the dsRNA into the seed.

As used herein the phrase "naked dsRNA" refers to a dsRNA nucleic acid molecule which is non-transcribable in the plant cell. Thus, the naked dsRNA molecule is not comprised in a nucleic acid expression construct such as a viral vector. According to some embodiments of the invention, the naked dsRNA molecule is not derived from a viral vector. According to other embodiments of the invention, the naked dsRNA molecule is not produced from a natural viral infection. The naked dsRNA may comprise regulatory elements for in-vitro transcription, such as the T7 promoter. According to some embodiments of the invention, the naked dsRNA may be modified e.g., chemically modified, to confer higher bioavailability, penetration into the seeds and/or improved shelf-life.

As used herein the term "dsRNA" relates to two strands of anti-parallel polyribonucleic acids held together by base pairing. The two strands can be of identical length or of different lengths provided there is enough sequence homology between the two strands that a double stranded structure is formed with at least 80%, 90%, 95% or 100% complementarity over the entire length. According to an embodiment of the invention, there are no overhangs for the dsRNA molecule. According to another embodiment of the invention, the dsRNA molecule comprises overhangs. According to other embodiments, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed.

As mentioned any dsRNA molecule can be used in accordance with the present teachings. In some embodiments, dsRNA used in the present application is subject to amplification by RNA-Dependant RNA Polymerase (RDRP). Without being limited, dsRNA can be siRNA, shRNA, pre-miRNA, or pri-miRNA.

The present teachings relate to various lengths of dsRNA, whereby the shorter version i.e., x is shorter or equals 50 bp (e.g., 17-50), is referred to as siRNA or miRNA. Longer dsRNA molecules of 51-600 are referred to herein as dsRNA, which can be further processed for siRNA molecules.

In one embodiment, the dsRNA in the present application is between 20 and 100 bp, between 25 and 90 bp, between 30 and 80 bp, between 30 and 70 bp, between 30 and 60 bp, or between 30 and 50 bp. In another embodiment, the dsRNA in the present application is about 50 bp. In a further embodiment, the 5' and/or 3' ends of the sense and/or antisense strands of the dsRNA comprise 1, 2, 3, 4, 5, 6, 7, 8, 9, 10 or more nucleotide overhangs. In some embodiments, the dsRNA comprises 1, 2, or 3 nucleotide overhangs on the 5' and/or 3' ends of the sense and/or antisense strands. In another embodiment, the ends of the dsRNA are blunt.

In one embodiment, the dsRNA in the present application is between 15 and 500 bp, between 15 and 450 bp, between 15 and 400 bp, between 15 and 350 bp, between 15 and 300 bp, between 15 and 250 bp, between 15 and 200 bp, between 15 and 150 bp, between 15 and 100 bp, between 15 and 90 bp, between 15 and 80 bp, between 15 and 70 bp, between 15 and 60 bp, between 15 and 50 bp, between 15 and 40 bp, between 15 and 35 bp, between 15 and 30 bp, or between 15 and 25 bp. In another embodiment, the dsRNA in the present application is at least about 20, 25, 30, 35, 40, 45, 50, 75, 100, 150, 200, 250, 300, 350, 400, 500, 600, 800, 900, 1000 nucleotides long. In a further embodiment, the dsRNA in the present application is between 100 and 1000 bp, between 200 and 1000 bp, between 300 and 1000 bp, between 400 and 1000 bp, between 500 and 1000 bp, between 600 and 1000 bp, between 700 and 1000 bp, between 800 and 1000 bp, or between 900 and 1000 bp. The term "siRNA" refers to small inhibitory RNA duplexes (generally between 17-30 basepairs, but also longer e.g., 31-50 bp) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550, SEQ ID NO: 22) and 5'-UUUGUGUAG-3' (Castanotto, D. et al. (2002) RNA 8:1454, SEQ ID NO: 23). It will be recognized by one of skill in the art that the resulting single chain oligonucleotide forms a stem-loop or hairpin structure comprising a double-stranded region capable of interacting with the RNAi machinery.

As used herein, the phrase "microRNA (also referred to herein interchangeably as "miRNA" or "miR") or a precursor thereof" refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule, wherein the other RNA molecule comprises a nucleotide sequence essentially complementary to the nucleotide sequence of the miRNA molecule.

Typically, a miRNA molecule is processed from a "pre-miRNA" or as used herein a precursor of a pre-miRNA molecule by proteins, such as DCL proteins, present in any plant cell and loaded onto a RISC complex where it can guide the cleavage of the target RNA molecules.

Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides which can adopt a secondary structure comprising an imperfect double stranded RNA stem and a single stranded RNA loop (also referred to as "hairpin") and further comprising the nucleotide sequence of the miRNA (and its complement sequence) in the double stranded RNA stem. According to a specific embodiment, the miRNA and its complement are located about 10 to about 20 nucleotides from the free ends of the miRNA double stranded RNA stem. The length and sequence of the single stranded loop region are not critical and may vary considerably, e.g. between 30 and 50 nt in length. The complementarity between the miRNA and its complement need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds. Exemplary hairpin sequences are provided in Tables 1-8, below.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds. Some pre-miRNA scaffolds may be preferred over others for their efficiency to be correctly processed into the designed microRNAs, particularly when expressed as a chimeric gene wherein other DNA regions, such as untranslated leader sequences or transcription termination and polyadenylation regions are incorporated in the primary transcript in addition to the pre-microRNA.

According to the present teachings, the dsRNA molecules may be naturally occurring or synthetic.

The dsRNA can be a mixture of long and short dsRNA molecules such as, dsRNA, siRNA, siRNA+dsRNA, siRNA+miRNA, or a combination of same. According to a specific embodiment, the dsRNA is an siRNA (100%). According to a specific embodiment the dsRNA is an siRNA+dsRNA combination in various ratios. Any dsRNA to siRNA ratio can be used for the siRNA+dsRNA combination. For example a ratio of 1 to 1:one dsRNA mixed with the same sequence after RNAse III treatment. According to another embodiment, the dsRNA to siRNA ratio is 2:1, 1.5:1, 1.3:1, 1:0.01, 1:0.05 or 1:0.1. According to a further embodiment, the dsRNA to siRNA ratio is 2:1 to 1:0.1. According to a specific embodiment, the dsRNA is purified dsRNA (100%). According to another embodiment, the dsRNA to siRNA ratio is 1:2, 1:5, 1:10, 1:20, or 1:50. According to a further embodiment, the dsRNA is purified siRNA (100%).

The dsRNA molecule is designed for specifically targeting a target gene of interest. It will be appreciated that the dsRNA can be used to down-regulate one or more target genes. If a number of target genes are targeted, a heterogenic composition which comprises a plurality of dsRNA molecules for targeting a number of target genes is used. Alternatively said plurality of dsRNA molecules are separately applied to the seeds (but not as a single composition). According to a specific embodiment, a number of distinct dsRNA molecules for a single target are used, which may be separately or simultaneously (i.e., co-formulation) applied.

According to an embodiment of the invention, the target gene is endogenous to the plant. Downregulating such a gene is typically important for conferring the plant with an improved, agricultural, horticultural, nutritional trait ("improvement" or an "increase" is further defined hereinbelow). It will be appreciated that the treatment with the dsRNA may result in an up-regulation of the target gene (which follows a suggested mechanism that is provided hereinbelow) however such an up-regulation may be transient. The present inventors are able to confer resistance to biotic stress by modulating expression of endogenous genes in cucumber and tomato thereby conferring resistance to infections as demonstrated in Examples 35 and 41.

As used herein "endogenous" refers to a gene which expression (mRNA or protein) takes place in the plant. Typically, the endogenous gene is naturally expressed in the plant or originates from the plant. Thus, the plant may be a wild-type plant. However, the plant may also be a genetically modified plant (transgenic).

Downregulation of the target gene may be important for conferring improved one of-, or at least one of (e.g., two of- or more), biomass, vigor, yield, abiotic stress tolerance, biotic stress tolerance or improved nitrogen use efficiency.

Exemplary target genes include, but are not limited to, an enzyme, a structural protein, a plant regulatory protein, a miRNA target gene, or a non-coding RNA such as a miRNA of the plant. WO2011067745, WO 2009125401 and WO 2012056401 provide examples of miRNA sequences or targets of miRNAs (e.g., mRNA167, miRNA 156, miR164 and targets thereof NFY, SPL17 and NAC, respectively) which expression can be silenced to improve a plant trait. Other examples of target genes which may be subject to modulation according to the present teachings are described in the Examples section which follows.

The target gene may comprise a nucleic acid sequence which is transcribed to an mRNA which codes for a polypeptide.

Alternatively, the target gene can be a non-coding gene such as a miRNA or a siRNA.

For example, in order to silence the expression of an mRNA of interest, synthesis of the dsRNA suitable for use with some embodiments of the invention can be selected as follows. First, the mRNA sequence is scanned including the 3' UTR and the 5' UTR.

Second, the mRNA sequence is compared to an appropriate genomic database using any sequence alignment software, such as the BLAST software available from the NCBI server (wwwdotncbidotnlmdotnihdotgov/BLAST/). Putative regions in the mRNA sequence which exhibit significant homology to other coding sequences are filtered out.

Qualifying target sequences are selected as template for dsRNA synthesis. Preferred sequences are those that have as little homology to other genes in the genome to reduce an "off-target" effect.

In one embodiment, the dsRNA of the present application may comprise a target sequence in an intron, exon, 3' UTR, 5' UTR, or a regulatory element of an endogenous gene, or combinations thereof. In one embodiment, the dsRNA of the present application may comprise a target site residing in a promoter.

It will be appreciated that the RNA silencing agent of some embodiments of the invention need not be limited to those molecules containing only RNA, but further encompasses chemically-modified nucleotides and non-nucleotides.

The dsRNA may be synthesized using any method known in the art, including either enzymatic syntheses or solid-phase syntheses. These are especially useful in the case of short polynucleotide sequences with or without modifications as explained above. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

As mentioned, the naked dsRNA molecule is directly contacted with the seed.

The seed may be of any plant, such as of the Viridiplantae super family including monocotyledon and dicotyledon plants. Other plants are listed hereinbelow. According to an embodiment of the invention, the cells of the plant comprise RNA dependent RNA polymerase activity and the target RNA molecule of the dsRNA to ensure amplification of the dsRNA.

The term "plant" as used herein encompasses whole plants, ancestors and progeny of the plants and plant parts, including seeds, shoots, stems, roots (including tubers), and isolated plant cells, tissues and organs. The plant may be in any form including suspension cultures, embryos, meristematic regions, callus tissue, leaves, gametophytes, sporophytes, pollen, and microspores. It will be appreciated, that the plant or seed thereof may be transgenic plants.

As used herein the phrase "plant cell" refers to plant cells which are derived and isolated from disintegrated plant cell tissue or plant cell cultures. Plant cells may be reproductive cells (i.e., cells from a tissue contributing directly to the sexual reproduction of a plant) or non-reproductive cells (i.e., cells from a tissue not involved in the sexual reproduction of a plant). Plant cells may be cells that are capable of regenerating into a whole plant or cells that cannot regenerate into a whole plant, for example, enucleated mature sieve tube cells.

As used herein the phrase "plant cell culture" refers to any type of native (naturally occurring) plant cells, plant cell lines and genetically modified plant cells, which are not assembled to form a complete plant, such that at least one biological structure of a plant is not present. Optionally, the plant cell culture of this aspect of the present invention may comprise a particular type of a plant cell or a plurality of different types of plant cells. It should be noted that optionally plant cultures featuring a particular type of plant cell may be originally derived from a plurality of different types of such plant cells.

Any commercially or scientifically valuable plant is envisaged in accordance with some embodiments of the invention. Plants that are particularly useful in the methods of the invention include all plants which belong to the super family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant used by the method of the invention is a crop plant including, but not limited to, cotton, *Brassica* vegetables, oilseed rape, sesame, olive tree, palm oil, banana, wheat, corn or maize, barley, alfalfa, peanuts, sunflowers, rice, oats, sugarcane, soybean, turf grasses, barley, rye, sorghum, sugar cane, chicory, lettuce, tomato, zucchini, bell pepper, eggplant, cucumber, melon, watermelon, beans, hibiscus, okra, apple, rose, strawberry, chili, garlic, pea, lentil, canola, mums, *Arabidopsis*, broccoli, cabbage, beet, quinoa, spinach, squash, onion, leek, tobacco, potato, sugarbeet, papaya, pineapple, mango, *Arabidopsis thaliana*, and also plants used in horticulture, floriculture or forestry, such as, but not limited to, poplar, fir, eucalyptus, pine, an ornamental plant, a perennial grass and a forage crop, coniferous plants, moss, algae, as well as other plants listed in World Wide Web (dot) nationmaster (dot) com/encyclopedia/Plantae.

According to a specific embodiment, the plant is selected from the group consisting of corn, rice, wheat, tomato, cotton and sorghum.

According to a specific embodiment, the seed is an uncoated or fresh seed that hasn't been subjected to chemical/physical treatments.

Washing of the seeds is effected for 30 min to 4 hours. Other exemplary wash ranges are 1 minute to 10 minutes, 10 minutes-30 minutes. According to some embodiments, washing of the seeds can be as short as 5, 10, 20, 30, 45, or 60 seconds. The wash solution may include a weak detergent such as Tween-20. The concentration of the detergent may be 0.01-0.2% or 0.2-1%. According to another embodiment, the detergent concentration can be about 0.001%, 0.005%, 0.01%, 0.05%, 0.1%, 0.5%, 1% or higher.

The seed may be subjected to priming or washing prior to contacting with the dsRNA.

As used herein the term "priming" refers to controlling the hydration level within seeds so that the metabolic activity necessary for germination can occur but radicle emergence is prevented. Different physiological activities within the seed occur at different moisture levels (Leopold and Vertucci, 1989; Taylor, 1997). The last physiological activity in the germination process is radicle emergence. The initiation of radicle emergence requires a high seed water content. By limiting seed water content, all the metabolic steps necessary for germination can occur without the irreversible act of radicle emergence. Prior to radicle emergence, the seed is considered desiccation tolerant, thus the primed seed moisture content can be decreased by drying. After drying, primed seeds can be stored until time of sowing.

Several different priming methods are used commercially. Among them, liquid or osmotic priming and solid matrix priming appear to have the greatest following (Khan et al., 1991).

According to an embodiment of the invention, priming is effected in the presence of salt, a chelating agent, polyethylene glycol or a combination of same (e.g., chelating agent and salt).

Alternatively priming is effected in the presence of water such as deionized water or double deionized water. According to a specific embodiment, the priming is effected in the presence of 100% ddW.

Several types of seed priming are commonly used:

Osmopriming (osmoconditioning)—is the standard priming technique. Seeds are incubated in well aerated solutions with a low water potential, and afterwards washes and dried. The low water potential of the solutions can be achieved by adding osmotica like mannitol, polyethyleneglycol (PEG) or salts like KCl.

Hydropriming (drum priming)—is achieved by continuous or successive addition of a limited amount of water to the seeds. A drum is used for this purpose and the water can also be applied by humid air. 'On-farm steeping' is a cheap and useful technique that is practiced by incubating seeds (cereals, legumes) for a limited time in warm water.

Matrixpriming (matriconditioning)—is the incubation of seeds in a solid, insoluble matrix (vermiculite, diatomaceous earth, cross-linked highly water-absorbent polymers) with a limited amount of water. This method confers a slow imbibition.

Pregerminated seeds—is only possible with a few species. In contrast to normal priming, seeds are allowed to perform radicle protrusion. This is followed by sorting for specific stages, a treatment that reinduces desiccation tolerance, and drying. The use of pregerminated seeds causes rapid and uniform seedling development.

Thus, according to an exemplary embodiment, the seeds are primed seeds.

Of note, it may be possible that the seeds are treated with water (double-distilled water, ddW), prior to contacting with the dsRNA without effecting any priming on the seeds. For instance, treatment for a short while with water (e.g., 30 seconds to 1 hours, 30 seconds to 0.5 hour, 30 seconds to 10 min, 30 seconds to 5 min or 45 seconds to 5 min). According to some embodiments, treatment with water can be as short as 5, 10, 20, or 30 seconds.

It will be appreciated that the dsRNA can be comprised in water (e.g., tap water, distilled water or double distilled water) i.e., free of any of the above mentioned priming effective concentration of salts, a chelating agents, polyethylene glycol or combinations of same (e.g., chelating agent and salt).

According to an exemplary embodiment, the seeds are non-primed seeds.

A non-limiting exemplary method of introducing the dsRNA into the seed is provided in Example 1, which is considered as an integral part of the specification.

The temperature at the washing/priming and drying steps may be the same or differ.

According to an exemplary embodiment, the washing/priming is effected at 4-28° C.

According to an exemplary embodiment, the priming/washing solution or the dsRNA containing solution is devoid of a solid carrier.

According to an exemplary embodiment, the priming/washing solution or the dsRNA containing solution is devoid of a transferring agent such as a surfactant or a salt.

According to a further embodiment of the invention, the seeds subject to contacting with the dsRNA molecule are washed in order to remove agents, to which the seeds have been subjected, such as a pesticide, a fungicide, an insecticide, a fertilizer, a coating agent and a coloring agent.

Thus, according to an exemplary embodiment, the seeds (prior to treatment with dsRNA) are substantially free (i.e., do not comprise effective amounts) of pesticide, a fungicide, an insecticide, a fertilizer, a coating agent and a coloring agent.

The seeds are then subjected to drying. In some embodiments, drying is optional.

According to an exemplary embodiment, the drying is effected at 20-37° C., 20-30° C., 22-37° C., 15-22° C. or 20-25° C. for 10-20 hours, 10-16 hours or even 2-5 hours.

Various considerations are to be taken when calculating the concentration of the naked dsRNA in the contacting solution.

These are dependent on at least one of seed size, seed weight, seed volume, seed surface area, seed density and seed permeability.

For example, related to seed size, weight, volume and surface area, it is estimated that corn seeds will require longer treatment than *Arabidopsis* and tomato seeds. Regarding permeability and density, it is estimated that wheat seeds will require longer treatments at higher concentrations than tomato seeds.

Exemplary concentrations of dsRNA in the treating solution include, but are not limited to, 0.01-0.3 µg/µl, 0.01-0.15 µg/µl, 0.04-0.15 µg/µl, 0.1-100 µg/µl; 0.1-50 µg/µl, 0.1-10 µg/µl, 0.1-5 µg/µl, 0.1-1 µg/µl, 0.1-0.5 µg/µl, 0.15-0.5 µg/µl, 0.1-0.3 µg/µl, 0.01-0.1 µg/µl, 0.01-0.05 µg/µl, 0.02-0.04 µg/µl, 0.001-0.02 µg/µl. According to a specific embodiment, the concentration of the dsRNA in the treating solution is 0.01-0.15 or 0.04-0.15 µg/µl.

In one embodiment, the dsRNA concentration in the treating solution is 0.01-0.3 µg/ml, 0.01-0.15 µg/ml, 0.04-0.15 µg/ml, 0.1-100 µg/ml; 0.1-50 µg/ml, 0.1-10 µg/ml, 0.1-5 µg/ml, 0.1-1 µg/ml, 0.1-0.5 µg/ml, 0.15-0.5 µg/ml, 0.1-0.3 µg/ml, 0.01-0.1 µg/ml, 0.01-0.05 µg/ml, 0.02-0.04 µg/ml, or 0.001-0.02 µg/ml.

In another embodiment, the dsRNA concentration in the treating solution is 0.0001-3 µg/µl, 0.0001-2.5 µg/µl, 0.0001-2 µg/µl, 0.0001-1.5 µg/µl, 0.0001-1 µg/µl, 0.0001-0.9 µg/µl, 0.0001-0.8 µg/µl, 0.0001-0.7 µg/µl, 0.0001-0.6 µg/µl, 0.0001-0.5 µg/µl, 0.0001-0.4 µg/µl, 0.0001-0.3 µg/µl, 0.0001-0.2 µg/µl, 0.0001-0.1 µg/µl, 0.0001-0.05 µg/µl, 0.0001-0.02 µg/µl, 0.0001-0.01 µg/µl, 0.0001-0.005 µg/µl, 0.0001-0.001 µg/µl, or 0.0001-0.0005 µg/µl.

In another embodiment, the dsRNA concentration in the treating solution is 0.0001-3 µg/µl, 0.0005-3 µg/µl, 0.001-3 µg/µl, 0.005-3 µg/µl, 0.01-3 µg/µl, 0.05-3 µg/µl, 0.1-3 µg/µl, 0.2-3 µg/µl, 0.3-3 µg/µl, 0.4-3 µg/µl, 0.5-3 µg/µl, 0.6-3 µg/µl, 0.7-3 µg/µl, 0.8-3 µg/µl, 0.9-3 µg/µl, 1-3 µg/µl, or 2-3 µg/µl.

In another embodiment, the dsRNA concentration in the treating solution is 0.0001-3 µg/µl, 0.0005-2.5 µg/µl, 0.001-2 µg/µl, 0.005-1.5 µg/µl, 0.01-1 µg/µl, 0.05-0.5 µg/µl, 0.1-0.4 µg/µl, or 0.2-0.3 µg/µl.

According to a specific embodiment, the contacting with the dsRNA is effected in the presence of a chelating agent such as EDTA or another chelating agent such as DTPA (0.01-0.1 mM).

The contacting solution may comprise a transferring agent such as a surfactant or a salt.

Examples of such transferring agents include but are not limited salts such as sodium or lithium salts of fatty acids (such as tallow or tallowamines or phospholipids lipofectamine or lipofectin (1-20 nM, or 0.1-1 nM)) and organosilicone surfactants. Other useful surfactants include organosilicone surfactants including nonionic organosilicone surfactants, e.g., trisiloxane ethoxylate surfactants or a silicone polyether copolymer such as a copolymer of polyalkylene oxide modified heptamethyl trisiloxane and allyloxypolypropylene glycol methylether (commercially available as Silwet™ L-77 surfactant having CAS Number 27306-78-1 and EPA Number. CAL.REG.NO. 5905-50073-AA, currently available from Momentive Performance Materials, Albany, N.Y.).

Useful physical agents can include (a) abrasives such as carborundum, corundum, sand, calcite, pumice, garnet, and the like, (b) nanoparticles such as carbon nanotubes or (c) a physical force. Carbon nanotubes are disclosed by Kam et al. (2004) J. Am. Chem. Soc., 126 (22):6850-6851, Liu et al. (2009) Nano Lett., 9(3):1007-1010, and Khodakovskaya et al. (2009) ACS Nano, 3(10):3221-3227. Physical force agents can include heating, chilling, the application of positive pressure, or ultrasound treatment. Agents for laboratory conditioning of a plant to permeation by polynucleotides include, e.g., application of a chemical agent, enzymatic treatment, heating or chilling, treatment with positive or negative pressure, or ultrasound treatment. Agents for conditioning plants in a field include chemical agents such as surfactants and salts.

Contacting of the seeds with the dsRNA can be effected using any method known in the art as long as a suppressive amount of the dsRNA enters the seeds. These examples include, but are not limited to, soaking, spraying or coating with powder, emulsion, suspension, or solution; similarly, the polynucleotide molecules are applied to the plant by any convenient method, e.g., spraying or wiping a solution, emulsion, or suspension.

As used herein "a suppressive amount" refers to an amount of dsRNA which is sufficient to down regulate the target gene by at least 20%, 30%, 40%, 50%, or more, say 60%, 70%, 80%, 90% or more even 100%. The suppressive amount can be a result of the formation of amplification in the plant.

According to a specific embodiment contacting may be effected by soaking (i.e., inoculation) so that shaking the seeds with the treating solution may improve penetration and soaking and therefore reduce treatment time. Shaking is typically performed at 50-150 RPM and depends on the volume of the treating solution. Shaking may be effected for 4-24 hours (1-4 hours, 10 minutes to 1 hour or 30 seconds to 10 minutes). The present teachings further envisage short incubation time such as up to 10 minutes. Examples include but are not limited to 30 seconds to 7 min, to 30 seconds to 5 min, to 30 seconds to 3 min, to 30 seconds to 2 min, to 30 seconds to 1 min, 1 min to 10 min or to 1 min to 5 min.

In one embodiment, the incubation time may be between 1 and 60, between 2 and 60, between 5 and 60, between 10 and 60, between 20 and 60, between 30 and 60, between 40 and 60, between 50 and 60, between 1 and 50, between 1 and 40, between 1 and 30, between 1 and 20, between 1 and 10, between 1 and 5, between 5 and 50, between 10 and 40, and between 20 and 30 seconds.

In another embodiment, the incubation time may be between 1 and 60, between 2 and 60, between 5 and 60, between 10 and 60, between 20 and 60, between 30 and 60, between 40 and 60, between 50 and 60, between 1 and 50, between 1 and 40, between 1 and 30, between 1 and 20, between 1 and 10, between 1 and 5, between 5 and 50, between 10 and 40, and between 20 and 30 minutes.

Dipping is also considered under the scope of the present invention. Thus, the seeds are dipped into the dsRNA solution for seconds e.g., 1-10 seconds, 1-5 seconds, 1-3 seconds or 1-2 seconds. During this period, the dsRNA may adsorb on the seed surface. The adsorbed dsRNA which coats the seed may penetrate the seed or the seedling during germination. The incubation takes place in the dark at 4-28° C. or 15-22° C. (e.g., 8-15° C., 4-8° C., 22-28° C.).

In one embodiment, the dipping time may be between 1 and 60, between 2 and 60, between 5 and 60, between 10 and 60, between 20 and 60, between 30 and 60, between 40 and 60, between 50 and 60, between 1 and 50, between 1 and 40, between 1 and 30, between 1 and 20, between 1 and 10, between 1 and 5, between 5 and 50, between 10 and 40, and between 20 and 30 minutes.

In one embodiment, the dipping time may be between 1 and 60, between 2 and 60, between 5 and 60, between 10 and 60, between 20 and 60, between 30 and 60, between 40 and 60, between 50 and 60, between 1 and 50, between 1 and 40, between 1 and 30, between 1 and 20, between 1 and 10, between 1 and 5, between 5 and 50, between 10 and 40, and between 20 and 30 seconds.

According to a specific embodiment, contacting occurs prior to breaking of seed dormancy and embryo emergence.

Following contacting, preferably prior to breaking of seed dormancy and embryo emergence, the seeds may be subjected to treatments (e.g., coating) with the above agents (e.g., pesticide, fungicide etc.).

Contacting is effected such that the dsRNA enters the embryo, endosperm, the coat, or a combination of the three.

After contacting with the treatment solution, the seeds may be subjected to drying for up to 30 hours at 25-37° C. For example, the seeds may be dried for 16 hours at 30° C.

According to a specific embodiment, the seed (e.g., isolated seed) comprises the exogenous naked dsRNA and wherein at least 10 or 20 molecules of the dsRNA are in the endosperm of the isolated seed.

As used herein the term "isolated" refers to separation from the natural physiological environment. In the case of seed, the isolated seed is separated from other parts of the plant. In the case of a nucleic acid molecule (e.g., dsRNA) separated from the cytoplasm.

According to a specific embodiment, the dsRNA is not expressed from the plant genome, thereby not being an integral part of the genome.

According to a specific embodiment there is provided an isolated seed comprising an exogenous dsRNA being present at a similar concentration (e.g., about 1:1, 2:1 or 1:2) in an embryo and an endosperm of the seed. It is suggested that the direct introduction of the naked dsRNA to the seed results in higher concentration of the dsRNA in the endosperm than that observed when the dsRNA is expressed from a nucleic acid expression construct.

According to a specific embodiment there is provided an isolated seed comprising an exogenous dsRNA being spatially distributed in an embryo and an endosperm of the plant seed in a spatial distribution that differs from a spatial distribution of the exogenous dsRNA in a seed derived from a transgenic plant that recombinantly expresses said exogenous dsRNA.

Methods of measuring the localization of RNA molecules in the seed are well known in the art. The use of siGlo as described in the Examples section is an example for such.

According to an alternative or an additional embodiment, there is provided an isolated seed comprising an exogenous dsRNA, wherein a concentration ratio of said exogenous dsRNA to siRNA maturing therefrom is higher in the seed as compared to a transgenic seed recombinantly expressing said exogenous dsRNA.

As used herein the term "higher" refers to at least about 3%, 5%, 7%, 10%, 15%, 20%, 25%, 30%, 50%, 60%, 70%, 80%, 90% or even a few folds higher.

According to an alternative or an additional embodiment, there is provided an isolated seed comprising an exogenous dsRNA, wherein the plant seed is devoid of a heterologous promoter for driving expression of said exogenous dsRNA, wherein a spatial distribution of said exogenous dsRNA and/or siRNA maturing therefrom is altered in the seed as compared to same in a transgenic seed recombinantly expressing said exogenous dsRNA.

The term "recombinantly expressing" refers to an expression from a nucleic acid construct.

According to a further embodiment there is provided a plant seed obtainable (or obtained) by any of the methods described herein.

Methods of qualifying successful introduction of the dsRNA include but are not limited to, RT-PCR (e.g., quantifying the level of the target gene or the naked dsRNA), phenotypic analysis such as biomass, vigor, yield and stress tolerance, root architecture, leaf dimensions, grain size and weight, oil content, cellulose, as well as cell biology techniques.

According to embodiments of the invention, up regulation of the gene targeted by the Seed treatment, as described herein, is sometimes observed. This has been mostly noted in genes that function as master regulators, such as targets of microRNAs (e.g. SPL and NAC) and other genes involved in regulating key processes (e.g. HY5). See for instance Examples 23 and 32 of the Examples section which follows.

Without being bound by theory, it is suggested that this phenomenon could be related to a potential feedback loop in the regulation of the expression of these genes. These genes are probably tightly regulated and therefore plants could react to changes in their expression in one direction by over compensating a strong change in the genes' expression in the opposite direction. Accordingly, it is possible for example that a gene will initially present down-regulation in the first hours or days following treatment, which could be altered into up-regulation later on in the plant's life cycle.

See for instance Example 32 of the Examples section which follows. Thus, the present inventors observed up regulation of the NAC gene in corn five days following treatment and down regulation 10 and 12 days following treatment. This is further substantiated in lettuce for the Hy 5.5 or 5.6 gene.

Seeds may be stored for 1 day to several months prior to planting (e.g., at 4-10° C.).

The resultant seed can be germinated in the dark so as to produce a plant.

Thus there is provided a plant or plant part comprising an exogenous naked dsRNA and devoid of a heterologous promoter for driving expression of the dsRNA in the plant.

As used herein "devoid of a heterologous promoter for driving expression of the dsRNA" means that the plant or plant cell doesn't include a cis-acting regulatory sequence (e.g., heterologous) transcribing the dsRNA in the plant. As used herein the term "heterologous" refers to exogenous, not-naturally occurring within the native plant cell (such as by position of integration, or being non-naturally found within the plant cell). Thus the isolated seed in the absence of a heterologous promoter sequence for driving expression of the dsRNA in the plant, comprises a homogenic (prior to amplification) or heterogenic (secondary siRNAs, following amplification) population of plant non-transcribable dsRNA.

The present methodology can be used for modulating gene expression such as in a plant, the method comprising: (a) contacting a seed of the plant with a naked dsRNA, under conditions which allow penetration of the dsRNA into the seed, thereby introducing the dsRNA into the seed; and optionally (b) generating a plant of the seed.

When used for down-regulating a plant gene, the naked dsRNA is designed of the desired specificity using bioinformatic tools which are well known in the art (e.g., BLAST).

This methodology can be used in various applications starting from basic research such as in order to asses gene function and lasting in generating plants with altered traits which have valuable commercial use.

Such plants can exhibit agricultural beneficial traits including altered morphology, altered flowering, altered tolerance to stress (i.e., viral biotic stress and/or abiotic), altered biomass vigor and/or yield and the like.

The phrase "abiotic stress" as used herein refers to any adverse effect on metabolism, growth, viability and/or reproduction of a plant. Abiotic stress can be induced by any of suboptimal environmental growth conditions such as, for example, water deficit or drought, flooding, freezing, low or high temperature, strong winds, heavy metal toxicity, anaerobiosis, high or low nutrient levels (e.g. nutrient deficiency), high or low salt levels (e.g. salinity), atmospheric pollution, high or low light intensities (e.g. insufficient light) or UV irradiation. Abiotic stress may be a short term effect (e.g. acute effect, e.g. lasting for about a week) or alternatively may be persistent (e.g. chronic effect, e.g. lasting for example 10 days or more). The present invention contemplates situations in which there is a single abiotic stress condition or alternatively situations in which two or more abiotic stresses occur.

According to an exemplary embodiment the abiotic stress refers to salinity.

According to another exemplary embodiment the abiotic stress refers to drought.

According to another exemplary embodiment the abiotic stress refers to a temperature stress.

As used herein the phrase "abiotic stress tolerance" refers to the ability of a plant to endure an abiotic stress without exhibiting substantial physiological or physical damage (e.g. alteration in metabolism, growth, viability and/or reproducibility of the plant).

As used herein the phrase "nitrogen use efficiency (NUE)" refers to a measure of crop production per unit of nitrogen fertilizer input. Fertilizer use efficiency (FUE) is a measure of NUE. Crop production can be measured by biomass, vigor or yield. The plant's nitrogen use efficiency is typically a result of an alteration in at least one of the uptake, spread, absorbance, accumulation, relocation (within the plant) and use of nitrogen absorbed by the plant. Improved NUE is with respect to that of a non-transgenic plant (i.e., lacking the transgene of the transgenic plant) of the same species and of the same developmental stage and grown under the same conditions.

As used herein the phrase "nitrogen-limiting conditions" refers to growth conditions which include a level (e.g., concentration) of nitrogen (e.g., ammonium or nitrate) applied which is below the level needed for optimal plant metabolism, growth, reproduction and/or viability.

As used herein the term/phrase "biomass", "biomass of a plant" or "plant biomass" refers to the amount (e.g., measured in grams of air-dry tissue) of a tissue produced from the plant in a growing season. An increase in plant biomass can be in the whole plant or in parts thereof such as aboveground (e.g. harvestable) parts, vegetative biomass, roots and/or seeds or contents thereof (e.g., oil, starch etc.).

As used herein the term/phrase "vigor", "vigor of a plant" or "plant vigor" refers to the amount (e.g., measured by weight) of tissue produced by the plant in a given time. Increased vigor could determine or affect the plant yield or the yield per growing time or growing area. In addition, early vigor (e.g. seed and/or seedling) results in improved field stand.

As used herein the term/phrase "yield", "yield of a plant" or "plant yield" refers to the amount (e.g., as determined by weight or size) or quantity (e.g., numbers) of tissues or organs produced per plant or per growing season. Increased yield of a plant can affect the economic benefit one can obtain from the plant in a certain growing area and/or growing time.

According to an exemplary embodiment the yield is measured by cellulose content, oil content, starch content and the like.

According to another exemplary embodiment the yield is measured by oil content.

According to another exemplary embodiment the yield is measured by protein content.

According to another exemplary embodiment, the yield is measured by seed number, seed weight, fruit number or fruit weight per plant or part thereof (e.g., kernel, bean).

A plant yield can be affected by various parameters including, but not limited to, plant biomass; plant vigor; plant growth rate; seed yield; seed or grain quantity; seed or grain quality; oil yield; content of oil, starch and/or protein in harvested organs (e.g., seeds or vegetative parts of the plant); number of flowers (e.g. florets) per panicle (e.g. expressed as a ratio of number of filled seeds over number of primary panicles); harvest index; number of plants grown per area; number and size of harvested organs per plant and per area; number of plants per growing area (e.g. density); number of harvested organs in field; total leaf area; carbon assimilation and carbon partitioning (e.g. the distribution/ allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

Improved plant NUE is translated in the field into either harvesting similar quantities of yield, while implementing less fertilizers, or increased yields gained by implementing the same levels of fertilizers. Thus, improved NUE or FUE has a direct effect on plant yield in the field.

As used herein the term "improving" or "increasing" refers to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90% or greater increase in NUE, in tolerance to stress, in yield, in biomass or in vigor of a plant, as compared to a native or wild-type plants [i.e., isogenic plants (not modified to comprise the dsRNA) of the invention].

As mentioned, the target gene of the dsRNA may not be an endogenous plant gene but rather a gene exogenous to the plant, such as that of a plant virus or bacteria which feeds on the plant or depends thereon for growth, replication and/or survival.

Thus, according to an aspect of the invention there is provided a method of inhibiting expression of a target gene in a plant virus, the method comprising providing (contacting under infecting conditions) to the plant virus the plant as described herein (at least part thereof includes the naked dsRNA), thereby inhibiting expression of a target gene in the plant virus.

A number of virus genera are transmitted, both persistently and non-persistently, by soil borne zoosporic protozoa. These protozoa are not viral pathogenic themselves, but parasitic. Transmission of the virus takes place when they become associated with the plant roots. Examples include *Polymyxa graminis*, which has been shown to transmit plant viral diseases in cereal crops and *Polymyxa betae* which transmits Beet necrotic yellow vein virus. Plasmodiophorids also create wounds in the plant's root through which other viruses can enter.

Specific examples of viruses which can be targeted according to the present teachings include, but are not limited to:

(1) Tobacco mosaic virus (TMV, RNA virus) which infects plants, especially tobacco and other members of the family Solanaceae).

(2) Tomato spotted wilt virus (TSWV, RNA virus) which causes serious diseases of many economically important plants representing 35 plant families, including dicots and monocots. This wide host range of ornamentals, vegetables, and field crops is unique among plant-infecting viruses. Belongs to tospoviruses in the Mediterranean area, affect vegetable crops, especially tomato, pepper and lettuce (Turina et al., 2012, *Adv Virus Res* 84; 403-437).

(3) Tomato yellow leaf curl virus (TYLCV) which is transmitted by whitefly, mostly affects tomato plants. Geminiviruses (DNA viruses) in the genus Begomovirus (including sweepoviruses and legumoviruses)—most devastating pathogens affecting a variety of cultivated crops, including cassava, sweet potato, beans, tomato, cotton and grain legumes (Rey et al 2012, Viruses 4; 1753-1791). Members include TYLCV above and tomato leaf curl virus (ToLCV).

(4) Cucumber mosaic virus (CMV)—CMV has a wide range of hosts and attacks a great variety of vegetables, ornamentals, and other plants (as many as 191 host species in 40 families). Among the most important vegetables affected by cucumber mosaic are peppers (*Capsicum annuum* L.), cucurbits, tomatoes (*Lycopersicon esculentum* Mill.), and bananas (*Musa* L. spp.).

Other vegetable hosts include: cucumber, muskmelon, squash, tomato, spinach, celery, peppers, water cress, beet, sweet potato, turnip, chayote, gherkin, watermelon, pumpkin, citron, gourd, lima bean, broad bean, onion, groundcherry, eggplant, potato, rhubarb, carrot, dill, fennel, parsnip, parsley, loofah, and artichoke (Chabbouh and Cherif, 1990, FAO Plant Prot. Bull. 38:52-53.).

Ornamental hosts include: China aster, chrysanthemum, delphinium, salvia, geranium, gilia, gladiolus, heliotrope, hyacinth, larkspur, lily, marigold, morning glory, nasturtium, periwinkle, petunia, phlox, snapdragon, tulip, and zinnia (Chupp and Sherf, 1960; Agrios, 1978).

(5) Potato virus Y (PVY)—one of the most important plant viruses affecting potato production.

(6) Cauliflower mosaic virus (CaMV, DNA virus (Rothnie et al., 1994)).

(7) African cassava mosaic virus (ACMV).

(8) Plum pox virus (PPV) is the most devastating viral disease of stone fruit from the genus *Prunus*.

(9) Brome mosaic virus (BMV)—commonly infects *Bromus inermis* and other grasses, can be found almost anywhere wheat is grown.

(10) Potato virus X (PVX)—There are no insect or fungal vectors for this virus. This virus causes mild or no symptoms in most potato varieties, but when Potato virus Y is present, synergy between these two viruses causes severe symptoms in potatoes.

Additional Viruses:

*Citrus* tristeza virus (CTV)—causes the most economically damaging disease to *Citrus*, including sour orange (*Citrus aurantium*), and any *Citrus* species grafted onto sour orange root stock, sweet orange (*C. sinensis*), grapefruit (*C. paradisi*), lime and Seville orange (*C. aurantifolia*), and mandarin (*C. reticulata*). CTV is also known to infect *Aeglopsis chevalieri, Afraegle paniculata, Pamburus missionis*, and *Passiflora gracilis*. CTV is distributed worldwide and can be found wherever citrus trees grow.

Barley yellow dwarf virus (BYDV)—most widely distributed viral disease of cereals. It affects the economically important crop species barley, oats, wheat, maize, triticale and rice.

Potato leafroll virus (PLRV) infects potatoes and other members of the family Solanaceae.

Tomato bushy stunt virus (TBSV), RNA virus, a member of the genus Tombusvirus and mostly affects tomatoes and eggplant.

Additional reviews:

Hamilton et al., 1981, J Gen Virol 54; 223-241—mentions TMV, PVX, PVY, CMV, CaMV.

Additional scientific papers:

Makkouk et al., 2012, *Adv Virus Res* 84; 367-402—Viruses affecting peas and beans with narrow (Faba bean necrotic yellow virus (FBNYN)) and wide (alfalfa mosaic virus (AMV) and CMV) host range.

The target gene of the plant virus encodes a product essential to the viability and/or infectivity of the viral pathogen, therefore its down-regulation (by the naked dsRNA) results in a reduced capability of the pathogen to survive and infect host cells. Hence, such down-regulation results in a "deleterious effect" on the maintenance viability and/or infectivity of the viral pathogen, in that it prevents or reduces the pathogen's ability to feed off and survive on nutrients derived from host cells. By virtue of this reduction in the viral pathogen's viability and/or infectivity, resistance and/or enhanced tolerance to infection by a pathogen is facilitated in the cells of the plant. Genes in the pathogen may be targeted at the mature (adult), immature (juvenile) or embryo stages.

As used herein, a "plant virus resistance" trait is a characteristic of a plant that causes the plant host to be resistant to attack from a viral pathogen that typically is capable of inflicting damage or loss to the plant. Once the viral pathogen is provided with the plant material comprising the naked dsRNA, expression of the gene within the target virus is suppressed by the dsRNA, and the suppression of expression of the gene in the target virus results in the plant being resistant to the virus.

To substantiate the anti-viral activity, the present teachings also contemplate observing reduced infectability or replicability and the degree of host symptomatology following said providing.

To improve the anti-viral activity, embodiments of the present invention further provide a composition that contains two or more different agents each toxic to the same plant virus, at least one of which comprises a dsRNA described herein. In certain embodiments, the second agent can be an agent selected from the group consisting of inhibitors of metabolic enzymes involved in amino acid or carbohydrate synthesis; inhibitors of cell division; cell wall synthesis inhibitors; inhibitors of DNA or RNA synthesis, gyrase inhibitors, tubulin assembly inhibitors, inhibitors of ATP synthesis; oxidative phosphorylation uncouplers; inhibitors of protein synthesis; MAP kinase inhibitors; lipid synthesis or oxidation inhibitors; sterol synthesis inhibitors; and melanin synthesis inhibitors.

In addition, plants generated according to the teachings of the present invention or parts thereof can exhibit altered nutritional or therapeutic efficacy and as such can be employed in the food or feed and drug industries. Likewise, the plants generated according to the teachings of the present invention or parts thereof can exhibit altered oil or cellulose content and as such can be implemented in the construction or oil industry.

The seeds of the present invention can be packed in a seed containing device which comprises a plurality of seeds at least some of which (e.g., 5%, 10% or more) containing an exogenous naked dsRNA, wherein the seed is devoid of a heterologous promoter for driving expression of the dsRNA.

The seed containing device can be a bag, a plastic bag, a paper bag, a soft shell container or a hard shell container.

Reagents of the present invention can be packed in a kit including the naked dsRNA, instructions for introducing the dsRNA into the seeds and optionally a priming solution.

Compositions of some embodiments of the invention may, if desired, be presented in a pack or dispenser device, which may contain one or more dosage forms containing the active ingredient. The pack may, for example, comprise metal or plastic foil, such as a blister pack. The pack or dispenser device may be accompanied by instructions for introduction to the seed.

According to an exemplary embodiment, the naked dsRNA and priming solution are comprised in separate containers.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Protocols for dsRNA Production and Seed Treatment

Generating the dsRNA/siRNA Sequences

The dsRNA sequences were custom-created for each gene using in vitro transcription of PCR products. Part of the mRNA, including either the ORF, 3' UTR or 5' UTR for which dsRNA to be produced was PCR-amplified using gene-specific primers, which contain the sequence of the T7 promoter on either side. This product was used as a template for dsRNA production using commercial kits such as the MaxiScript dsRNA kit (Life Technologies) or T7 High Yield RNA Synthesis kit (NEB). Next, the sample is treated with DNase Turbo at 37° C. for 15-30 min followed by phenol treatment and nucleic acid precipitation. Next, one of two different reactions is carried out: (1) dsRNA is ready to use, (2) processing of the dsRNA with Dicer (Shortcut RNase III (NEB)) to create small interfering RNAs (siRNA).

Either dsRNA or a combination of dsRNA and siRNA were used for seed treatments as described below. All dsRNA sequences provided herein are listed as DNA (simple transformation is done by converting T>U).

General Seed Treatment Protocol for Gene Silencing Using a dsRNA/siRNA Mixture

Uncoated organic corn seeds were from variety "popcorn", uncoated organic whole grain rice seeds and organic soybean were purchased from Nitsat Haduvdevan (Israel). Wheat seeds were from A.B. Seeds (Israel). Lettuce seeds were from the variety Sun Valley. Fresh tomato seeds were retrieved from M82 tomato fruits, which are propagated in-house. Uncoated or fresh plant seeds were washed with double distilled water (DDW) prior to treatment for four hours. Next, seeds were dried at 20-30° C. for up to 24 hours. Following the drying step, seeds were treated with a solution containing the dsRNA formulation, which is made of dsRNA at a final concentration of 1-261 μg/ml in 0.1 mM EDTA. Treatment was performed by gently shaking the seeds in the solution for up to 60 hours in a dark growth chamber at 15-25° C. Finally, seeds were washed up to three times briefly and planted on soil or germinated at 25° C. in a dark growth chamber and planted in soil or dried for 0-30 hours and germinated at 25° C. in a dark growth chamber and planted in soil or planted directly in soil. Control seeds were treated in a similar way, with a formulation that lacked the dsRNA or with non-specific dsRNA.

Example 2

Stability of the dsRNA in Seedlings of Rice, Tomato and *Sorghum*

As an example for an exogenous gene that is not present/expressed in plants, the ORFs encoding the replicase and coat protein of CGMMV (Cucumber green mottle mosaic virus, accession number AF417242) were used as targets for dsRNA treatment of plant seeds using the protocol described in Example 1. Rice, tomato and sorghum seeds were washed for 4 hours at 20° c., tomato and sorghum were dried at 30° C. and rice at 20° C. for overnight. Seeds were immediately treated at 15° C. with 132.7 μg/ml dsRNA (final concentration) for 39 hours for rice, as shown in FIG. 1; 93.8 μg/ml dsRNA (final concentration) for 48 hours for tomato as shown in FIG. 2A and 75 μg/ml dsRNA (final concentration) for 40 hours for sorghum as shown in FIG. 2B. Briefly, the virus-derived ORFs were amplified by PCR with specifically designed forward and reverse primers that contain the T7 sequence (5'-TAATACGACTCACTATAGGG-3', SEQ ID NO: 1) at their 5' (see Table 1, below). PCR products were purified from agarose gel and since they carry T7 promoters at both ends they were used as templates for T7-dependent in-vitro transcription, resulting in dsRNA product of the CGMMV genes. PCR on a housekeeping gene, tubulin, was used as a positive control (forward primer 5'-GGTGCTCT-GAACGTGGATG-3' (SEQ ID NO: 2), and reverse primer 5'-CATCATCGCCATCCTCATTCTC-3'(SEQ ID NO: 3)).

TABLE 1

PCR primers served as Templates for in vitro Transcription and detection of CGMMV, and CGMMV dsRNA products.

| Virus Name | Product Name | Product Sequence/SEQ ID NO: | Forward primer/SEQ ID NO: | Reverse primer/SEQ ID NO: |
|---|---|---|---|---|
| 1) CGMMV (NCBI Accession number AF417242) | CGMMV dsRNA product 1 | TAATACGACTCACTATAGGGGGTAAG CGGCATTCTAAACCTCCAAATCGGAG GTTGGACTCTGCTTCTGAAGAGTCCA GTTCTGTTTCTTTTGAAGATGGCTTAC AATCCGATCACACCTAGCAAACTTAT TGCGTTTAGTGCTTCTTATGTTCCCGT CAGGACTTTACTTAATTTTCTAGTTGC TTCACAAGGTACCGCTTTCCAGACTC AAGCGGGAAGAGATTCTTTCCGCGAG TCCCTGTCTGCGTTACCCTCGTCTGTC GTAGATATTAATTCTAGATTCCCAGA TGCGGGTTTTTACGCTTTCCTCAACGG TCCTGTGTTGAGGCCTATCTTCGTTTC GCTTCTCAGCTCCACGGATACGCGTA ATAGGGTCATTGAGGTTGTAGATCCT AGCAATCCTACGACTGCTGAGTCGCT TAACGCCGTAAAGCGTACTGATGACG CGTCTACGGCCGCTAGGGCTGAGATA GATAATTTAATAGAGTCTATTTCTAA GGGTTTTGATGTTTACGATAGGGCTTC ATTTGAAGCCGCGTTTTCGGTAGTCTG GTCAGAGGCTACCACCTCGAAAGCTT AGTTTC TABLE 1-continued PCR primers served as Templates for in vitro Transcription and detection of CGMMV, and CGMMV dsRNA products.

| Virus Name | Product Name | Product Sequence/SEQ ID NO: | Forward primer/SEQ ID NO: | Reverse primer/SEQ ID NO: |
|---|---|---|---|---|
| | | CAAGGGATCTGGCGGGTGCAGACCTC TTCCAACTTTCCAGATAGATGCATTCA GGAGGTACGATAGTTCTCCCTGTGCG GTCACCTGTTCAGACGTTTTCCAAGA GTGTTCCTATGATTTTGGGAGTGGTA GGGATAATCATGCAGTCTCGTTGCAT TCAATCTACGATATCCCTTATTCTTCG ATCGGACCTGCTCTTCATAGGAAAAA TGTGCGAGTTTGTTATGCAGCCTTTCA TTTCTCGGAGGCATTGCTTTTAGGTTC GCCTGTAGGTAATTTAAATAGTATTG GGGCTCAGTTTAGGGTCGATGGTGAT GCCCTATAGTGAGTCGTATTA/11 | | |

Figure 2A:
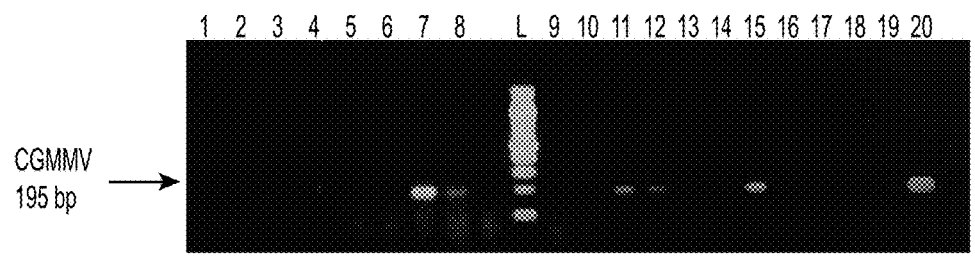
FIGS. 2A-B show the identification of CGMMV dsRNA by RT-PCR on tomato and sorghum seedlings, 10 days and 4 weeks after germination, respectively.
Figure 2B:
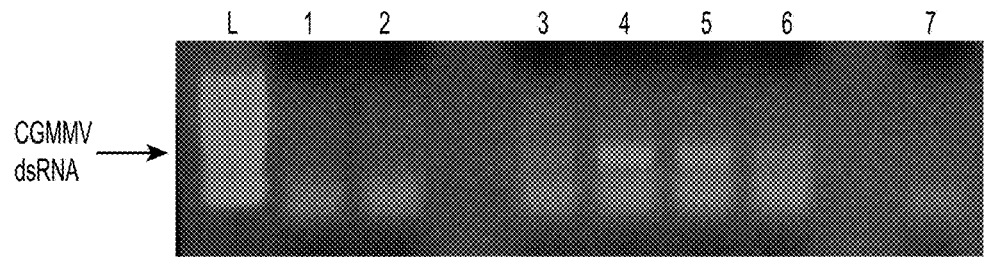

The exogenous dsRNA was found to be stable for at least three weeks in rice seedlings as can be seen in FIGS. 1A-C and at least 10 days in tomato seedlings and four weeks in *Sorghum* plants as can be seen in FIGS. 2A-B.

Example 3

The dsRNA is not Intergrated into the Genome of Rice

Figure 3:
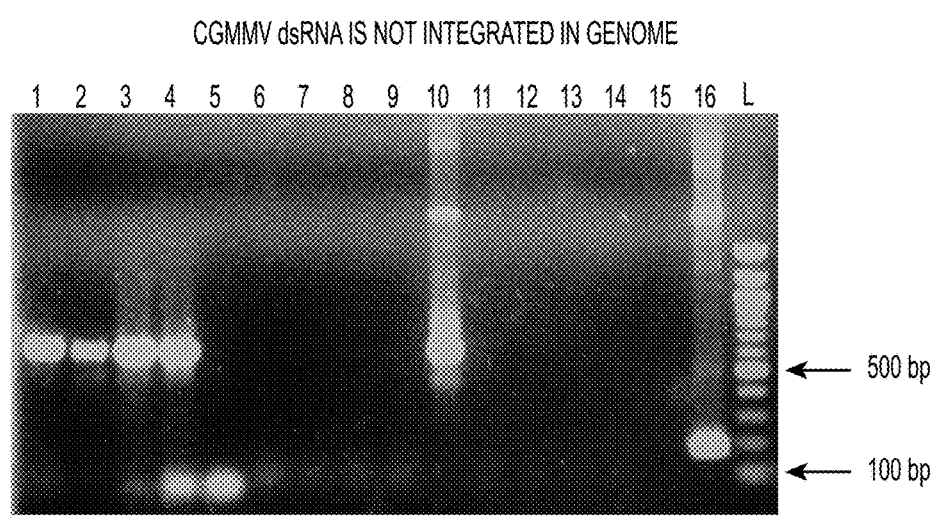
FIG. 3 shows that CGMMV-derived dsRNA does not integrate into the genome of treated rice seeds, 5 weeks after germination. Three different DNA PCR reactions were carried out: (1) Tubulin PCR (lanes 1-5); 1-2 are control plants, 3-4 are dsRNA-treated plants, 5 is a negative control (ddW), (2) First PCR for DNA CGMMV (lanes 6-10); 6-7 are control plants, 8-9 are dsRNA-treated plants, 10 is a positive control (plasmid carrying the CGMMV sequence), (3) Second PCR for DNA CGMMV (lanes 11-16); 11-12 are control plants, 13-14 are dsRNA-treated plants, 15 is a negative control (ddW), and 16 is a positive control (plasmid carrying the CGMMV sequence). L—100 bp DNA ladder.

Rice seeds were treated with an exogenous dsRNA as in Example 2. Plants were germinated and grown for five weeks, DNA was extracted and PCR reactions were performed to demonstrate that the dsRNA did not integrate into the Rice's genome (FIG. 3). Two sets of primers that gave a positive reaction when checked on the RNA level were used, set 1 (see Table 1) of primers were the set of primers used to amplify the template (all the dsRNA sequence). Set 2 (see Table1) are the primers that were used in the PCR on FIG. 1. A Rice endogenous housekeeping gene (tubulin) was used as a positive control for the PCR reaction (see Table 2).

TABLE 2

Tubulin Primers Used for PCR Amplification.

| Primer Name and Direction | Primer Sequence/ (SEQ ID NO:) | Primer Length |
|---|---|---|
| osa_TubA1_736F | GGTGCTCTGAACGTGGATG/12 | 19 |
| osa_TubA1_1342R | CATCATCGCCATCCTCATTCTC/13 | 22 |

Example 4

Figure 4A:
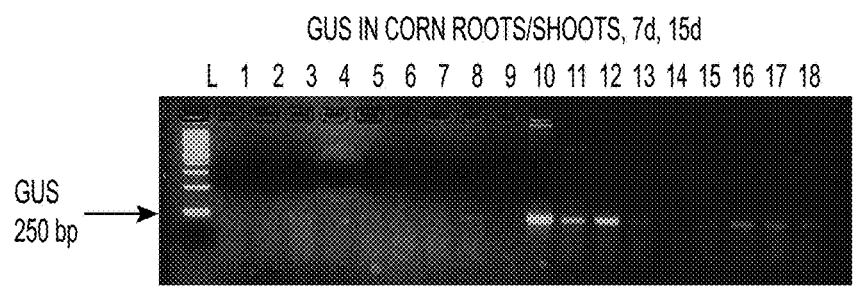
FIGS. 4A-C show the stability of GUS dsRNA in corn seedlings by RT-PCR, 7 and 15 days after germination.
Figure 4B:
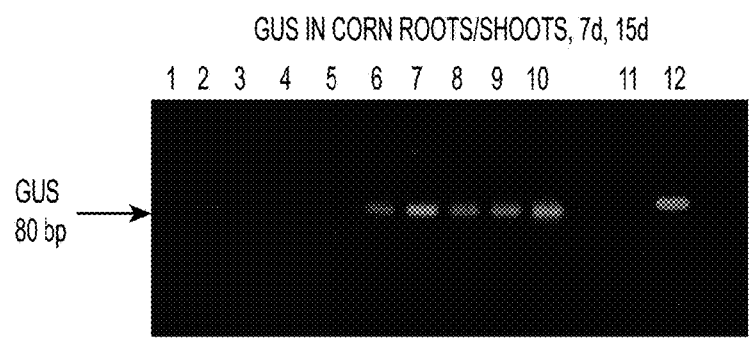
Figure 4C:
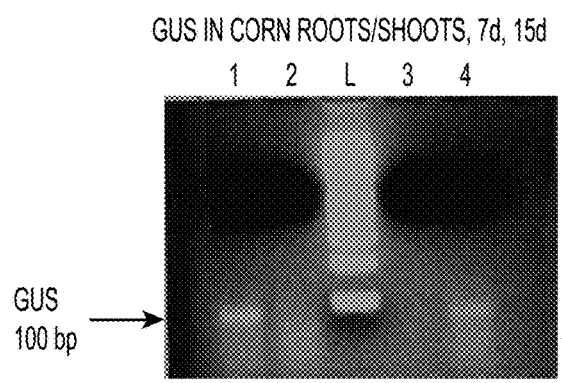
Figure 5A:
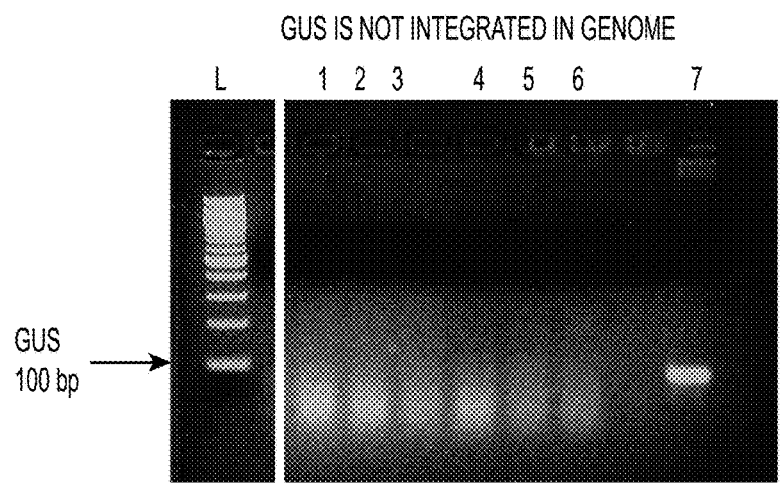
FIGS. 5A-B show that GUS dsRNA does not integrate into the genome of treated corn seeds 1 week after germination. Upper gel shows a DNA PCR on GUS gene: 1-3 are control plants, 4-6 are dsRNA treated plants and 7 is a positive control (plasmid). Bottom gel is a positive control for DNA extraction showing a DNA PCR on ubiquitin gene: 1-3 are control plants, 4-6 are dsRNA treated plants and 7 is a negative control (ddW).
Figure 5B:
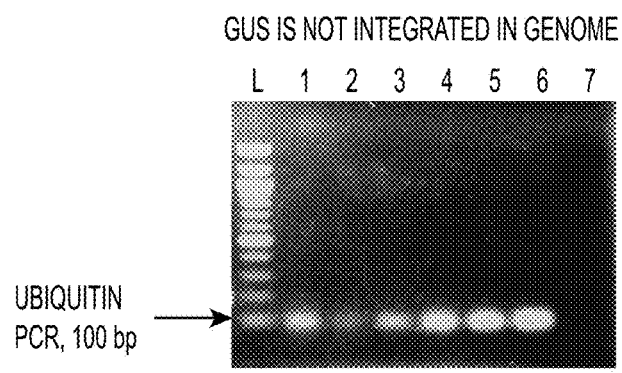

Exogenous dsRNA Molecules are Highly Stable and do not Get Incorporated into the Genome of Treated Plants Corn seeds were treated using the protocol described in Example 1, seeds were washed for 4 h at 20° c., dried at 30° c. overnight and immediately treated with 40 µg/ml dsRNA (final concentration) directed against the 3-glucuronidase (GUS) reporter gene for 60 hours at 15° C., dried and were germinated. Leaves and roots were harvested from control and dsGUS-treated plants 7 and 15 days following germination. RNA was extracted from the harvested tissues and RT-PCR with specific GUS primers was run (Table 3). In addition, a corn endogenous housekeeping gene (ubiquitin) was used as a positive control for the PCR reaction. The GUS dsRNA molecules were found to be extremely stable in the treated seeds, and can be detected in corn plants 7 and 15 days post germination of the seeds (FIGS. 4A-C). Also, the GUS dsRNA molecules do not get incorporated in the genome of treated corn plants one week after germination (FIGS. 5A-B).

TABLE 3

Primers for PCR Amplification of GUS and Ubiquitin Genes and GUS dsRNA product.

| Primer Name | Primer Sequence/SEQ ID NO: | Primer Length |
|---|---|---|
| GUST7_For | TAATACGACTCACTATAGGGAGATCGACGGCCTGTGGGCATTC/15 | |
| GUST7_Rev | TAATACGACTCACTATAGGGAGCATTCCCGGCGGGATAGTCTG/16 | 43 |
| GUS208For | CAGCGCGAAGTCTTTATACC/17 | 43 |
| GUS289Rev | CTTTGCCGTAATGAGTGACC/18 | 20 |

TABLE 3-continued

Primers for PCR Amplification of GUS and Ubiquitin Genes and GUS dsRNA product.

| Primer Name | Primer Sequence/SEQ ID NO: | Primer Length |
|---|---|---|
| zmaUBQ-947F | CCATAACCCTGGAGGTTGAG/19 | 20 |
| zmaUBQ1043R | ATCAGACGCTGCTGGTCTGG/20 | 20 |
| GUS dsRNA product | TAATACGACTCACTATAGGGAGATCGACGGCCTGTGGGCATTC AGTCTGGATCGCGAAAACTGTGGAATTGATCAGCGTTGGTGG GAAAGCGCGTTACAAGAAAGCCGGGCAATTGCTGTGCCAGGC AGTTTTAACGATCAGTTCGCCGATGCAGATATTCGTAATTATG CGGGCAACGTCTGGTATCAGCGCGAAGTCTTTATACCGAAAG GTTGGGCAGGCCAGCGTATCGTGCTGCGTTTCGATGCGGTCAC TCATTACGGCAAAGTGTGGGTCAATAATCAGGAAGTGATGGA GCATCAGGGCGGCTATACGCCATTTGAAGCCGATGTCACGCC GTATGTTATTGCCGGGAAAAGTGTACGTATCACCGTTTGTGTG AACAACGAACTGAACTGGCAGACTATCCCGCCGGGAATGCTC CCTATAGTGAGTCGTATTA/21 | |

Example 5

Fluorescence Microscopy of siRNA Sequences in Various Plant Seeds

Plant seeds were treated as per the protocol described in Example 1. Seeds were washed for 4 h at 20° C., dried at 25° C. and were immediately treated with a fluorescent siRNA (siGLO, 2 μM final concentration, Thermo Scientific) at 15° C. for 24 h.

Figure 6:
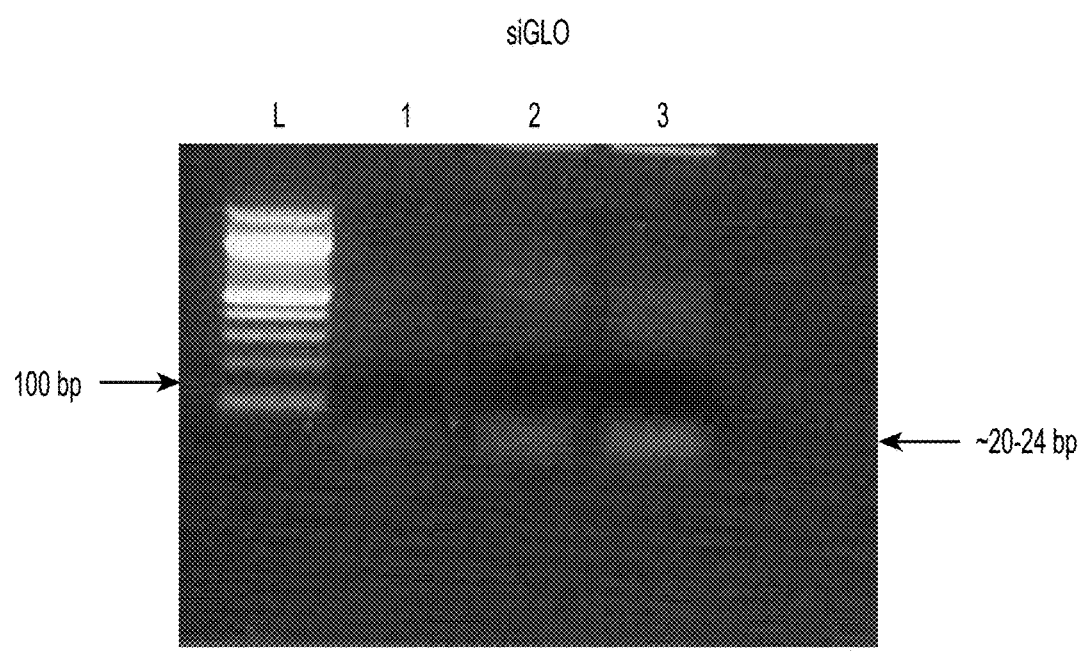
FIG. 6 shows gel electrophoresis analysis of siGLO before experiment. L—100 bp ladder, 1-5 µl of 2 µM siGLO solution, 2-15 µl of 2 µM siGLO solution, 3-30 µl of 2 µM siGLO solution. Bands can be seen that correspond with the expected size of 20-24 bp of the fluorescent siRNA molecules.

The quality of the siGLO was verified by gel electrophoresis analysis as can be seen on FIG. 6.

Figure 8A:
FIGS. 8A-C show rice seeds 24 hours following treatment with siGLO dsRNA. The figures show treated seeds on the left of each image alongside control untreated seeds, at various magnifications.
Figure 8B:
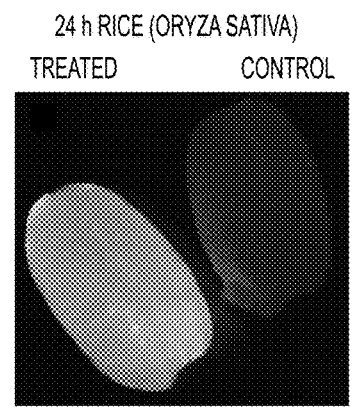
Figure 8C:
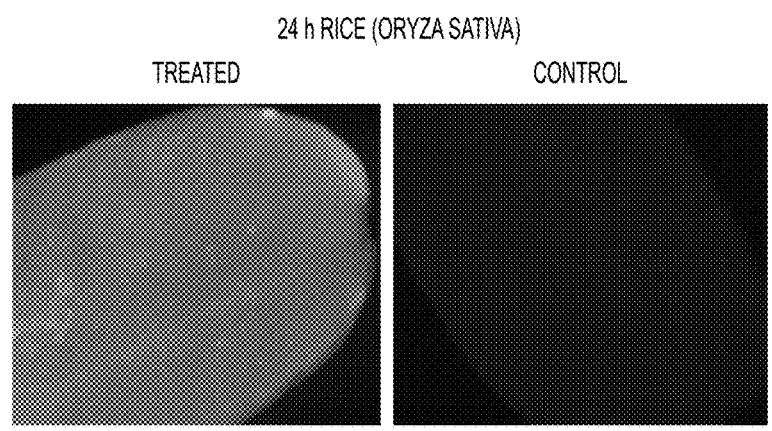
Figure 9A:
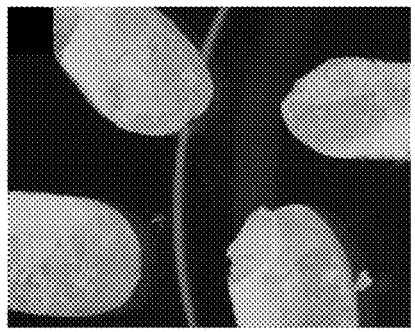
FIGS. 9A-F are light and fluorescent images of sliced rice seeds 48 hours following treatment with siGLO dsRNA. siGLO-treated and control rice seeds are sliced to view the interior distribution of the fluorescent dsRNA using a fluorescent binocular.
Figure 9B:
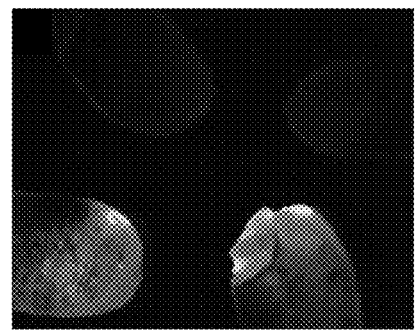
Figure 9C:
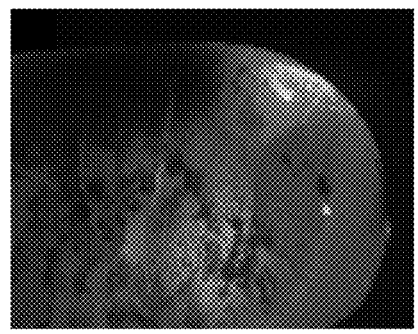
Figure 9D:
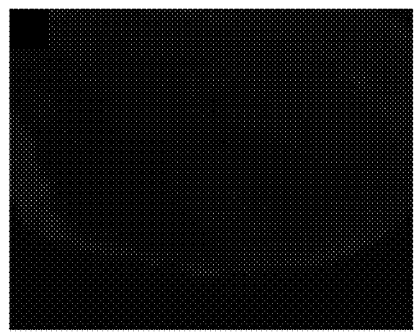
Figure 9E:
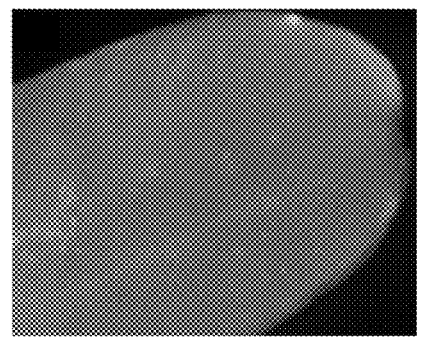
Figure 9F:
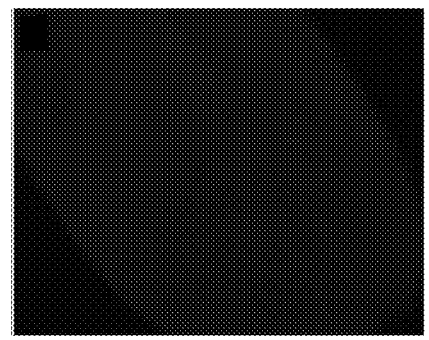
Figure 10D:
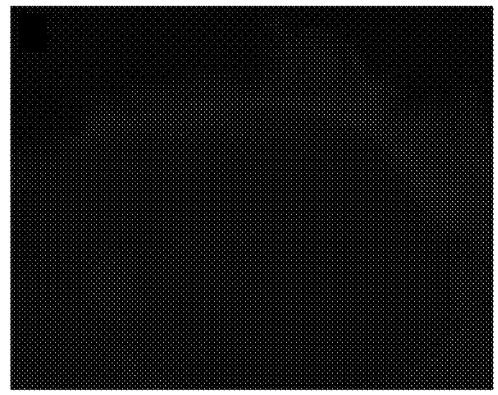
Figure 10E:
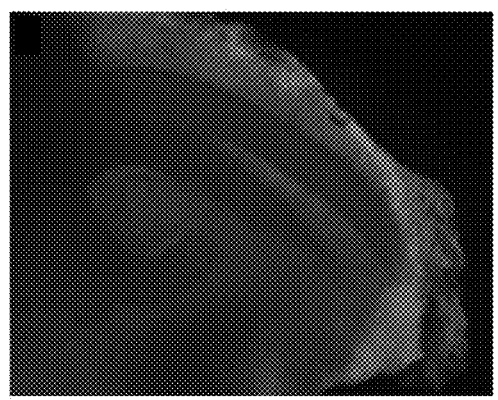
Figure 11A:
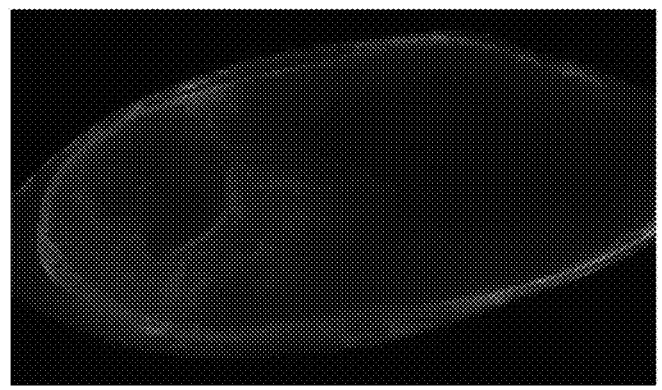
Figure 11B:
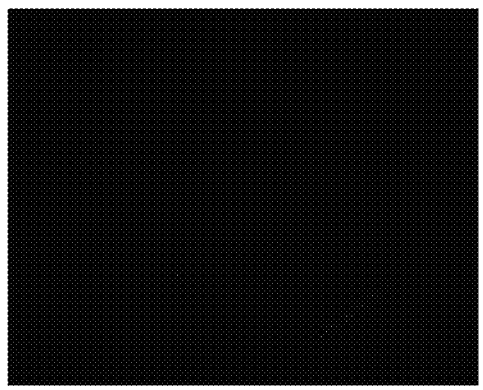
Figure 11C:
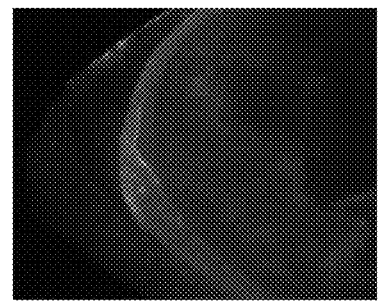
Figure 11G:
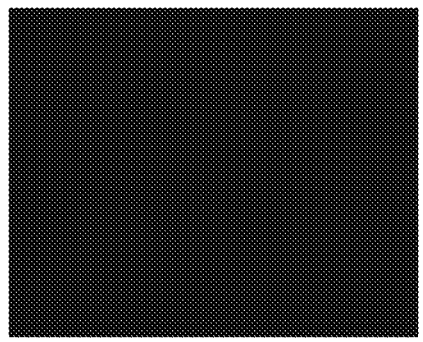
Figure 11H:
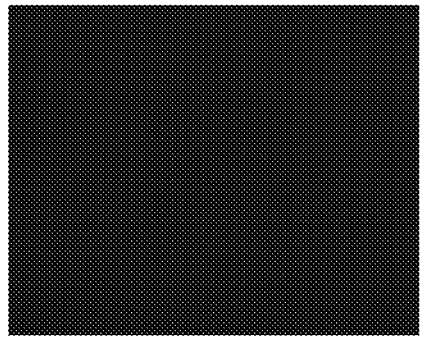
Figure 12B:
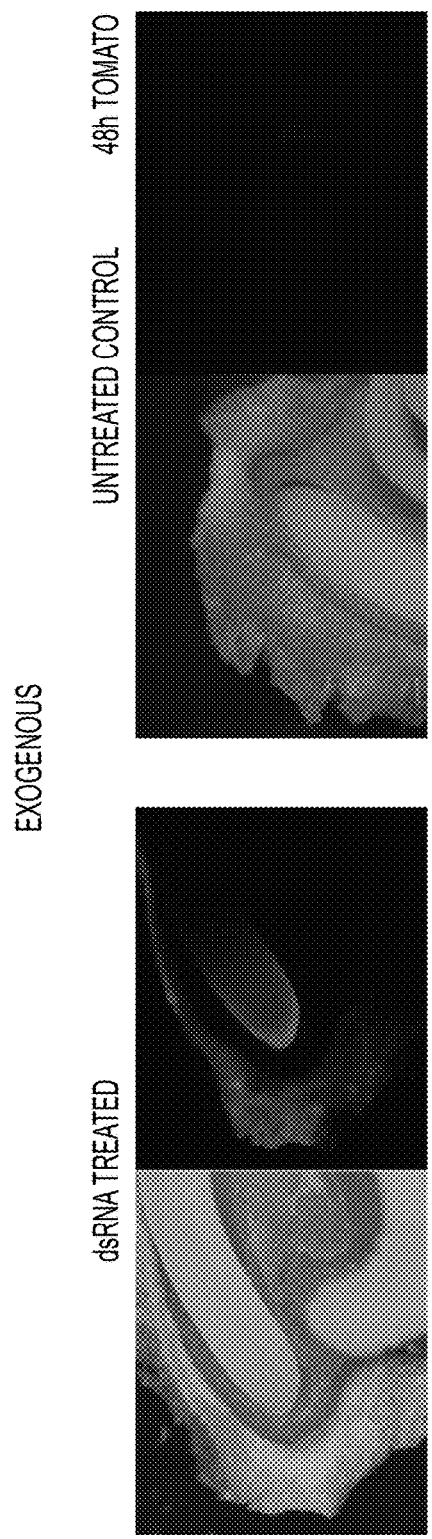
Figure 12C:
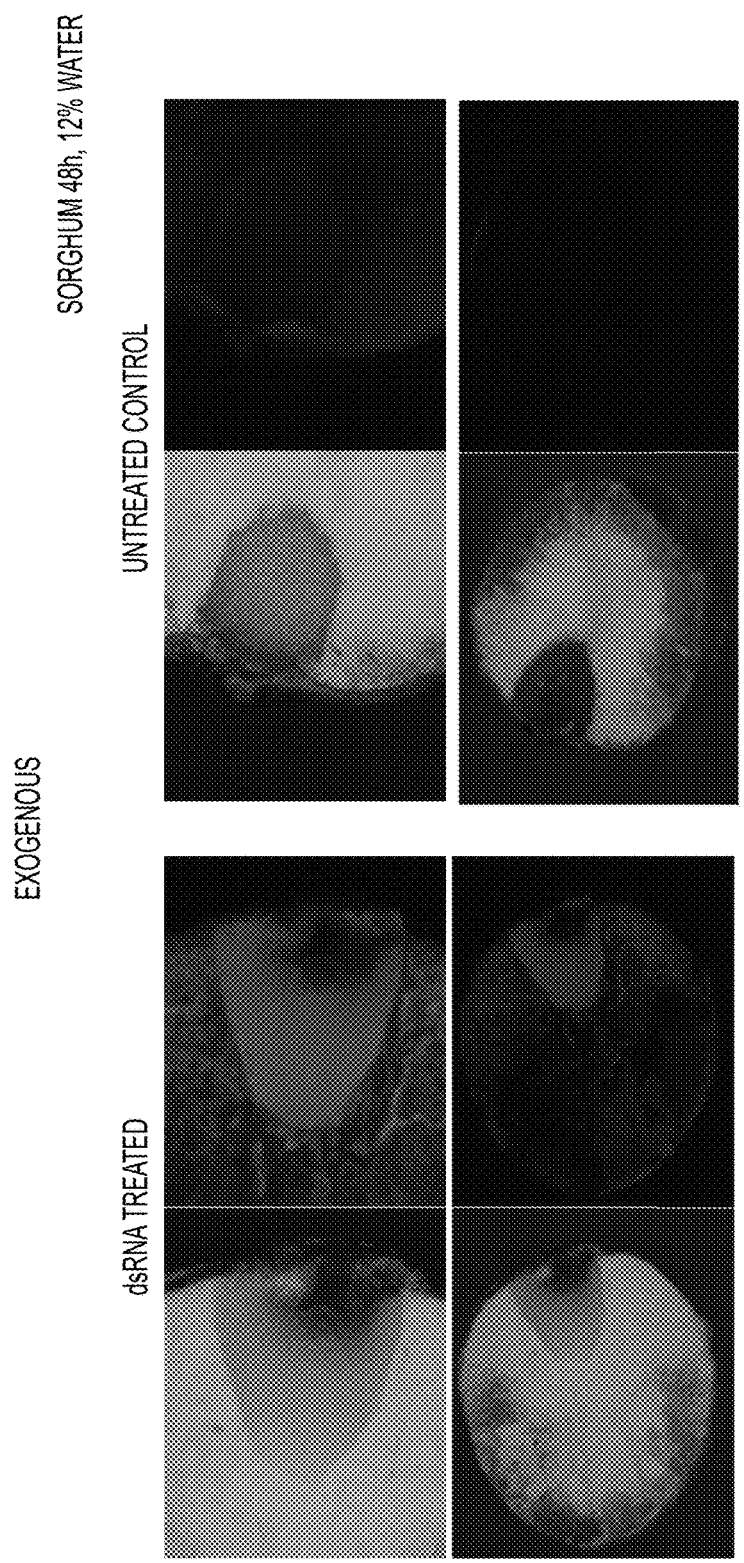
Figure 12D:
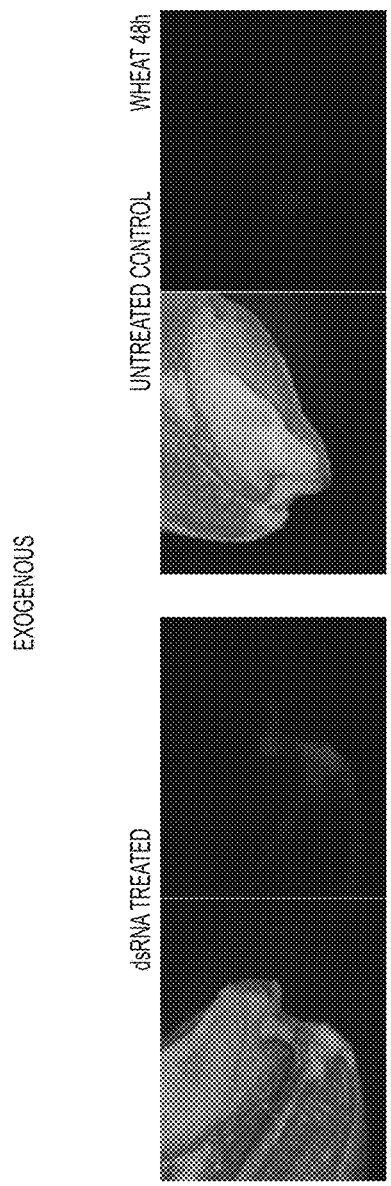

Fluorescent pictures of the seeds were taken 24-48 hours post treatment using an Olympus microscope at the lowest objective magnification (5× for bigger seeds such as rice and tomato seeds, and 10× for smaller seeds such as arabidopsis seeds). To eliminate the possibility of non-specific autofluorescence, each dsRNA-treated seed is shown alongside a control seed that was left untreated (FIGS. 7-8).

In order to evaluate the distribution efficiency of the fluorescent siRNA inside the seeds, different plant seeds were cut into slices and imaged with a fluorescent binocular 48 hours after treatment. Each treated seed was imaged alongside a control untreated seed. Light and fluorescent images were taken where applicable for rice, tomato, cucumber, bean, sorghum and wheat seed samples (FIGS. 9-12). It is clear that the siRNA is distributed at various levels between the embryo and the endosperm. This supports the following models:

The dsRNA molecules enter the embryo directly, carried by the water-based solution which is used for the seed treatment.

The dsRNA molecules enter the endosperm as part of the endosperm's water-absorption process. These molecules then feed the embryo as it develops as part of the nutrient flow from the endosperm during germination and seed development.

These present findings suggest the RNA molecules used to treat the seeds both penetrate the embryo and function in the embryo as it develops and also penetrate the endosperm and feed the embryo following germination.

Example 6

Time Course Experiment with siGLO Treatment

Figure 13:
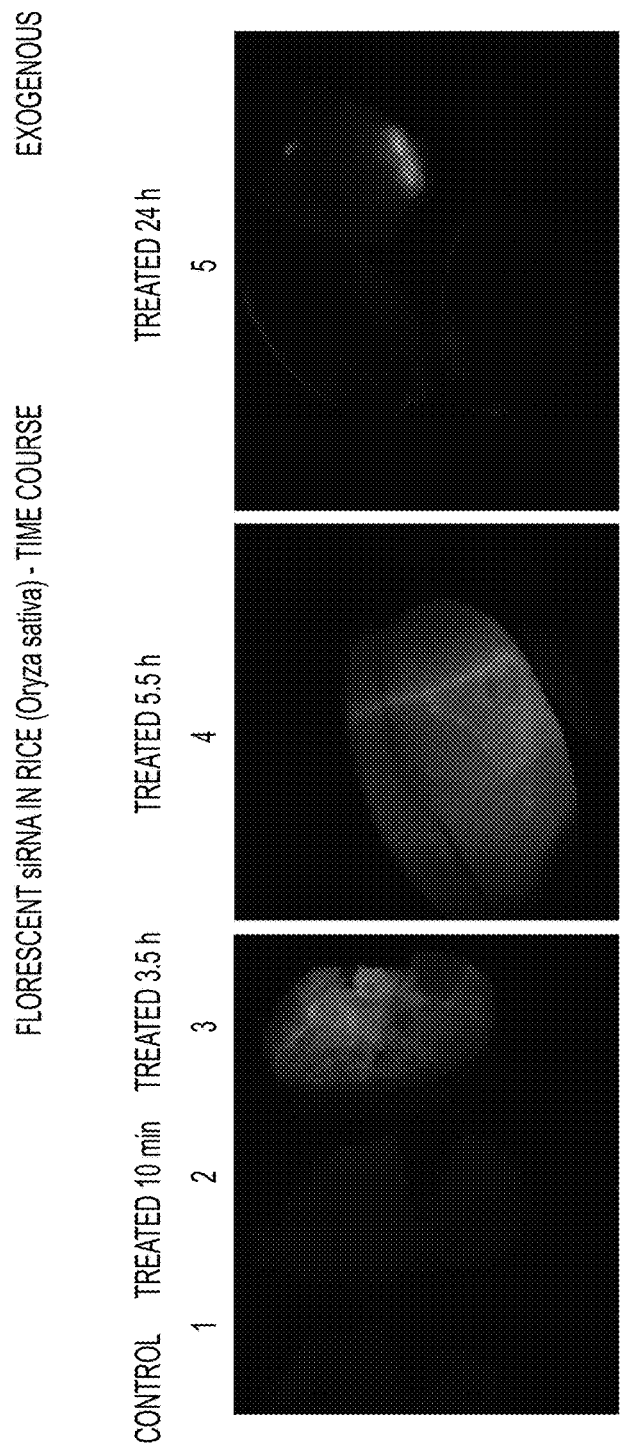
FIG. 13 shows a time-course siGLO-treatment results on rice seeds. The effect of incubation time with siGLO dsRNA on fluorescence intensity, indicating quantity and quality of dsRNA penetration, was tested. Untreated control (1) are shown along with seeds treated with siGLO dsRNA for four different incubation times: 10 min (2), 3.5 hours (3), 5.5 hours (4), and 24 hours (5).
Figure 14A:
FIGS. 14A-D show silencing the PDS-1 gene in rice by a dsRNA/siRNA mixture.
Figure 14B:
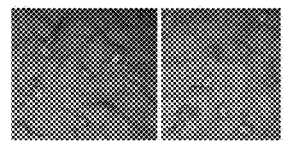
Figure 14C:
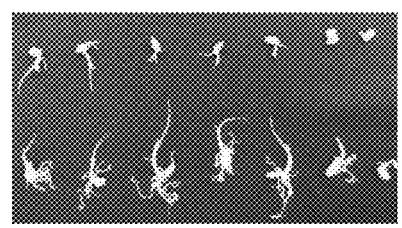
Figure 14D:
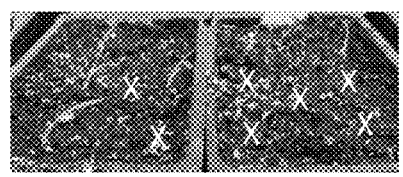

A time course experiment was performed on rice seeds to monitor the kinetics of siGLO penetration into the seeds following the seed treatment (FIG. 13). The results indicate that the siRNA efficiently penetrates the plant seeds using the protocol described in Example 1.

Example 7

Silencing the PDS-1 Gene in Rice by a dsRNA/siRNA Mixture

Rice seeds were washed in wash solution for 4 h at 20° C., dried at 25° C. and immediately treated with a mixture of dsRNA/siRNA at a total concentration of 60 μg/ml at 15° C. for 40 hours. Seeds were germinated at room temperature for several days and seed development was monitored. Seeds treated with the PDS and dsRNA/siRNA mixture exhibited stunted and delayed development, as seen by smaller seedlings and reduced rooting. In these experiments, two products of the PDS-1 gene are combined (see Table 4).

TABLE 4

Two PDS-1 Gene Products to be Silenced by dsRNA/siRNA Mixture.

| Gene Name | Organism | NCBI Accession Number | Nucleotide Sequence - Product 1/SEQ ID NO: | Nucleotide Sequence - Product 2/SEQ ID NO: |
|---|---|---|---|---|
| Phytoene Desaturase (PDS-1) | Zea mays | BT084155.1 | TAATACGACTCACTATA GGGAGATTGGCGAGCT TAGGATTGAGGATCGTT TACAGTGGAAAGAACA CTCTATGATATTCGCCA TGCCAAACAAGCCAGG AGAATTCAGCCGGTTTG | TAATACGACTCACTATA GGGTGATCGGGTGAACG ATGAGGTTTTTATTGCAA TGTCCAAGGCACTCAATT TCATAAATCCTGATGAG CTATCTATGCAGTGCATT TTGATTGCTTTGAACCGA |

TABLE 4-continued

Two PDS-1 Gene Products to be Silenced by dsRNA/siRNA Mixture.

| Gene Name | Organism | NCBI Accession Number | Nucleotide Sequence - Product 1/SEQ ID NO: | Nucleotide Sequence - Product 2/SEQ ID NO: |
|---|---|---|---|---|
| | | | ATTTCCCAGAAACTTTG<br>CCAGCACCTATAAATGG<br>GATATGGGCCATATTGA<br>GAAACAATGAAATGCT<br>TACCTGGCCCGAGAAG<br>GTGAAGTTTGCAATCGG<br>ACTTCTGCCAGCAATGG<br>TTGGTGGTCAACCTTAT<br>GTTGAAGCTCAAGATG<br>GCTTAACCGTTTCAGAA<br>TGGATGAAAAAGCAGG<br>GTGTTCCTGATCGGGTG<br>AACGATGAGGTTTTTAT<br>TGCAATGTCCAAGGCAC<br>TCAATTTCATAAATCCT<br>GATGAGCTATCTATGCA<br>GTGCATTTTGATTGCTT<br>TGAACCGATTTCTTCAG<br>GAGAAGCATGGTTCTA<br>AAATGGCATTCTTGGAT<br>GGTAATCCGCCTGAAA<br>GGCTATCTCCCTATAGT<br>GAGTCGTATTA/44 | TTTCTTCAGGAGAAGCAT<br>GGTTCTAAAATGGCATTC<br>TTGGATGGTAATCCGCCT<br>GAAAGGCTATGCATGCC<br>TATTGTTGATCACATTCG<br>GTCTAGGGGTGGAGAGG<br>TCCGCCTGAATTCTCGTA<br>TTAAAAAGATAGAGCTG<br>AATCCTGATGGAACTGT<br>AAAACACTTCGCACTTA<br>GTGATGGAACTCAGATA<br>ACTGGAGATGCTTATGTT<br>TGTGCAACACCAGTCGA<br>TATCTTCAAGCTTCTTGT<br>ACCTCAAGAGTGGAGTG<br>AAATTACTTATTTCAAGA<br>AACTGGAGAAGTTGGTG<br>GGAGTTCCTGTTATCAAT<br>GTTCATATATGGTTTGAC<br>AGAAAACTGAACAACAC<br>ATATGACCACCTTCTTTT<br>CAGCAGGAGTTCACTTTT<br>AAGTGTCTATGCAGACA<br>TGTCAGTAACCTGCAAG<br>GAATACTATGACCCAAA<br>CCGTTCAATGCTGGCCCT<br>ATAGTGAGTCGTATTA/45 |

The experiment was performed in three biological repeats and the results are presented in FIGS. 14A-D.

Example 8

Chlorophyll Bleaching and Growth Inhibition Following PDS Silencing

Figure 15:
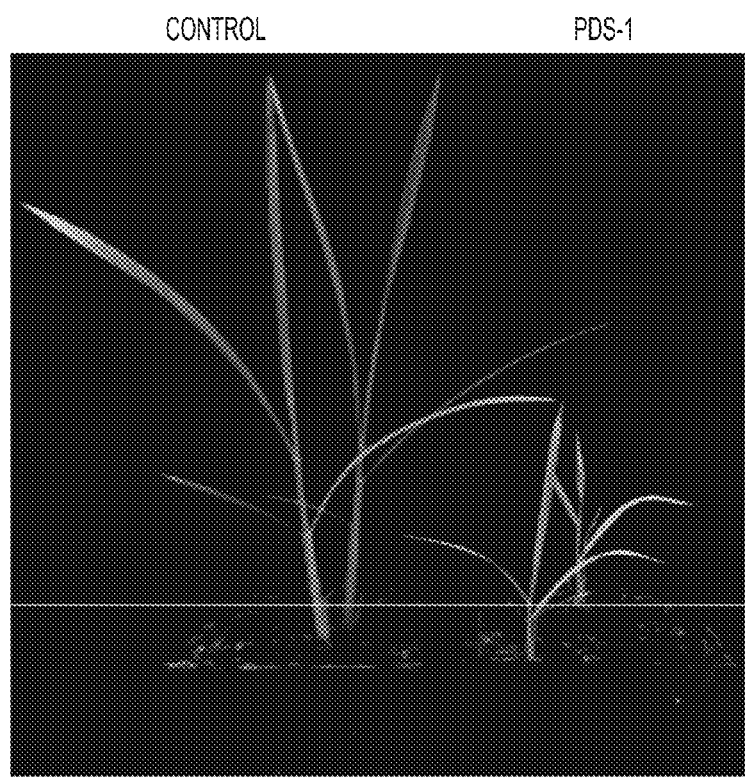
FIG. 15 is a photograph showing that PDS-1 silencing treatment results in chlorophyll bleaching and growth inhibition. Control plants (on left) display normal coloring and growth rate while PDS-silenced plants (on right) look paler in color and smaller in size, indicating signs of chlorophyll bleaching and growth inhibition, 30 days post treatment.

Rice seeds were treated as described in Example 7 and their subsequent development and seedling growth were monitored. Thirty days post PDS-1 silencing treatment the overall phenotype of the two plant groups, control and PDS-silenced, was recorded. PDS silencing has been reported to cause chlorophyll bleaching and growth inhibition (Peretz et al., 2007, Plant Physiol 145: 1251-1263), which correlates with the phenotype of the PDS-silenced plants of the invention, as they appeared smaller in size and paler in color, respectively, compared to control plants (see FIG. 15).

Example 9

Detection of the Two PDS-1 Gene Products by Real-Time PCR

Figure 16A:
FIGS. 16A-C show PDS-1 expression levels as determined by Real-Time PCR.
Figure 16B:
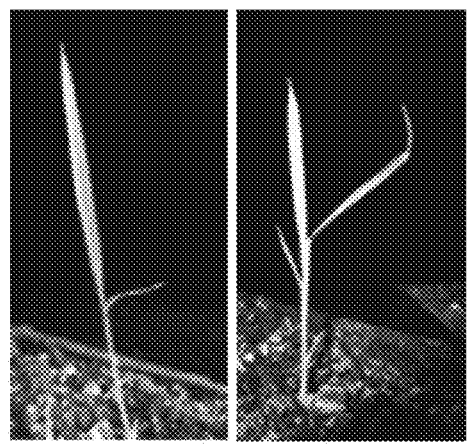
Figure 16C:
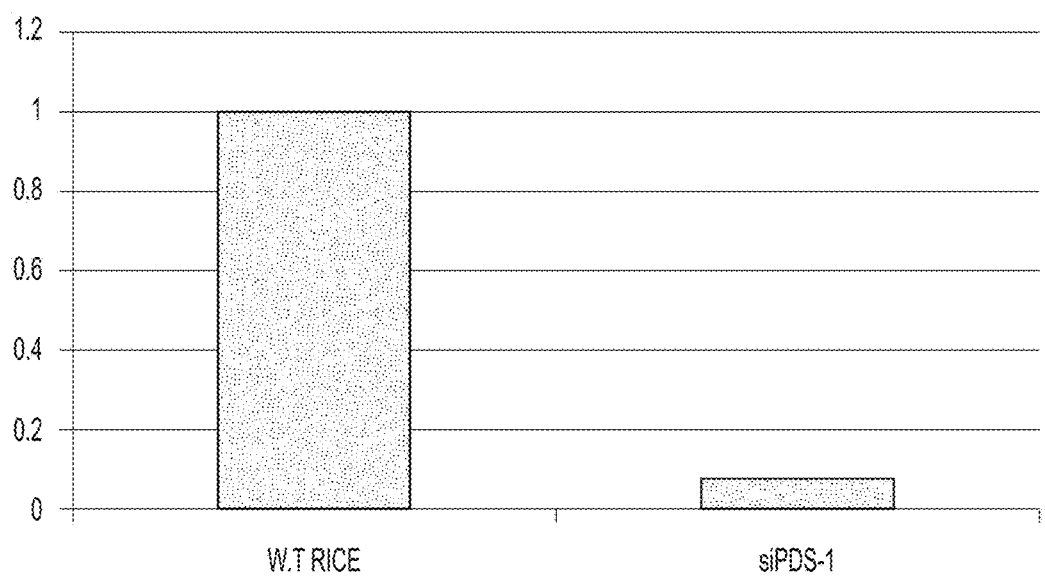

Following treatment with the dsRNA/siRNA mixture (ratio 1:1) as described in Example 7, expression levels of PDS-1 gene products are determined by real-time PCR using specifically designed primers (Forward: GATTGCTGGAGCAGGATTAG SEQ ID NO: 46, Reverse: CCCTTGCCTCAAGCAATATG, SEQ ID NO: 47). For normalization purposes, UBQ5 expression was also determined using primers (forward—ACCACTTCGACCGCCACTACT, SEQ ID NO: 48, reverse—ACGCCTAAGCCTGCTGGTT, SEQ ID NO: 49). The results are shown in FIGS. 16A-C.

Example 10

HAP2E Target Gene Silencing

Figure 17:
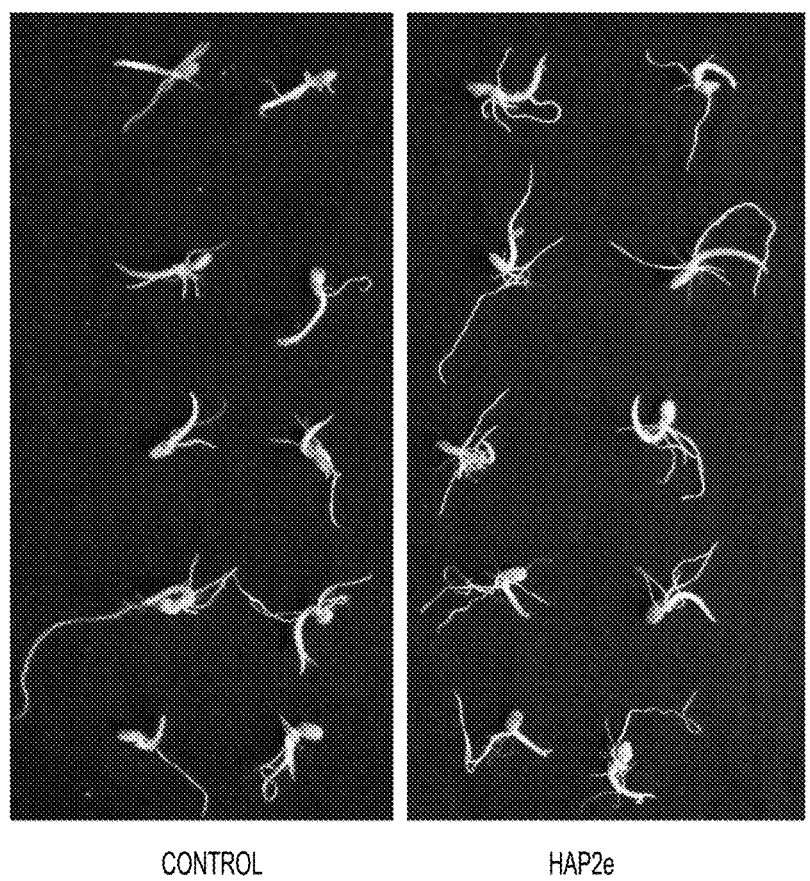
FIG. 17 shows no phenotypic differences in root development of control (left) and Hap2e dsRNA-treated (right) germinated seeds 5 days post treatment. This demonstrates that the seed treatment does not have any negative effect on seed germination and initial development.
Figure 18A:
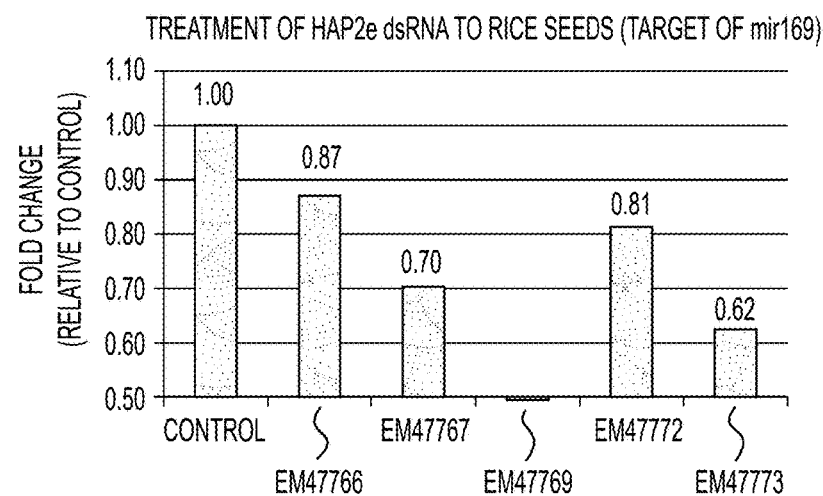
FIGS. 18A-C show the successful dsRNA-derived expression changes of Hap2e (miR169 target gene) using RT-PCR testing 3 different primer sets on RNA extracted from leaves of rice seedlings 5 days post germination.
Figure 18B:
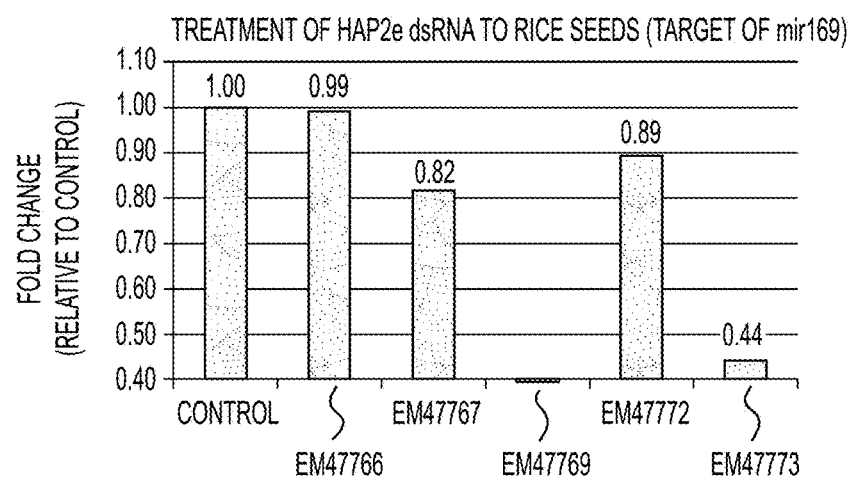
Figure 18C:
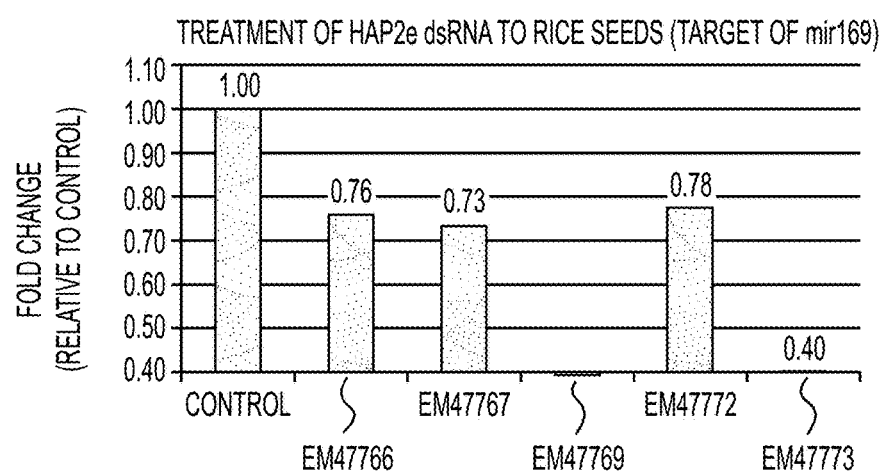
Figure 19:
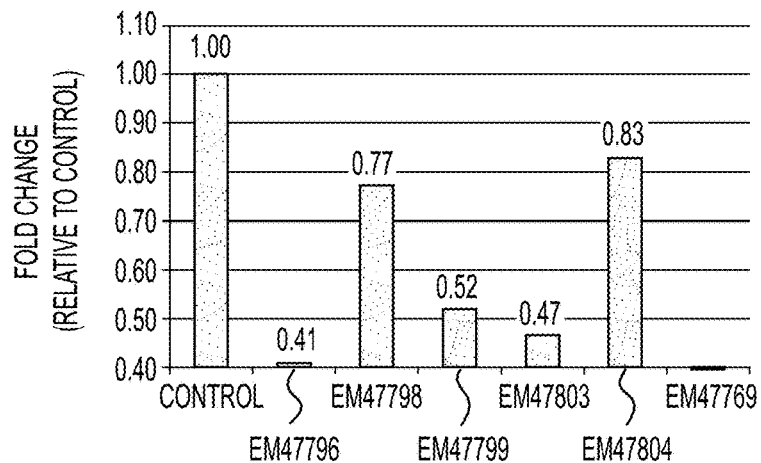
FIG. 19 shows the final dsRNA-derived expression changes of Hap2e (miR169 target gene) detected by RT-PCR, using the third primer set from FIG. 18C above, on RNA extracted from leaves of rice seedlings 7 days post germination. The average fold change of Hap2e expression of 4 control plants is used as a threshold reference and is plotted as having a value of 1. Treated samples are plotted separately and their respective fold change of Hap2e target gene is calculated relative to expression in control plants. Six representative treated plants, out of 16 plants total, are selected and plotted alongside control plants, with 4 treated plants exhibiting Hap2e down-regulation of approximately 50% and over compared to control (4/16 equals 25% efficiency), including complete silencing in one plant.

Rice seeds were treated using the protocol described in Example 1, Seeds were washed for 4 h at room temperature, dried overnight at 25° C. and immediately treated with a Hap2e dsRNA concentration of 152 μg/ml, for 41 hours at 15° C. (for Hap2e dsRNA sequences see Table 11, below). Control and Hap2e dsRNA-treated rice seeds that were germinated 5 days post treatment did not exhibit any differences in their root development (FIG. 17). RNA was extracted from shoots of germinated seeds, 5 and 7 days post germination, and RT-PCR was run. After testing 3 different sets of primers (see Table 6), located in various regions of the dsRNA molecules (FIG. 18), the best primer set (primer set 3) was used to evaluate the endogenous Hap2e expression levels in dsRNA-treated plants versus control (untreated) plants. Down-regulation of Hap2e mRNA expression in the treated plants, at a level of about 50% silencing or more compared to control plants, was achieved with an efficiency of 25% (FIG. 19).

Figure 20:
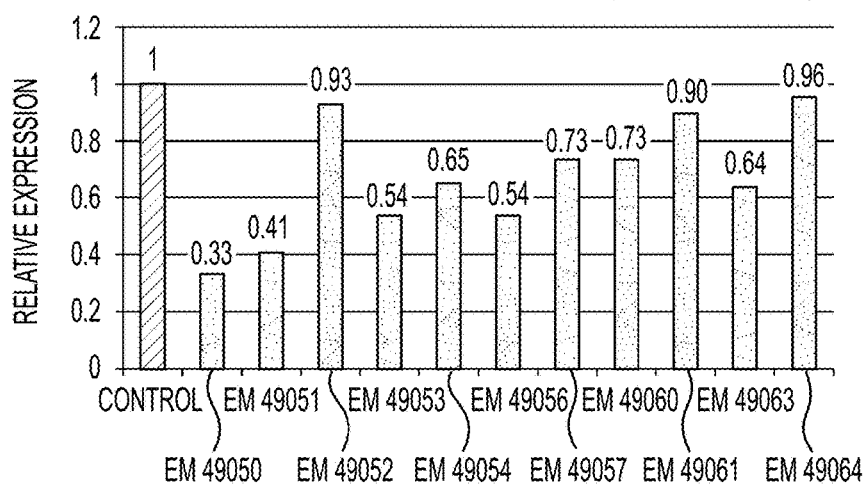
FIG. 20 shows the dsRNA-derived down-regulation of Hap2e (miR169 target gene) detected by RT-PCR, on RNA extracted from leaves of rice seedlings 18 days post germination. The average fold change of Hap2e expression of 4 control plants is used as a threshold reference and is plotted as having a value of 1 (shown in a red bar). Treated samples are plotted separately and their respective fold change of Hap2e target gene is calculated relative to expression in control plants. Eleven out of 16 treated plants exhibit some Hap2e down-regulation (shown in blue bars), and 8 of those exhibiting Hap2e down-regulation of over 25% compared to control (8/16 equals 50% efficiency).

Other rice seeds were treated under the same conditions as in FIG. 17 with a Hap2e dsRNA concentration of 145.7 g/ml, for 42 hours. RT-PCR using random primers+Oligo dT on RNA extracted from seedlings 18 days post germination also exhibited down-regulation of Hap2e mRNA in dsRNA-treated plants (FIG. 20), with 50% efficiency of reaching down-regulation of over 25% compared to control.

TABLE 5

Primers used for RT-PCR of Hap2e dsRNA Molecules

| Primer Set | Primer Set Location | Primer Name and Direction | Primer Sequence/SEQ ID NO: | Primer Length |
|---|---|---|---|---|
| 1 | In dsRNA | osaHAP2E501F3<br>osaHAP2E589R3 | ACCGGCATCAGCTCAGTCTC/50<br>TGCTGTTCTCTGGGCACAGG/51 | 20<br>20 |
| 2 | Junction | osaHAP2E11F5<br>osaHAP2E108R5 | TCCCCTCAGATATTAACAAC/52<br>AGGAGGAAAGGCAGCTTCTGTG/53 | 20<br>22 |
| 3 | Out of dsRNA | osaHAP2E122F7<br>osaHAP2E202R7 | GTGACTCGTCACCAACAAAG/54<br>TGTGTTGTCCGTTGAGACTG/55 | 20<br>20 |

Example 11

NFY Target Gene Silencing in Corn Seeds

Figure 21:
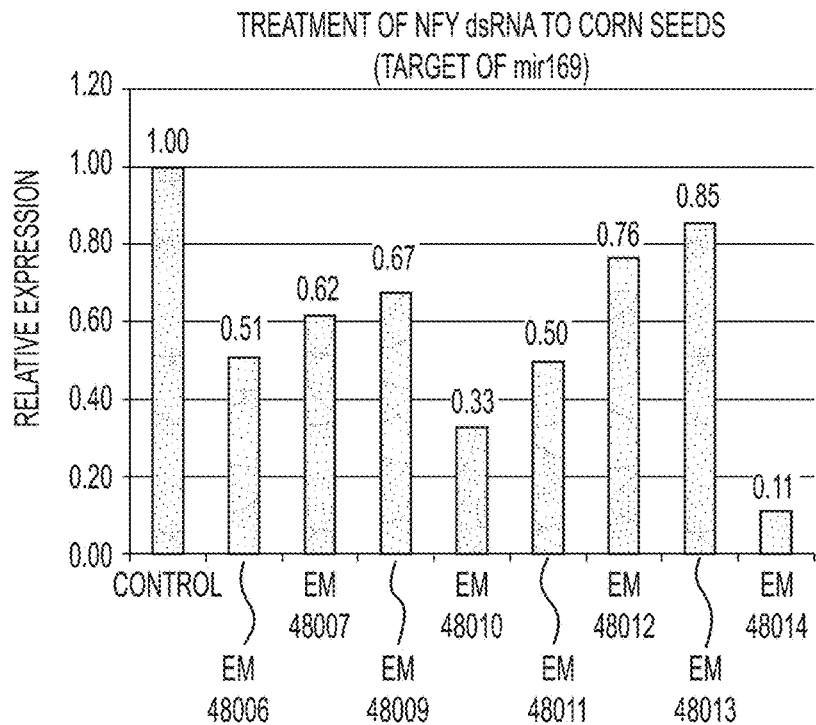
FIG. 21 shows results of RT-PCR on RNA extracted from control and NFY dsRNA-treated corn seeds 10 days after germination. The expression level of NFY target gene in control plants is averaged and recorded as "1" for comparison reference to that seen in dsRNA-treated plants. Four out of 8 treated plants that appear on the graph exhibit NFY down-regulation of 50% and over (4/8 efficiency of 50%).

Corn seeds were treated using the protocol described in Example 1, Seeds were washed for 4 h at room temperature, dried overnight at 30° C. and immediately treated with a NFY dsRNA concentration of 56 g/ml, for 40 hours at 15° C. (for NFY dsRNA sequence see table 11). RT-PCR on RNA extracted from shoots of control and NFY dsRNA-treated corn seeds 10 days after germination was performed to determine the expression level of NFY target gene (see Table 6). Down-regulation of the gene was successfully achieved as exhibited in FIG. 21.

TABLE 6

Primers used for RT-PCR of NFYA dsRNA Molecules in Corn Seeds 3 10 Days after Germination.

| Primer Name and Direction | Primer Sequence | Primer Length |
|---|---|---|
| zma-NFYA3_345 F3 | TCGGAAGCCGTACCTTCGTG/57 | 20 |
| zma-NFYA3 _442R3 | CCTGGAGCTGCTGCTTTGTG/58 | 20 |
| zma-NFYA3_457F4 | TACCAGGCGTCGAGTGGTTC/59 | 20 |
| zma-NFY-A3_542R4 | GAAGAGGGCGTGCAAATGGG/60 | 20 |

Example 12

NFY Target Gene Silencing in Tomato Seeds

Figure 22:
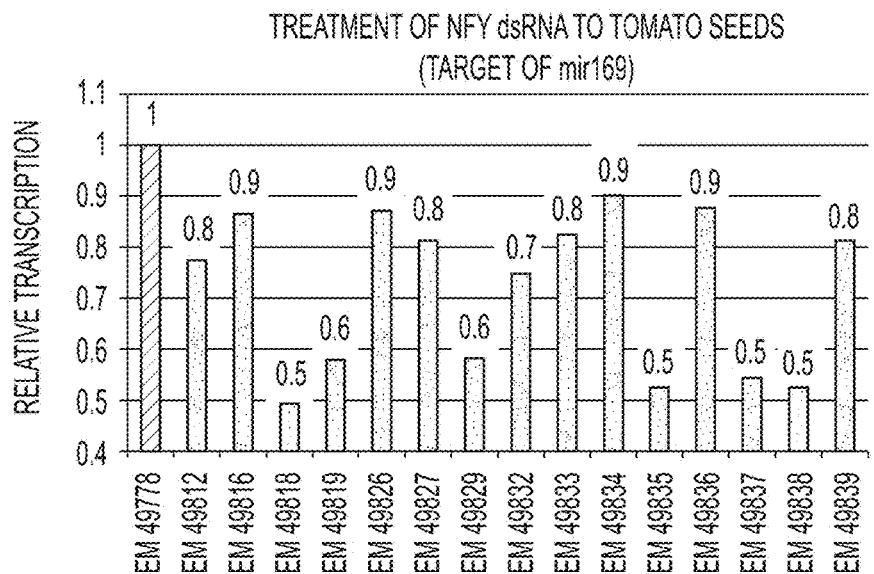
FIG. 22 shows results of RT-PCR on RNA extracted from control and NFY dsRNA-treated tomato seeds 3 weeks after germination. The expression level of NFY target gene in 8 control plants (shown in red) is averaged and recorded as "1" for a comparison reference to that seen in dsRNA-treated plants (shown in blue bars). Down-regulation of 40% and over is successfully achieved with 23% efficiency (6 out of 26) in treated plants relative to control plants.

Tomato seeds were treated using the protocol described in Example 1. Un washed seeds were treated with a NFY dsRNA concentration of 200 μg/ml, for 24 hours at 15° C., seeds were washed twice briefly and immediately planted in soil without drying. RT-PCR on RNA extracted from shoots of control and NFY dsRNA-treated tomato seeds 3 weeks after germination was performed to determine the expression level of NFY target gene (see Table 7). Down-regulation of the gene was successfully achieved as exhibited in FIG. 22.

Figure 23A:
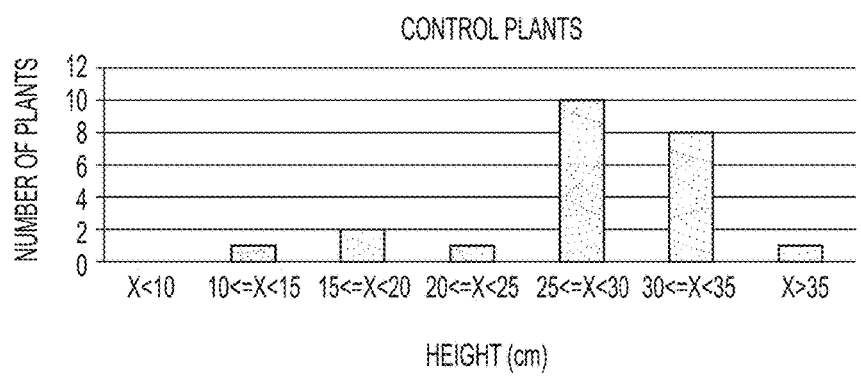
FIGS. 23A-B show height distribution of control and NFY dsRNA-treated tomato plants 55 days post inoculation.
Figure 23B:
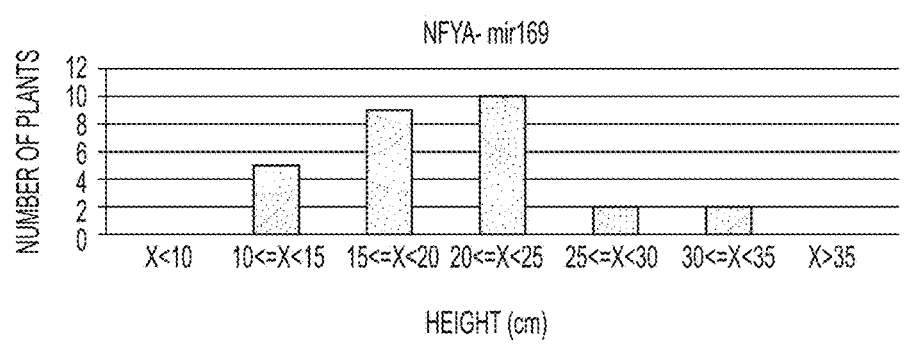
Figure 24:
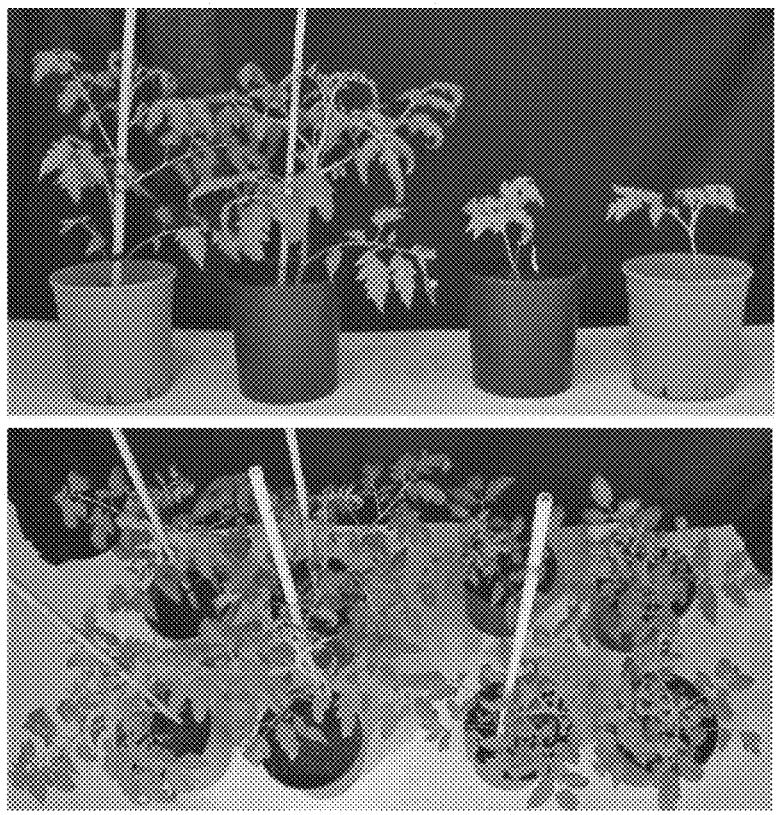
FIG. 24 shows major phenotypic differences of control and NFY dsRNA-treated tomato plants 55 days post inoculation. Control plants are seen on the left and treated plants are on the right of each picture. A delayed development is apparent in the shorter treated plants compared to control plants. Top picture is a side view and bottom picture is a top view of the same plants.

Tomato plants 55 days post treatment with NFY dsRNA molecules were compared to same age control plants. Major phenotypic differences were evident upon comparison, most notably was a shift in height, where treated plants appeared significantly shorter than untreated control plants (FIGS. 23, 24).

TABLE 7

Primers used for RT-PCR of NFYA dsRNA Molecules in Tomato and NFY dsRNA product

| Primer Name and Direction | Primer Sequence/ SEQ ID NO: | Primer Length |
|---|---|---|
| slyNFYA125F3 | CTATTGCGTGTGCTCCAAAC/61 | 20 |
| slyNFYA212R3 | ACATGAGGAGGAACCAAAGG/62 | 20 |
| NFY dsRNA product 1 | CTAATACGACTCACTATAGGGAGAGGCTCAAGAACCAG<br>TTTATGTTAATGCTAAGCAGTATCGAAGGATCCTGCAGC<br>GAAGACAGTCACGTGCTAAAGCAGAACTTGAAAAGAAG<br>CAAATAAAGGGTAGAAAGCCATATCTTCACGAGTCTCG<br>ACATCAGCATGCACTGAGGAGGGTAAGGGCCTCGGGTG<br>GACGTTTTGCCAAAAAGACAGATGCTTCTAAGGGTACT<br>GGTTCTGTGAGTTCATCGGGTTCTGAACCTTTGCAGTTC<br>AATGCTGCTGATATTCAAAAGAGGAATGAAAATGGAAG<br>GTTGGCCGAGCTTCAGCAGTCTTATTCAAATGGTAGCAG<br>TTATGGCAATCAAAGTAGCTTTCAAGAATCCAAGGATG | Product 1 |

TABLE 7-continued

Primers used for RT-PCR of NFYA dsRNA Molecules in Tomato and NFY dsRNA product

| Primer Name and Direction | Primer Sequence/ SEQ ID NO: | Primer Length |
|---|---|---|
| | AGTACCAGTTTGCTAAAAGCAGGGAAGGAGGTTTTTTT GTCAAGTAATTGGAGATACGTTCATGTGTAAACTAGCTC TTGCCCTCTCCCTATAGTGAGTCGTATTAG/63 | |
| NFY dsRNA product 2 | CTAATACGACTCACTATAGGGAGAGCAGTTATGGCAAT CAAAGTAGCTTTCAAGAATCCAAGGATGAGTACCAGTT TGCTAAAAGCAGGGAAGGAGGTTTTTTTGTCAAGTAATT GGAGATACGTTCATGTGTAAACTAGCTCTTGCCCTGCAA CGAGGGTAGAGTATGAGCAAGAGGAGTTTACAGGGATT GTTTCATTTCTTGGCTTTTCAAGATAGGCGGCAATTCAT TCTTGGCTTTTTACTTTAGTGTTAAAGGGAGCAACAGAG GTGACGAGGGTATCAGTGTTGCAGCATTTGCTTGGAGAT TACATCTTCCCTTATGTACAGAGATGGATGAACTTAGAA CTAGGATTAGAAAGTTTTTCAGTAAGTTTATGTTTGGCC AGTTACTGTAGTTTTAGTTTAGGAGACCATGTAAAAAGG TTGTTAGTTTTGCAAAAGGATCTTTTTTCTTTCCCTAATT GGTGCATTCTCCCTATAGTGAGTCGTATTAG/64 | Product 2 |

Example 13

NAC Target Gene Silencing in Corn Seeds

Figure 25:
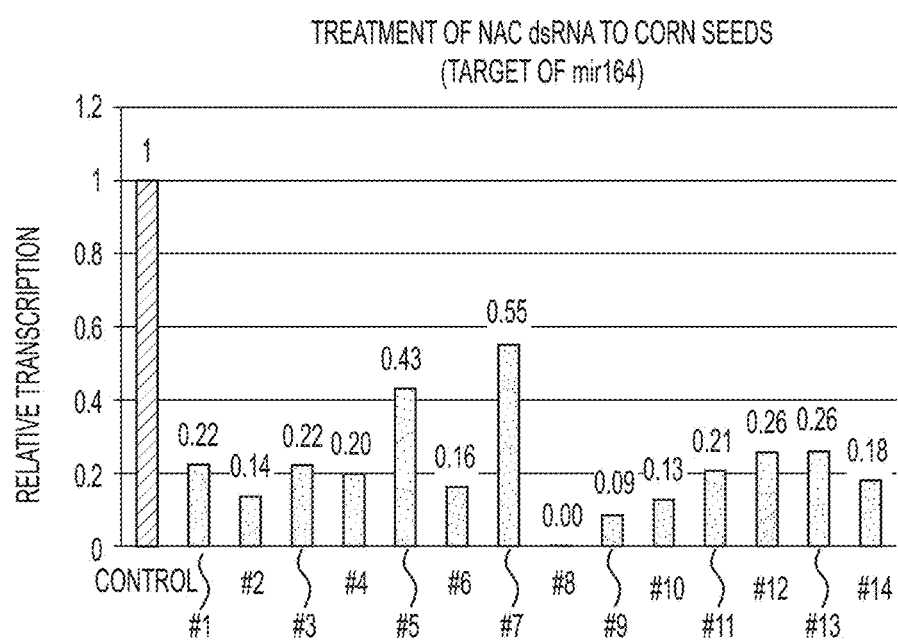
FIG. 25 shows results of RT-PCR on RNA extracted from control and NAC dsRNA-treated corn seeds 10 days after germination. The expression level of NAC target gene in control plants is averaged and recorded as "1" for a comparison reference to that seen in dsRNA-treated plants. All 14 dsRNA treated plants exhibit NAC gene down-regulation, with one plant showing complete silencing of the gene (#8).

Corn seeds were treated using the protocol described in Example 1, seeds were washed for 4 h at room temperature, dried overnight at 30° C. and immediately treated with a NAC dsRNA concentration of 90 µg/ml, for 40 hours at 15° C. and immediately germinated (for NAC dsRNA sequence see Table 11). RT-PCR on RNA extracted from shoots of control and NAC dsRNA-treated corn seeds 10 days after germination was performed to determine the expression level of NAC target gene (see Table 8). Down-regulation of the gene was successfully achieved as exhibited in FIG. 25.

TABLE 8

Primers used for RT-PCR of NAC dsRNA Molecules in Corn.

| Primer Name and Direction | Primer Sequence | Primer Length |
|---|---|---|
| zmaNAC5_267F3 | CGAGTCGGGATACTGGAAGG/65 | 20 |
| zmaNAC5_342R3 | CTTCTTCATGCCGACGAGGG/66 | 20 |
| zmaNAC5_187F4 | ACGATGGGCGAGAAGGAGTG/67 | 20 |
| zmaNAC5_250R4 | TCAGTCCCGTCGGGTACTTG/68 | 20 |

Example 14

ARF-8 Target Gene Silencing in Rice Seeds

Figure 26A:
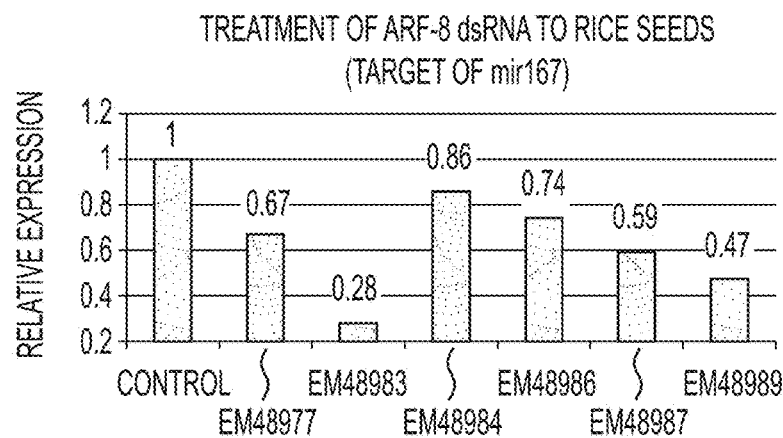
FIGS. 26A-B show results of RT-PCR, using cDNA prepared with either random primers (FIG. 26A) or oligo-dT (FIG. 26B), on RNA extracted from control and ARF-8 dsRNA-treated rice seeds 18 days after germination. The expression level of ARF-8 target gene in 9-10 control plants is averaged and recorded as "1" for a comparison reference to that seen in dsRNA-treated plants.
Figure 26B:
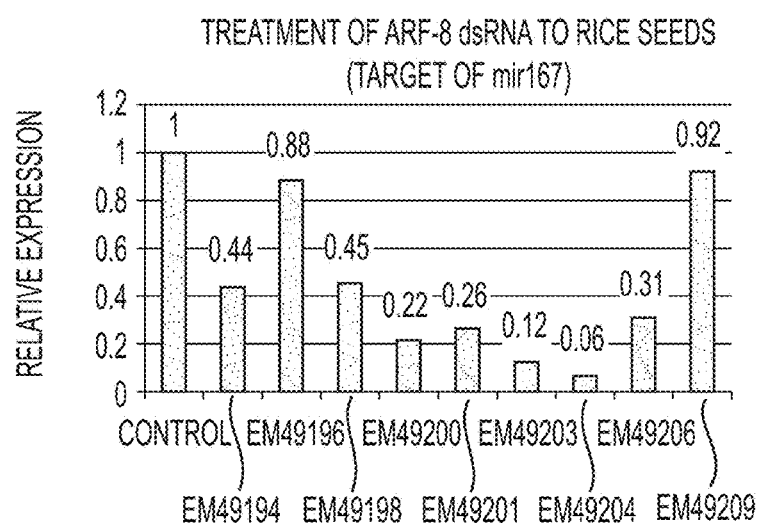

Rice seeds were treated using the protocol described in Example 1, seeds were washed for 4 h, dried overnight at 20° C. and immediately treated with an ARF-8 dsRNA concentration of 66.2 µg/ml, for 42 hours at 15° C. RT-PCR on RNA extracted from control and ARF-8 dsRNA-treated rice seeds 18 days after germination was performed to determine the expression level of ARF-8 target gene (see Table 9). Down-regulation of the gene was successfully achieved as exhibited in FIG. 26.

TABLE 9

Primers used for RT-PCR of ARF-8 mRNA Molecules in Rice and ARF-8 dsRNA product

| Primer Name and Direction | Primer Sequence | Primer Length |
|---|---|---|
| osaARF8_140F3 | AGGGTCACATCCCGAACTAC/69 | 20 |
| osaARF8_233R3 | ACCTCGTCAGTCTCCACATC/70 | 20 |
| osaARF8_1674F4 | GTTGGATTCGAGCTTCCTTC/71 | 20 |
| osaARF8_1757R4 | TGCTGCTGCTCACTAGCTAC/72 | 20 |
| ARF8 dsRNA product | CTAATACGACTCACTATAGGGAGACAGTCCGTTGGCCTAGT TCCTATTGGAGATCTGTGAAGGTTGGTTGGGATGAATCAAC TGCAGGGGAAAGACCACCAAGAGTTTCTTTATGGGAAATT GAACCATTGACAACCTTTCCAATGTATCCATCTCTGTTCCC ACTGAGAGTTAAGCATCCTTGGTATTCAGGAGTTGCTTCCC | |

TABLE 9-continued

Primers used for RT-PCR of ARF-8 mRNA Molecules in Rice and ARF-8 dsRNA product

| Primer Name and Direction | Primer Sequence | Primer Length |
|---|---|---|
| | TGCATGATGACAGCAATGCTTTAATGTGGCTGAGAGGAGT TGCTGGTGAGGGAGGTTTTCAGTCTCTGAACTTTCAGTCAC CTGGTATTGGCTCCTGGGGACAACAGAGGCTCCATCCATCC TTACTGAGCAGCGATCACGATCAGTACCAAGCAGTAGTTG CTGCTGCTGCTGCTTCCCAATCTGGTGGTTACTTAAAACAG CAATTCTTGCACCTTCAGCAACCTATGCAGTCCCCTCAAGA ACACTGCAACCTCAACCCTCTCCCTATAGTGAGTCGTATTA G/73 | |

Example 15

SPL17 Target Gene Silencing in Rice Seeds

Figure 27:
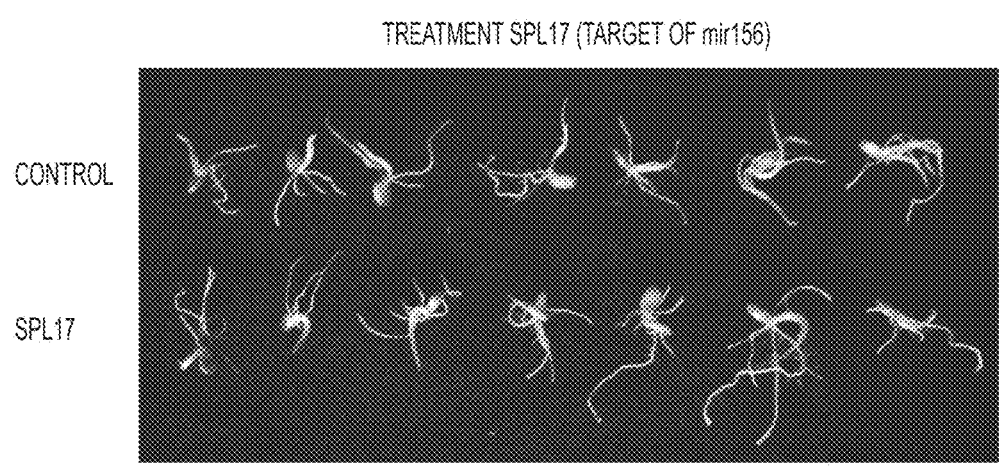
FIG. 27 shows no phenotypic differences in root development of control (top row) and SPL17 dsRNA-treated (bottom row) germinated rice seeds 5 days post treatment.
Figure 28A:
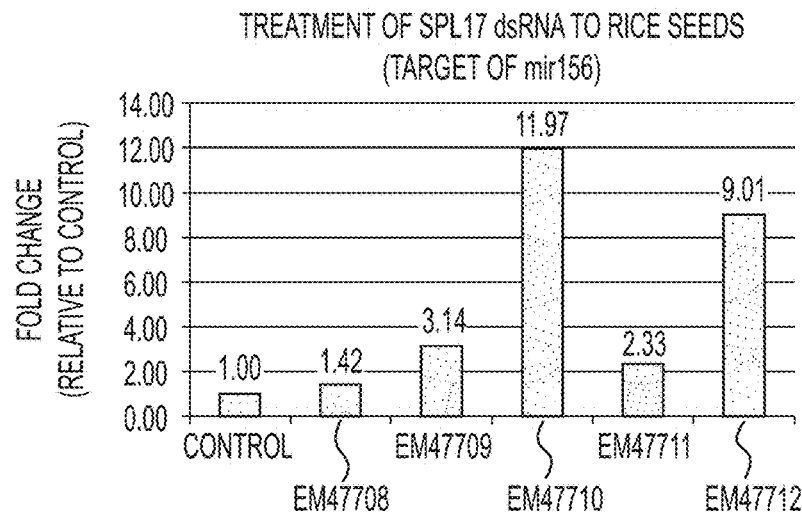
FIGS. 28A-B show the results of RT-PCR testing 2 different primer sets on RNA extracted from leaves of control and SPL17 (miR156 target gene) dsRNA treated rice seedlings 5 days post germination.
Figure 28B:
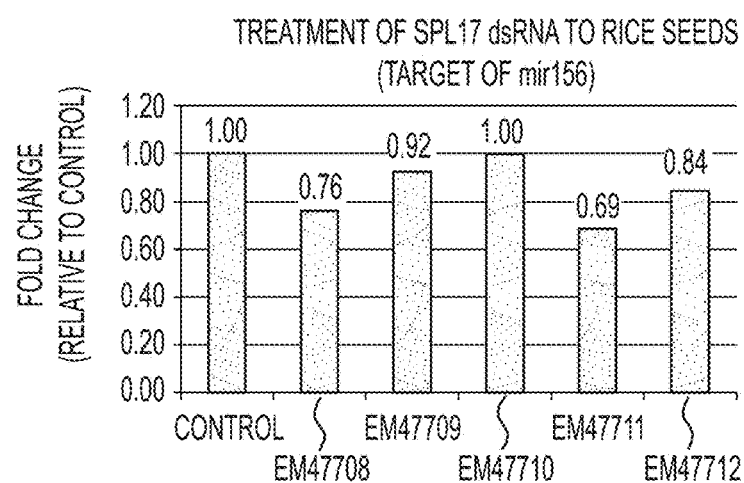
Figure 29:
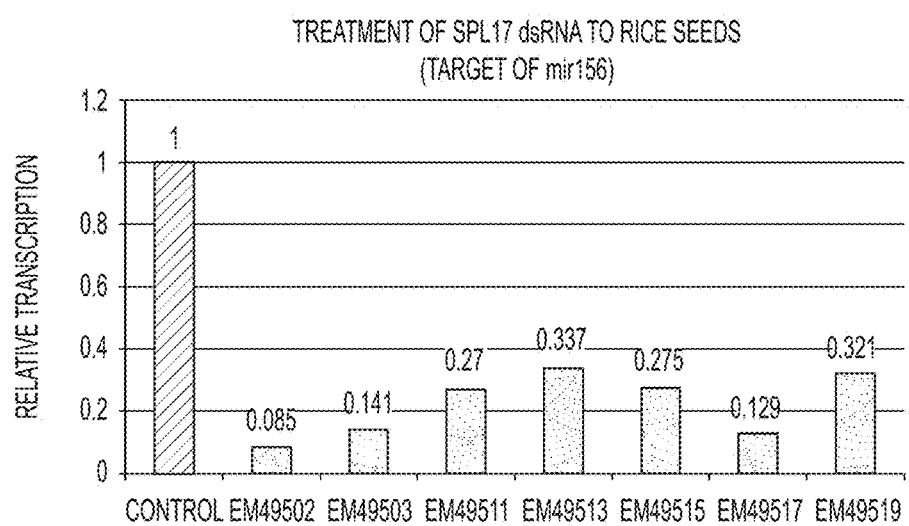
FIG. 29 shows the results of RT-PCR on RNA extracted from leaves of control and SPL17 (miR156 target gene) dsRNA-treated rice plants 14 weeks post germination. The average fold change of SPL17 expression of 4 control plants is used as a threshold reference and is plotted as having a value of 1. Treated samples are plotted separately and their respective fold change of SPL7 target gene is calculated relative to expression in control plants. Down-regulation of up to 90% of SPL17 gene expression is observed. Seven out of 10 dsRNA-treated plants exhibit SPL17 down-regulation of over 65% (7/10 efficiency of 70%).

Rice seeds were treated using the protocol described in Example 1, seeds were washed for 4 h, dried overnight at 20° C. and immediately treated with a SPL17 dsRNA concentration of 200 µg/ml, for 41 hours at 15° C. (for SPL17 dsRNA sequence see table 11). Control and SPL17 dsRNA-treated rice seeds that were germinated 5 days post treatment did not exhibit any visual differences (FIG. 27). RNA was extracted from 5 days old shoots of these germinated seeds and RT-PCR was run to determine SPL17 expression levels in control and treated plant groups. Two different sets of primers (see Table 10), located in various regions of the dsRNA molecules, were tested (FIG. 28). When RT-PCR was run on RNA extracted from 14-week old plants, down-regulation of SPL17 mRNA expression in the treated plants was achieved with high efficiency compared to control plants, (FIG. 29).

TABLE 10

Primers used for RT-PCR of SPL17 dsRNA Molecules in Rice Seeds 5 Days after Germination.

| Primer Set and Location | Primer Name and Direction | Primer Sequence | Primer Length |
|---|---|---|---|
| 1 - in dsRNA | osaSPL17_119F3 | CTCAGCCATGGGATACTACC/74 | 20 |
| | osaSPL17_189R3 | GCTGGCCGTTGACGACATTG/75 | 20 |
| 2 - out of dsRNA | osa spl17 454Fwd | TTCAGCCACTCCACCAATG/76 | 19 |
| | osa spl17 512Rev | AAGAAGATGATCAATGGTCTC/77 | 21 |

Example 16

Silencing of MicroRNA Target Genes with Complementary dsRNA/siRNA

The high specificity and efficiency of posttranscriptional gene silencing by target gene-specific dsRNA has become a preferred method to generate preferred phenotype eukaryotic organisms, wherein expression of one or more genes is reduced or inactivated. Specific dsRNA sequences designed to silence corn (*Zea mays*) and rice (*Oryza sative*) microRNA target genes. Specifically, microRNAs shown to associate with improved abiotic stress tolerance will be used. Table 11 below provides several examples for target gene sequences that are produced using PCR amplification to test the gene silencing capabilities of their respective dsRNA/siRNA mixture. These dsRNA molecules will then be used to knock down the endogenous level of the selected target genes.

TABLE 11

Target Gene Sequences and Primers for PCR

| Target for Mir | Target Gene | Organism | Accession number | Target Sequence/SEQ ID NO: | Forward Primer/SEQ ID NO: | Reverse Primer/SEQ ID NO: | Product Length |
|---|---|---|---|---|---|---|---|
| miR169 | NFY-A3 | *Zea mays* | NM_001153839 | GATGAAGATCATGGGAAGG ATAATCAGGACACATTGAA | TAATACG ACTCACT | TAATAC GACTCA | 537 bp |

TABLE 11-continued

Target Gene Sequences and Primers for PCR

| Target for Mir | Target Gene | Organism | Accession number | Target Sequence/SEQ ID NO: | Forward Primer/SEQ ID NO: | Reverse Primer/SEQ ID NO: | Product Length |
|---|---|---|---|---|---|---|---|
| | | | | GCCAGTATTGTCCTTGGGGA AGGAAGGGTCTGCCTTTTTG GCCCCAAAAATAGATTACA ACCCGTCTTTTCCTTATATTC CTTATACTGCTGACGCTTAC | ATAGGGC CGCATGC CATTGTC CATCC/84 | CTATAG GGTGCA TGCCGTT CACGAC CAG/85 | |
| | | | | TATGGTGGCGTTGGGGTCTT GACAGGATATGCTCCGCAT GCCATTGTCCATCCCCAGCA AAATGATACAACAAATAGT CCGGTTATGTTGCCTGCGGA ACCTGCAGAAGAAGAACCA ATATATGTCAATGCAAAAC AATACCATGCGATCCTTAGG AGGAGGCAGACACGTGCTA AACTGGAGGCGCAAAACAA GATGGTGAAAGGTCGGAAG CCGTACCTTCGTGAGTCTCG ACACCGTCATGCCATGAAG CGGGCCCGTGGCTCAGGAG GGCGGTTCCTCAACACAAA GCAGCAGCTCCAGGAGCAG AACCAGCAGTACCAGGCGT CGAGTGGTTCAATGTGCTCA AAGACCATTGGCGACAGCG TAATCTCCCAAAGTGGCCCC ATTTGCACGCCCTCTTCTGA CGCTGCAGGTGCTTCAGCAG CCAGCCAGGACCGCGGCTG CTTGCCCTCGGTTGGCTTCC GCCCCACAGCCAACTTCAGT GAGCAAGGTGGAGGCGGCT CGAAGCTGGTCGTGAACGG CATGCAGCAGCGTGTTTCCA CCATAAGGTGAAGAGAAGT GGGCACGACACCATTCCCA GGCGCGCACTGCCTGTGGC AACTCATCCTTGGCTTTTGA AACTATGAATATGCAATGG ACATGTAGCTTTGAGTTCCT CAGAATAA/78 | TAATACG ACTCACT ATAGGGC AAATAGT CCGGTTA TGTTG/86 | TAATAC GACTCA CTATAG GGGCTA CATGTCC ATTGCAT ATTC/87 | 619 bp |
| | HAP2E | Oryza sativa | AB288031.1 | TCAGTGTTTGTCCCCTCAGA TATTAACAACAATGATAGTT GTGGGGAGCGGGACCATGG CACTAAGTCGGTATTGTCTT TGGGGAACACAGAAGCTGC CTTTCCTCCTTCAAAGTTCG ATTACAACCAGCCTTTTGCA | TAATACG ACTCACT ATAGGGC TGCCTTT CCTCCTT CAAAGTT C/88 | TAATAC GACTCA CTATAG GGTGCT GTTCTCT GGGCAC AGG/89 | 535 bp |
| | | | | TGTGTTTCTTATCCATATGG TACTGATCCATATTATGGTG GAGTATCAACAGGATACAC TTCACATGCATTTGTTCATC CTCAAATTACTGGTGCTGCA AACTCTAGGATGCCATTGGC TGTTGATCCTTCTGTAGAAG AGCCCATATTTGTCAATGCA AAGCAATACAATGCGATCC TTAGAAGAAGGCAAACGCG TGCAAAATTGGAGGCCCAA AATAAGGCGGTGAAAGGTC GGAAGCCTTACCTCCATGAA TCTCGACATCATCATGCTAT GAAGCGAGCCCGTGGATCA GGTGGTCGGTTCCTTACCAA AAAGGAGCTGCTGGAACAG CAGCAGCAGCAGCAGCAGC AGAAGCCACCACCGGCATC AGCTCAGTCTCCAACAGGTA GAGCCAGAACGAGCGGCGG TGCCGTTGTCCTTGGCAAGA ACCTGTGCCCAGAGAACAG CACATCCTGCTCGCCATCGA CACCGACAGGCTCCGAGAT CTCCAGCATCTCATTTGGGG | TAATACG ACTCACT ATAGGGC ATTGGCT GTTGATC CTTCTG/90 | TAATAC GACTCA CTATAG GGTTCGT TCAGTCA TAGCTTA C/91 | 722 bp |

TABLE 11-continued

Target Gene Sequences and Primers for PCR

| Target for Mir | Target Gene | Organism | Accession number | Target Sequence/SEQ ID NO: | Forward Primer/SEQ ID NO: | Reverse Primer/SEQ ID NO: | Product Length |
|---|---|---|---|---|---|---|---|
| | | | | GCGGCATGCTGGCTCACCA AGAGCACATCAGCTTCGCAT CCGCTGATCGCCACCCCACA ATGAACCAGAACCACCGTG TCCCCGTCATGAGGTGAAA ACCTCGGGATCGCGGGACA CGGGCGGTTCTGGTTTACCC TCACTGGCGCACTCCGGTGT GCCCGTGGCAATTCATCCTT GGCTTATGAAGTATCTACCT GATAATAGTCTGCTGTCAGT TTATATGCAATGCAACCTCT GTCAGATAAACTCTTATAGT TTGTTTTATTGTAAGCTATG ACTGAACGAACTGT/79 | | | |
| miR156 | SPL17 | Oryza sativa | JN192988.1 | CATGGTGGCTCAGCGGCTG GGGCACCAATGCTCCACCA CCCAGCCTTTGAGCTCACCT CAGGTGGATGTCTCGCGGG AGTCGCCACCGACTCCAGCT GTGCTCTCTCTCTTCTGTCA ACTCAGCCATGGGATACTAC CCAAAGCACCAGCAGCCAC AACCGGTCCCCGCCAATGTC GTCAACGGCCAGCGCCTTCG GAGGCGGCAACAACCCGGT GTCGCCCTCGGTCATGGCAA GCAACTACATGGCGGCGAG CCCCGGCTGGAACAGCTCC AGCCGGGGCCATGACGGCG CCAGGAACGTGCACCTGCC GCCACCGCACGGGGTTGTG CTGAACGAGGTCCCTCCGG GCTCTGTCCACCACGGCCAT TTCTCCGGCGAGCTCGAGCT CGCACTGCAGGGAGGTGCC CCGTCCAACCGGCCGGAAG CCAAGCATGGCTCCGGCAG CGGCGCCTTCAGCCACTCCA CCAATGCCATGAACTGGTCT CTGTAGAGACCATTGATCAT CTTCTT/80 | TAATACG ACTCACT ATAGGGT CACCTCA GGTGGAT GTCTC/92 | TAATAC GACTCA CTATAG GGCATT GGTGGA GTGGCT GAAG/93 | 500 bp |
| | | | | | TAATACG ACTCACT ATAGGGC CAATGCT CCACCAC CCAGCCT TT/94 | TAATAC GACTCA CTATAG GGAGTT CATGGC ATTGGTG GAGTGG/ 95 | 497 bp |
| | SBP-A3 | Zea mays | HQ858696.1 | ATGGAAGGAAACGGTGGCG CGGGCGGCGGTAGCGGAAG CGCGGCACCGCCCTGGGAT CTCGCCATGCACTGGGCACC CGCCGTAGTGTCGTCCTACC CGCCGCAGCCCTTGGAGCTG CAGCAGCAGGAGCTTACCT GCCTCAAGCTGGGGAAGCG GCCCGCCTGCTGCTGGGCAG GGGCGCCGGGCAACCAAGC GGCGCAGGTCCACGGCAAT GGCGGCGCTGGTGGCGCAG CTGCTGAGGGTAAGAGGAA GGACAAGGCGCCTGCCGCG GCGGCCGTGACGAGGTGCC AGGTGGAGGGGTGCCACCT GTCGCTGGCGGACGCCAAG GAGTACCACCGGCGGCACA AGGTGTGCGAGGCGCACTC CAAGTCGCCCCGGGTCGTCG TCCTCGGCGCCGAGCAGCG CTTCTGCCAGCAGTGCAGCC GGTTCCACGCGATCTCGGAG TTCGACGACGCGAAGCGGA GCTGCCGACGCGTCTGGCC GGGCACAACGAGCGGCGGC GGAAGAGCAACGCCAGCGA GGCCATGGCAAGAGGCGTC GCGCACCCACACGGAGTGA CGGCTTTCGGCCACGGCGGC | TAATACG ACTCACT ATAGGGC GCCGTAG TGTCGTC CTACC/96 | TAATAC GACTCA CTATAG GGAAAG CCGTCAC TCCGTGT GG/97 | 529 bp |
| | | | | | TAATACG ACTCACT ATAGGGC GCAGGTC CACGGCA ATG/98 | TAATAC GACTCA CTATAG GGCGGT CGGAGA CGAAGT ACTGC/99 | 650 bp |

TABLE 11-continued

Target Gene Sequences and Primers for PCR

| Target for Mir | Target Gene | Organism | Accession number | Target Sequence/SEQ ID NO: | Forward Primer/SEQ ID NO: | Reverse Primer/SEQ ID NO: | Product Length |
|---|---|---|---|---|---|---|---|
| | | | | TTCCTGCCCTCGCGCGGCCT CGTCCCCGCAGGGTCGTCCC CGGCGGCGGCTGGTGCTCTC TCTCTTCTGTCATCGGCCAG AGGCAGCGTGGCGGGCGCC AGCGGGCCCTGGCTGGTCA CGGCGGCGCGGGAGGACAT CCCGGCGCGCTCCAGCGCG GCGCTCGACGACCTTATCGC CGAGAACCGCGCCGCCGCG CTCCTCGCGCGGCAGTACTT CGTCTCCGACCGCTCGCCGG CGCCCAGACGGGATTTCGTC GCCTCT/81 | | | |
| miR164 | NAC (TF homolog) | Oryza sativa | NM_001064881.1 | ATGAGCGGGATGAATTCGC TGAGCATGGTGGAGGCGAG GCTGCCGCCGGGGTTCAGGT TCCACCCGCGAGACGACGA GCTCGTGCTGGACTACCTGG AAAGGAAGCTCCTCGACGG CGGCGTGGGCGGCGCCGCG GCGGCGGCGGCGGCGGTCA CCATCTACGGCTGCCCGGTG ATGGTCGACGTCGATCTCAA CAAGTGCGAGCCATGGGAC CTTCCTGAGATCGCTTGCGT TGGTGGCAAGGAGTGGTAC TTCTATAGCCTTAGGGATAG GAAGTATGCAACTGGCCAA CGAACAAATAGAGCAACCG AATCGGGCTACTGGAAGGC CACAGGAAAAGATCGCCCA ATAAGCCGGAAAGGATTGC TCGTCGGTATGCGAAAAAC CCTGGTGTTCTACAAAGGTA GAGCCCCTAAGGGGAAGAA GACCGAGTGGGTCATGCAT GAATTCCGCAAAGAAGGAC AAGGGGATCCGATGAAGTT GCCTCTCAAGGAGGACTGG GTCTTGTGTAGAGTCTTCTA CAAGAGTAGGACAACCATT GCCAAGCTGCCAACGGAGG GTAGCTACAACAATATTGAC AGTGTGGCCACAACTTCACT GCCTCCCCTCACTGACAACT ACATTGCATTTGATCAGCCT GGTTCAATGCAAAACCTAG AGGGTTATGAGCAAGTGCC CTGCTTCTCCAATAATCCCT CTCAACAGCCATCGTCGTCG ATGAATGTTCCGTTGACATC GGCCATGGTTGATCAAGAG CAAAACAATATGGGTAGGG CGATCAAGGATGTGCTGAG CCAATT/82 | TAATACG ACTCACT ATAGGGT TCAGGTT CCACCCG CGAGAC/ 100 | TAATAC GACTCA CTATAG GGCCGTT GGCAGC TTGGCA ATGG/101 | 545 bp |
| | | | | | TAATACG ACTCACT ATAGGGC GTGCTGG ACTACCT GGAAAG/ 102 | TAATAC GACTCA CTATAG GGCAAC CATGGC CGATGTC AAC/103 | 708 bp |
| | NAC5 | Zea mays | NM_001154298.1 | ATGGAGCACGACGTGCACC ACCAGCAGGCCATGGAGCT GCCGCCGGGGTTCCGATTCC ACCCCACCGACGAGGAGCT CATCACGCACTACCTCGCCA GGAAGGCCGCCGACGCCCG CTTCGCCCCCGCGCCGTCG GCGAGGCCGACCTCAACAA GTGCGAGCCATGGGACCTG CCATCCCGGGCGACGATGG GCGAGAAGGAGTGGTACTT CTTCTGCGTCAAGGACCGCA AGTACCCGACGGGACTGAG GACGAACCGGGCCACCGAG TCGGGATACTGGAAGGCGA CGGGCAAGGACAGGGAGAT | TAATACG ACTCACT ATAGGGC CACCGAC GAGGAG CTCATC/104 | TAATAC GACTCA CTATAG GGCGAC GTCCTCC ACCAAC ATC/105 | 565 bp |
| | | | | | TAATACG ACTCACT ATAGGG AGGCCG ACCTCAA CAAGTG/ 106 | TAATAC GACTCA CTATAG GGTCAG GAAGAA CTGGCCC TCCAG/107 | 664 bp |

TABLE 11-continued

Target Gene Sequences and Primers for PCR

| Target for Mir | Target Gene | Organism | Accession number | Target Sequence/SEQ ID NO: | Forward Primer/SEQ ID NO: | Reverse Primer/SEQ ID NO: | Product Length |
|---|---|---|---|---|---|---|---|
| | | | | CTTCAGGAGCAAGGCCCTC | | | |
| | | | | GTCGGCATGAAGAAGACGC | | | |
| | | | | TCGTCTTCTACACGGGGAGG | | | |
| | | | | GCGCCCAGGGGAGGCAAGA | | | |
| | | | | CCGGCTGGGTCATGCACGA | | | |
| | | | | GTACCGCCTCCACGGCAAG | | | |
| | | | | CACGCCAGCAGCAGCCGCC | | | |
| | | | | TCATGCCGTCGTCGGTCAGA | | | |
| | | | | GCTGGCGCGTCAAAGGACG | | | |
| | | | | AGTGGGTGCTGTGCAGGGT | | | |
| | | | | GTTCAAGAAGAGCATCGAG | | | |
| | | | | CCGCCGCCGTCAGTGGGCA | | | |
| | | | | AGAGGTCGTCGGTCGCGTGT | | | |
| | | | | ACGGGGATGATGTTGGTGG | | | |
| | | | | AGGACGTCGTGGGACCGCC | | | |
| | | | | GTCCATGTCCATGGAGGAC | | | |
| | | | | GACCTCGCCGCGTGCGCGCT | | | |
| | | | | GCCTCCGCTGATGGACGTGT | | | |
| | | | | CCGGCGGTGGCGGCGCCAA | | | |
| | | | | CATGGCGGCGGCGTCCATC | | | |
| | | | | GAGCTGCTGGCGCCACCGG | | | |
| | | | | CACCACACGTGACCTGCTTC | | | |
| | | | | TCCAACGCGCTGGAGGGCC | | | |
| | | | | AGTTCTTCCTGAACCCACCC | | | |
| | | | | TGCCTCCACCCCTCCACGTC | | | |
| | | | | GCCGCTCC/83 | | | |

Example 17

ARF-8 Gene Silencing in Tomato Seeds

Figure 30A:
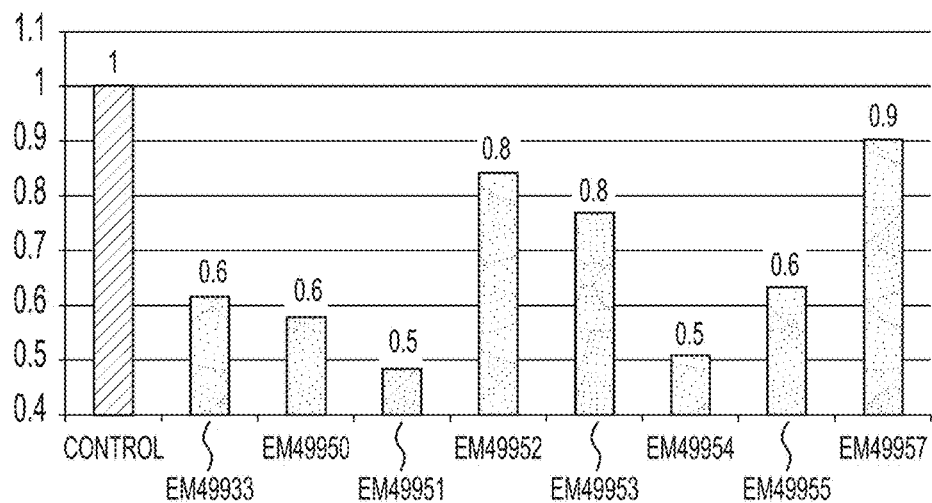
FIGS. 30A-B show the results of RT-PCR on RNA extracted from leaves of control and ARF8 (miR167 target gene) dsRNA treated tomato seeds in plants 3 weeks and 8 weeks (FIGS. 30A and 30B, respectively) post germination. The expression level of ARF-8 target gene in 8 or 20 control plants (FIGS. 30A and 30B, respectively) is averaged and recorded as "1" for a comparison reference to that seen in dsRNA-treated plants FIG. 30A—The fold change of ARF8 expression in control (shown in a red bar) and dsRNA-treated (shown in blue bars) tomato plants 3 weeks after germination is plotted for each individual plant to demonstrate the large variation of ARF-8 expression in dsRNA-treated plants. Five out of the 8 treated plants shown in the graph exhibit ARF-8 down-regulation of over 40% (5/8 efficiency of 62.5%), FIG. 30B—same as in FIG. 30A for tomato plants 8 weeks after germination. Six out of 9 treated plants shown in the graph exhibit ARF-8 down-regulation of over 30% (6/9 efficiency of 66.7%).
Figure 30B:
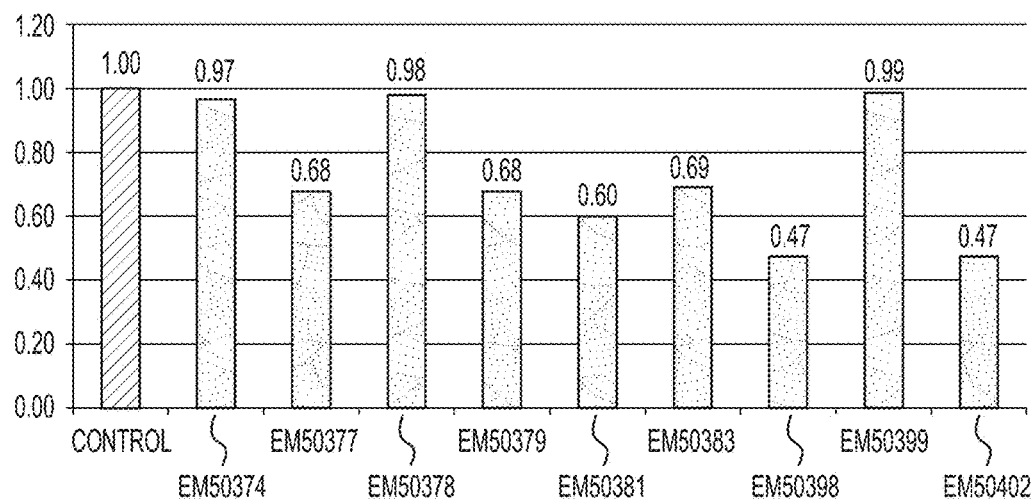

Tomato seeds were treated using the protocol described in Example 1, unwashed seeds were treated with an ARF-8 dsRNA concentration of 200 µg/ml, for 24 hours at 15° C. and immediately planted in soil. Expression levels of the gene were examined using RT-PCR, 3 and 8 weeks after treatment (see Table 12). Changes in expression were observed in dsRNA-treated plants 3 weeks after treatment (FIG. 30A-B).

Figure 31A:
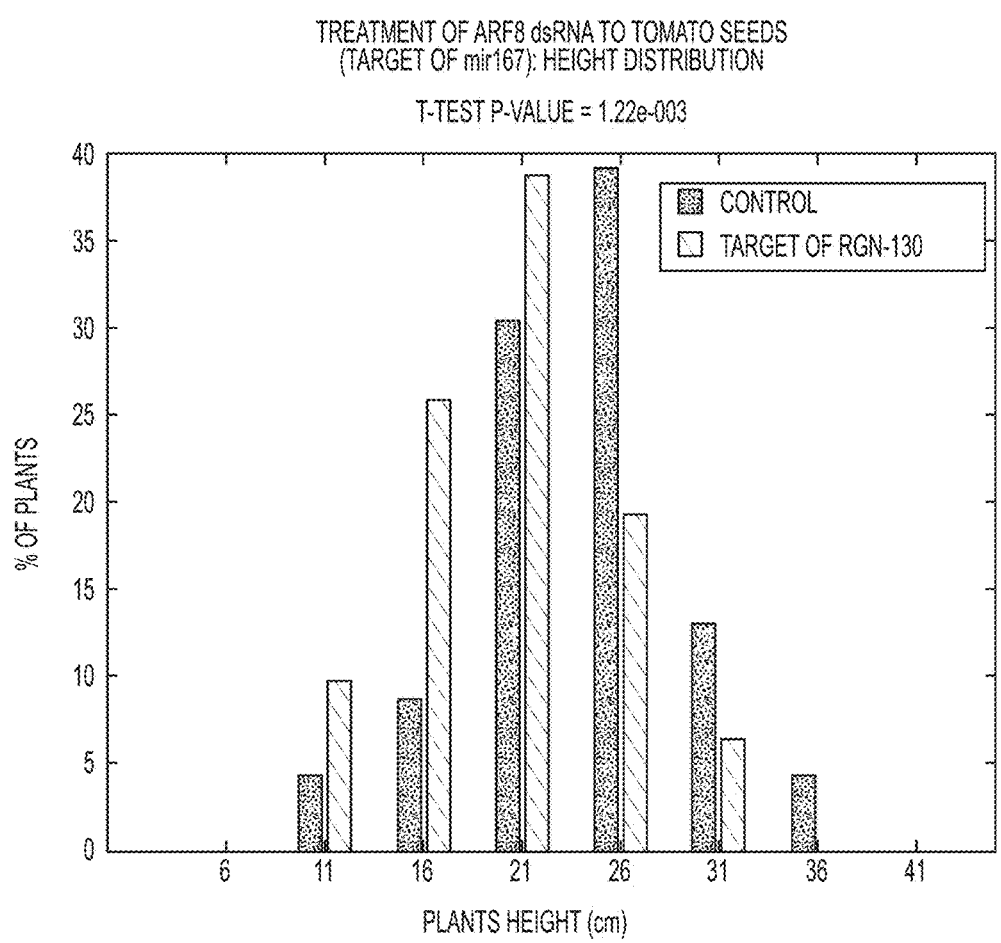
FIGS. 31A-D show the specific distribution of height in control (blue bars) and ARF8 dsRNA-treated (maroon bars) tomato plants 55 (FIG. 31A), 62 (FIG. 31B) and 72 days (FIG. 31C) following treatment.
Figure 31B:
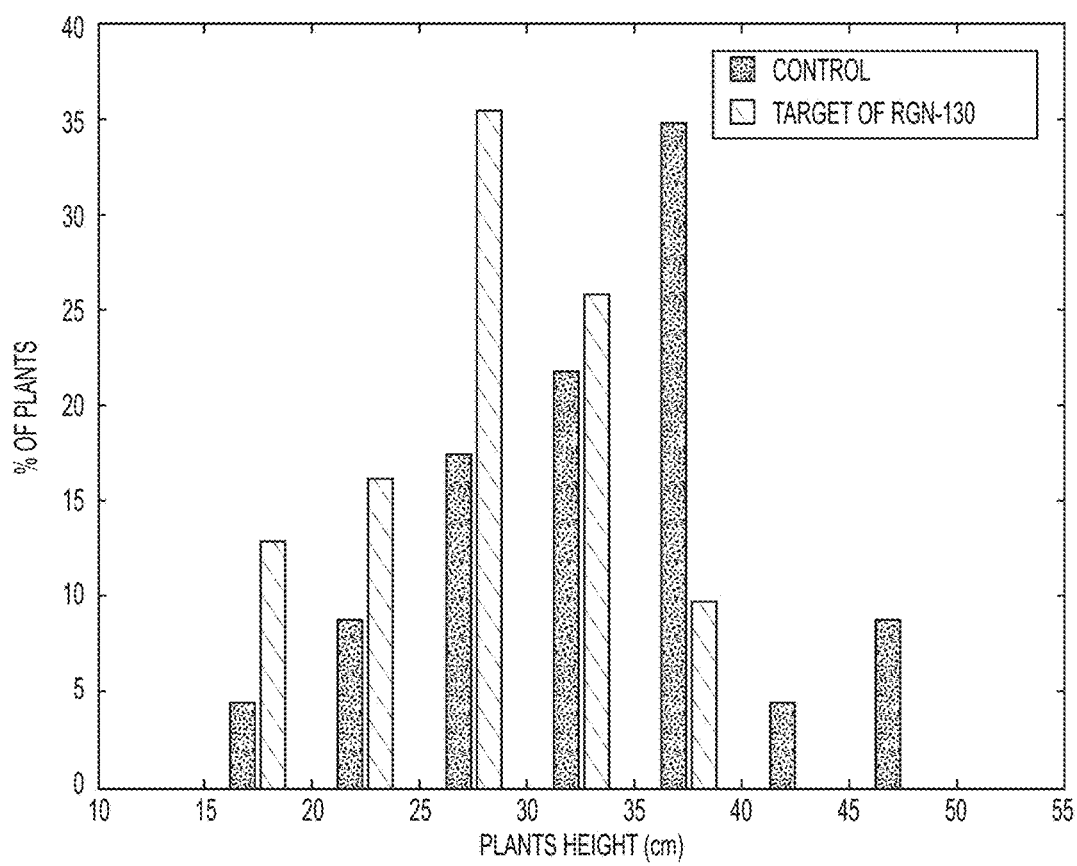
Figure 31C:
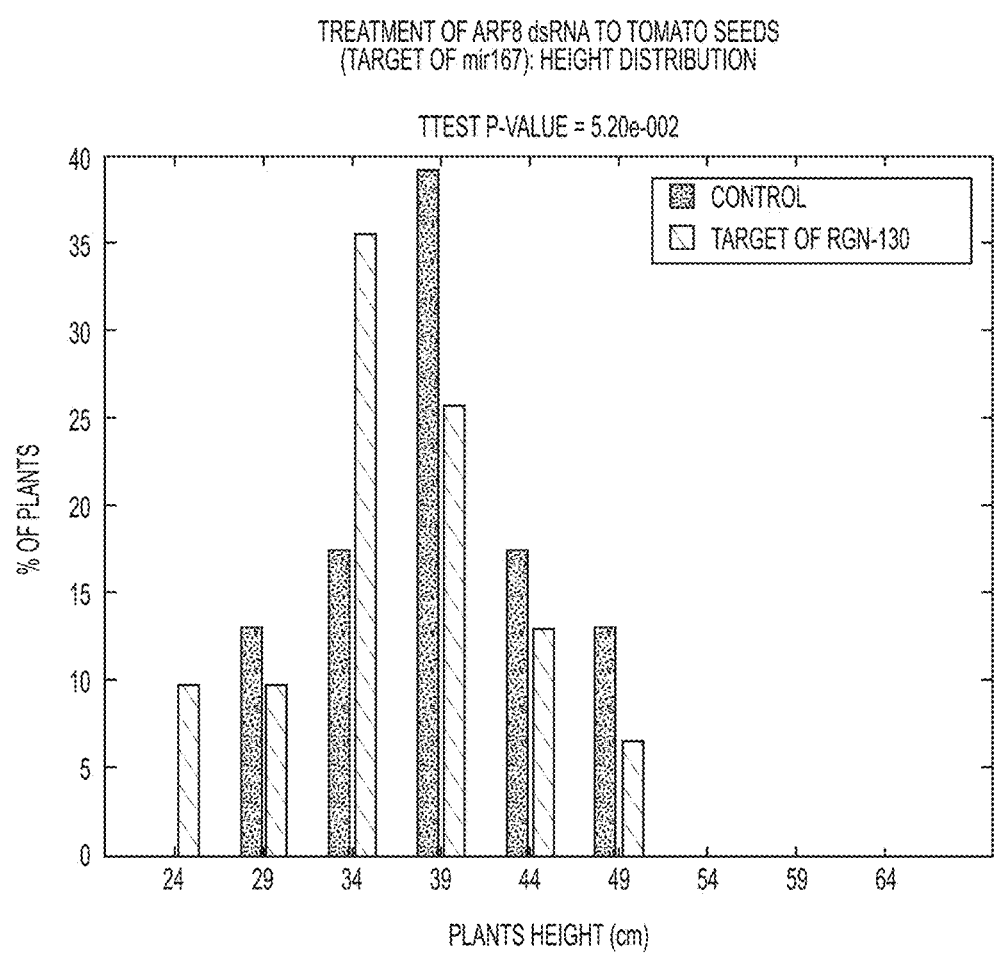
Figure 31D:
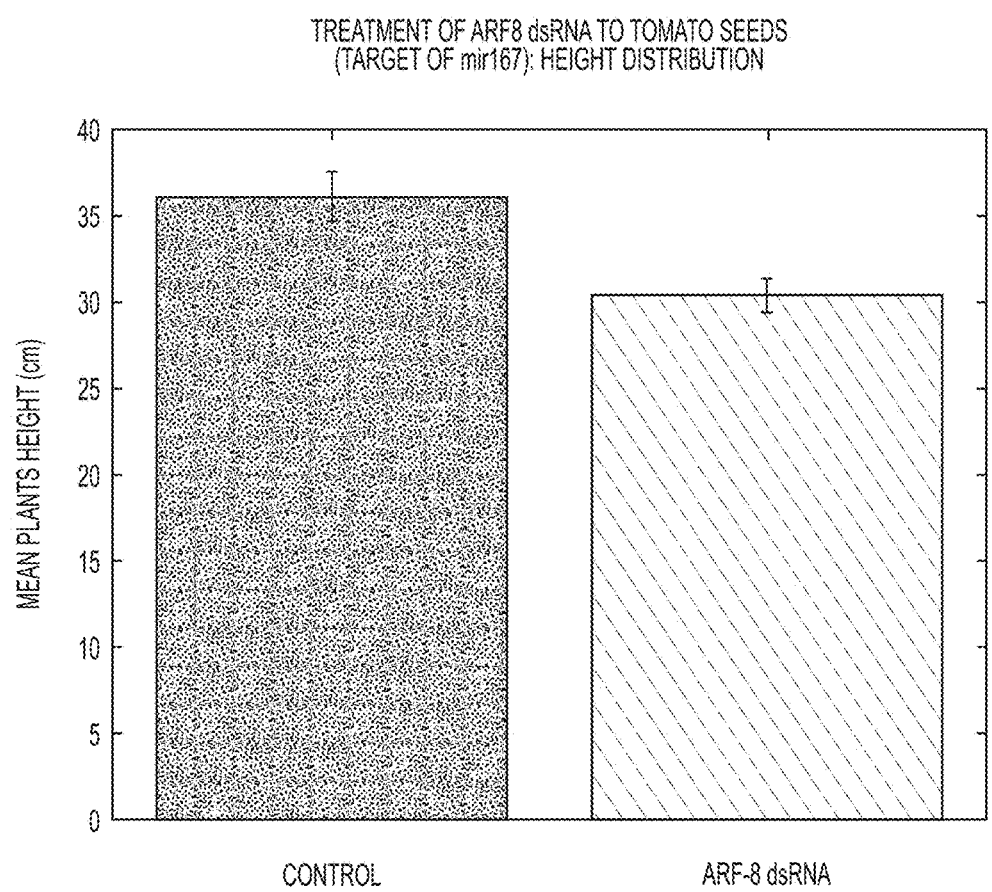
Figure 32A:
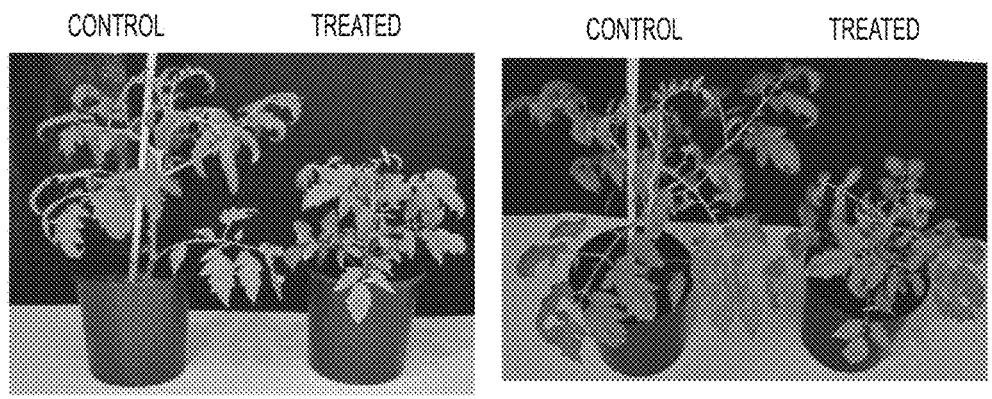
FIGS. 32A-B show phenotypic differences between control and ARF8 dsRNA-treated plants, 55 (FIG. 32A) and 72 days (FIG. 32B) after seed treatment. Control plants are seen on the left and treated plants are seen on the right of each picture.
Figure 32B:
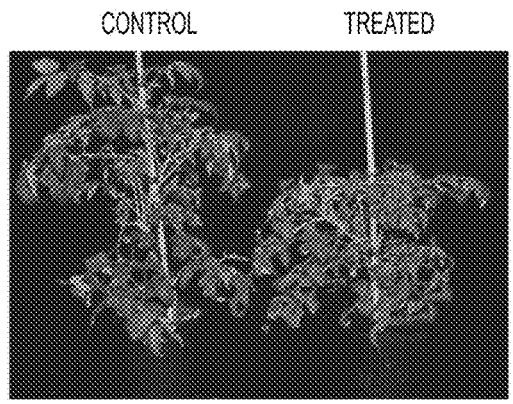

Plants that were treated with dsRNA molecules specific for the ARF8 gene showed a phenotypic difference compared to control plants. This phenotypic difference was observed at different time points (55, 62 and 72 days) and was demonstrated by a decrease in height (FIGS. 31A-C). While the average height of control plants was ~36 cm, the dsRNA treated plants were ~30 cm tall on average (FIG. 31D). In addition to their decreased height (delayed vertical development), dsRNA-treated plants appeared more branched (increased horizontal development) compared to control plants. Thus, plants treated with dsRNA specific for ARF8 appeared shorter and more branched relative to their control counterparts 55 and 72 days after treatment, as can be visualized in FIGS. 32A and 32B.

TABLE 12

Primers used for RT-PCR of ARF-8 mRNA Molecules in Tomato and ARF-8 dsRNA product

| Primer Name and Direction | Primer Sequence | Primer Length |
|---|---|---|
| slyARF_8_1816F4 | CCTCAACAGTCCTGGATGTC/108 | 20 |
| sly ARF_8_1896R4 | CCCGTAAGTTGGAAGTGATG/109 | 20 |
| ARF 8 dsRNA product 1 | CTAATACGACTCACTATAGGGAGAGCTTCTCCTCCCTA CAACTGTGTCTAACGTCGCTACTACATCAATTGATGCT GATATATCCTCTATGCCACTAGGGACTTCTGGATTTCC GAATCCCTTGTATAGTTATGTGCAAGATTCTACTGACT TGTTGCATAATGTAGGGCAAGCTGATGCACAAACTGT GCCCCGTACATTTGTCAAGGTTTACAAATCAGCGTCCC TTGGGAGGTCATTGGACATCACTCGGTTCAACAGCTAT CATGAGCTGCGACAGGAATTAGGGCAGATGTTCGGTA TCGAAGGGTTGCTTGAAGACCCTCAAAGATCAGGCTG GCAGCTTGTATTTGTTGACAGGGAGAATGATGTCCTTC TCCTTGGAGACGATCCGTGGGAGGAATTTGTCAATAA TGTTTGGTACATCAAAATTCTTTCACCCGAGGATGTGC AGAAACTGGGGAAAGAGGAGGTTGGATCCCTCTCCCT ATAGTGAGTCGTATTAG/110 | Product 1 |

TABLE 12-continued

Primers used for RT-PCR of ARF-8 mRNA Molecules in Tomato and ARF-8 dsRNA product

| Primer Name and Direction | Primer Sequence | Primer Length |
|---|---|---|
| ARF 8 dsRNA product 2 | CTAATACGACTCACTATAGGGAGATGGGAGATTGAGC CTTTGACTACTTTTCCGATGTATCCATCTCTTTTTCCTC TAAGGCTAAAGAGGCCTTTCTATCAAGGAACCTCATCT TATCAGGATAGTAACAATGAAGCTATTAATCGAATGT CATGGTTAAGAGGGAATGCTGGTGAGCTAGGACATCA TTCAATGAATCTTCAGTCTTTTGGCATGCTTCCTTGGAT GCAACAGAGAGTCGATTCAACAATTCTCCCAAATGAT ATTAATCAGCACTATCAAGCTATGCTGGCTACTGGC TTGCAAAGTTTTGGGAGTGGAGATTTACTGAAACAGC AATTAATGCAGTTTCAGCAGCCTGTCCAATATCTGCAA CATGCAAGTACTGAGAATTCAATTTTGCATCAGCAGC AGCAGCAGCAGCAGCAAATAATGCAGCAAGCAGTTCA TCAGCATATGCTGCCTGCTCAAACCCAAATGCTGTCAG AGAACCTTCAAAGGCAATCCCAGCATCAATCCATCTC CCTATAGTGAGTCGTATTAG/111 | Product 2 |

Example 18

FW2.2 Gene Silencing in Tomato Seeds

Figure 33A:
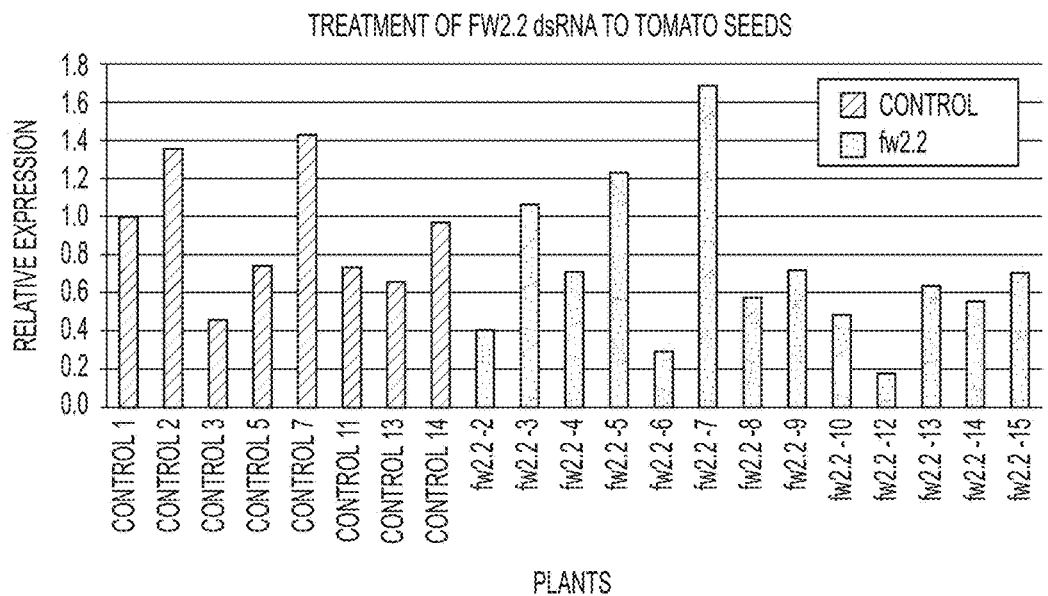
FIGS. 33A-B show the results of RT-PCR on RNA extracted from leaves of control and FW2.2 dsRNA treated tomato plants 9 weeks post germination.
Figure 33B:
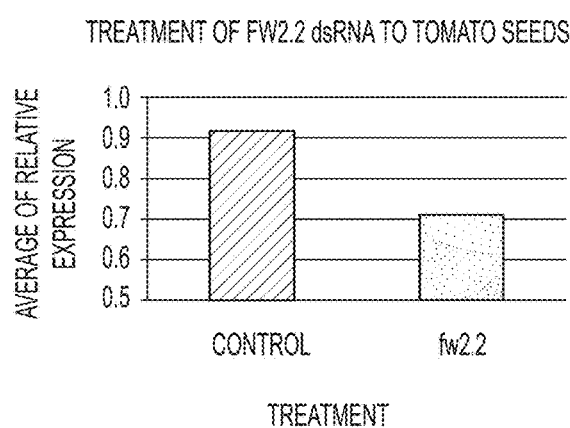

Tomato seeds were treated using the protocol described in Example 1, unwashed seeds were treated with a FW2.2 dsRNA concentration of 100 μg/ml, for 24 hours at 15° C. and immediately planted in soil Expression levels of the gene were examined using RT-PCR, 9 weeks following germination (primers are listed in Table 13). An approximate 2-fold reduction in the expression level of FW2.2 in dsRNA treated plants compared to control plants was detected (FIG. 33).

Even so, plants that were treated with dsRNA molecules specific for the FW2.2 gene showed no phenotypic differences compared to control plants, ruling out a toxic effect as an alternative explanation for the phenotypic effects seen in the previous example. The plants presented similar height and appearance 72 days after treatment (FIG. 34).

Example 19

Figure 35:
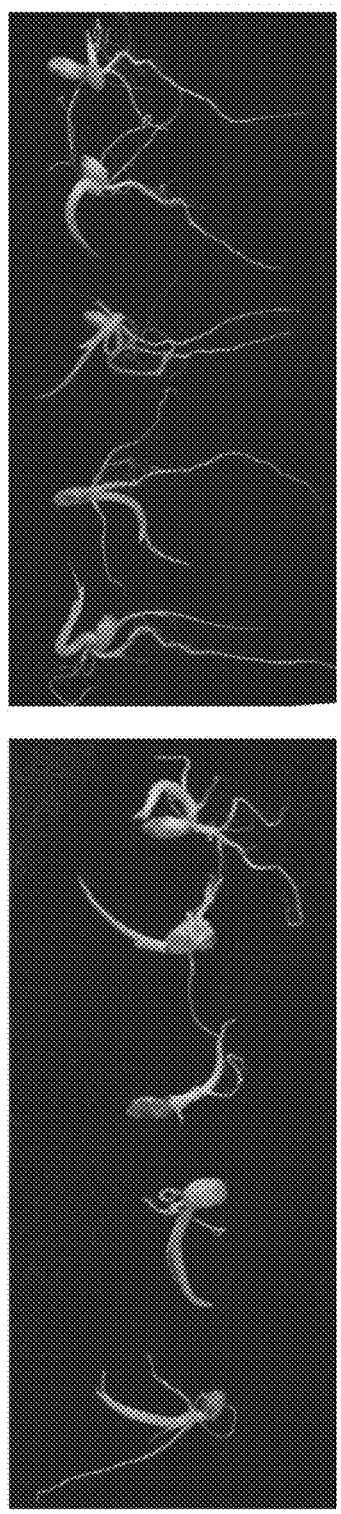
FIG. 35 shows a longer and more developed root system in rice seedlings grown from rice seeds treated against the Della gene compared to control plants.

Della Gene Down-Regulation in Rice Results in More Developed Roots of Germinated Seeds Rice seeds were treated using the protocol described in Example 1, seeds were washed for 4 h, dried for 24 h at room temperature and immediately treated with a DELLA dsRNA concentration of 66 g/ml, for 36 hours at 15° C. Rice seeds were treated with dsRNA directed against the Della gene (see Table 15 below), which is a known plant growth repressor. *Arabidopsis* seedlings with mutant Della gene are larger with a longer root system (Josse, E. M., Gan, Y., Bou-Torrent, J., Stewart, K. L., Gilday, A. D., Jeffree, C. E., Vaistij, F. E., Martinez-Garcia, J. F., Nagy, F., Graham, I. A., and Halliday, K. J. (2011). A DELLA in disguise: SPATULA restrains the growth of the developing *Arabidopsis* seedling. Plant Cell 23: 1337-1351.). FIG. 35 shows mimicking of the *Arabidopsis* phenotypes using dsRNA seed treatment, with treated seedlings being larger with longer roots than control seedlings.

TABLE 13

Primers used for RT-PCR of FW2.2 dsRNA Molecules in Tomato and FW2.2 dsRNA product

| Primer Name and Direction | Primer Sequence | Primer Length |
|---|---|---|
| slyFW2_316F2 | GAGGCACCTTGTGTTGATTG/112 | 20 |
| slyFW2_406R2 | CAAAGCCACGGTTCTTAAGC/113 | 20 |
| FW2.2 dsRNA product | CTAATACGACTCACTATAGGGAGATCCAGGTCCAATGAAA CAACCTTATGTTCCTCCTCACTATGTATCTGCCCCCGGCAC CACCACGGCGCGGTGGTCGACTGGTCTTTGTCATTGTTTTG ATGACCCTGCTAACTGTTTAGTTACTAGTGTTTGCCCTTGTA TCACCTTTGGACAGATTTCTGAAATACTAAACAAAGGAAC AACTTCATGTGGGAGTAGAGGTGCATTATATTGTTTGCTGG GATTGACAGGATTGCCTAGCCTATATTCCTGCTTCTACAGG TCTAAAATGAGGGGGCAATATGATCTGGAAGAGGCACCTT GTGTTGATTGTCTTGTACATGTATTCTGTGAACCTTGTGCTC TTTGCCAAGAATACAGAGAGCTTAAGAACCGTGGCTTTGA TATGGGAATAGGGTGGCAAGCTAATATGGATAGACAAAGC CGAGGAGTTACCATGCCCCCTTATCATGCAGGCATGACCTC TCCCTATAGTGAGTCGTATTAG/114 | |

Example 20

NRR Gene Down-Regulation in Rice Results in More Developed Roots and Shoots of Germinated Seeds Rice seeds were treated using the protocol described in Example 1, seeds were washed for 4 h, dried for 24 h at room temperature and immediately treated with a NRR dsRNA concentration of approximately 13 μg/ml, for 36 hours at 15° C. Rice seeds were treated with dsRNA directed against the NRR gene, which was found to regulate root growth in response to macronutrients in rice (Zhang et al., 2012, *Mol Plant* 5(1):63-72). Transgenic rice seedlings, with reduced NRR levels using RNAi were shown to have longer roots when grown under nitrogen limiting conditions. FIG. 36 shows mimicking of this phenotype using dsRNA seed treatment, with resulting treated seedlings being larger and with longer roots than control seedlings.

TABLE 14

Products of NRR dsRNA Molecules in rice

| Primer Name and Direction | Primer Sequence | Primer Length |
|---|---|---|
| NRR dsRNA product 1 | CTAATACGACTCACTATAGGGAGAAGCTCCTGAACCCAT CATTGAAGAACCAGTGCTTAGCCTTGATCCAGTTGCAGCA GCCATTTCGATGATGTCTGGCAGTGAGAACGTAATGGAT GAAACTATAGAGGTTGCAGATATCAGCGACATTCAGAAT GACTCTCTTTTAAGCGAAGTATTATACGAGTGCGAGAAG GAACTCATGGAGAAGTCCGCAATCGAAGAGACTATTTCT GAACTGCTGGACGTCAAGATTCCTATGCTGCAAGTGGAA GAGTTCCCTAGGGAAACCCAAGTACAACTACCGGCCATG GAGAAGGAGAAGCCATCAGTTCCTGAATGTTGTTCACTC CAGAAAAGTGTCAGTTCTGGGTGCCTCAACTCAGCTGATT GGATCAATGGACCAGCCAGGCCAAACTTCCTGGACTTCC AAGGATTGGACTTTGAGACAGCGTTTGGGTTGAGGAGGG CATACAGCGAAGGAGACATTCTCCCTATAGTGAGTCGTA TTAG/115 | Product 1 |
| NRR dsRNA product 2 | CTAATACGACTCACTATAGGGAGACATGGAGAAGTCCGC AATCGAAGAGACTATTTCTGAACTGCTGGACGTCAAGAT TCCTATGCTGCAAGTGGAAGAGTTCCCTAGGGAAACCCA AGTACAACTACCGGCCATGGAGAAGGAGAAGCCATCAGT TCCTGAATGTTGTTCACTCCAGAAAAGTGTCAGTTCTGGG TGCCTCAACTCAGCTGATTGGATCAATGGACCAGCCAGG CCAAACTTCCTGGACTTCCAAGGATTGGACTTTGAGACAG CGTTTGGGTTGAGGAGGGCATACAGCGAAGGAGACATTC AGAATCTTGGAGCTAGCACCCCTCGACCCGGGAACTCAG GAAACGCTCAATTAGCATCTTGCGAGAGGCTTGTAACCA TCAGTGACCTGAAATCTGAAGAAAGGAAGCAGAAGCTAT CTAGGTACAGAAAGAAGAAGGTGAAGAGAAACTTTGGC AGAAAGATCAAGTATGCTTGCAGGAAGGCTCTCTCCCTA TAGTGAGTCGTATTAG/116 | Product 2 |

Example 21

Simultaneous Silencing of Three Endogenous Genes

Figure 37A:
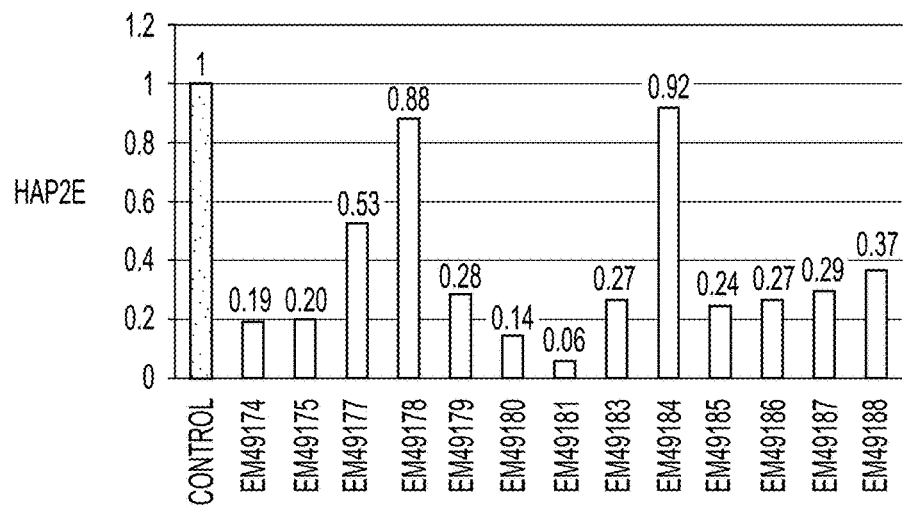
FIGS. 37A-C show the results of RT-PCR (using oligo dT) on RNA extracted from leaves of control rice seeds and seeds treated with a mix containing dsRNA molecules for down-regulation of three endogenous genes: Hap2e, Della and SQS, 18 days post germination. The expression level of each individual gene is averaged in 8 control plants (shown in a red bar) and used as a threshold reference (received value of 1) for expression in treated plants. Treated samples (shown in blue bars) are plotted separately and their respective fold change in expression level of each target gene is calculated relative to expression in control plants.
Figure 37B:
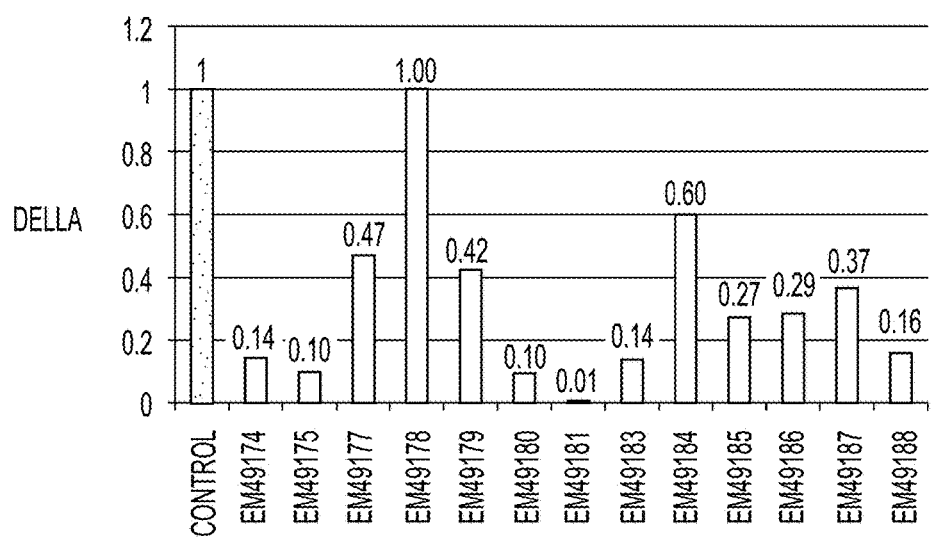
Figure 37C:
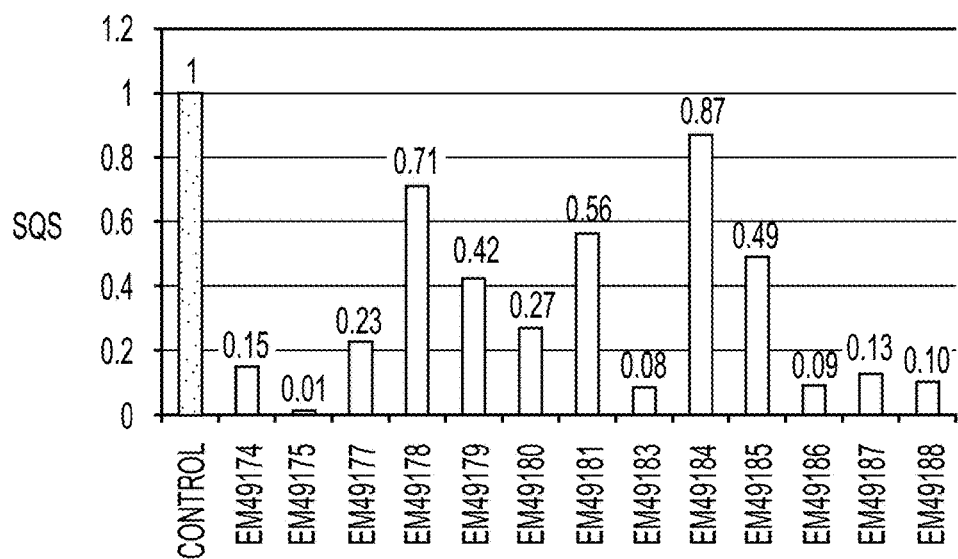

In the present example, the effect of silencing three genes simultaneously is tested. Rice seeds were treated using the protocol described in Example 1, seeds were washed for 4 h, dried overnight at room temperature and immediately treated with a solution containing a mixture (152.3 g/ml final concentration) of dsRNA against three genes: Hap2e (59.9 μg/ml, see Table 11), Della (44 μg/ml see table 15 below) and SQS (48.4 g/ml see table 16 below) for 42 h at 15° C. RNA was extracted from shoots of germinated seeds, 18 days post germination, and RT-PCR for each of the three genes was run (see Table 15 below). As can be seen in FIG. 37, down-regulation of all three genes was highly effective, with treated plants exhibiting decrease in expression of each individual gene at various amounts, ranging from a minimum of 10% decrease to total silencing of the gene (equals 100% down-regulation).

TABLE 15

Primers Used for RT-PCR Analysis for Expression Level of Hap2e, Della and SQS Genes and dsRNA products.

| Primer Name and Direction | Primer Sequence | Primer Length |
|---|---|---|
| osaHAP2E122F7 | GTGACTCGTCACCAACAAAG/117 | 20 |
| osaHAP2E202R7 | TGTGTTGTCCGTTGAGACTG/118 | 20 |
| osaDella1410F5 | CAGTTCGCGCACACCATTCG/119 | 20 |
| osaDella1494R5 | GCAGCATGAACGGCTCCAAG/120 | 20 |
| osaSQS465F3 | TCCGCAATGCCGTGTGCATC/121 | 20 |
| osaSQS543R3 | GCGGCAGGAATGCTAGTGTC/122 | 20 |
| Della dsRNA product | CTAATACGACTCACTATAGGGAGAGCCCACTTCTACGAGTCCTGCCCCTACCTCAAGTTCGCCCACTTCACCGCAAATCAAGCCATCCTCGAGGCTTTCGCCGGCTGCCACCGCGTCCACGTCGTCGACTTCGGCATCAAGCAGGGGATGCAATGGCCAGCTCTCCTCCAGGCCCTCGCCCTTCGTCCCGGCGGCCCCCCATCGTTCCGCCTCACCGGCGTCGGCCCCCCGCAGCCGGACGAGACCGACGCCTTGCAGCAGGTGGGTTGGAAGCTTGCCCAGTTCGCGCACACCATTCGCGTCGACTTCCAGTACCGGGGACTCGTCGCCGCCACTCTCGCGGACTTGGAGCCGTTCATGCTGCAGCCGGAGGGCGAGGCGGACGCGAACGAGGAGCCTGAGGTGATCGCCGTCAACTCGGTGTTCGAGCTGCACCGGCTGCTCGCGCAGCCCGGCGCGCTGGAGAAGGTCCTGGGCACGGTGCACGCGGTGCGGCCAAGGATCGTCACCGTGGTAGAGTCTCCCTATAGTGAGTCGTATTAG/123 | |
| SQS dsRNA product 1 | CTAATACGACTCACTATAGGGAGAATATCTACAACCGCGACTGGCATTATTCATGTGGAACAAAAGACTACAAATTACTGATGGATAAGTTTCGCCTTGTCTCCACGGCTTTCTTGGAGCTTGGTCAAGGTTATCAAGAGGCAATTGAAGAAATCACTAGGCTAATGGGAGCAGGAATGGCAAAATTTATCTGCAAGGAGGTTGAAACTGTTGATGACTACAATGAGTACTGTCACTATGTAGCAGGGCTAGTGGGGTATGGGCTTTCCAGGCTCTTTCATGCTGGTGGGACGGAAGATCTGGCTTCAGATTCACTTTCAAATTCAATGGGCTTGTTTCTGCAGAAAATCAATATAATTAGGGATTATTTGGAGGACATAAACGAGATACCAAAGTCACGTATGTTCTGGCCTCGAGAAATATGGAGTAAATATGTCAATAAACTCGAGGATTTGAAATACGAGGAAAATTCAGAAAAGGCAGTTCAGTGTTTGAATGATATGGTGACTAACGCTCTGTCTCATCTCCCTATAGTGAGTCGTATTAG/56 | Product 1 |
| SQS dsRNA product 2 | CTAATACGACTCACTATAGGGAGACGCTCTGTCTCATGCTGAAGACTGCCTCCAATACATGTCAGCATTGAAGGATCATGCCATTTTCCGTTTTTGTGCAATACCTCAGATAATGGCAATTGGGACATGTGCTATTTGCTACAATAATGTGAATGTCTTTAGAGGAGTTGTTAAGATGAGGCGTGGGCTCACTGCACGAGTAATTGATGAGACAAACACAATGTCAGATGTCTATACTGCTTTCTATGAGTTCTCTTCGCTGATAGAATCGAAGATTGATAATAATGATCCAAATGCTTCCCTAACGCGGAAACGTGTTGATGCGATAAAGAGAACCTGCAAGTCATCTTGCTCACTAAAGAGAAGGGGATACGATTTGGAGAAGTCAAAGTACAACTCCATGCTGATAATGGTTGTACTTCTGTTGGTGGCTCTCCCTATAGTGAGTCGTATTAG/14 | Product 2 |

Example 22

Fluorescence Microscopy of siRNA Fragments in Tomato

Tomato seeds were treated with a fluorescent siRNA (siGLO, 1 μM final concentration, Thermo Scientific) at 15° C. for 24 h.

Figure 38A:
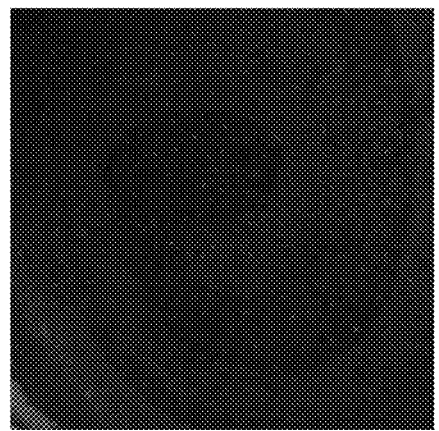
FIGS. 38A-D are confocal images showing penetration of fluorescent siRNA molecules (red, siGlo) to tomato seeds. Cells nuclei are stained with Hoechst 33342 (blue). Seeds treated with fluorescent siRNA are shown on FIGS. 38A and 38C, while the untreated control seeds are shown FIGS. 38B and 38D.
Figure 38B:
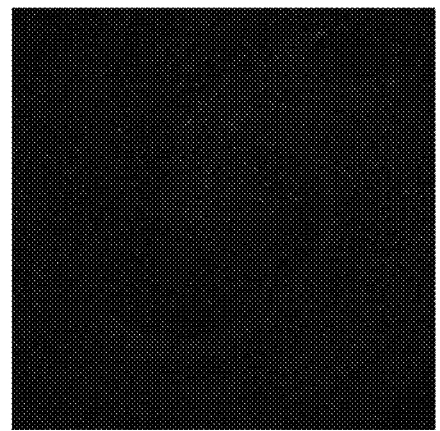
Figure 38C:
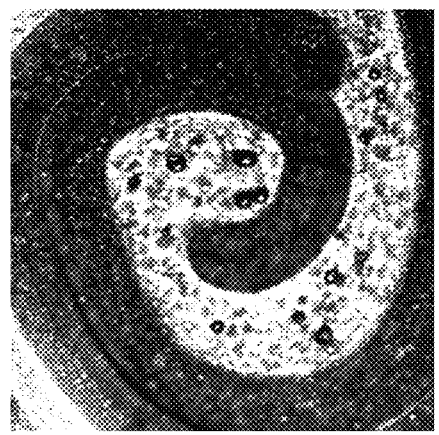
Figure 38D:
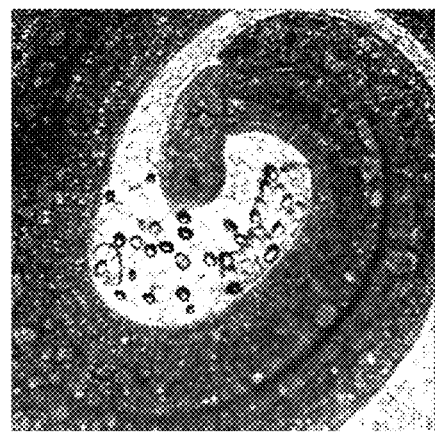

The seeds were cut into slices and fluorescent pictures were taken 24 hours post treatment using Leica confocal microscope. As shown in FIGS. 38A-D, a treated seed is shown (FIG. 38A, C) alongside a control seed that was treated with buffer (FIG. 38B, D). It is clear that the siRNA is distributed at various levels in the embryo and in the endosperm.

Examples 23-27

SPL Expression Affected by Dose and Kinetics of dsRNA Seed Treatment

Example 23

Altered SPL Expression Following Treatment with 50 µg/ml dsRNA in Tomato

Figure 39A:
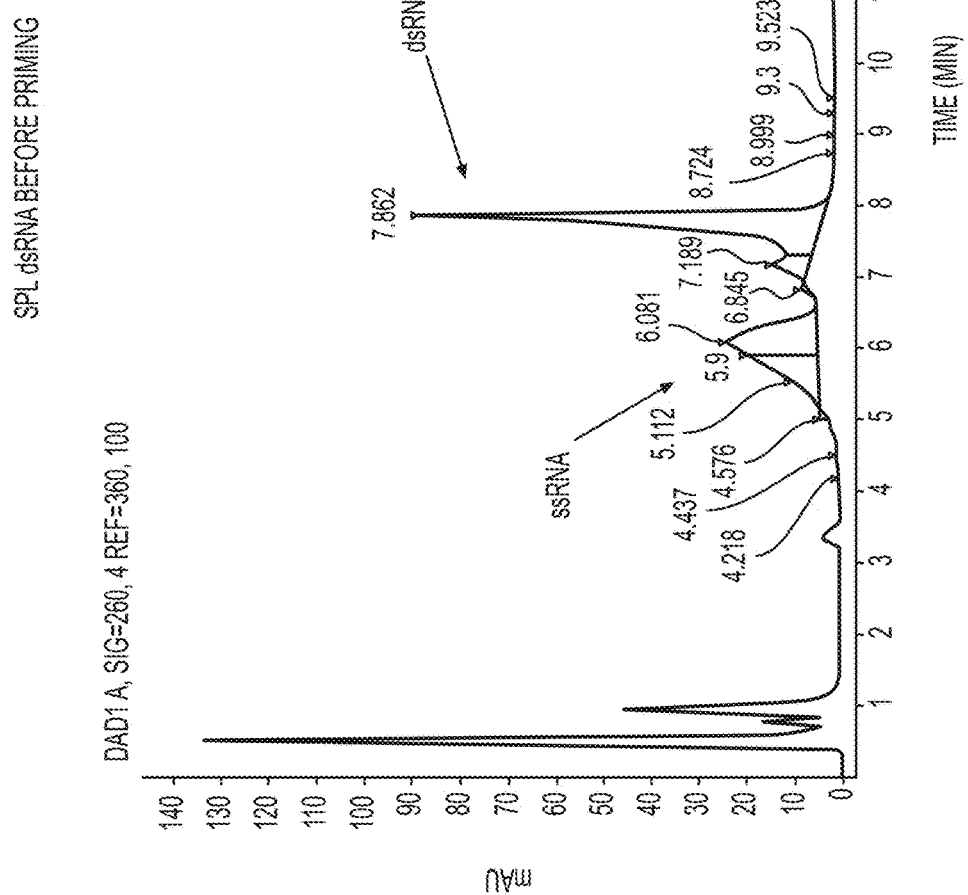
FIGS. 39A-D are graphs of HPLC analyses of SPL (SEQ ID NO: 126, FIGS. 39A and B) and GUS (SEQ ID NO: 21, FIGS. 39C and D) dsRNAs before (FIGS. 39A and C) and after (Figures B and D) seed treatment. The arrows indicate ssRNA and dsRNA.
Figure 39B:
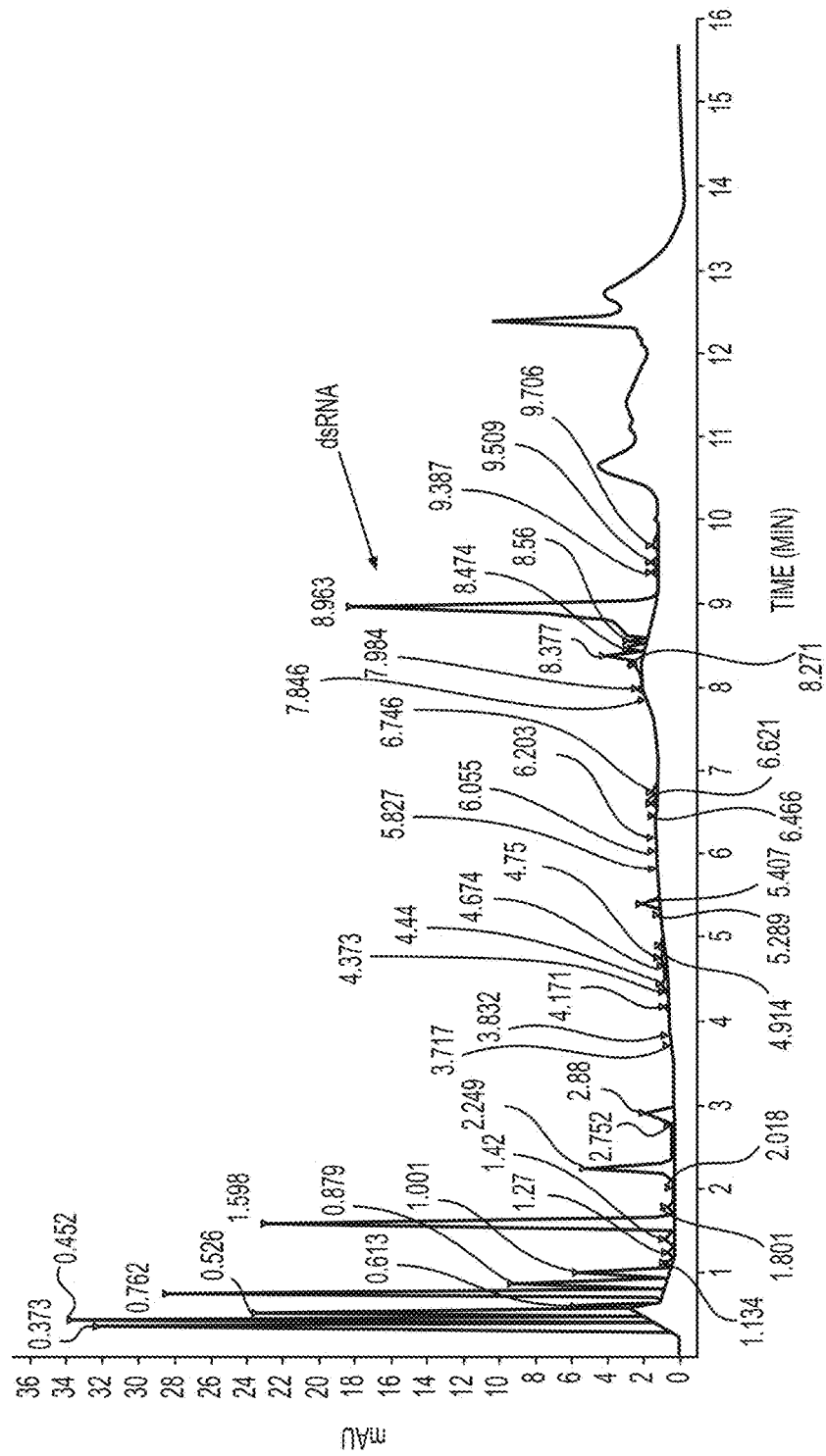
Figure 39C:
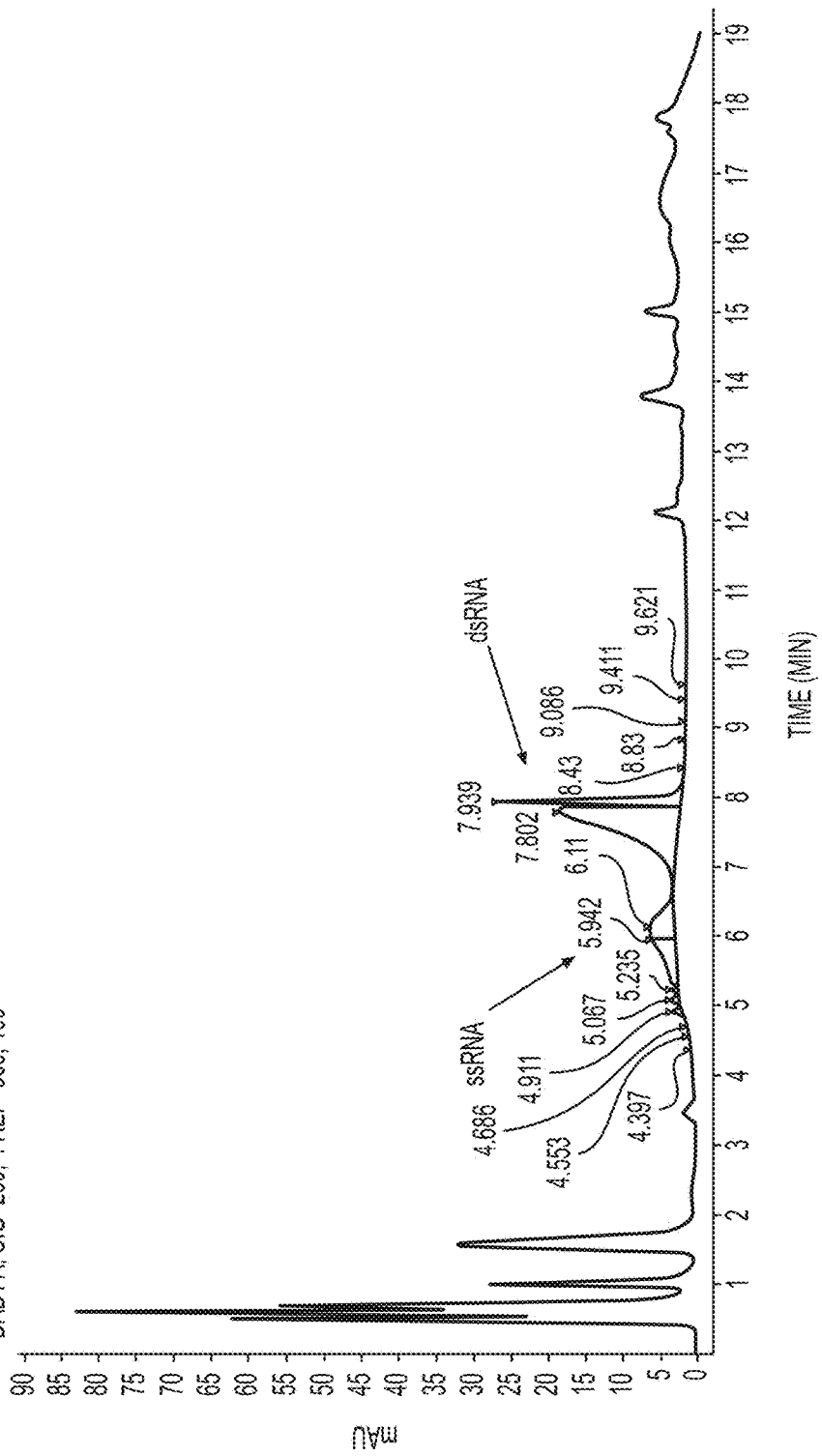
Figure 39D:
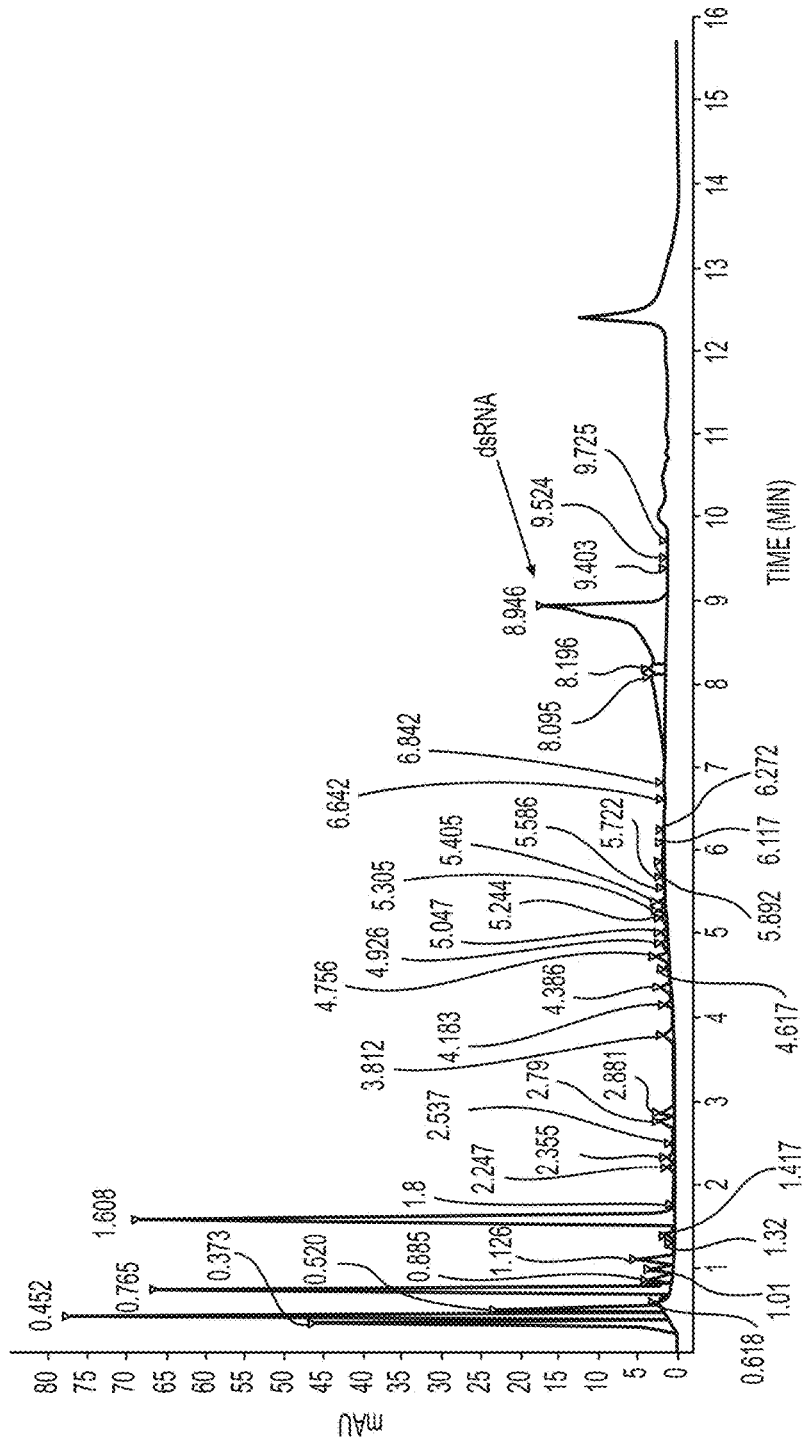

Tomato seeds were treated with a dsRNA (SEQ ID NO: 126) derived from the SPL gene and with GUS dsRNA as a control according to the protocol described in Example 1. Treatment was performed by gently shaking the seeds in the solution for up to 24 hours in a dark growth chamber at 15-25° C. followed by washing with water three times for one minute. After treatment, seeds were planted in soil and grown at about 25° C. with 16 hours photoperiod. The plants were watered with tap water as necessary. The primers used for in-vitro transcription of SPL dsRNA and the sequence of the dsRNA are listed in Table 16. The sequence of GUS dsRNA appears in Table 3.

measurement was 1864 µg/ml for SPL and 1964 µg/ml for GUS. HPLC showed that the sample contains mostly dsRNA but other molecules (including nucleotides and ssRNA) were present in the solution as well. According to the HPLC analysis, the SPL solution contained 1219 µg/ml of dsRNA and 838 µg/ml of ssRNA. The GUS solution contained 633 µg/ml of dsRNA and 167 µg/ml of ssRNA (see FIGS. 39A-B).

Seeds were treated with dsRNA at a concentration of 50 µg/ml (determined by the HPLC measurement) for 10 minutes, 2, 6 and 24 hours. An additional HPLC analysis of the SPL and GUS dsRNA solutions following seed incubation revealed that the ssRNA peak has disappeared (see FIG. 39).

Total RNA was extracted from leaves of germinated seeds, 17 days (in plants treated for 24 hours) and 18 days (in plants treated for 10 minutes, 2 and 6 hours) post treatment. cDNA was prepared using oligo-dT primers and the expression level of SPL mRNA was determined in treated and control plants by real-time PCR with SYBR Green (Quanta BioSciences). Primers used for real-time PCR of SPL were located outside of the dsRNA region, at the 3' UTR. Primers sequences are listed in Table 17 together

TABLE 16

Primers used for in-vitro transcription of SPL dsRNA and the resulting dsRNA product.

| Target | | Sequence/SEQ ID NO: | Length (nt) |
|---|---|---|---|
| SPL | Forward primer | CTAATACGACTCACTATAGGGAGATGGCCCAATAGG TTCTCCTCA/124 | 45 |
| | Reverse primer | CTAATACGACTCACTATAGGGAGAGCTGCCATTGAT GCTGATGC/125 | 44 |
| | dsRNA | CTAATACGACTCACTATAGGGAGATGGCCCAATAGG TTCTCCTCATATGGATGGAAACTAACAAATGGGAAG GGAAGAGAAGCATTACTGAAGCTGAAAAGGAAGAG GATGAACATGGAAGTGTTGAAGAGGATAGCAAAAG AAAAAGGGTATTGACTCTCTCTGGTAGGAAGCTAGT TGGTGAAGGGTCGGCACATCCTTCTTGCCAGGTCGAT CAGTGCACTGCAGATATGGCAGATGCCAAGCCATAC CATCGCCGCCACAAGGTGTGTGAGTTCCATTCAAAG TCTCCAATAGTACTTATTAGTGGACTCCAGAAGCGAT TCTGTCAGCAATGTAGCAGATTTCATCTGTTAGCAGA GTTTGATGATGCTAAGAGGAGTTGCCGAAGGCGTTT GGCAGGTCACAATGAGCGCCGCCGTAAAATTACATA TGACTCTCATGGAGAAAATTTGGGCTGAAGAAGCAT CAGCATCAATGGCAGCTCTCCCTATAGTGAGTCGTAT TAG/126 | 509 |

Prior to treatment, the dsRNA concentration and purity were assessed by absorbance (NanoDrop) and by HPLC. The concentration of the dsRNA according to the NanoDrop with the house-keeping genes (Expressed and CAC) that were used as normalizers (in the case of SPL Expressed was used as the normalizer).

TABLE 17

Primers used to determine expression level of SPL mRNA by real-time PCR.

| Target | Real-time PCR method | | Sequence/SEQ ID NO: | Length (nt) |
|---|---|---|---|---|
| SPL | SYBR Green | Forward primer | CAATTCCCGGATTTCTAAGC/127 | 20 |
| | | Reverse primer | CCCTTTACACAAGGGAAATG/128 | 20 |
| | Taqman | Forward primer | TTCTGAAGCAACATAAACAAGATGTG/129 | 26 |
| | | Reverse primer | AATTTGCTTAGAAATCCGGGAAT/130 | 23 |
| | | Taqman probe | 6FAM-TTAAGCATGCTCTCTATCT-MGBNFQ/131 | 19 |

TABLE 17-continued

Primers used to determine expression level of SPL mRNA by real-time PCR.

| Target | Real-time PCR method | | Sequence/SEQ ID NO: | Length (nt) |
|---|---|---|---|---|
| Expressed | SYBR Green | Forward primer | GCTAAGAACGCTGGACCTAATG/132 | 22 |
| | | Reverse primer | AGAATAGCATCCGGTCTCAG/133 | 20 |
| CAC | Taqman | Forward primer | GGTGGCGCCTTTGATGAA/134 | 18 |
| | | Reverse primer | TCCAATAGCTCGTAAATCAGAACAA/135 | 25 |
| | | Taqman probe | VIC-ATGCCATCCGCAATAA-MGBNFQ/136 | 16 |

This analysis showed a significant (Wilcoxon rank-sum test, p-value <0.05) up-regulation of SPL mRNA at all incubation times. The median expression level of SPL in plants treated with SPL dsRNA for 10 minutes, 2 hours, 6 hours and 24 hours was 2.54, 2.85, 2.69 and 2.73-fold higher than in control plants treated with GUS dsRNA, respectively (FIGS. 40A-B to 43A-B).

Figure 40B:
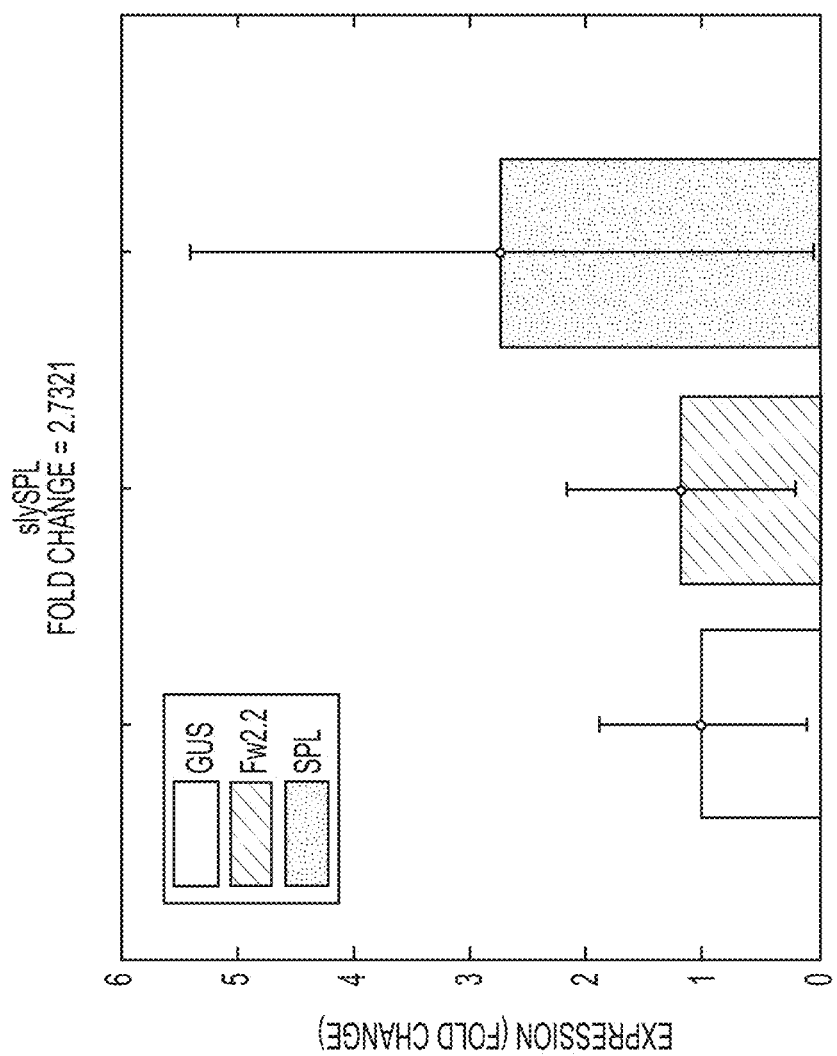
Figure 41A:
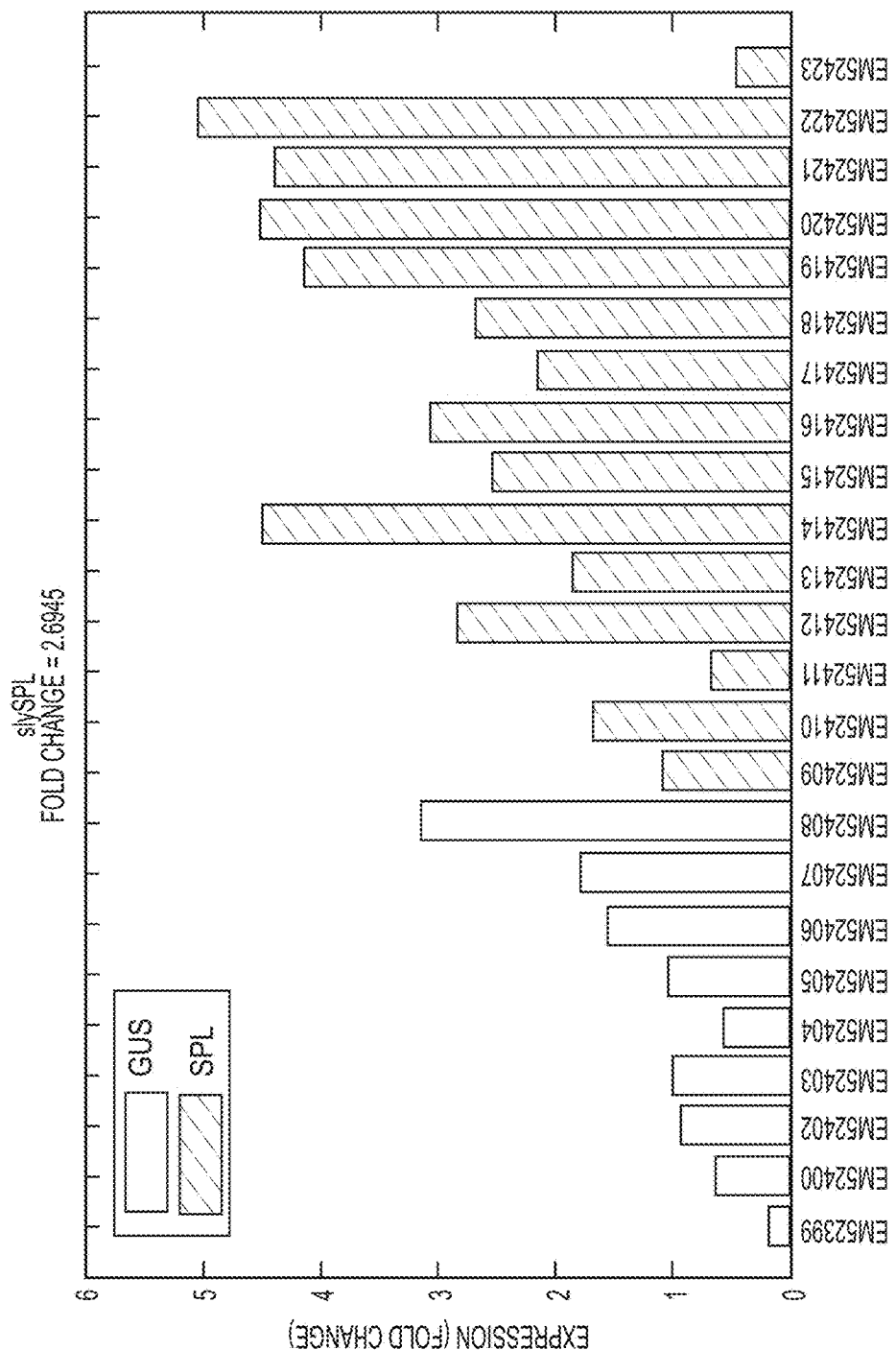
Figure 42B:
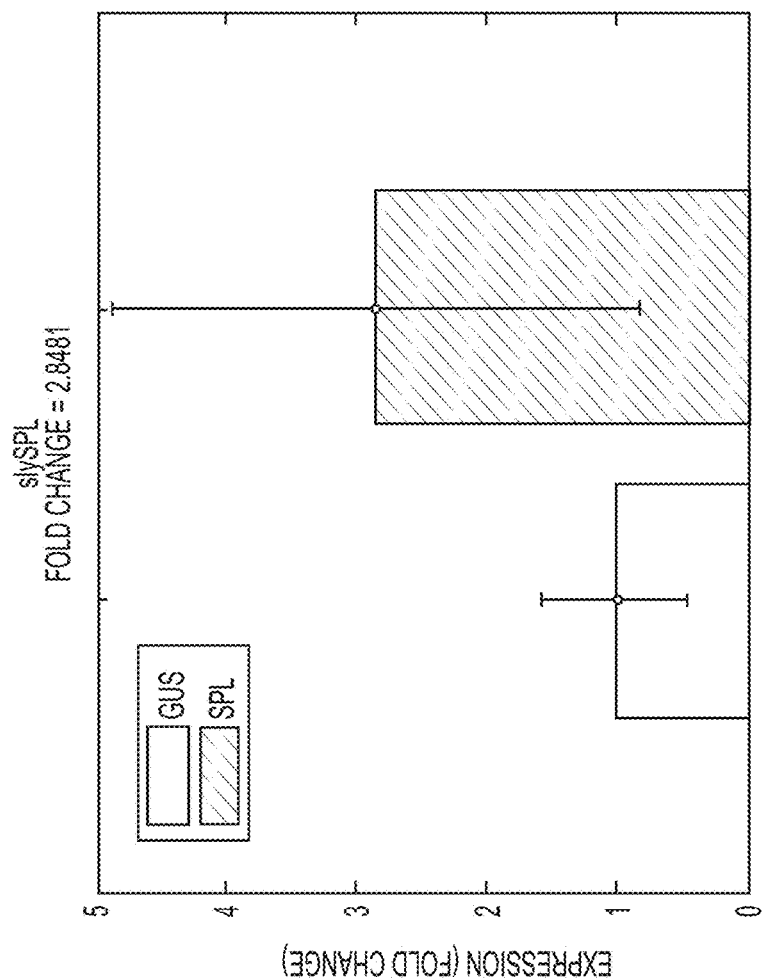
Figure 43A:
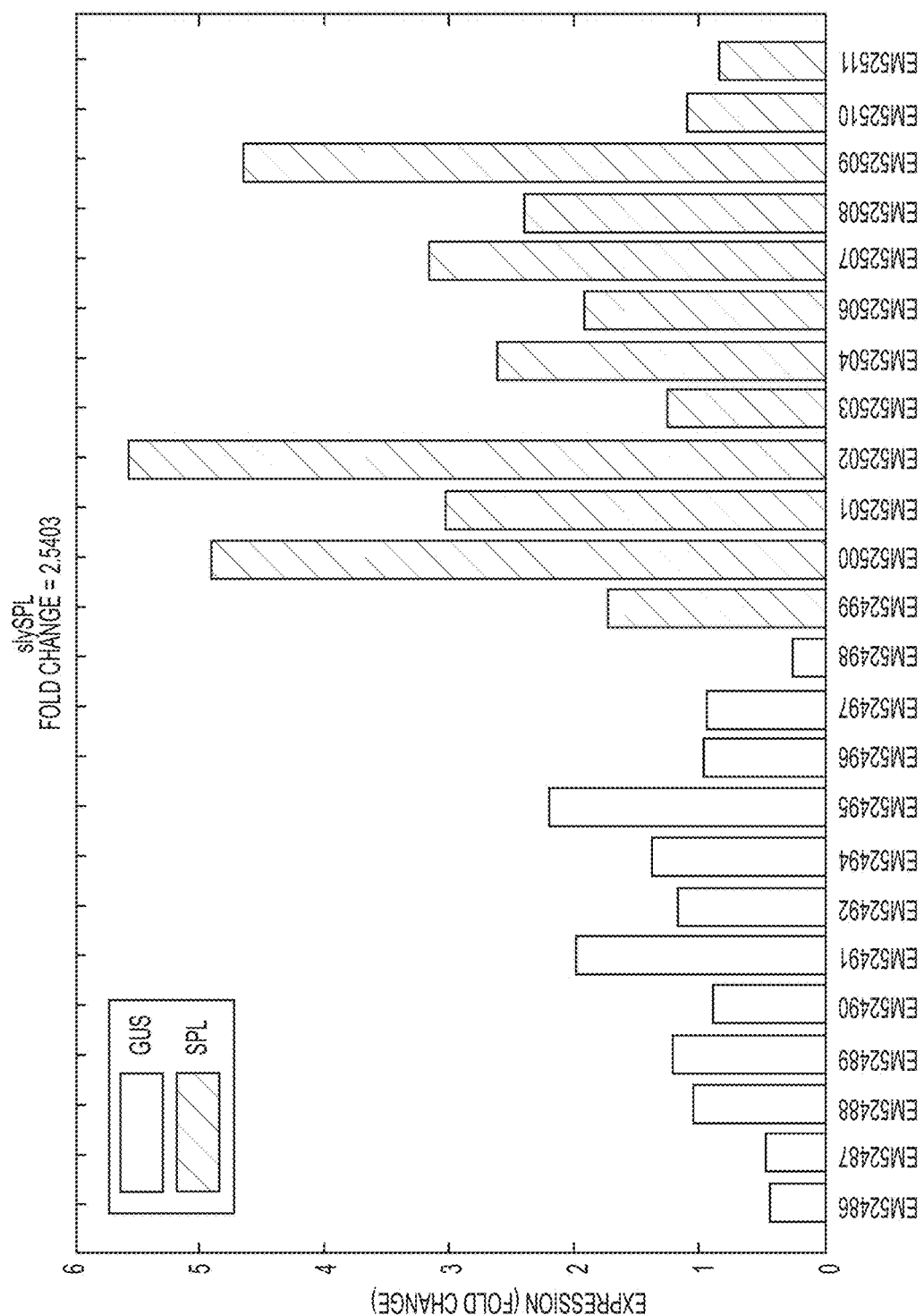

To verify that the effect on SPL mRNA results specifically from treatment with SPL dsRNA, the level of SPL mRNA was measured after treatment with both GUS dsRNA (a control sequence having no silencing relevant homology in the tomato genome) and FW2.2 dsRNA (which is a tomato endogenous sequence, see Table 13). Plants treated with 50 µg/ml dsRNA for 24 hours showed up-regulation of SPL when treated with SPL sequence, but not when treated with GUS or FW2.2 sequences (FIGS. 40A-B). FIGS. 41A-B to 43A-B shows the effect of varying treatment periods on SPL expression. All tested treatment times i.e., 24 h-10 minutes, showed an effect of SPL mRNA levels.

In another experiment, tomato seeds of the Oregon Spring variety were treated with an independently made dsRNA for the SPL gene at a concentration of 50 µg/ml for 24 hours. The seeds were then washed 3 times with water, and transferred to seed germination boxes (9 seeds per box) containing 12 ml water. Seeds in boxes were germinated in a growth chamber in the light at 25° C. for 7 days, and shoot tissue was then harvested for RNA analysis. RNA analysis was conducted by Taqman, using a tomato CAC assay for normalization of the values to correct for differences in sample concentration (Table 17). Table 18 shows that in seedlings germinated from seeds treated with SPL dsRNA, mRNA levels of the SPL gene was elevated about 7-fold compared to seedlings germinated from seeds treated with GUS dsRNA. Treatment with AFR8 dsRNA and 0.1 mM EDTA (buffer) had no significant effect on SPL mRNA levels compared to treatment with GUS dsRNA.

TABLE 18 mRNA concentrations for SPL gene in tomato seedling shoot tissue.

| Treatment | Number | Mean RQ | Std Dev | % change from GUS control | fold change | Dunnett's p value |
|---|---|---|---|---|---|---|
| Buffer | 12 | 0.298 | 0.551 | 330% | 4.3 | 0.4723 |
| GUS | 15 | 0.069 | 0.059 | 0% | 1.0 | 1 |
| Sl.ARF8-1 | 11 | 0.196 | 0.338 | 183% | 2.8 | 0.846 |
| Sl.SPL | 18 | 0.463 | 0.655 | 568% | 6.7 | 0.0577 |

Example 24

Altered SPL Expression Following Tomato Seed Dipping in dsRNA

Tomato seeds were treated with a dsRNA derived from the SPL gene as described in Examples 1 and 23.

Treatment with dsRNA at a concentration of 50 µg/ml was done by dipping the seeds in the dsRNA solution at room temperature and immediately washing with double distilled water (DDW). Total RNA was extracted from leaves of germinated seeds, 13 days post treatment. cDNA was prepared using oligo-dT primers and the expression level of SPL mRNA was determined in treated and control plants by real-time PCR, as described in Example 23.

Figure 44B:
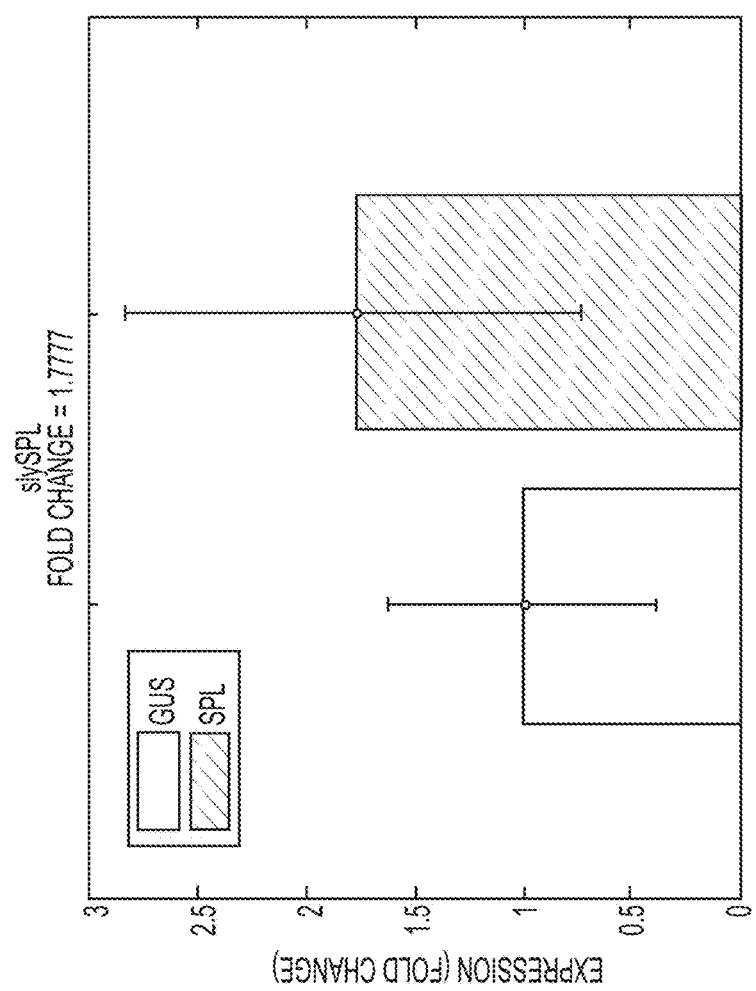
Figure 45B:
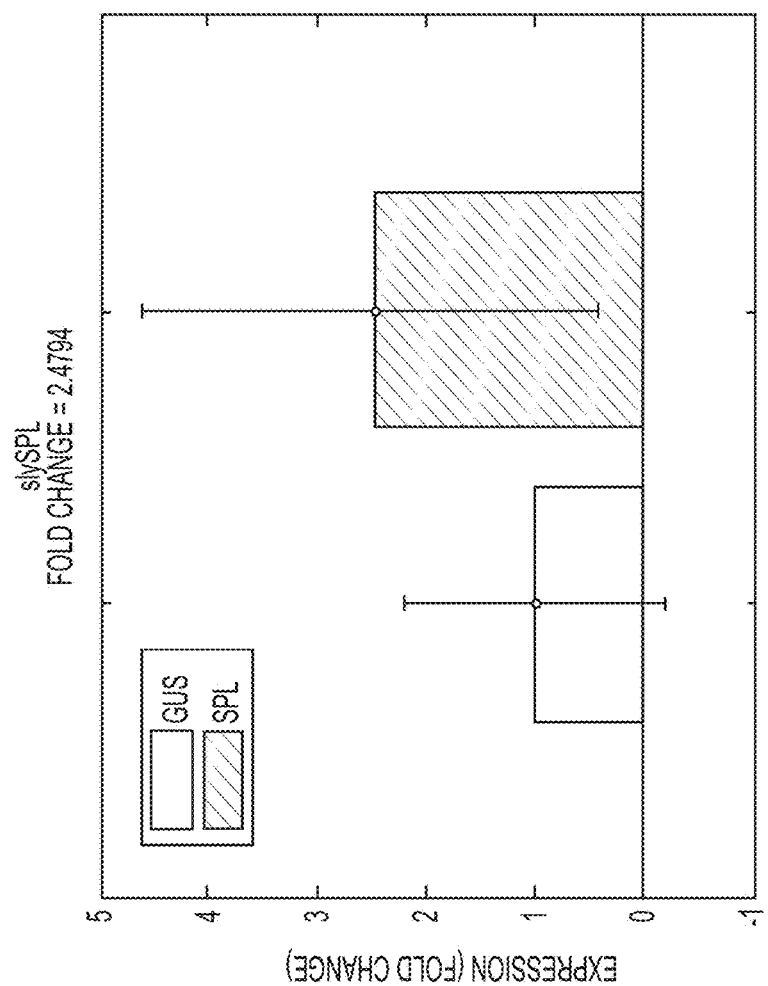
Figure 46A:
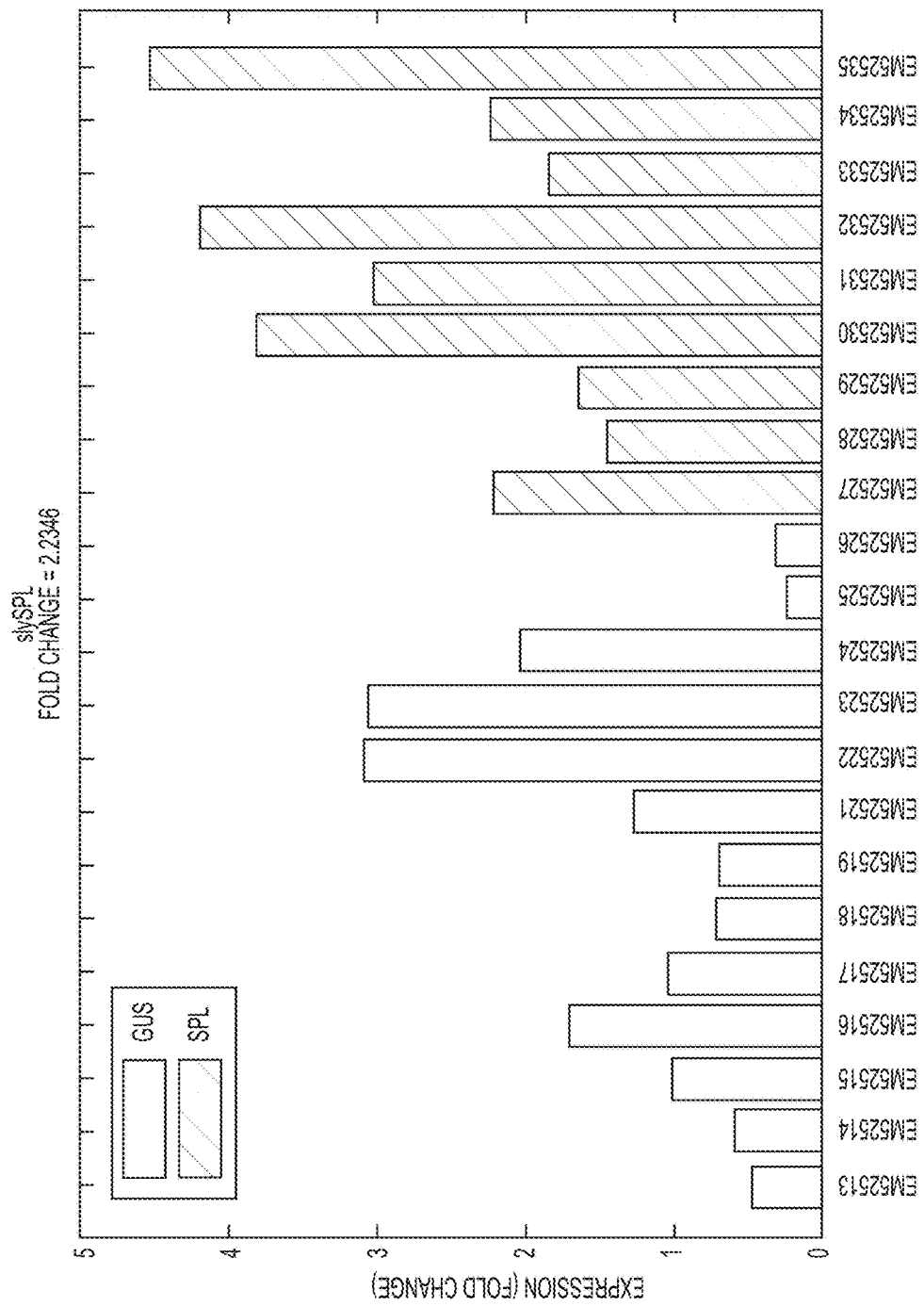
FIGS. 46A-B are bar graphs showing real-time PCR analyses of SPL mRNA expression in 18-days old tomato plants germinated from seeds treated with 25 µg/ml dsRNA for 2 hours (the dsRNAs are as in FIGS. 40A-B).
Figure 46B:
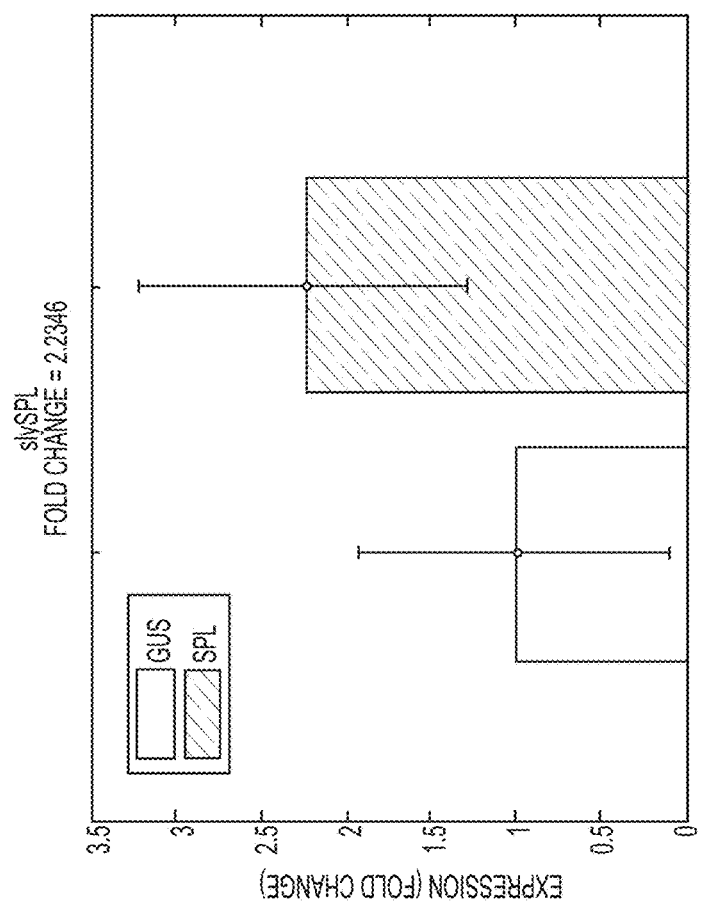
Figure 47A:
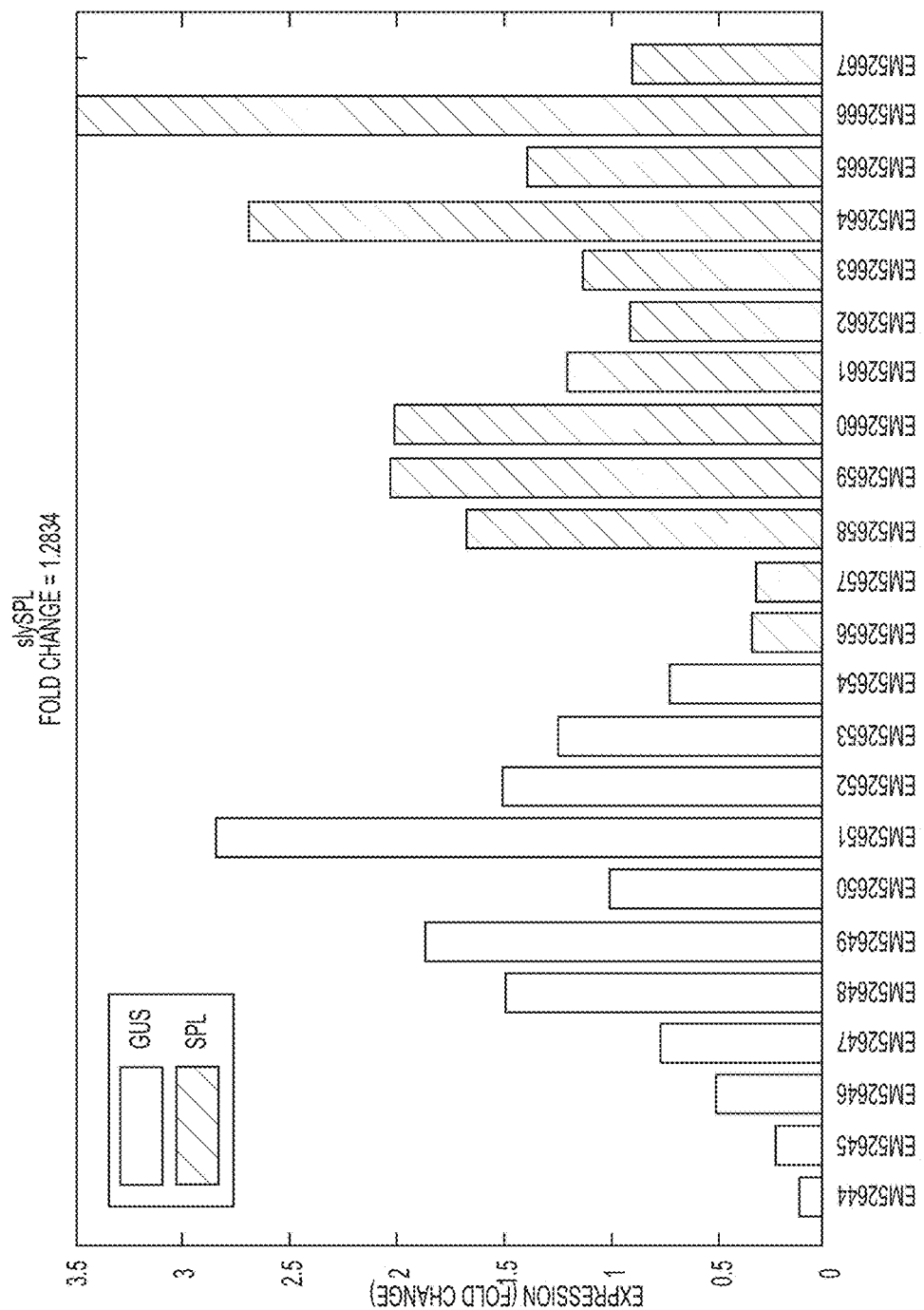
FIGS. 47A-B are bar graphs showing real-time PCR analyses of SPL mRNA expression in 18-days old tomato plants germinated from seeds treated with 25 µg/ml dsRNA for 10 minutes (the dsRNAs are as in FIGS. 40A-B).
Figure 47B:
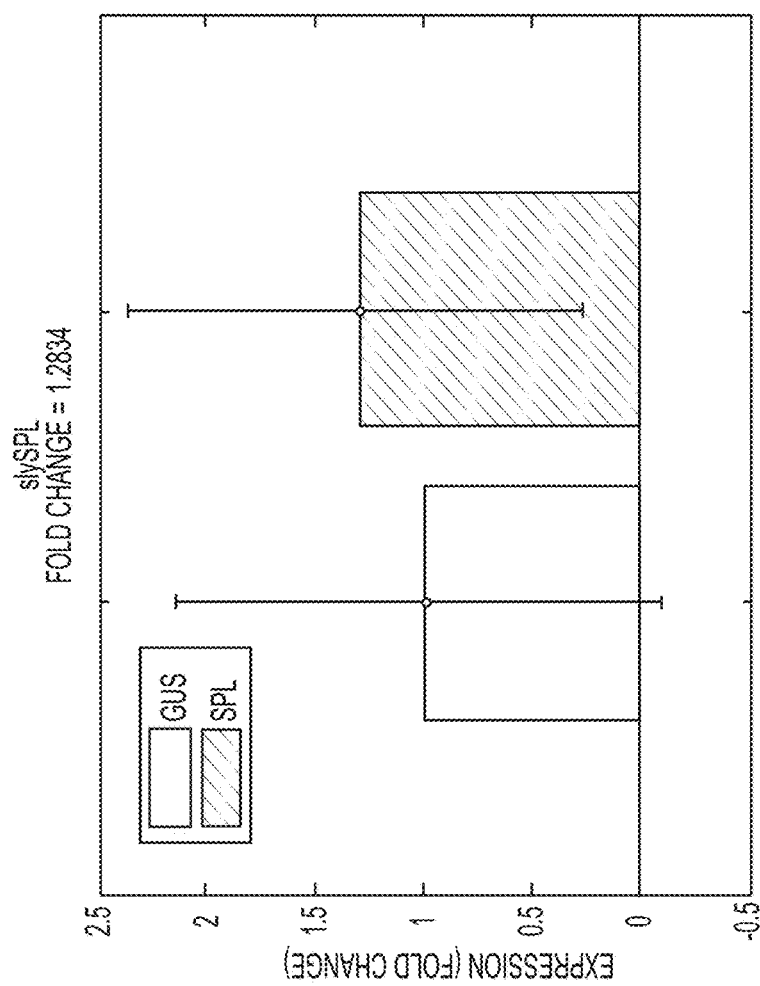
Figure 48A:
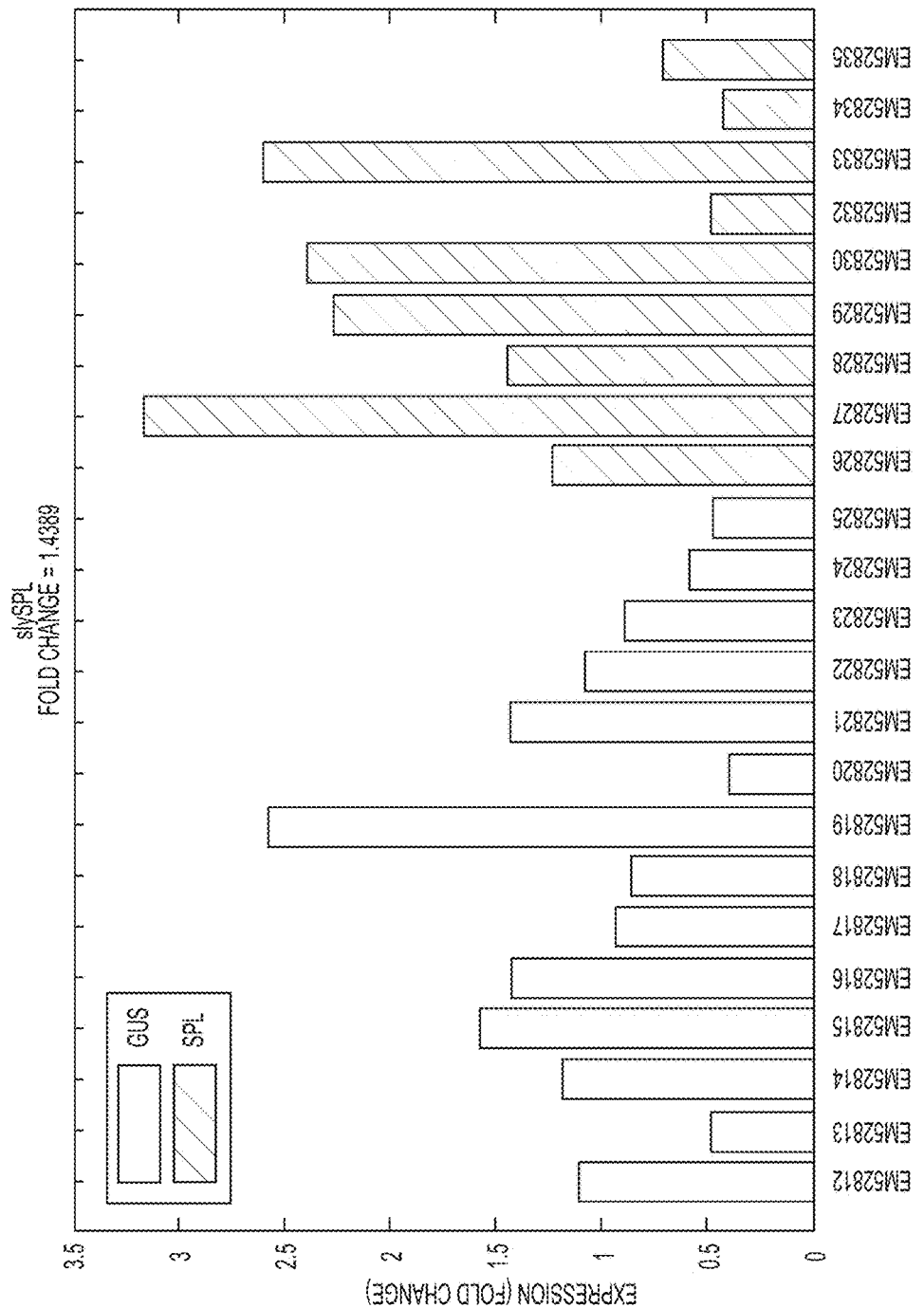
FIGS. 48A-B are bar graphs showing real-time PCR analyses of SPL mRNA expression in 17-days old tomato plants germinated from seeds treated with 1 µg/ml dsRNA for 24 hours (the dsRNAs are as in FIGS. 40A-B).
Figure 48B:
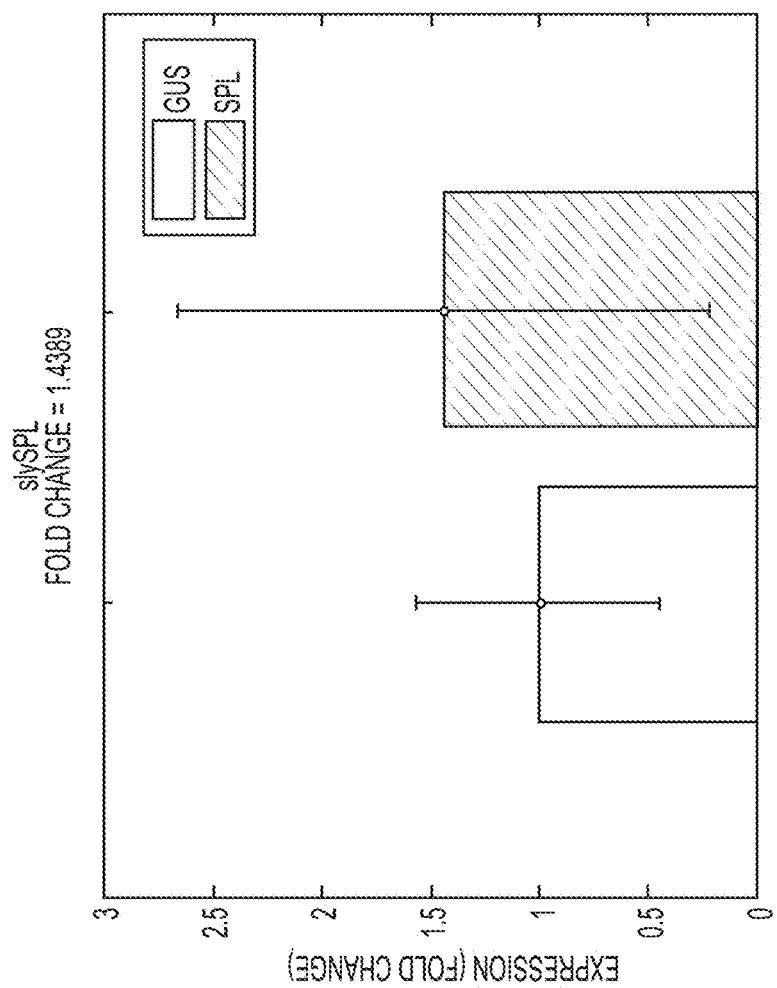
Figure 49A:
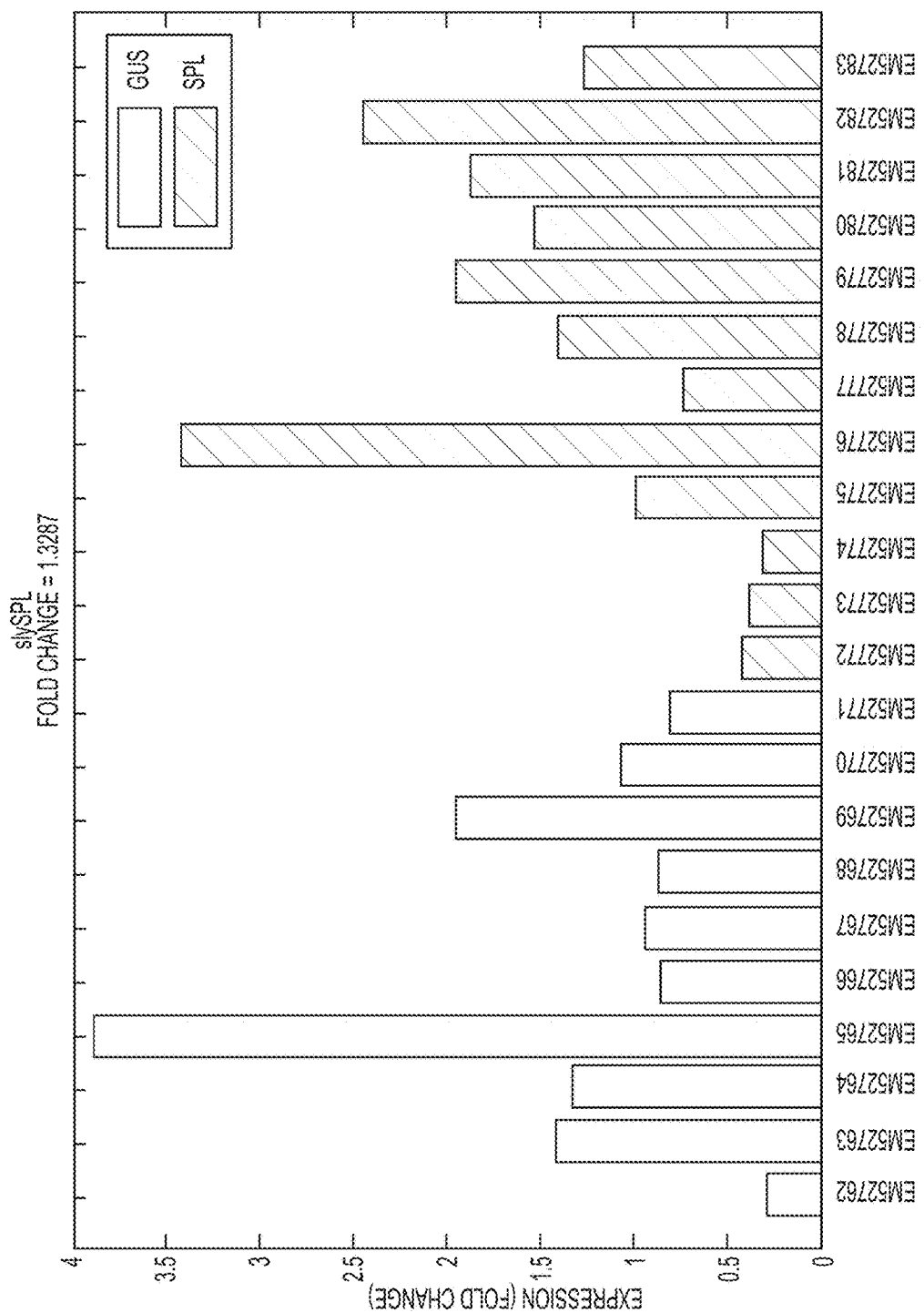
FIGS. 49A-B are bar graphs showing real-time PCR analyses of SPL mRNA expression in 18-days old tomato plants germinated from seeds treated with 1 µg/ml dsRNA for 2 hours (the dsRNAs are as in FIGS. 40A-B).
Figure 49B:
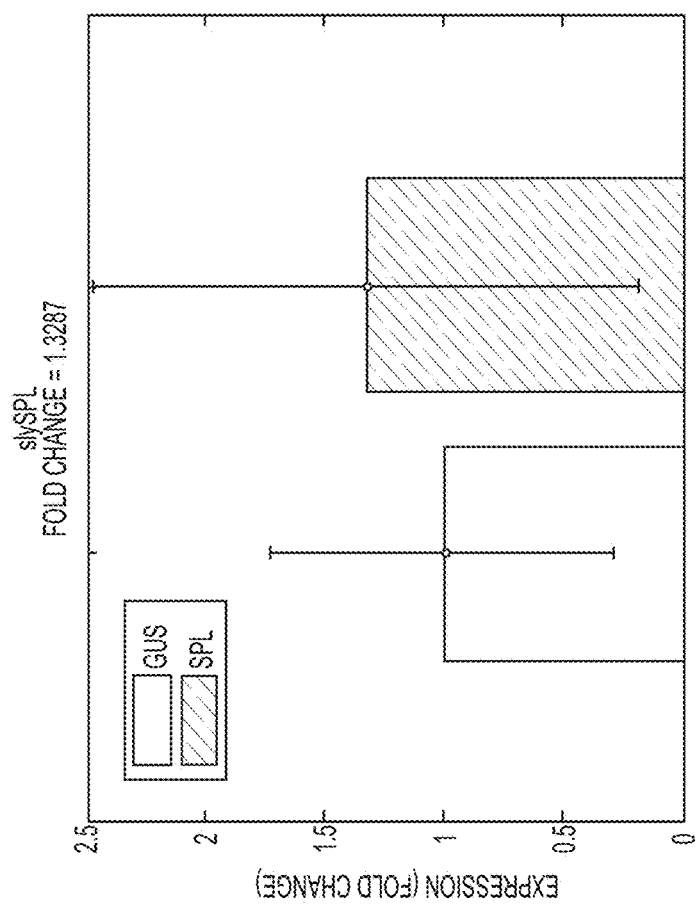
Figure 50A:
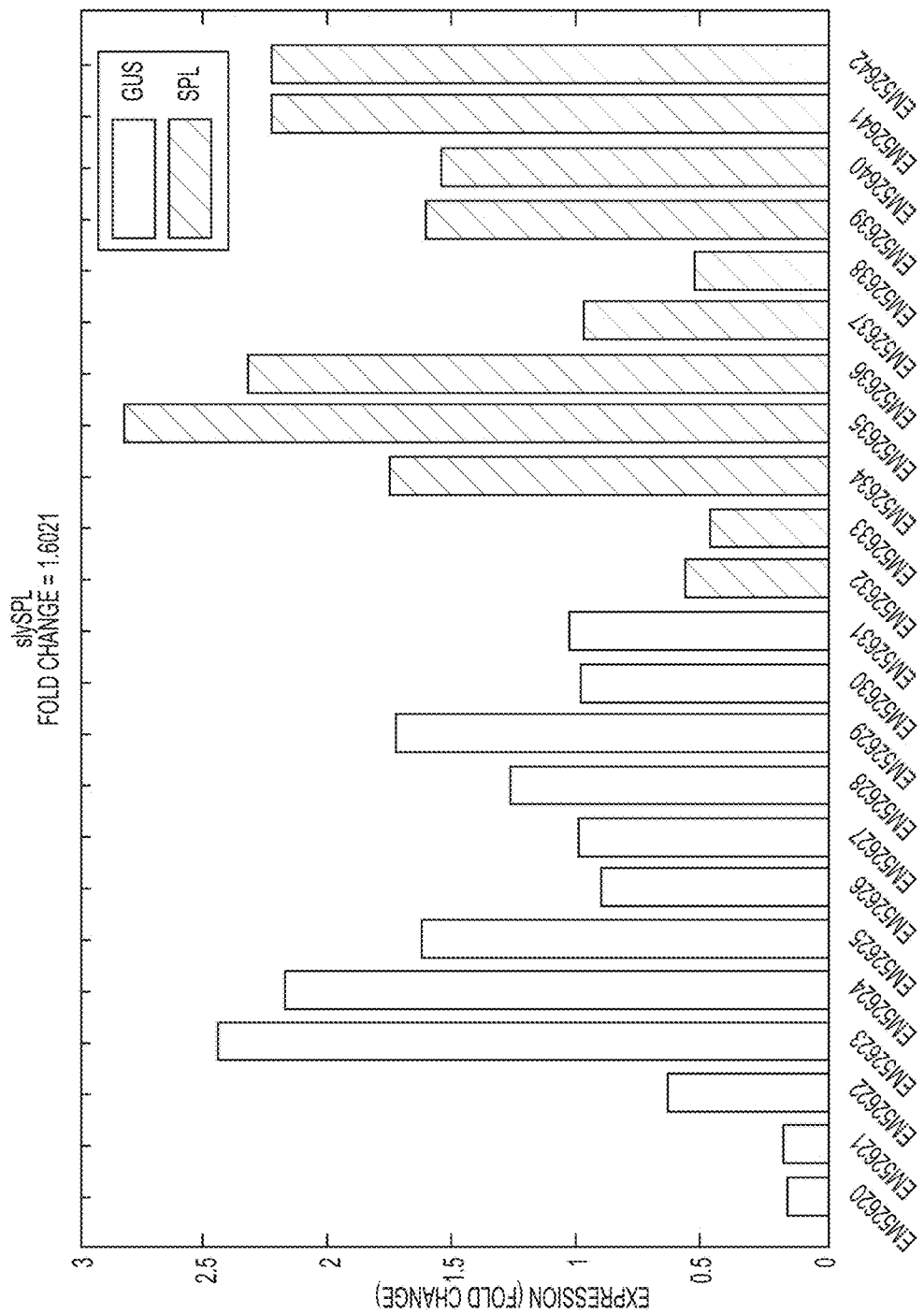

This analysis showed a significant (p-value <0.05) up-regulation of SPL mRNA (FIGS. 44A-B). The median expression level of SPL in plants treated with SPL dsRNA was 1.78 fold higher than in control plants dipped with 50 µg/ml GUS dsRNA.

Example 25

Altered SPL Expression Following Treatment with 25 µg/ml dsRNA in Tomato

Tomato seeds were treated with a dsRNA derived from the SPL gene as described in Examples 1 and 23.

Seeds were treated with dsRNA at a concentration of 25 µg/ml for 10 minutes, 2 and 24 hours. Total RNA was extracted from leaves of germinated seeds, 17 days (in plants treated for 24 hours) and 18 days (in plants treated for 10 minutes and 2 hours) post treatment. cDNA was prepared using oligo-dT primers and the expression level of SPL mRNA was determined in treated and control plants by real-time PCR, as described in Example 23.

This analysis showed a significant (p-value <0.05) up-regulation of SPL mRNA for incubation times of 2 and 24 hours, and an up-regulation trend for 10 minutes incubation time (FIGS. 45A-B to 47A-B). The median expression level of SPL in plants treated with SPL dsRNA for 2 and 24 hours was 2.23 and 2.48-fold higher than in control plants treated with GUS dsRNA, respectively.

Example 26

Altered SPL Expression Following Treatment with 1 or 5 µg/ml dsRNA in Tomato

Tomato seeds were treated with a dsRNA derived from the SPL gene as described in Examples 1 and 23.

Seeds were treated with dsRNA at a concentration of 1 or 5 µg/ml for 10 minutes, 2 and 24 hours. Total RNA was extracted from leaves of germinated seeds, 17 days (in plants treated for 24 hours) and 18 days (in plants treated for 10 minutes and 2 hours) post treatment. cDNA was prepared using oligo-dT primers and the expression level of SPL mRNA was determined in treated and control plants by real-time PCR, as described in Example 23.

An up-regulation trend in SPL mRNA expression was detected for all incubation times treated with 1 µg/ml dsRNA (FIGS. 48A-B to 50A-B).

Example 27

Altered SPL Expression Following Treatment with SPL siRNA in Tomato dsRNA derived from the SPL gene (Table 16) was processed with ShortCut® RNase III (NEB) as described in Example 1.

Tomato seeds were treated with the resulting siRNA at a concentration of 50 µg/ml for 2 hours at 25° C. Total RNA was extracted from leaves of germinated seeds 13 days post treatment. cDNA was prepared using oligo-dT primers and the expression level of SPL mRNA was determined in treated and control plants by real-time PCR, as described in Example 23.

Figure 51A:
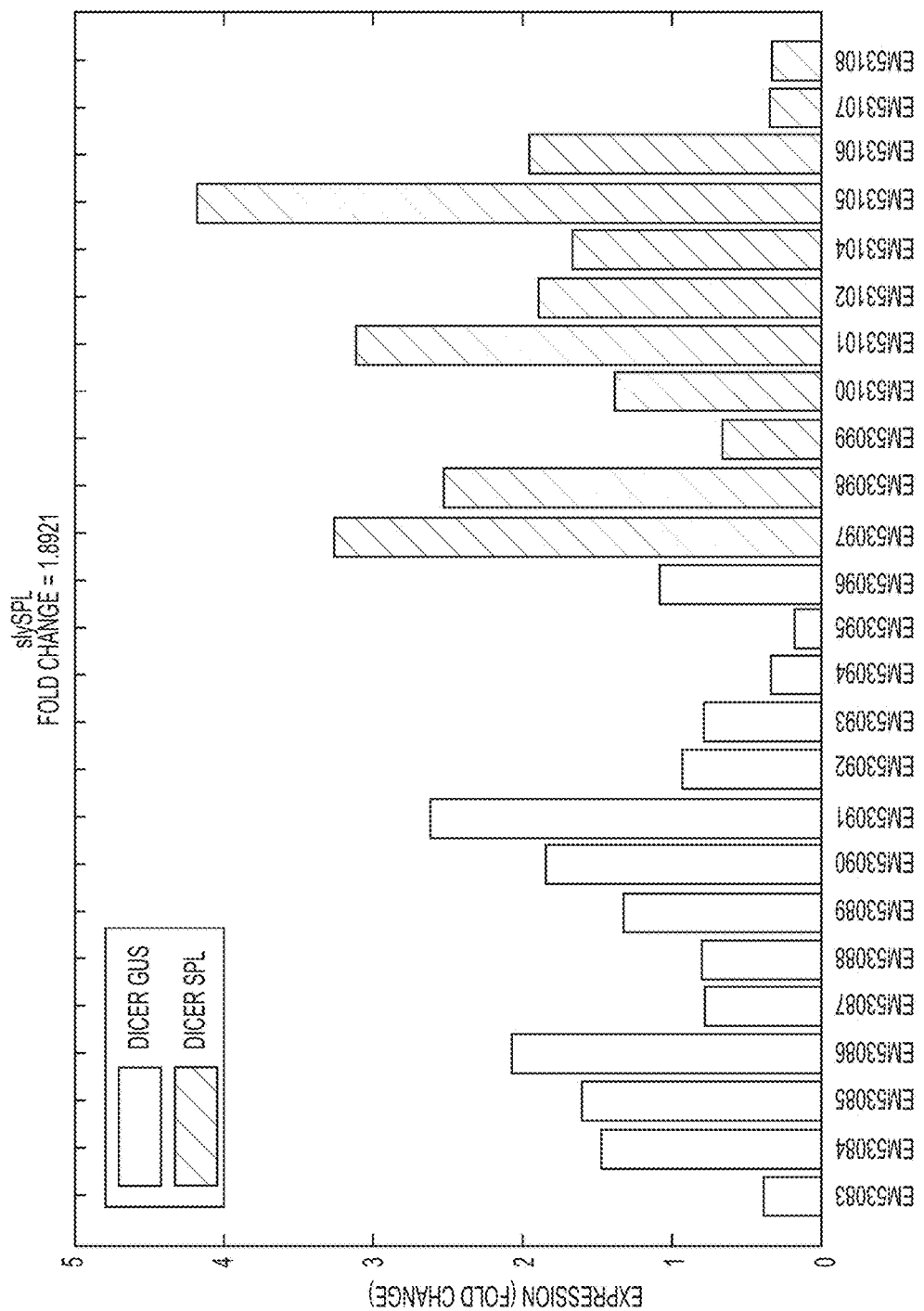
FIGS. 51A-B are bar graphs showing real-time PCR analyses of SPL mRNA expression in 13-days old tomato plants germinated from seeds treated with 50 µg/ml siRNA for 2 hours (the dsRNAs are as in FIGS. 40A-B).
Figure 51B:
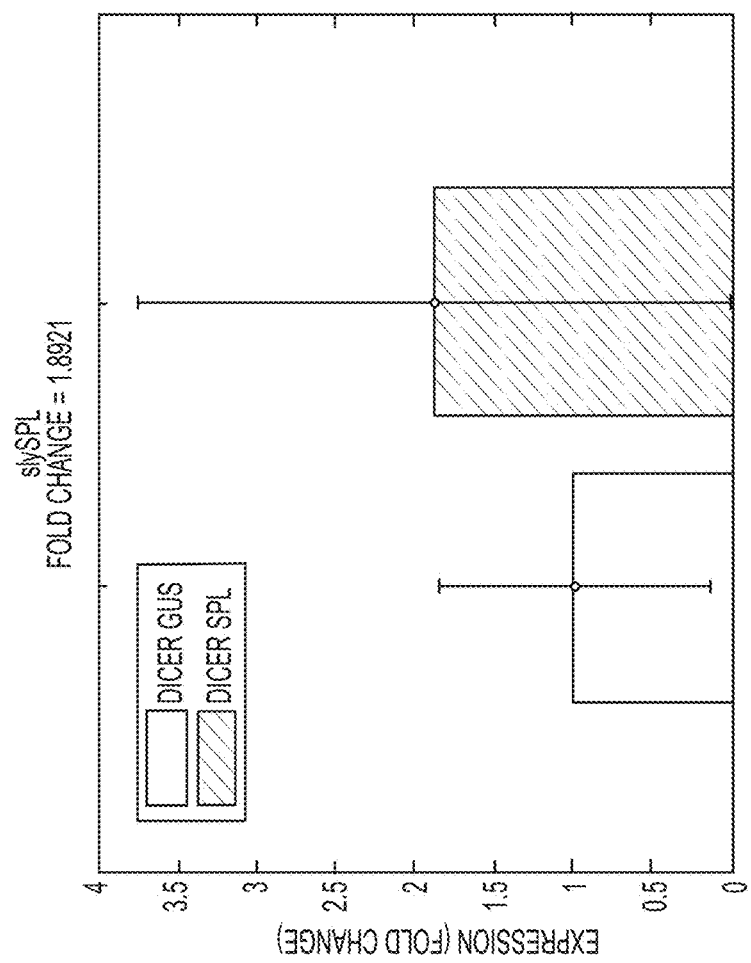

An up-regulation trend in SPL mRNA expression was detected. The median expression level of SPL in plants treated with SPL siRNA was 1.89 higher than in control plants treated with GUS siRNA (FIGS. 51A-B).

Example 28

Altered FW2.2 Expression Following Treatment with 50 µg/ml dsRNA in Tomato

Tomato seeds were treated with a dsRNA derived from the FW2.2 gene as described in Examples 1 and 23. As a control, seeds were treated with GUS dsRNA at the same concentration. The FW2.2 dsRNA sequence appears in Table 13.

Figure 52:
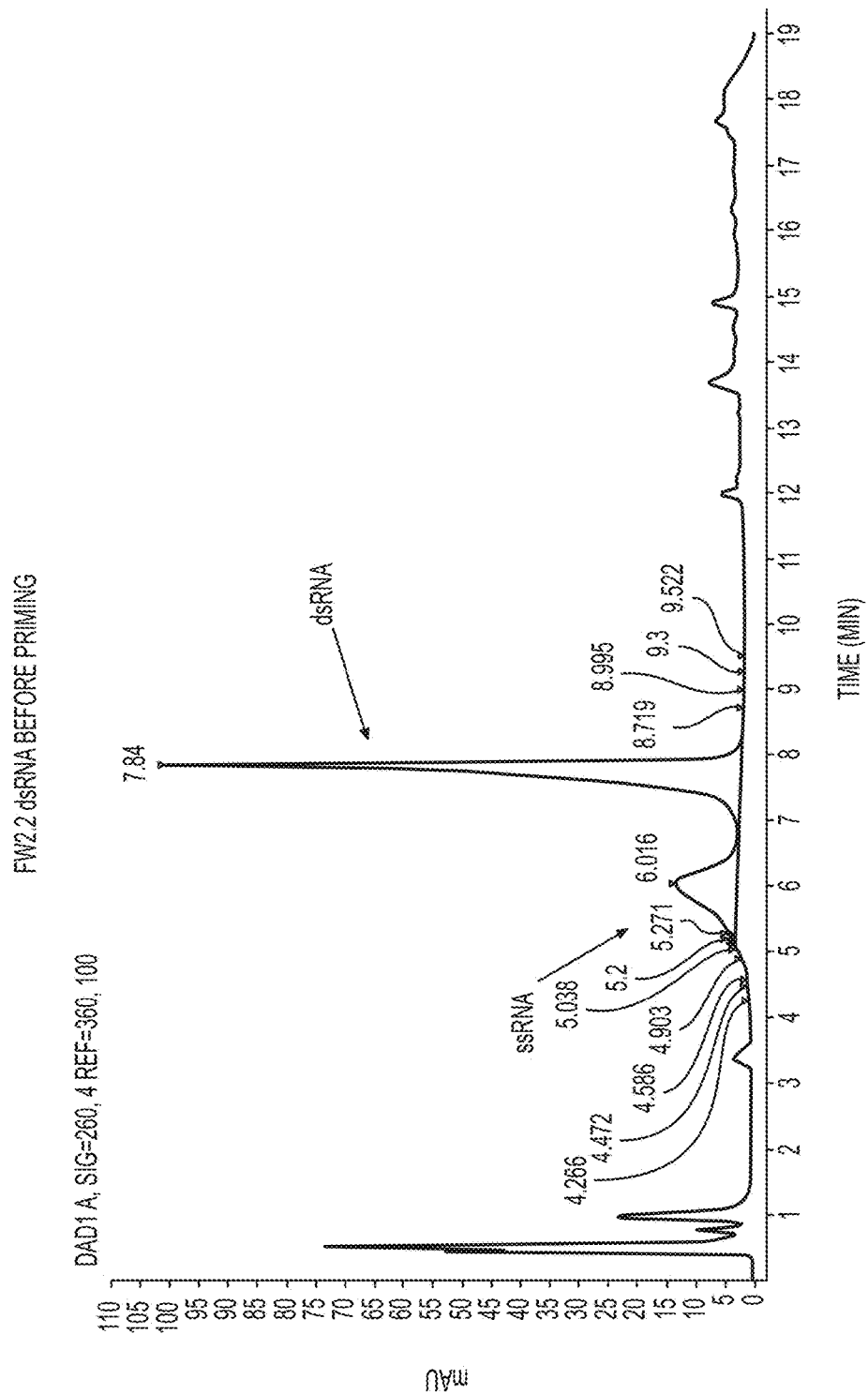
FIG. 52 is graphs showing HPLC analyses of FW2.2 ssRNA/dsRNA (SEQ ID NO: 114) mixture before treatment. Arrows indicate the ssRNA and dsRNA fractions.
Figure 53A:
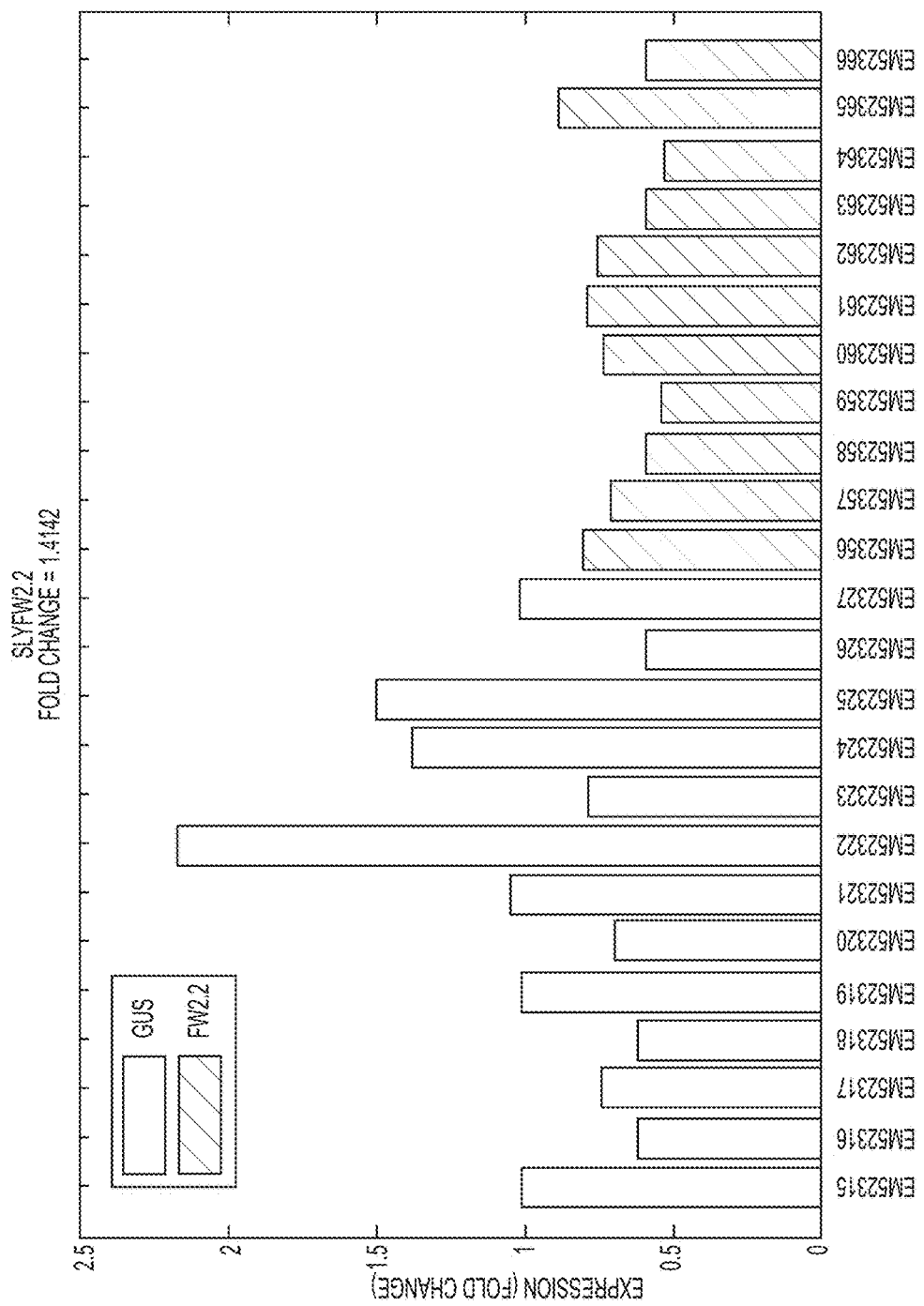
FIGS. 53A-B are bar graphs showing real-time PCR analyses of FW2.2 mRNA expression in 17-days old tomato plants germinated from seeds treated with 50 µg/ml dsRNA for 24 hours.
Figure 53B:
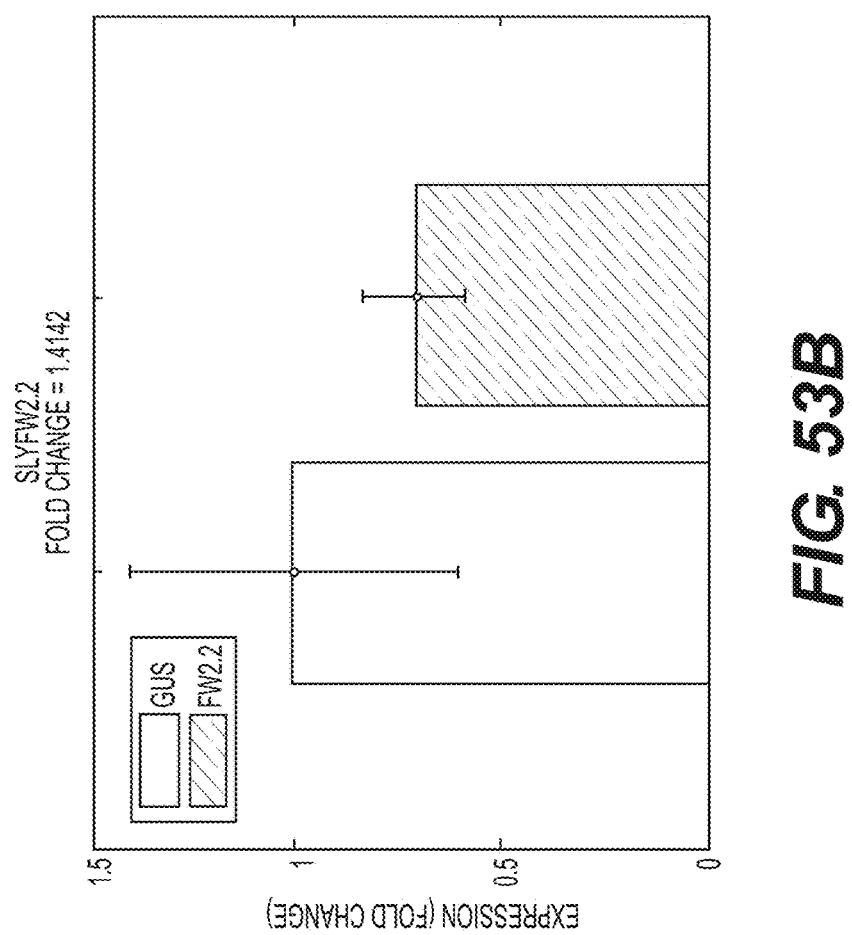
Figure 54A:
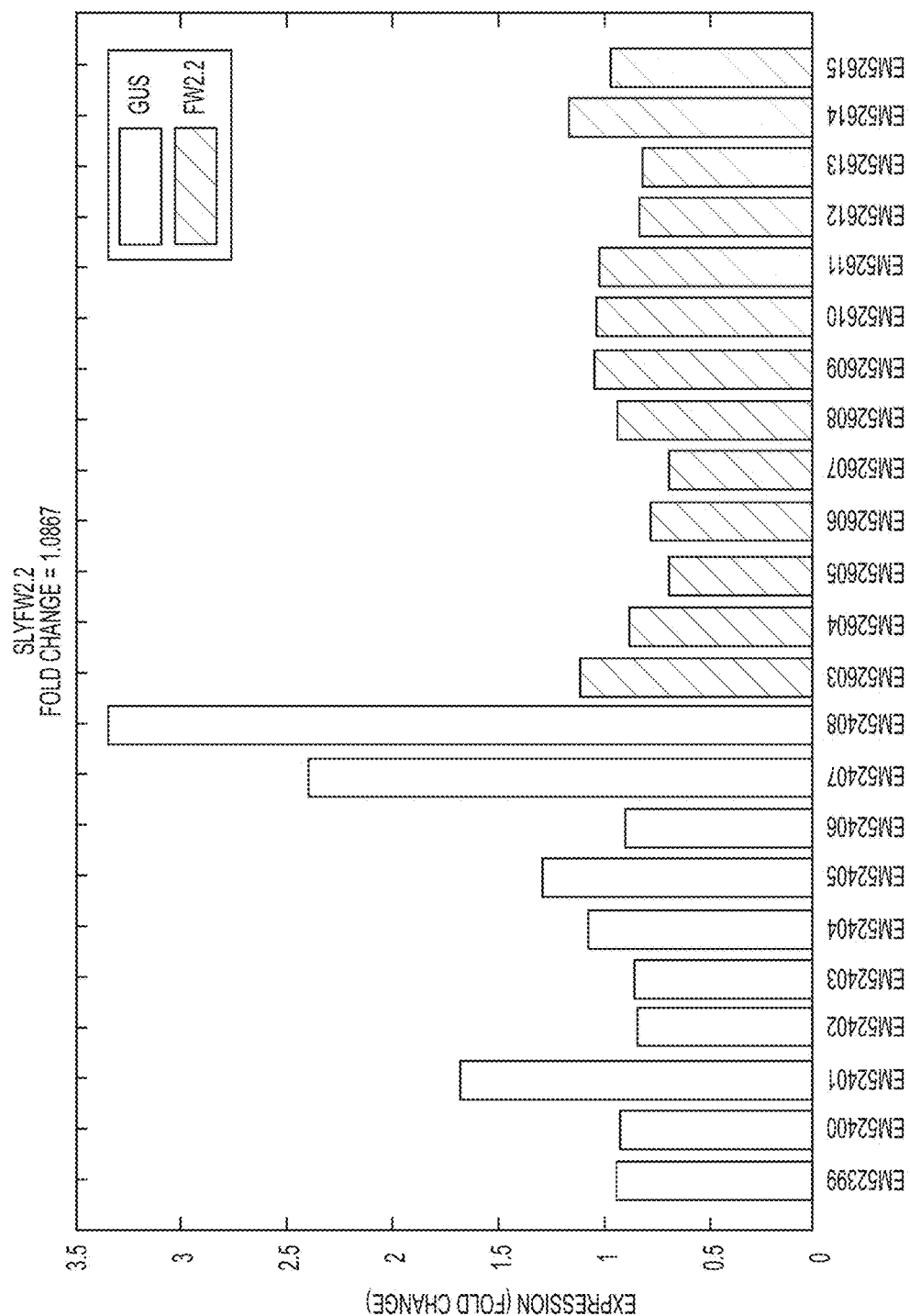
FIGS. 54A-B are bar graphs showing real-time PCR analysis of FW2.2 mRNA expression in 18-days old tomato plants germinated from seeds treated with 50 µg/ml dsRNA for 6 hours (the dsRNAs are as in FIGS. 53A-B).
Figure 54B:
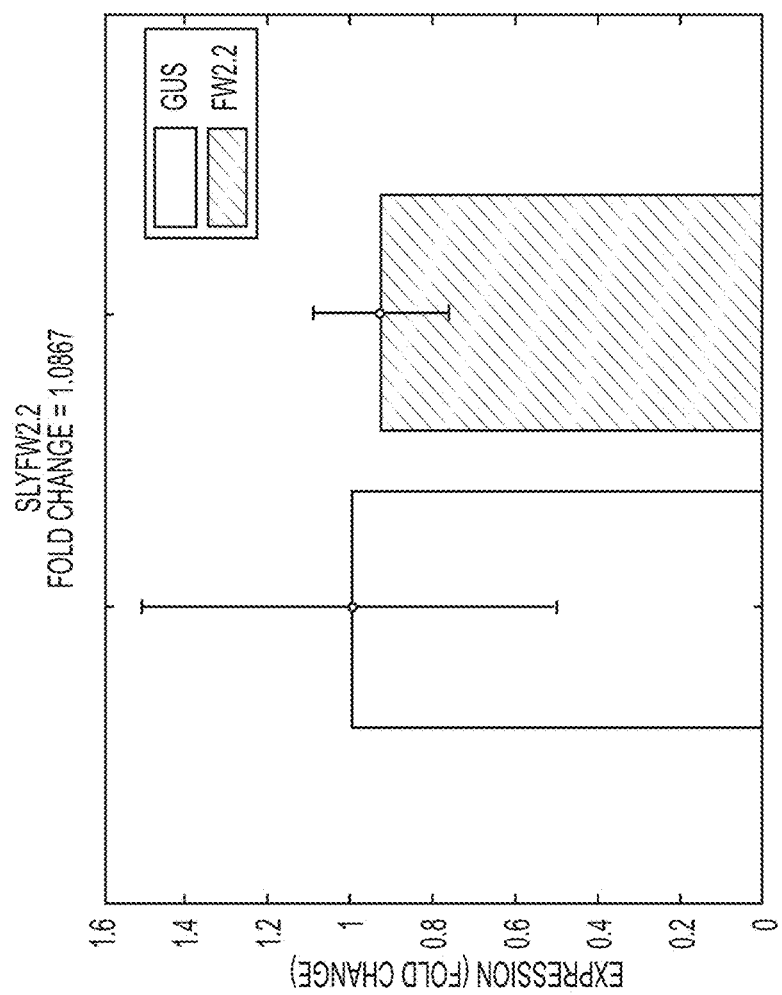
Figure 55A:
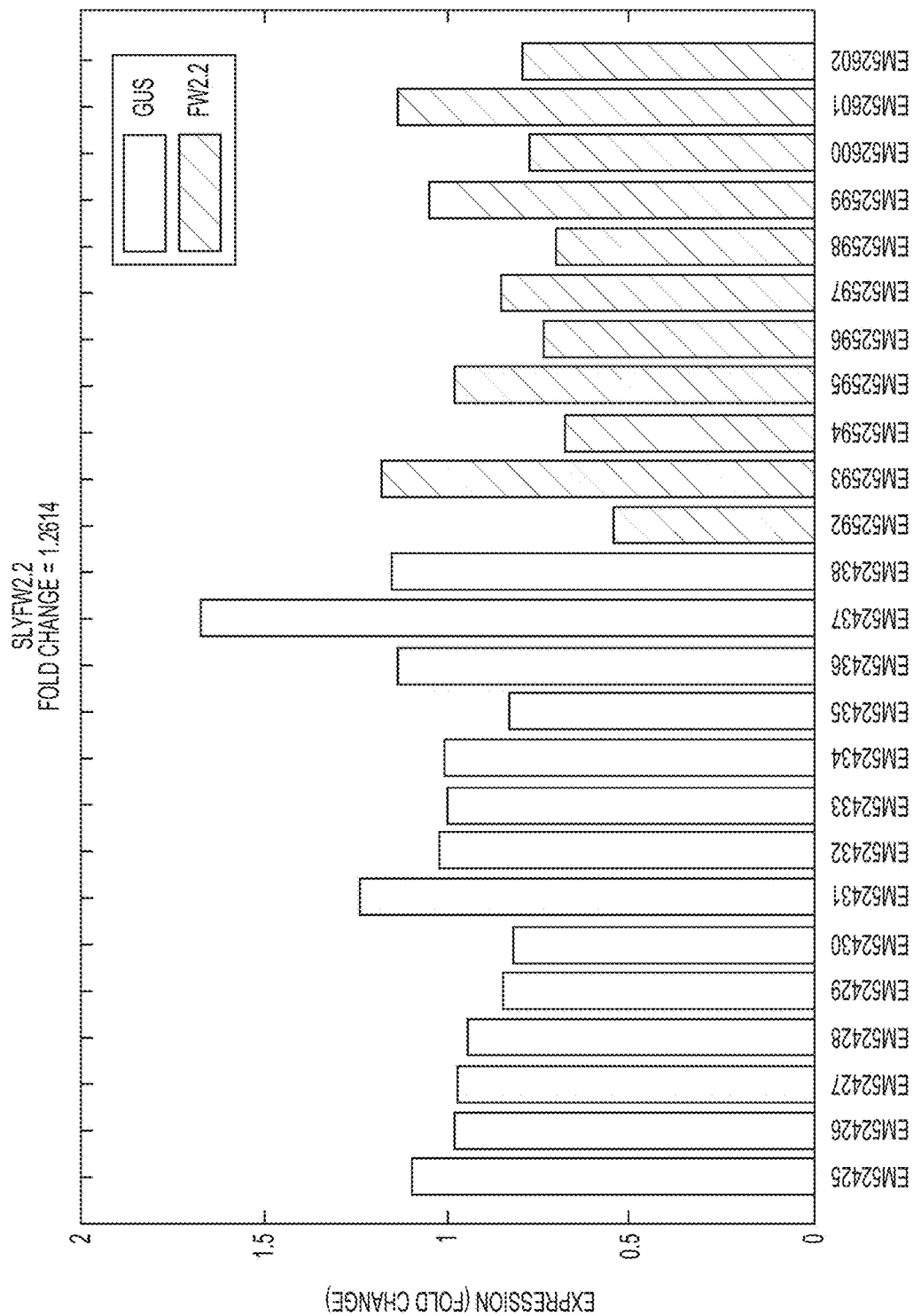
FIGS. 55A-B are bar graphs showing real-time PCR analyses of FW2.2 mRNA expression in 18-days old tomato plants germinated from seeds treated with 50 µg/ml dsRNA for 2 hours (the dsRNAs are as in FIGS. 53A-B).
Figure 55B:
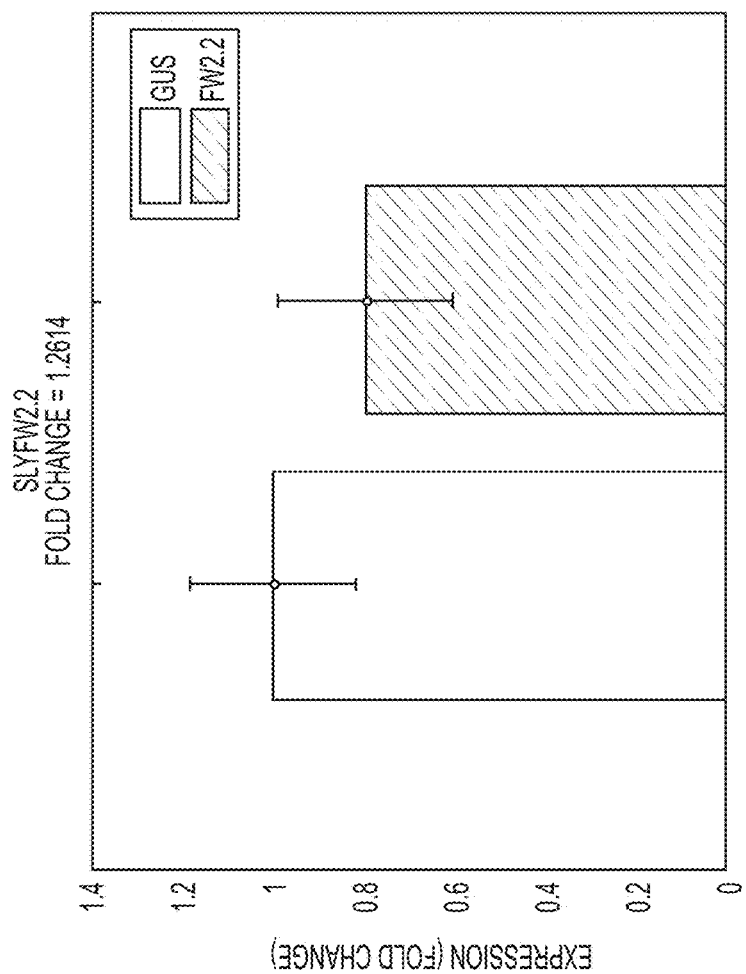

Before treatment, the dsRNA concentration and purity were assessed by absorbance (NanoDrop) and by HPLC. The concentration of the dsRNA according to the NanoDrop measurement was 1791 µg/ml. HPLC showed that the sample contains mostly dsRNA but other species (nucleotides and ssRNA) were present in the solution as well. According to the HPLC analysis, the FW2.2 solution contained 1410 µg/ml of dsRNA and 473 µg/ml of ssRNA (see FIGS. 52A-B).

Seeds were treated with dsRNA at a concentration of 50 µg/ml (determined by the HPLC measurement) for 2, 6 and 24 hours. Total RNA was extracted from leaves of germinated seeds, 17 days (in plants treated for 24 hours) and 18 days (in plants treated for 2 and 6 hours) post treatment. cDNA was prepared using oligo-dT primers and the expression level of FW2.2 mRNA was determined in treated and control plants by real-time PCR. Primers used for real-time PCR of FW2.2 were TCTCTGGGCTTGTATCATCC (Forward primer, SEQ ID NO: 137) and GCTGCTCAAGGT-GTTTGTG (Reverse primer, SEQ ID NO: 138). These primers are located outside of the dsRNA region, at the 3'UTR.

Down-regulation of FW2.2 mRNA following seed treatment was achieved at all incubation times (p-value ≤0.1). The median expression level of FW2.2 in plants treated with FW2.2 dsRNA for 2, 6 and 24 hours was 1.26, 1.09 and 1.41-fold lower than in control plants treated with GUS dsRNA, respectively (FIGS. 53A-B to 55A-B).

Example 29

Altered Della Expression Following Treatment with Della dsRNA in Rice

Rice seeds were treated using the protocol described in Example 1. Seeds were washed for 4 h, dried over night at room temperature and treated with DELLA dsRNA (see Table 15) at a concentration of 142 µg/ml, for 24 hours at 15° C. Total RNA was extracted from leaves of germinated seeds 13 days post treatment. cDNA was prepared using oligo-dT primers and the expression level of DELLA mRNA was determined in treated and control plants by real-time PCR (see Table 15).

Figure 56B:
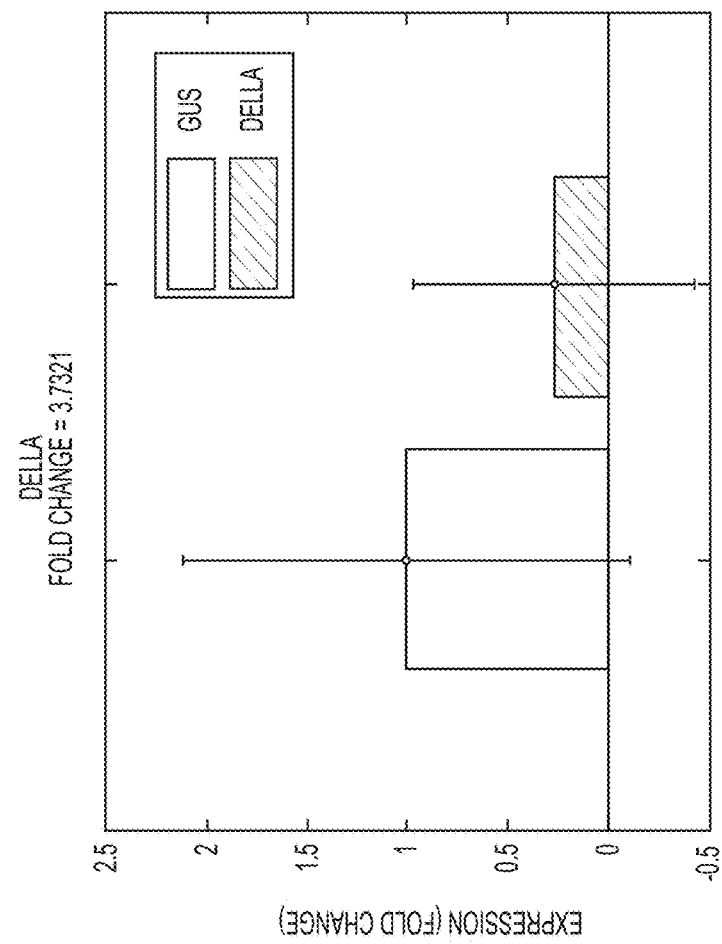

This analysis showed a significant (p-value <0.05) down-regulation of DELLA mRNA. The median expression level of DELLA in plants treated with DELLA dsRNA was 3.73-fold lower than in control plants treated with GUS dsRNA (FIGS. 56A-B).

Example 30

Figure 57:
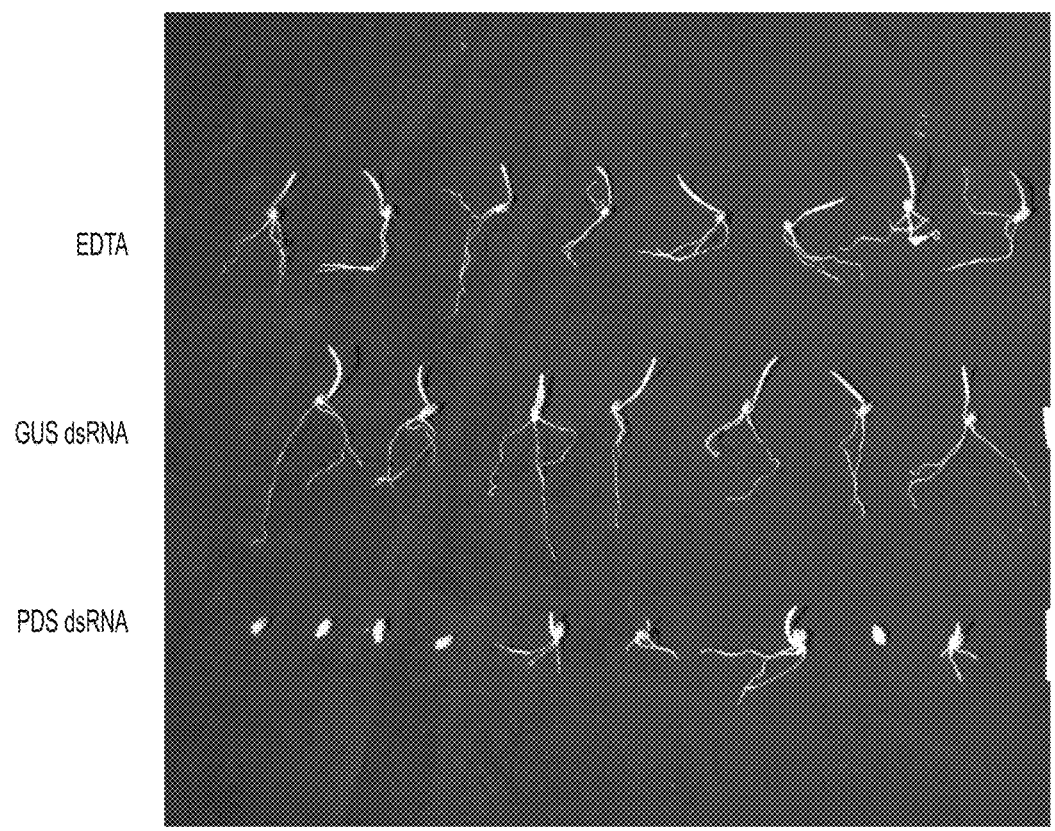
FIG. 57 is an image showing germinated wheat seeds three days after treatment. Top—control seeds treated with 0.1 mM EDTA, middle—control seeds treated with GUS dsRNA (SEQ ID NO: 21), bottom—seeds treated with PDS dsRNA (SEQ ID NOs: 44 and 45).

Delayed Seedling Development and Altered PDS Expression Following PDS dsRNA Treatment in Wheat Wheat seeds were treated using the protocol described in Example 1. Seeds were treated with a mixture of two PDS dsRNA fragments (see Table 19) for 4 hours at 15° C. and then germinated on a wet paper towel. The concentration of dsRNAs in the mixture was 136 µg/ml for fragment #1 (SEQ ID NO: 141) and 125 µg/ml for fragment #2 (SEQ ID NO: 144). Three days post treatment, seeds treated with the PDS dsRNA mixture exhibited stunted and delayed development, as seen by smaller seedlings and reduced rooting compared with control seeds treated with either 200 µg/ml GUS dsRNA or 0.1 mM EDTA (FIGS. 57A-B).

TABLE 19

Primers used for in-vitro transcription of Wheat PDS dsRNAs and the resulting dsRNA products.

| Target | | Sequence/SEQ ID NO: | Length (nt) |
|---|---|---|---|
| PDS | Forward primer #1 | CTCGTAATACGACTCACTATAGGGCGAACAAGA ATCTGCCGGACTAC/139 | 47 |
| | Reverse primer #1 | CTCGTAATACGACTCACTATAGGGCGACATCCTT CCATGCAGCTAAC/140 | 47 |

TABLE 19-continued

Primers used for in-vitro transcription of Wheat PDS dsRNAs and the resulting dsRNA products.

| Target | Sequence/SEQ ID NO: | Length (nt) |
|---|---|---|
| dsRNA #1 | CTCGTAATACGACTCACTATAGGGCGAACAAGA ATCTGCCGGACTACTTGCTTCAGTATGGATACCA GCTGCCTATCATCTATGAACATAGCTGGAGCGA AGCAAGTAAGATCTTTTGCTGGACAACTTCATA CGCAGAGGTGTTTCACAAGTAGCAGCGTCCAGG CACTAAAAACTAGTCATCGTACGACCTCCCTTG GCTTAAGGAATAAAGTAAAAGGATCACGTCATG GACTTCGTGCTCTGCAGGTTGTTTGCCAAGATTT TCCAAGGCCTCCACTAGAGAACACGATTAACTA TTTGGAAGCTGGCCAGCTTTCTTCGTCGTTTAGA AGCAGTGAACGCCCCAGTAAACCATTACAGGTC GTGATTGCTGGTGCAGGACTGGCTGGTCTATCA ACTGCAAAATACCTGGCAGACGCTGGCCACAAA CCCATAGTGCTTGAGGCAAGAGATGTGTTGGGC GGAAAGTTAGCTGCATGGAAGGATGTCGCCCTA TAGTGAGTCGTATTACGAG/141 | 517 |
| Forward primer #2 | CTCGTAATACGACTCACTATAGGGCGACGGAAC AGTGAAGCACTTTG/142 | 47 |
| Reverse primer #2 | CTCGTAATACGACTCACTATAGGGCGATTCGGG ACGGTCTTGTAAAC/143 | 47 |
| dsRNA #2 | CTCGTAATACGACTCACTATAGGGCGACGGAAC AGTGAAGCACTTTGCACTTACTGATGGGACTCA AATAACTGGAGATGCATATGTTTTTGCAGCACC AGTTGATATCTTCAAGCTTCTTGTACCACAAGAG TGGAGAGAGATCTCTTATTTCAAAAGGCTGGAT AAGTTGGTGGGAGTTCCTGTCATCAATGTTCATA TATGGTTTGACAGAAAACTGAAGAACACGTATG ACCACCTTCTTTTCAGCAGGAGTTCACTTTTAAG CGTTTATGCAGACATGTCTTTAGCGTGCAAGGA GTACTATGATCCAAACCGTTCGATGCTGGAGTT GGTTTTTGCTCCAGCAGAGGAATGGATCGGACG GAGTGACACCGAAATCATCGAAGCAACTATGCT AGAGCTAGCCAAGTTGTTTCCTGATGAAATCGC TGCTGACCAGAGTAAAGCAAAGATTCTTAAATA CCATGTTGTGAAGACACCGAGGTCCGTTTACAA GACCGTCCCGAATCGCCCTATAGTGAGTCGTATT ACGAG/144 | 537 |

Example 31

Altered TB1 Expression Following Treatment with TB1 dsRNA in Corn

Corn seeds were treated using the protocol described in Example 1. Seeds were washed for 4 h, dried over night at 30° C. and treated with TB1 dsRNA (see Table 20) at a concentration of 25 μg/ml, for 24 hours at 15° C. As a control, seeds were treated with CGMMV dsRNA (Table 1, product 1, SEQ ID NO: 8) at the same concentration. Total RNA was extracted from leaves of germinated seeds 7.5 weeks post germination. cDNA was prepared using oligo-dT primers and the expression level of TB1 mRNA was determined in treated and control plants by real-time PCR, using GPM 120 as a normalizer (see Table 20).

Figure 58A:
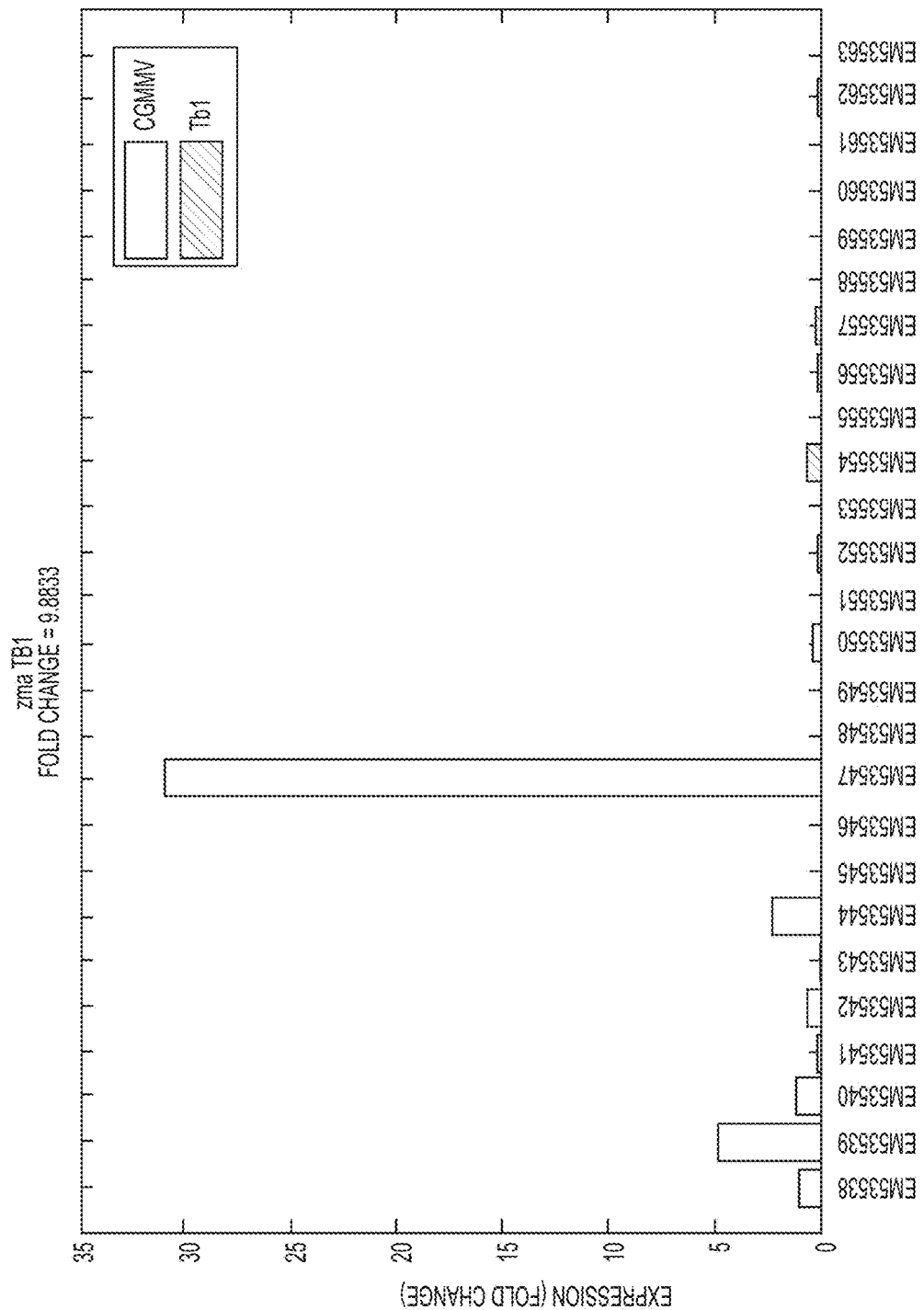
FIGS. 58A-B are bar graphs showing real-time PCR analysis of TB1 mRNA expression in 7.5-week old corn plants germinated from seeds treated with 25 µg/ml dsRNA for 24 hours.
Figure 58B:
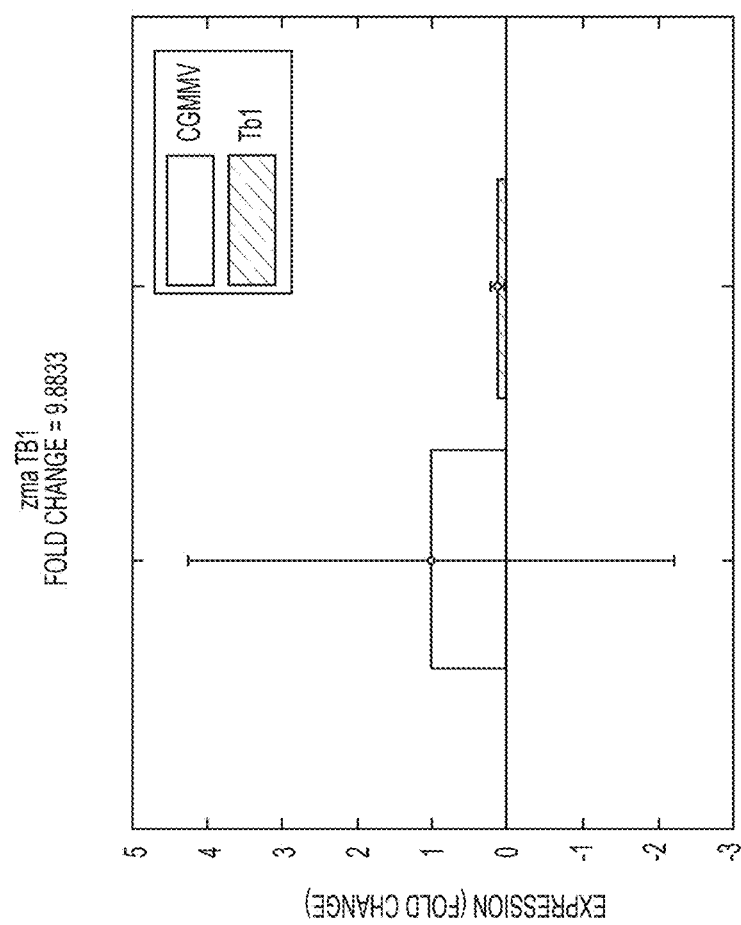

This analysis showed down-regulation of TB1 mRNA following dsRNA treatment. The median expression level of TB in plants treated with TB1 dsRNA was 9.88-fold lower than in control plants treated with CGMMV dsRNA (FIGS. 58A-B).

TABLE 20 dsRNA of Corn TB1 and Primers used for real-time PCR of TB1 and GPM120 mRNAs.

| Target | Sequence/SEQ ID NO: | Length (nt) |
|---|---|---|
| TB1 dsRNA | CTAATACGACTCACTATAGGGAGGT GATCAACTCGCCGGACCTGCCGGTGC AGGCGCTGATGGACCACGCGCCGGC GCCGGCTACAGAGCTGGGCGCCTGC GCCAGTGGTGCAGAAGGATCCGGCG CCAGCCTCGACAGGGCGGCTGCCGC GGCGAGGAAAGACCGGCACAGCAAG ATATGCACCGCCGGCGGGATGAGGG ACCGCCGGATGCGGCTCTCCCTTGAC GTCGCGCGCAAATTCTTCGCGCTGCA | 481 |

TABLE 20-continued dsRNA of Corn TB1 and Primers used for real-time PCR of TB1 and GPM120 mRNAs.

| Target | | Sequence/SEQ ID NO: | Length (nt) |
|---|---|---|---|
| | | GGACATGCTTGGCTTCGACAAGGCA<br>AGCAAGACGGTACAGTGGCTCCTCA<br>ACACGTCCAAGTCCGCCATCCAGGA<br>GATCATGGCCGACGACGCGTCTTCGG<br>AGTGCGTGGAGGACGGCTCCAGCAG<br>CCTCTCCGTCGACGGCAAGCACAACC<br>CGGCAGAGCAGCTGGGAGGAGGAGG<br>AGATCAGAAGCCCAAGGGTAATTGC<br>CGTCTCCCTATAGTGAGTCGTATTAG/<br>145 | |
| | Forward primer | AATCGGTGTCGTCGATTTGG/146 | 20 |
| | Reverse primer | GGCGGATACTGTTTGATCTC/147 | 20 |
| GPM120 | Forward primer | GCTGCGTGTTGTGCGTTCTG/148 | 20 |
| | Reverse primer | TCGTCGCGTGCTGTCTGTTC/149 | 20 |

Example 32

Altered NAC Expression Following Treatment with NAC dsRNA in Corn

The two indicated NAC dsRNA sequences (Table 11) were synthesized in vitro using a convergent T7 RNA polymerase method, and diluted in 0.1 mM EDTA to a concentration of 50 µg/ml total nucleic acid. Fifteen inbred (LH244) maize seeds were incubated in 7.5 ml of this dsRNA solution in a 15 ml tube in the dark at 15° C., with gentle oscillation, for 24 hours. One set of seeds was washed 3 times with water after treatment with dsRNAs, and then dried overnight at 30° C. A second set of seeds was planted directly after imbibition in the dsRNA solution.

Following treatment, seeds were either transferred to seed germination boxes (15 seed per box) containing moistened filter paper and germinated in a growth chamber set at 25° C. in the dark, or were planted in soil and germinated in a greenhouse.

Shoot tissues, including mesocotyl and coleoptile base, were harvested from the germinating seeds in the germination boxes 5 days after treatment for RNA analysis. Seeds that had been dried had only 4 days to germinate, while seeds that were germinated without the drying step had 5 days for germination. However, drying resulted in improved synchronicity in germination so that the 2 sets of plants spanned similar developmental stages. RNA analysis was conducted by Taqman, using the Zm.GPM 120 gene for normalization of the values to correct for differences in sample concentration (Table 21). RQ values were transformed to log 10 for analysis. Outlier data points are defined as being 3 standard deviations from the mean, and were removed from the dataset before analysis.

Figure 59A:
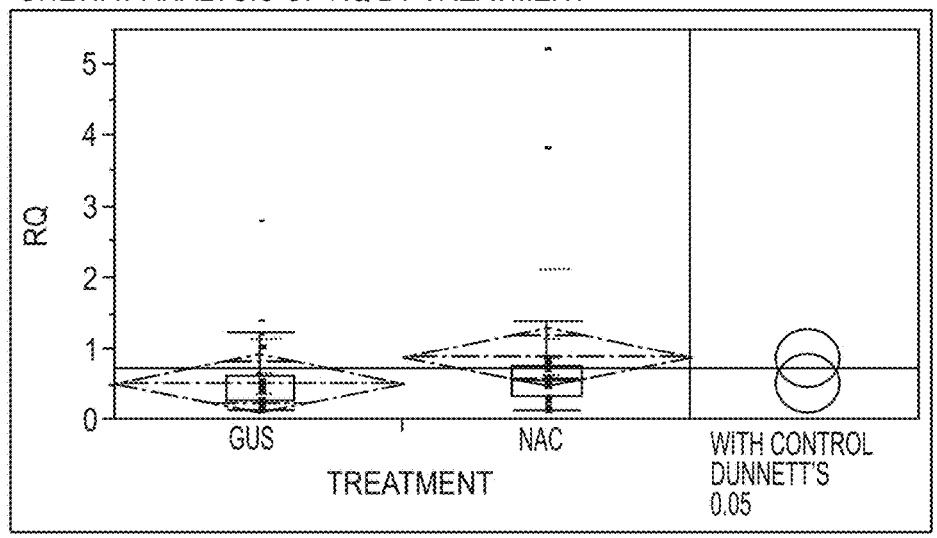
FIGS. 59A-C are bar graphs showing real-time PCR analyses of NAC mRNA expression in five-days old corn shoots and 12-days old leaves germinated from seeds treated with 50 µg/ml dsRNA for 24 hours.
Figure 59B:
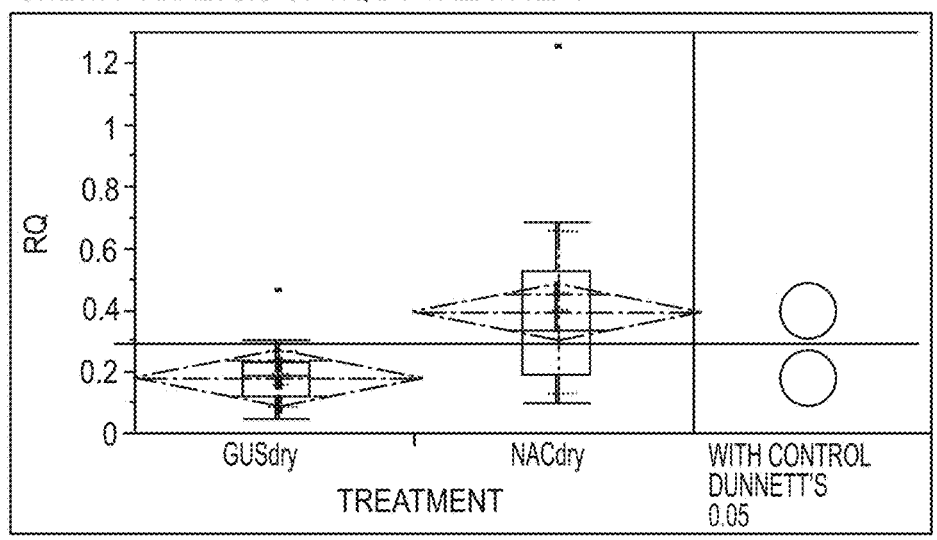

Treatment of seeds with NAC dsRNAs resulted in increased NAC expression so that NAC mRNA levels were 1.7 to 2.2 times those of GUS control values (Table 22 and FIGS. 59A and 59B).

Figure 59C:
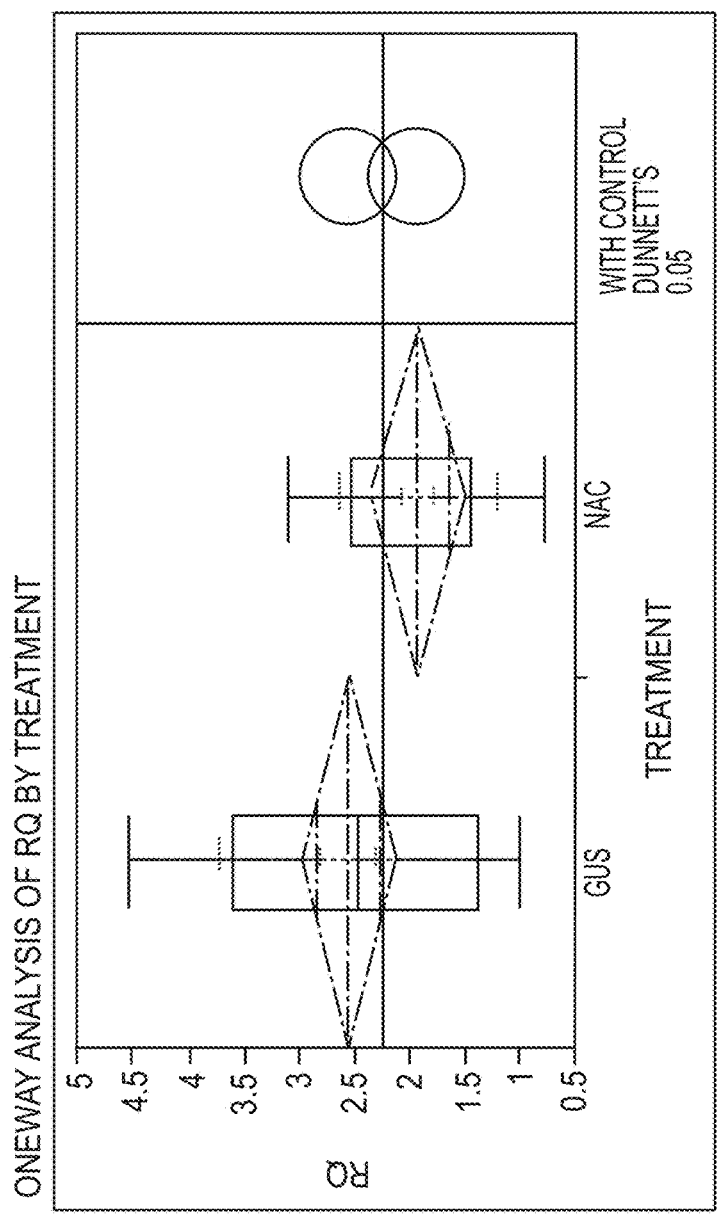

In another experiment, seeds were treated as described above and directly planted in soil. 12 days after planting, there was a decreased NAC mRNA expression in the V1 leaf in seeds that were not washed and dried before planting (FIG. 59C and Table 23). These plants also showed a decrease in plant height 16 days after planting (Table 24).

TABLE 21

Primers used to determine expression level of NAC mRNA by real-time PCR.

| Target | | Sequence/SEQ ID NO: | Length (nt) |
|---|---|---|---|
| NAC | Forward primer | CTGGATTGGAAACTGGGATTGT/150 | 22 |
| | Reverse primer | TTGCCCCATTTTGCATATAGC/151 | 21 |
| | Taqman probe | 6FAM-ATTGTGCCGTTGAATAT-MGBNFQ/152 | 17 |
| GPM120 | Forward primer | AGGCTTTCGCTGCGTGTT/153 | 18 |
| | Reverse primer | TGGCCCATCCAAACTCAGA/154 | 19 |
| | Taqman probe | VIC-TGCGTTCTGCTTGAAT-MGBNFQ/155 | 16 |

TABLE 22 mRNA concentrations for NAC gene in corn 5 days-old seedling shoot tissue.

| Treatment | Number | Mean RQ | Std Dev | Std Err Mean | Lower 95% | Upper 95% | fold change | Dunnett's comparison to control on log10 transformed RQ values (signficant if pVal < 0.05) |
| --- | --- | --- | --- | --- | --- | --- | --- | --- |
| NAC | 22 | 0.904 | 1.225 | 0.261 | 0.361 | 1.447 | 1.7 | 0.0882 |
| GUS | 22 | 0.543 | 0.623 | 0.133 | 0.267 | 0.819 | | 1.0000 |
| NAC_Dry | 21 | 0.401 | 0.267 | 0.058 | 0.279 | 0.522 | 2.2 | 0.0004 |
| GUS_Dry | 21 | 0.185 | 0.092 | 0.020 | 0.142 | 0.227 | | 1.0000 |

GUS_dry and NAC_dry, seeds were washed and dried after treatment with dsRNAs. The other set was put directly into seed germination boxes after treatment with dsRNAs. Comparisons with a control using Dunnett's Method, Control Group=GUS_dry or GUS, as appropriate.

TABLE 23 mRNA concentrations for NAC gene in corn 12 days-old leaf tissue.

| Treatment | Number | Mean RQ | Std Dev | Std Err Mean | Lower 95% | Upper 95% | % change from GUS control | fold change | Dunnett's p value |
| --- | --- | --- | --- | --- | --- | --- | --- | --- | --- |
| GUS | 22 | 2.56 | 1.17 | 0.25 | 2.04 | 3.08 | | | 1 |
| NAC | 21 | 1.94 | 0.72 | 0.16 | 1.62 | 2.27 | −24.2% | 0.76 | 0.0441 |

TABLE 24

Height of 16 days old corn plants.

| Treatment | N | Mean Height (cm) | Std Dev | Std Err Mean | Upper 95% Mean | Lower 95% Mean | % change | Dunnett's p-value |
| --- | --- | --- | --- | --- | --- | --- | --- | --- |
| GUS | 43 | 48.91 | 3.37 | 0.51 | 49.94 | 47.87 | | 1.0000 |
| NAC | 43 | 45.47 | 2.86 | 0.44 | 46.34 | 44.59 | −7.04% | 0.0001 |

Example 33

Altered Expression of HY5 mRNAs in Lettuce Plants after Treatment of Seeds with HY5 dsRNA The LONG HYPOCOTYL 5 (HY5) gene encodes a key positive regulator of plant response to light (Oyama, Shimura et al. 1997). Lettuce contains 2 genes related to *Arabidopsis* HY5 on chromosomes 5 and 6 which have 79% DNA sequence identity to each other. A ~500 bp region was selected from the cDNA sequence of each gene as a trigger (Table 25), and dsRNA was made in vitro using the convergent T7 RNA polymerase method. The dsRNAs were solubilized in 0.1 mM EDTA at a concentration of 50 µg/ml. Thirty lettuce seeds of the variety Sun Valley were incubated in 1.5 ml of this dsRNA solution in a 2 ml eppendorf tube in the dark at 15° C., with gentle shaking, for 24 hours. The seeds were then washed 3 times with water, and then either transferred to seed germination boxes (9 seeds per box) containing 12 ml water, or to soil. Seeds in boxes were germinated in the light at 25° C. for 7 days, and shoot tissue was then harvested for RNA analysis. RNA analysis was conducted by Taqman, using a lettuce ubiquitin assay for normalization of the values to correct for differences in sample concentration (Table 25).

TABLE 25 dsRNA of HY5.5 and HY5.6 and primers used for real-time PCR.

| Target | | Sequence/SEQ ID NO: | Length (nt) |
| --- | --- | --- | --- |
| HY5.5 | dsRNA | AGAGTTTCGGCTCAACAAGCAAGGGAGAGGAAGAA GGCATACTTGAATGAATTGGAAGTGCGAGTAAAAGA AATTGAAAAGAAGAACTCCGAGCTTGAAGAGCGACT TTCAACTCTCCAAAATGAGAATCAAATGCTTAGACA TATCTTGAAAAACACTACAGCCGGTATGCAAGAAAA GAAGTAGACATATGATTAGAAGAGGAAAAGCATTAC ATGTGCAATCCGATCATAGCTTGAAAATCGAAGGG TTTGGTTTAGGATCGAGACTTGTTATTGTGGTTATTT CTTTTCCTAGCAAACATAATGAGAATCCAACCATCTT TACGTACGATTCGATTAAAGATCTTTAAGTCATGTAG | 440 |

TABLE 25-continued dsRNA of HY5.5 and HY5.6 and primers used for real-time PCR.

| Target | | Sequence/SEQ ID NO: | Length (nt) |
|---|---|---|---|
| | | GTGGTAATGGGCTGTGTTTCTAAATGACCAAAAAAG ATGTAAAGTATTGCATATGATATGGGTTTTAATTTGT AGCAC/156 | |
| | F primer | CATGTGCAATCCGAATCATAGC/157 | 22 |
| | R primer | ACCACAATAACAAGTCTCGATCCTAA/158 | 26 |
| | Taqman probe | 6FAM-TGAAAATCGAAGGGTTTG-MGBNFQ/159 | 18 |
| HY5.6 | dsRNA | ATGCAGGAGCAAGCAGCAACGAGTTCCATGGCGGCT AGTCTACCTTCAAGTAGCGAGAGATCTTCAAGCTCTG CTCTACAAATTGAAATTAAAGAAGGAATGGAAAGTG ATGACGAGATCAGAAGAGTGCCGGATATGGGCGGA GAAGCCGCCGGAGCATCAAGATCCGGCAGAGAAAC CGGTTCAAATCAAAATAATCCAGACCGGGTTCAACA CTCAGCTGAAGGAACAAAGAAAAGAGGGAAAACTC CTGCTGATAGAGAAAGCAAGCGATTAAAGAGATTGT TGAGGAATAGAGTATCGGCTCAACAAGCAAGAGAG AGAAAGAAGGCGTACATGACCGAGTTGGAGAGCCG AGTTAAAGAGTTGGAGAAGAAGAACTCGGAGCTTGA AGAACGTTT/160 | 401 |
| | F primer | CCACAATGCAAAATGAAAACCA/161 | 22 |
| | R primer | GCATCCCAGACGTTGTGTTCT/162 | 21 |
| | Taqman probe | 6FAM-TGCTTAGACACATCTTG-MGBNFQ/163 | 17 |
| Ubiquitin | F primer | TTGTCTTGAATTTTAGCTTTGACGTT/164 | 26 |
| | R primer | CCTTGACCGGAAAAACAATCA/165 | 21 |
| | Taqman probe | VIC-TCAATGGTGTCGGAGCTTTCCACTTCC-TAMRA/166 | 27 |

Figure 60A:
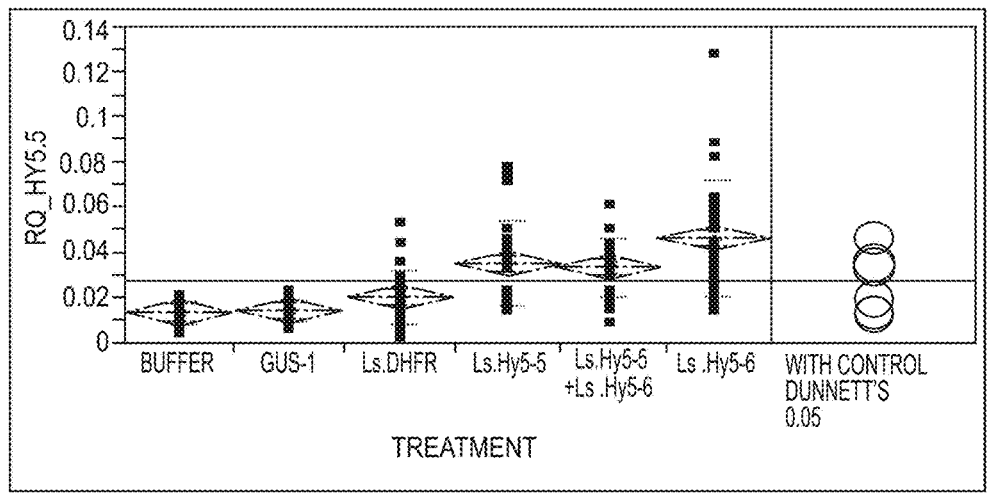
FIGS. 60A-D are graphs showing real-time PCR analyses of HY5 mRNA expression in one-week old and two-week old lettuce plants germinated from seeds treated with 50 µg/ml dsRNA for 24 hours.
Figure 60B:
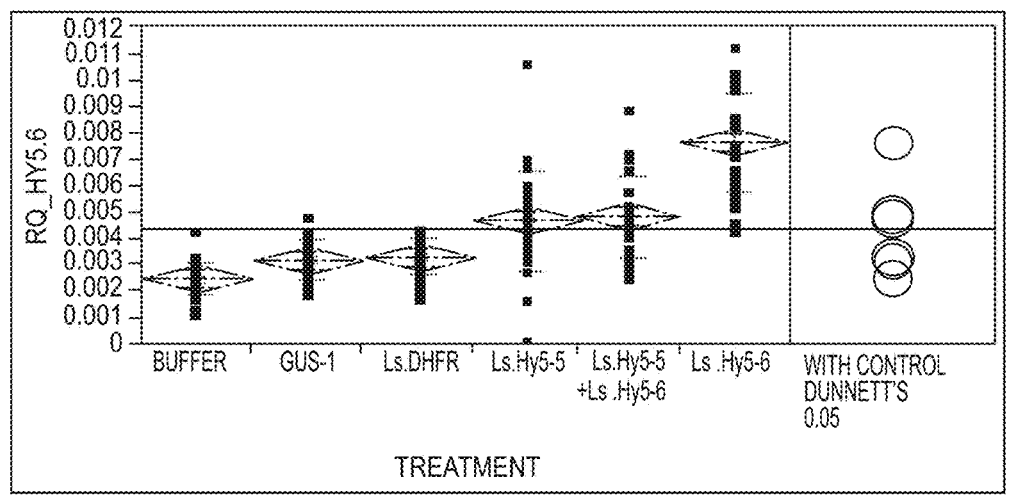

Table 26 and FIG. 60A shows that mRNA levels of the HY5.5 gene was elevated 2-3 fold when seeds were treated with dsRNAs from the HY5.5 or HY5.6 genes compared to seedlings from seeds treated with GUS dsRNA. mRNA levels of the HY5.6 gene were elevated about 2-fold after treatment with HY5 dsRNAs compared to treatment with GUS dsRNA (Table 27 and FIG. 60B).

TABLE 26

Concentration of HY5.5 mRNA in shoots of 1 week old seedlings treated with different dsRNAs.
HY5.5, Means for Oneway Anova, α = 0.05

| Treatment | Number | Mean RQ | Std Dev | Std Err Mean | Lower 95% | Upper 95% | % change from GUS control | Dunnett's p value |
|---|---|---|---|---|---|---|---|---|
| buffer control | 28 | 0.013 | 0.005 | 0.001 | 0.011 | 0.015 | −8% | 0.9960 |
| GUS-1 dsRNA | 29 | 0.014 | 0.005 | 0.001 | 0.012 | 0.016 | 0% | 1.0000 |
| Sl.Hy5-5 + Sl.Hy5-6 dsRNA | 25 | 0.033 | 0.013 | 0.003 | 0.028 | 0.038 | 135% | <.0001 |
| Sl.Hy5-5 dsRNA | 27 | 0.035 | 0.019 | 0.004 | 0.028 | 0.042 | 148% | <.0001 |
| Sl.Hy5-6 dsRNA | 30 | 0.046 | 0.026 | 0.005 | 0.037 | 0.056 | 227% | <.0001 |

Comparisons with a control using Dunnett's Method, Control Group = GUS-1.

TABLE 27

Concentration of HY5.6 mRNA in shoots of 1 week old seedlings treated with different dsRNAs.
HY5.6, Means for Oneway Anova, α = 0.05

| Treatment | Number | Mean RQ | Std Dev | Std Err Mean | Lower 95% | Upper 95% | % change from GUS control | Dunnett's p value |
|---|---|---|---|---|---|---|---|---|
| buffer control | 28 | 0.002 | 0.001 | 0.000 | 0.002 | 0.003 | −22% | 0.2116 |
| GUS-1 dsRNA | 29 | 0.003 | 0.001 | 0.000 | 0.003 | 0.003 | 0% | 1.0000 |
| Sl.Hy5-5 + Sl.Hy5-6 dsRNA | 25 | 0.005 | 0.002 | 0.000 | 0.004 | 0.005 | 53% | 0.0002 |
| Sl.Hy5-5 dsRNA | 27 | 0.005 | 0.002 | 0.000 | 0.004 | 0.005 | 48% | 0.0006 |
| Sl.Hy5-6 dsRNA | 29 | 0.008 | 0.002 | 0.000 | 0.007 | 0.008 | 142% | 0.0000 |

Comparisons with a control using Dunnett's Method, Control Group = GUS-1.

Figure 60C:
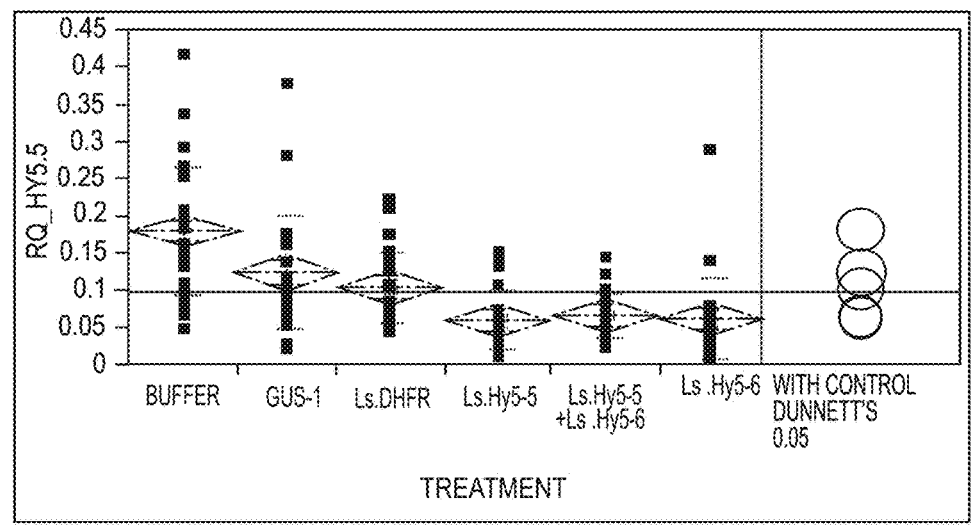
Figure 60D:
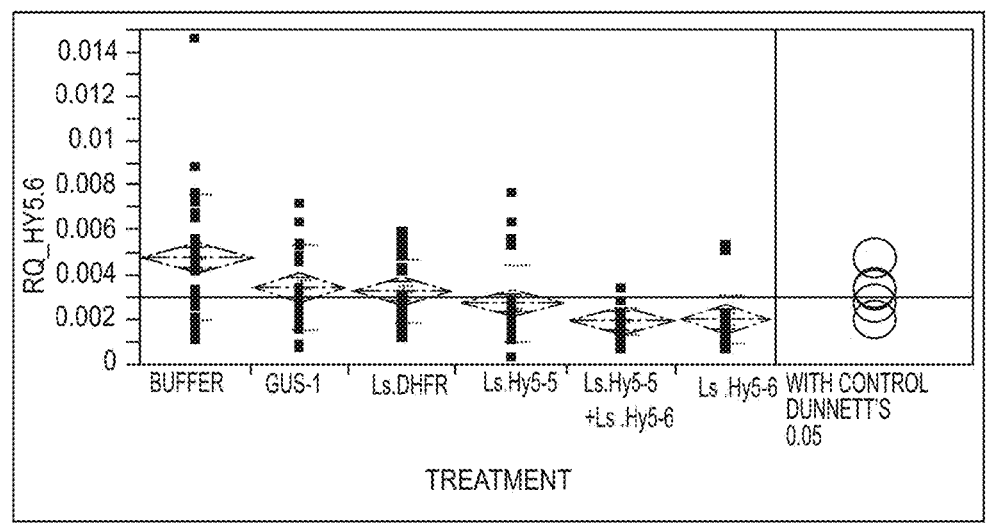

In another experiment, plants were treated as described above and were grown for 2 weeks in the greenhouse. Then, a leaf punch was harvested and analyzed for mRNA concentration. In these older plants, a decrease in HY5 expression was observed. Table 28 and FIG. 60C shows the mRNA levels of the HY5.5 gene in plants when seeds were treated with dsRNAs from the HY5.5 or HY5.6 genes compared to plants grown from seeds treated with GUS dsRNA and with lettuce DHFR dsRNA (Table 30) as controls. Table 29 and FIG. 60D shows the mRNA levels of the HY5.6 gene in plants when seeds were treated with dsRNAs from the HY5.5 or HY5.6 genes compared to plants grown from seeds treated with GUS dsRNA and with lettuce DHFR dsRNA (Table 30) as controls.

TABLE 28

Concentration of HY5.5 mRNA in leaves of 2 week old plants treated with different dsRNAs.

| Treatment | Number | Mean RQ | Std Dev | Std Err Mean | Lower 95% | Upper 95% | % change from GUS control | fold change | Dunnett's p value |
|---|---|---|---|---|---|---|---|---|---|
| Buffer | 29 | 0.179 | 0.086 | 0.016 | 0.146 | 0.212 | 45% | 1.4 | 0.0028 |
| GUS-1 | 26 | 0.124 | 0.076 | 0.015 | 0.093 | 0.154 | 0% | 1.0 | 1 |
| Ls.DHFR | 29 | 0.103 | 0.048 | 0.009 | 0.084 | 0.121 | −17% | 0.8 | 0.533 |
| Ls.Hy5-5 | 28 | 0.058 | 0.038 | 0.007 | 0.043 | 0.073 | −53% | 0.5 | 0.0003 |
| Ls.Hy5-5 + Ls.Hy5-6 | 29 | 0.065 | 0.030 | 0.006 | 0.054 | 0.076 | −47% | 0.5 | 0.0013 |
| Ls.Hy5-6 | 27 | 0.061 | 0.054 | 0.010 | 0.040 | 0.082 | −51% | 0.5 | 0.0007 |

TABLE 29

Concentration of HY5.6 mRNA in leaves of 2 week old plants treated with different dsRNAs.

| Treatment | Number | Mean RQ | Std Dev | Std Err Mean | Lower 95% | Upper 95% | % change from GUS control | fold change | Dunnett's p value |
|---|---|---|---|---|---|---|---|---|---|
| Buffer | 29 | 0.005 | 0.003 | 0.001 | 0.004 | 0.006 | 41% | 1.4 | 0.0166 |
| GUS-1 | 26 | 0.003 | 0.002 | 0.000 | 0.003 | 0.004 | 0% | 1.0 | 1.000 |
| Ls.DHFR | 28 | 0.003 | 0.001 | 0.000 | 0.003 | 0.004 | −4% | 1.0 | 0.9984 |
| Ls.Hy5-5 | 29 | 0.003 | 0.002 | 0.000 | 0.002 | 0.003 | −20% | 0.8 | 0.4458 |
| Ls.Hy5-5 + Ls.Hy5-6 | 29 | 0.002 | 0.001 | 0.000 | 0.002 | 0.002 | −43% | 0.6 | 0.009 |
| Ls.Hy5-6 | 26 | 0.002 | 0.001 | 0.000 | 0.002 | 0.002 | −41% | 0.6 | 0.0188 |

Example 34

Altered Expression of Dihydroflavonol 4-Reductase (DHFR) mRNA in Lettuce Plants after Treatment of Seeds with DHFR dsRNA Dihydroflavonol 4-Reductase (DHFR) is an enzyme in the anthocyanin biosynthetic pathway. One DHFR gene was identified in lettuce, and a 524 bp region was selected from the cDNA sequence as a trigger (Table 30). dsRNA was made in vitro using the convergent T7 RNA polymerase method for DFR and for the GUS control sequence.

TABLE 30 dsRNA of DHFR and primers used for real-time PCR.

| Target | | Sequence/SEQ ID NO: | Length (nt) |
|---|---|---|---|
| DHFR | dsRNA | AGAGGATTCTCCGACCACCGTGTGTGTCACTGGAGC TGCCGGATTCATTGGTTCATGGCTCGTTATGAGACTT CTTGAACGTGGGTATAATGTTCATGCCACTGTTCGTG ACCCTGATGACATAAAGAAAGTGAAACATTTATTGG AACTACCAAAAGCAGCAACAAACTTGACGTTATGGA AGGCAGATTTGACACAAGAAGGAAGCTTTGATGAAG CCATTGAAGGTTGTCATGGAGTCTTTCATGTGGCTAC GCCTATGGACTTTCAGTCCAAGGATCCTGAGAATGA GATCATAAAGCCAACAATAGAAGGTGTATTAAGCAT CGTAAGATCATGTGTGAAAGTCAAAACAGTCAAGAA | 524 |

TABLE 30-continued dsRNA of DHFR and primers used for real-time PCR.

| Target | Sequence/SEQ ID NO: | Length (nt) |
|---|---|---|
|  | ATTGGTGTTTACATCCTCTGCGGGGACAGTGAACGTG CACGGAAATGATCAACTTCCGGTCTATGACGAGTCT CATTGGAGCGATTTGGACTTCATCTACTCCAAGAAA ATGACTGCATGGATGTATTTCGTATCAAAAACATTGG CAGAAAAAGCAGCAT/167 |  |
| F primer | GGAGATGTTCAAAGGAGCAATTG/168 | 23 |
| R primer | TTGATTGTGGAATATGGAAGCATT/169 | 24 |
| Taqman probe | 6FAM-TAGTTGCAGAGAGAAAG-MGBNFQ/170 | 17 |

Figure 61:
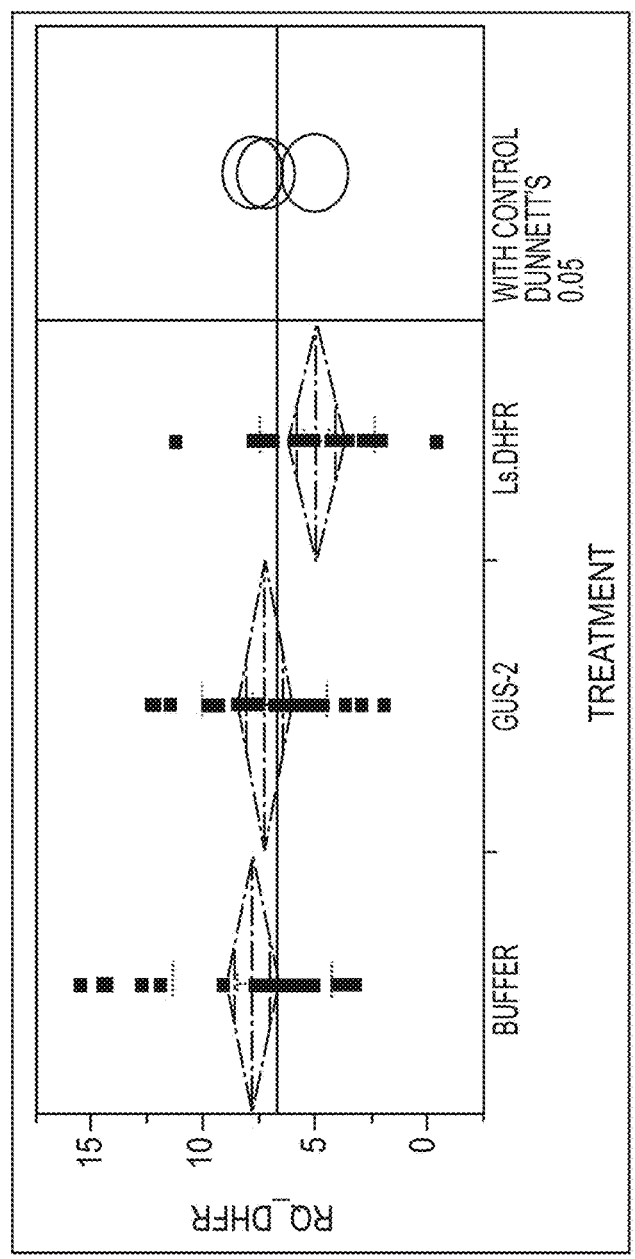
FIG. 61 is a graph showing real-time PCR analysis of DHFR mRNA expression in one-week old lettuce plants germinated from seeds treated with 50 µg/ml dsRNA (SEQ ID NO: 167) for 24 hours. GUS dsRNA (SEQ ID NO: 21) or 0.1 mM EDTA (buffer) served as controls. Each dot represents one plant.

The dsRNAs were solubilized in 0.1 mM EDTA at a concentration of 50 μg/ml. Lettuce variety 8N LLF 65-2713141 Batavia is a highly pigmented red variant used for these studies. Thirty lettuce seeds were incubated in 1.5 ml of the dsRNA solution in a 2 ml eppendorf tube in the dark at 15° C., with gentle shaking, for 24 hours. The seeds were then washed 3 times with water, and then either transferred to seed germination boxes (10 seeds per box) containing 12 ml water, or to soil. Seeds in boxes were germinated in the light at 20° C. for 7 days, and shoot tissue was then harvested for RNA analysis. RNA analysis was conducted by Taqman, using a lettuce ubiquitin assay for normalization of the values to correct for differences in sample concentration (Tables 25 and 30).

mRNA levels for DHFR were significantly reduced when seeds were treated with dsRNA for DHFR compared to seeds treated with GUS dsRNA or the buffer control (Table 31 and FIG. 61).

TABLE 31

Concentration of DHFR mRNA in shoots of 1 week old seedlings treated with dsRNA.

| Treatment | Number | Mean RQ | Std Dev | Std Err Mean | Lower 95% | Upper 95% | fold change | Dunnett's comparison to control |
|---|---|---|---|---|---|---|---|---|
| buffer control | 25 | 7.800 | 3.555 | 0.711 | 6.333 | 9.268 | 1.1 | 0.7386 |
| GUS-2dsRNA | 28 | 7.256 | 2.792 | 0.528 | 6.173 | 8.338 | 1.0 | 1 |
| Ls.DHFR dsRNA | 23 | 4.966 | 2.548 | 0.531 | 3.864 | 6.068 | 0.7 | 0.0159 |

Comparisons with a control using Dunnett's Method, Control Group = GUS-2.

Example 35

Altered Expression of DND1 mRNA and Reduced RKN Root Galling in Cucumber Following Seed Treatment with DND1 dsRNAs

DND1, defense no death, is a negative regulator of plant defenses. Mutations in DND1 lead to constitutive systemic resistance and elevated levels of salicylic acid (Clough et al. 2000). Seeds of Straight 8 cucumber variety were placed in a monolayer in a plastic box and covered with 5-12 volumes of water at room temperature (~20 C). Seeds were washed for 4 hours in water with gentle agitation. Following the washing, seed were air dried on filter paper at ~30 C for 12-24 hr. Cucumber DND1 dsRNAs (Table 32) were resuspended in 0.1 mM EDTA (diluted from a 0.5M pH8.0 stock solution) to 100 μg/ml. A 1:5 (w/v) ratio of dsRNA solution to seed (e.g. for 1 gr of seed a 5 mL solution of dsRNA in EDTA) was used. Seeds were placed in a 50 mL conical tube and incubated in the dark at 15 C with gentle agitation for 24 hr. Following incubation, seeds were washed three times with gentle agitation for 1 minute each in a volume of water to completely fill the plastic container, and dried on filter paper before planting.

TABLE 32 dsRNAs of GFP and cucumber DND1 and primers used for real-time PCR.

| Target | | Sequence/SEQ ID NO: | Length (nt) |
|---|---|---|---|
| DND1 | dsRNA #1 (T33787) | GTCTTGGAATGCTACGCCTGTACCCAAGTGGGCGTTC CAGCCTTCCACTCCACCAGCTGCGACCACGCCCACC AACAACCCGAATGGGAAGCCTCCGCGGGCTCTTCCC TGGTTCCAATCCAACCCACAAAATCCTCACCAGCGC CCCGACATTCTTCGGCGGGTTGCTTCGGGACGGTTCT GGACCCAAGAAAGAAACCGGTTCAGAGATGGAACC GGGTTCTGTTATTGGCCCGGGGAATGTCTCTTGCGGT TGATCCGCTTTACTTCTATGCTCTGTCTATTGGAAGA GGAGGATGGCCTTGCCTGTACATGGATGGTGGGTTG GCTGCCGGAGTTACGGTGGTTCGAACGTGTCTTGATA TAGTGCACTTGTGGCACGTGTGGCTTCAGTTCAGGCT TGCTTACGTGTCGAAAGAGAGTATGGTGATTGGGTG TGGGAAACTGGTGTGGGATGCACGTGATATTGCTTCT CACTATGTTCGTTCTTTCAAAGGC/171 | 498 |
| | dsRNA #2 (T33788) | GTACGGTGCTTAGTGGATTGTTGCTTTTCACTCTTTTG ATTGGTAATATTCAGGTACTTTTGCACGCTGTCATGG CAAGGAGGCGAAAAATGCAGCTGAGATGTCGAGATT TGGAGTGGTGGATGAGGAGACGACAATTGCCATCTC GTTTGAAACATCGAGTTCGACACTATGAGCACCAGA GATGGGCAGCTATGGGAGGAGAAGATGAGATGGAA CTAATCAATGATTTGCCAGAAGGTCTTAGAAGAGAT ATCAAACGTCATCTTTGTGTTGACCTAATCAGAAAGG TGCCTCTCTTTCAAAACCTGGAGGAGCTGATTCTAGA CAACATATGTGACAAAGTCAAGCCACTTGTATTCTCC AAAGATGAAAAGATAATCAGAGAAGGAGATCCTGTT CCAAGGATGTTATTCATAGTGTGTGGACGAGTAAAA CGTAGCCAAAGCCTGAGCAAGGGCATGACAGCGACA AGTTTTATTGAACCGGGAGGATTTCTTGGTGAC/172 | 506 |
| | F primer | CAGCGAGTTGCTTCTTGTATCCA/173 | 23 |
| | R primer | TCCTCAGAGCAAGACAAAGATAAGTTG/174 | 27 |
| | Taqman probe | 6FAM-ACATTGTGAGAGAAACAAGT-MGBNFQ/175 | 20 |
| GFP | dsRNA | GGTGATGCAACATACGGAAAACTTACCCTTAAATTT ATTTGCACTACTGGAAAACTACCTGTTCCATGGCCAA CACTTGTCACTACTTTCTCTTATGGTGTTCAATGCTTT TCAAGATACCCAGATCATATGAAGCGGCACGACTTC TTCAAGAGCGCCATGCCTGAGGGATACGTGCAGGAG AGGACCATCTTCTTCAAGGACGACGGGAACTACAAG ACACGTGCTGAAGTCAAGTTTGAGGGAGACACCCTC GTCAACAGGATCGAGCTTAAGGGAATCGATTTCAAG GAGGACGGAAACATCCTCGGCCACAAGTTGGAATAC AACTACAACTCCCACAACGTATACATCATGGCCGAC AAGCAAAAGAACGGCATCAAAGCCAACTTCAAGACC CGCCACAACATCGAAGACGGCGGCGTGCAACTCGCT GATCATTATCAACAAAATACTCCAATTGGCGATGGC CCTGTCCTTTTACCAGACAACCATTACC/176 | 499 |
| ELF1a | F primer | ATGGCTTGCTGCCTGATGTATC/177 | 22 |
| | R primer | GGTGGCAACAGCAGCATTCA/178 | 20 |
| | Taqman probe | VIC-ATGTTGTGCCTAAGGAC-MGBNFQ/179 | 17 |

Figure 62A:
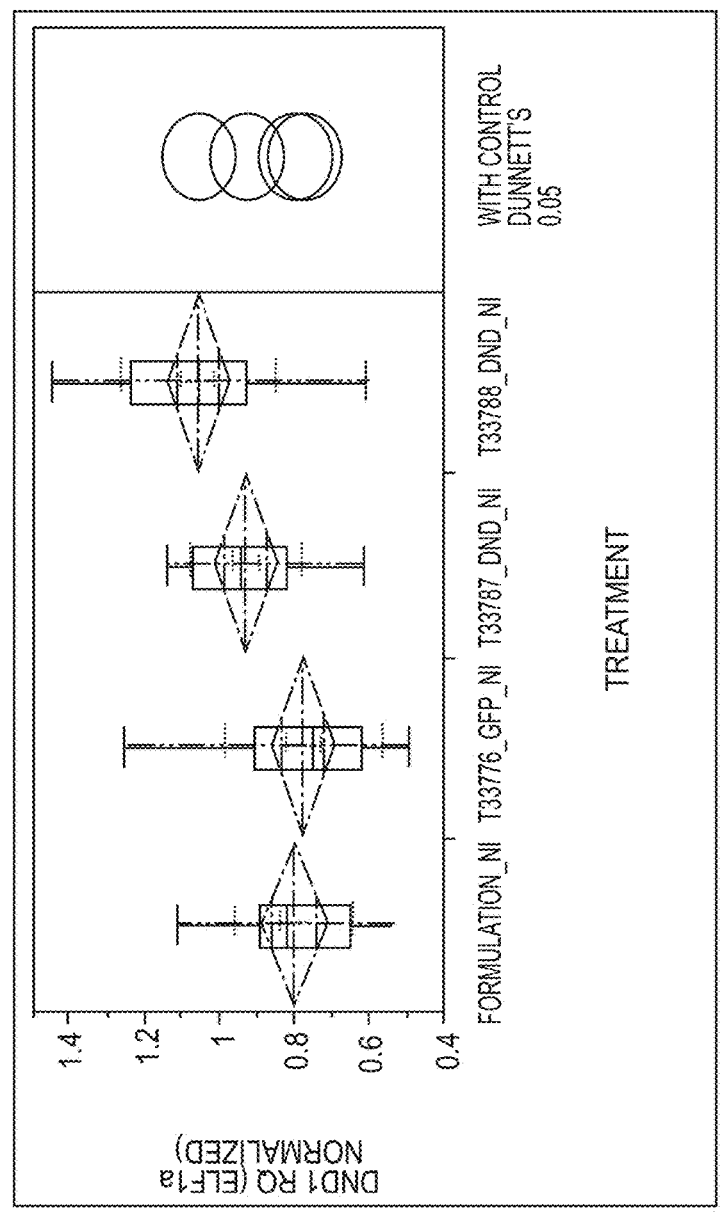
FIGS. 62A-B shows the effect of cucumber seed treatment with DND1 dsRNA.

RNA analysis was conducted by Taqman real time PCR using a cucumber ELF1a assay for normalization of the values to correct for differences in sample concentration (see Table 32 for primers and Taqman probes sequences). Analysis on samples from fifteen days old cucumber leaves germinated from seeds treated with DND1 dsRNAs have demonstrated altered expression of the DND1 gene compared to control seeds treated with GFP dsRNA (see Table 32 for GFP dsRNA sequence and Table 33 and FIG. 62A for real time PCR analysis).

TABLE 33

Concentration of DND1 mRNA in 15 days old cucumber leaves treated with DND1 dsRNAs.
Means and Std Deviations, Cs.DND1

| Treatment | Number | Mean RQ | Std Dev | Std Err Mean | Lower 95% | Upper 95% | % change from GFP control | fold change | Dunnett's p-value on LOG10 RQ |
|---|---|---|---|---|---|---|---|---|---|
| Formulation_NI | 19 | 0.806 | 0.157 | 0.036 | 0.730 | 0.881 | 3% | 1.0 | 0.8571 |
| T33776_GFP_NI | 20 | 0.782 | 0.209 | 0.047 | 0.684 | 0.879 | 0% | 1.0 | 1.0000 |

TABLE 33-continued

Concentration of DND1 mRNA in 15 days old cucumber leaves treated with DND1 dsRNAs.
Means and Std Deviations, Cs.DND1

| Treatment | Number | Mean RQ | Std Dev | Std Err Mean | Lower 95% | Upper 95% | % change from GFP control | fold change | Dunnett's p-value on LOG10 RQ |
|---|---|---|---|---|---|---|---|---|---|
| T33787_DND_NI | 20 | 0.934 | 0.150 | 0.033 | 0.864 | 1.004 | 19% | 1.2 | 0.0117 |
| T33788_DND_NI | 20 | 1.060 | 0.204 | 0.046 | 0.965 | 1.156 | 36% | 1.4 | <.0001 |

Comparisons with a control using Dunnett's Method, Control Group = GFP-1.

Figure 62B:
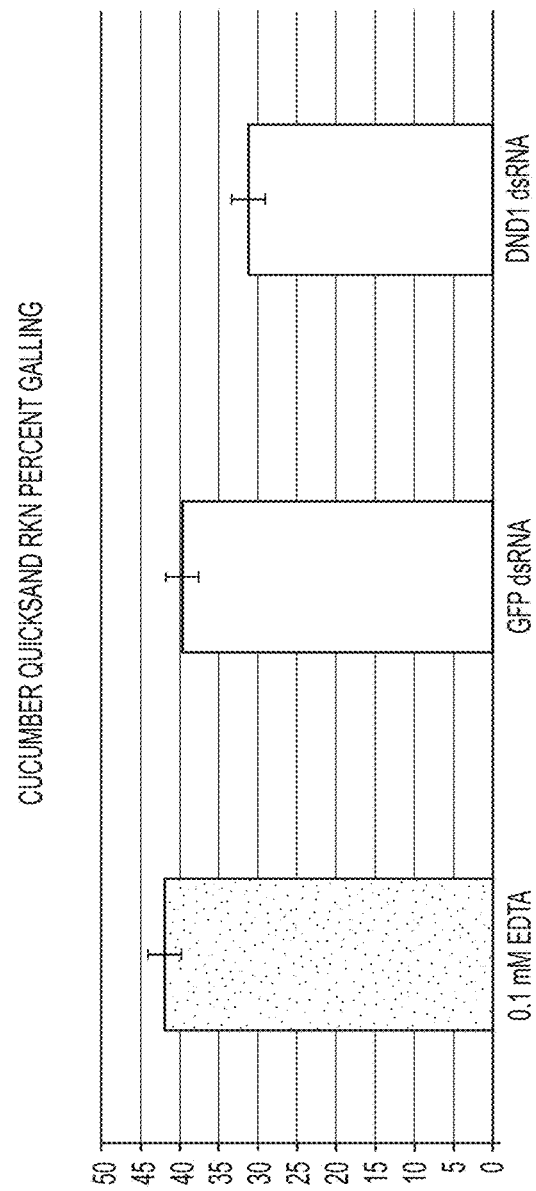

In another experiment, One hundred cucumber seeds were treated with dsRNA containing the cucumber DND1 transcribed sequence (Table 32, dsRNA #2 T33788) as described above. Treated seeds were plated on 1/4 MS plates for 3 days. Ten ml dry sand was added to each glass vial and seedlings were planted by tilting the vial and laying the seedling in the correct orientation so that the cotyledons are just above the sand and then tilting back to cover the radicles with sand. 3.3 ml water was added to each vial and the vials placed in racks under fluorescent light banks. 250 vermiform eggs or 300 J2 RKN were inoculated in each tube in 50 ul of deionized or spring water. Plants were watered as needed. Harvest of the cucumber plants was performed at 11 days after inoculation by washing sand off the roots. A percent gall rating of the roots was taken for each sample, demonstrating a 26% and 21% reduction in RKN galling when compared to control treatments with 0.1 mM EDTA and GFP dsRNA, respectively (FIG. 62B).

Example 36

Altered Expression of PMR5 mRNA in Cucumber Following Seed Treatment with PMR5 dsRNAs PMR5 belongs to a family of plant-specific genes of unknown function. Mutations in the *Arabidopsis* gene PMR5, powdery mildew resistance, have pectin enriched cell walls and confer powdery mildew resistance (Vogel et al. 2004).

Figure 63:
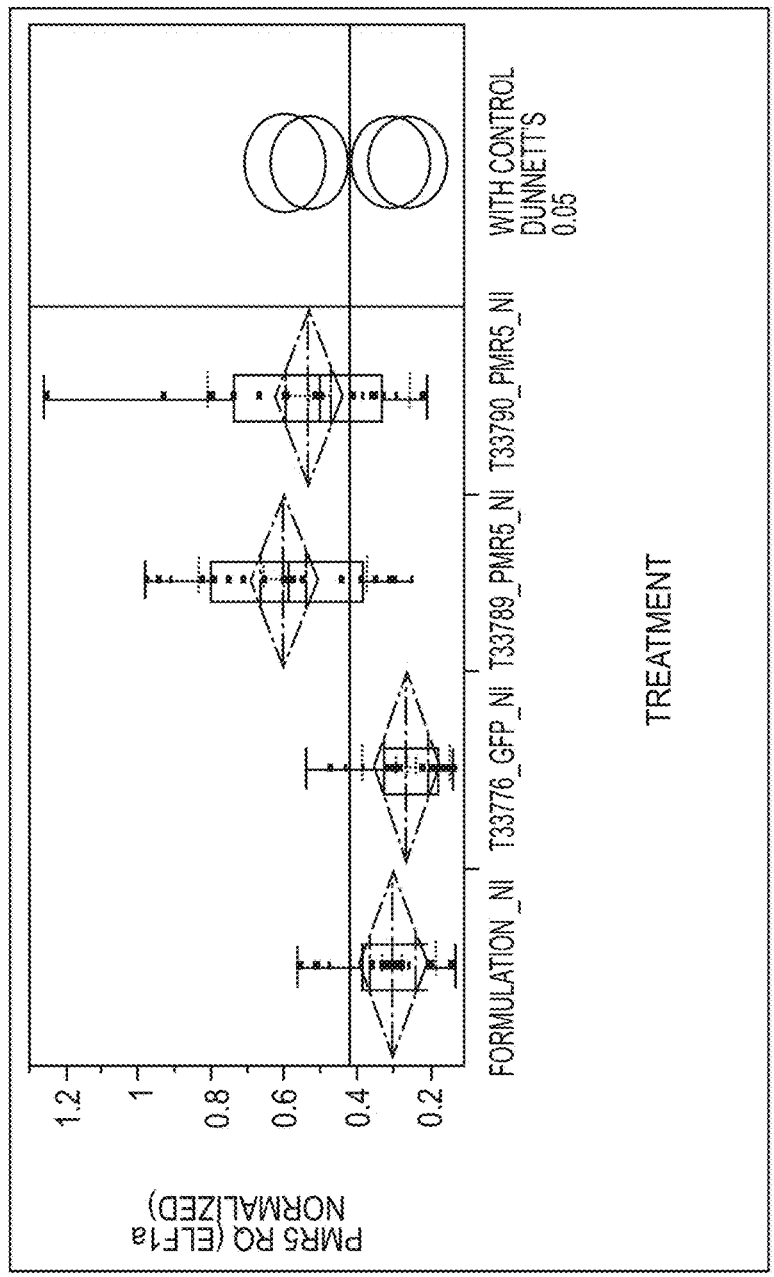
FIG. 63 is a graph showing real-time PCR analysis of PMR5 mRNA expression in 15-days old cucumber plants germinated from seeds treated with 100 µg/ml dsRNA (SEQ ID NOs: 180 and 181) for 24 hours. GFP dsRNA (SEQ ID NO: 176) or 0.1 mM EDTA (formulation) served as controls. Each dot represents one plant.

Cucumber seeds were treated with PMR5 dsRNAs (Table 34) as described in Example 35. Leaves germinated from treated seeds were analyzed as described in Example 35. An altered expression of the PMR5 gene was demonstrated in PMR5 treated seeds compared to GFP treated seeds (Table 35 and FIG. 63).

TABLE 34 dsRNAs of cucumber PMR5 and primers used for real-time PCR.

| Target | | Sequence/SEQ ID NO: | Length (nt) |
|---|---|---|---|
| PMR5 | dsRNA #1 (T33789) | GATCCTGAGTTCAACTGCCAAGCTTACGGCAGACCC GATTCAAATTACCTCAAGTACCGTTGGCAGCCGCTCG ATTGTGAGCTCCCAAGGTTCGATGGGGCTGAGTTTTT GATGAGAATGAGAGGAAGAACTGTGATGTTTGTTGG TGATTCATTGGGGAGAAACCAATGGGAGTCATTGAT TTGTTTGATCGTGTCATCTTCTCCTCAAACTCCTACTC AAATGACTAGAGGAGAACCTCTTTCAACCTTCAGAT TCCTGGAATATGAGTTAACTGTGTCCTATTACAAAGC CCCGTATCTTGTGGACATAGAGATAGAGAATGGGAA GAGAGTGTTGAAGCTGGAGGAGATATCAATGAATGG AAATGCTTGGGTTGGAGCTGATGTTATTTCCTTCAAC ACTGGACATTGGTGGAGCCACACTGGCTCTCTACAA GGGTGGGATTACATGGAATCAGGAGGATCATACTAT CAAGACATGGATCGGTTGGGTGCAATGGAAAAGGC/ 180 | 509 |
| | dsRNA #2 (T33790) | GGCTCTCTACAAGGGTGGGATTACATGGAATCAGGA GGATCATACTATCAAGACATGGATCGGTTGGGTGCA ATGGAAAAGGCTTTAAGAACATGGGCTGATTGGGTT GAGAAGAACATTGATGTCTCTAGAACAAGGGTTTTC TTCCAAGCTATCTCCCCCACACATTACAATCCATCTG AATGGAACACGGGGACAGCATCGATGATGACATCAA CGAAAAATTGTTATGGGGAAACGGCACCAATGGGGG GGACGACGTACCCGGGAGGGTACCCTATTCAAATGA GGGTTGTGGATGAAGTGATAAGGGAGATGAGGAAG CCAGTATACTTATTGGACATAACAATGTTATCTGAGC TAAGAAAAGATGGACACCCTTCCATTTATAGTGGTG ATTTGAATCCTCAACAAAGGGCTAACCCAGATAGAT CAGCGGATTGTAGCCATTGGTGTCTTCCTGGCTTACC AGATACTTGGAACCAATTGTTTTATACTGC/181 | 500 |

TABLE 34-continued dsRNAs of cucumber PMR5 and primers used for real-time PCR.

| Target | Sequence/SEQ ID NO: | Length (nt) |
|---|---|---|
| F primer | AGCTTCCTCAGCTTTGATTCTCAGT/182 | 25 |
| R primer | GCGATTATGGTGGTCGCTGTT/183 | 21 |
| Taqman probe | 6FAM-TGAAGCACCATTACCG-MGBNFQ/184 | 16 |

TABLE 35

Concentration of PMR5 mRNA in 15 days old cucumber leaves germinated from seeds treated with PMR5 dsRNAs.
Means and Std Deviations, Cs.PMR5

| Treatment | Number | Mean RQ | Std Dev | Std Err Mean | Lower 95% | Upper 95% | % change from GFP control | fold change | Dunnett's p-value on LOG10 RQ |
|---|---|---|---|---|---|---|---|---|---|
| Formulation_NI | 20 | 0.304 | 0.118 | 0.026 | 0.249 | 0.359 | 13% | 1.1 | 0.6213 |
| T33776_GFP_NI | 20 | 0.268 | 0.119 | 0.027 | 0.212 | 0.323 | 0% | 1.0 | 1.0000 |
| T33789_PMR5_NI | 18 | 0.604 | 0.233 | 0.055 | 0.488 | 0.721 | 126% | 2.3 | <.0001 |
| T33790_PMR5_NI | 19 | 0.536 | 0.279 | 0.064 | 0.401 | 0.670 | 100% | 2.0 | <.0001 |

Example 37

Figure 64:
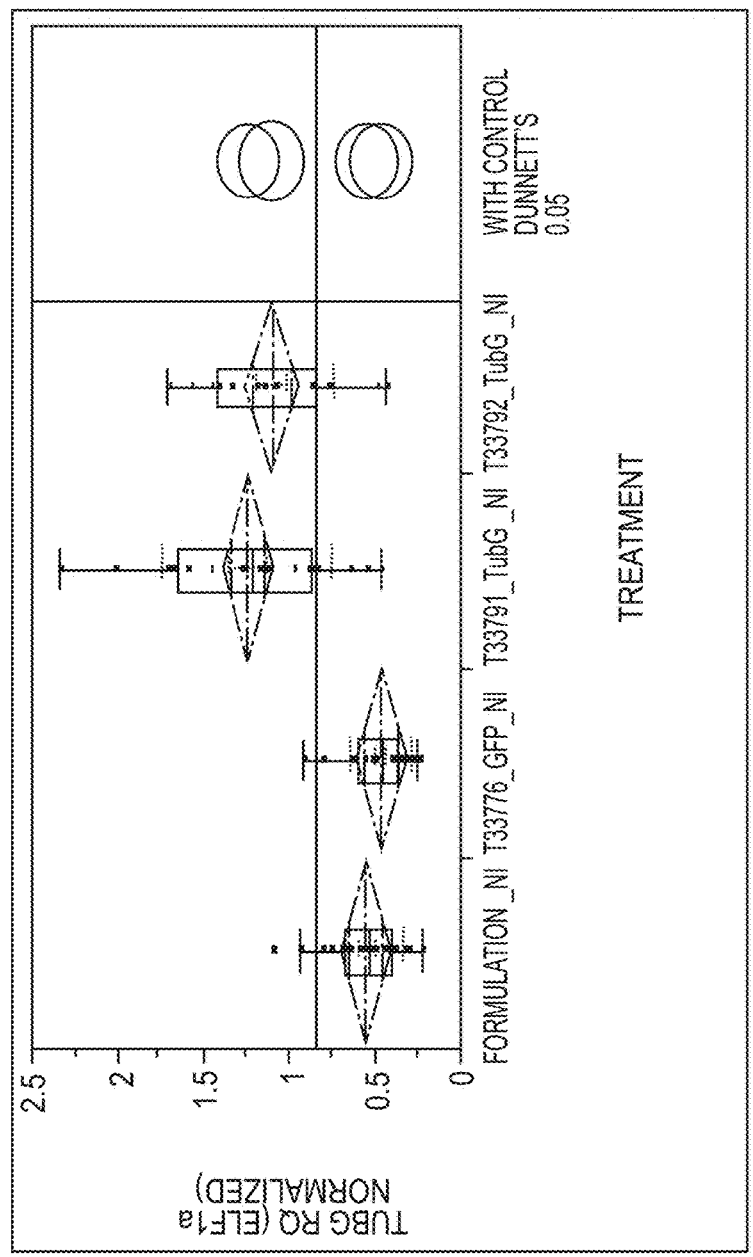
FIG. 64 is a graph showing real-time PCR analysis of TubG mRNA expression in 15-days old cucumber plants germinated from seeds treated with 100 µg/ml dsRNAs (SEQ ID NO: 185 and 186) for 24 hours. GFP dsRNA (SEQ ID NO: 176) or 0.1 mM EDTA (formulation) served as controls. Each dot represents one plant.

Altered Expression of TubG mnRNA in Cucumber Following Seed Treatment with TubG dsRNAs TubG encodes a γ-tubulin protein (Snustad, D. P., et al. 1992). Cucumber seeds were treated with TubG dsRNAs (Table 36) as described in Example 35. Leaves germinated from treated seeds were analyzed as described in Example 35. An altered expression of the TubG gene was demonstrated in leaves of treated seeds compared to GFP treated seeds (Table 37 and FIG. 64).

TABLE 36 dsRNAs of cucumber TubG and primers used for real-time PCR.

| Target | | Sequence/SEQ ID NO: | Length (nt) |
|---|---|---|---|
| TubG | dsRNA #1 (T33791) | GTGGGAACCAGATCGGAATGGAGTTCTGGAAGCAGC TTTGCCTCGAGCATGGAATCAGCAAAGACGGCATTC TTGAAGATTTTGCTACTCAGGGAGGTGACCGGAAAG ATGTATTCTTCTATCAAGCCGATGATCAGCACTACAT ACCAAGAGCTTTACTTATTGACCTGGAGCCCAGGGT CATTAATGGTATCCAGAACAGTGAATATCGAAATCT CTACAACCACGAGAACATCTTTGTTTCAGATCATGGA GGTGGTGCTGGAAATAACTGGGCCAGTGGATATCAT CAGGGAAAGGGCGTTGAAGAGGATATCATGGACATG ATTGACAGAGAAGCAGATGGAAGCGATAGCCTTGAG GGTTTTGTTCTATGCCACTCAATTGCTGGAGGGACAG GATCGGGCATGGGTTCATATCTTCTGGAGACTCTGAA TGATCGCTACAGCAAAAAACTGGTTCAGACGTACAG TGTTTTTCCTAATCAGATGGAAACAAGTGATGTTGTA GTC/185 | 512 |
| | dsRNA #2 (T33792) | GCCTTACAACTCACTTTTGACTTTAAAGCGACTAACA CTCAATGCTGATTGTGTTGTTGTTCTTGATAATACTG CCCTAAATAGAATAGCTGTAGAACGCCTTCATCTATC AAATCCAACCTTTGCACAAACAAACTCCTTAGTGTCG ACTGTAATGTCAGCTAGCACAACCACTTTGAGATAC CCAGGATATATGAACAATGACTTGGTTGGACTCTTG GCCTCTCTAATTCCAACACCAAGATGCCATTTTCTAA TGACAGGATACACACCACTCACGGTTGAGCGCCAGG CTAATGTGATAAGGAAAACCACTGTTCTTGATGTCAT GAGAAGACTTCTCCAGACAAAAAATATTGGTCTC CTCGTATGCTCGAACAAAAGAAGCTAGTCAAGCAAA ATACATATCAATATTGAATATCATACAGGGAGAAGT GGACCCTACACAGGTTCATGAAAGTTTGCAGAGAAT ACGTGAAAGAAAGCTGGTGAATTTTATTGAGTGGGG GC/186 | 512 |

TABLE 36-continued dsRNAs of cucumber TubG and primers used for real-time PCR.

| Target | Sequence/SEQ ID NO: | Length (nt) |
|---|---|---|
| F primer | GGGTCAGTGGTCTTATGTTAGC/187 | 22 |
| R primer | TTCTCAACTTCTCATACTGGCTC/188 | 23 |
| Taqman probe | 6FAM-AGTATCCGGCATCTTTTCAGCAAGTGT-3IABkFQ/189 | 27 |

TABLE 37

Concentration of TubG mRNA in 15 days old cucumber leaves germinated from seeds treated with TubG dsRNAs.
Means and Std Deviations, Cs.TubG

| Treatment | Number | Mean RQ | Std Dev | Std Err Mean | Lower 95% | Upper 95% | % change from GFP control | fold change | Dunnett's p-value on LOG10 RQ |
|---|---|---|---|---|---|---|---|---|---|
| Formulation_NI | 20 | 0.562 | 0.215 | 0.048 | 0.462 | 0.663 | 18% | 1.2 | 0.4562 |
| T33776_GFP_NI | 20 | 0.478 | 0.177 | 0.040 | 0.395 | 0.561 | 0% | 1.0 | 1.0000 |
| T33791_TubG_NI | 20 | 1.252 | 0.493 | 0.110 | 1.021 | 1.483 | 162% | 2.6 | <.0001 |
| T33792_TubG_NI | 18 | 1.117 | 0.360 | 0.085 | 0.938 | 1.297 | 134% | 2.3 | <.0001 |

Example 38

Figure 65:
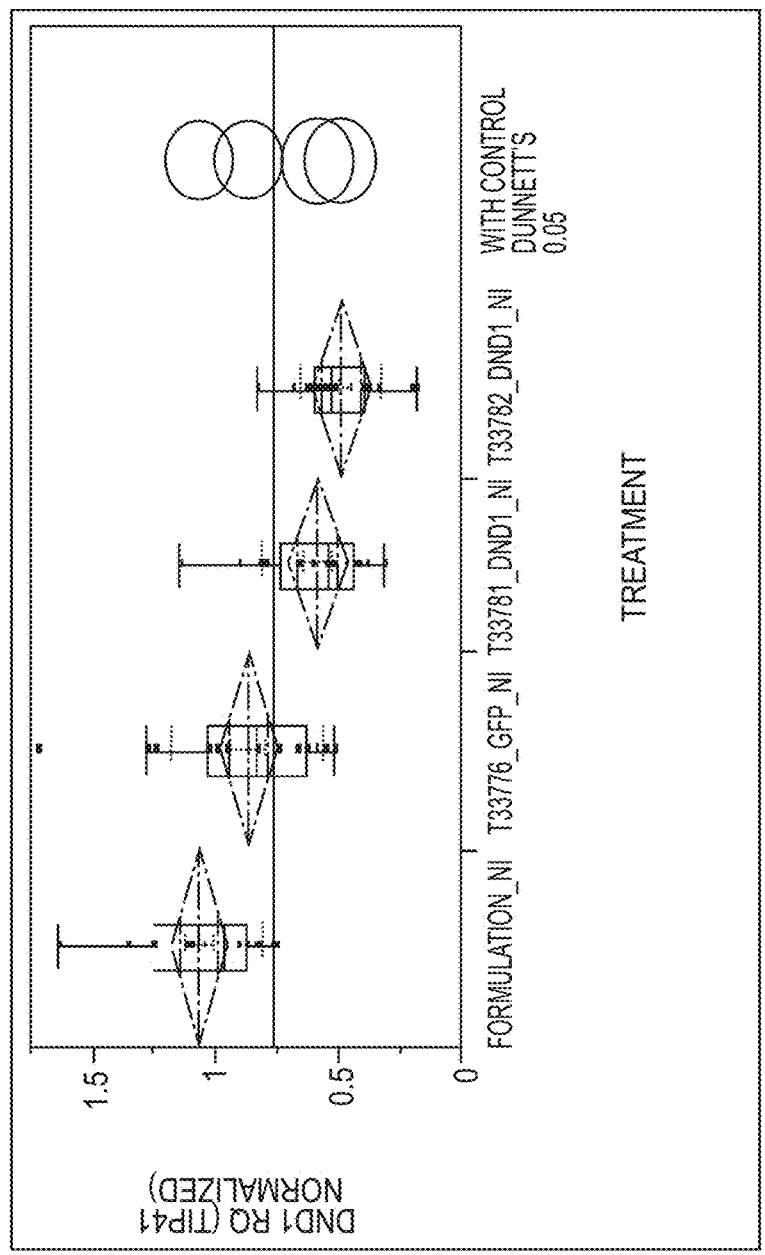
FIG. 65 is a graph showing real-time PCR analysis of DND1 mRNA expression in 15-days old tomato plants germinated from seeds treated with 100 µg/ml dsRNA (SEQ ID NOs: 24 and 25) for 24 hours. GFP dsRNA (SEQ ID NO: 176) or 0.1 mM EDTA (formulation) served as controls. Each dot represents one plant.

Altered Expression of DND1 mRNA in Tomato Following Seed Treatment with DND1 dsRNAs Microtom variety tomato seeds were treated with DND1 dsRNAs (Table 38) as described in Example 35 (except for using 2 ml Eppendorf tube instead of a 50 ml Conical tube in the dsRNA incubation step). RNA analysis was conducted by Taqman real time PCR using a tomato TIP41 assay for normalization of the values to correct for differences in sample concentration (see Table 38 for primers and Taqman probes sequences). An altered expression of the DND1 gene was demonstrated in leaves of treated seeds compared to GFP treated seeds (Table 39 and FIG. 65).

TABLE 38 dsRNAs of tomato DND1 and primers used for real-time PCR.

| Target | | Sequence/SEQ ID NO: | Length (nt) |
|---|---|---|---|
| DND1 | dsRNA #1 (T33781) | GATGACGACATCAATCCAATCTCAAATTCCATTGAATGTTATGCATGTACTCAAGTTGGCGTCCCTGTTTTCCACTCCACCAGTTGCGATGGAGCTAACCAACCGGAGTGGGAAGCTTCAGCCGGTTCTTCTCTAGTTCCAATTCAAAACCGGACGGATTCAAAAACCGGAAAATCCCGGTCCAGTCGCAGCCGGCACACATCGGGGCCGTTCGGGCGTGTATTAGACCCTCGAAGCAAGCGCGTGCAGAGATGGAACCGAATGATTTTATTGGCACGTGGCATGGCTTTAGCCGTTGATCCTCTATTCTTTTACGCCTTATCCATCGGCCGCGGTGGATCGCCGTGTTTGTACATGGACGGCAGCCTGGCGGCTATCGTCACCGTGATTCGGACTAGCGTCGACGCCGTGCACCTCTTCCATTTGTGGTTGCAGTTTCGTTTGGCTTACGTGTCGAGAGAATCGCTGGTGGTTGGTTGTGGGAAACTCGTGTGGGATGC/24 | 500 |
| | dsRNA #2 (T33782) | GATTTTGGTTCGATGCTTTTGTCATCCTTCCCGTTCCACAGGCTGTATTCTGGCTGGTGGTTCCAAAACTAATAAGAGAAGAGCAGATAAAGCTTATAATGACGATCCTTTTATTAATGTTCTTGTTCCAGTTCCTTCCCAAAGTTTATCACTGTATAAGCTTAATGAGAAGGATGCAAAAGGTTACAGGATATATTTTGGTACCATCTGGTGGGGATTTGGACTTAATCTCATTGCTTATTTTATTGCTTCTCATGTTGCTGGGGATGCTGGTATGTTCTTGCAATACAAAGAGTGGCTTCATGTCTAAGGCAGCAGTGTGAGCGCAACCCTTCGTGTAATCTATCTTTGTCTTGCTCAGAGGAGGTGTGTTATCAGTTTCTGTTGCCAACAGGAACTGTGGGAAATCCATGTGCTGGGAACTCAACAACAGTGACCAGGAAGCCAATGTGTTTGGATGTCAATGGACCATTTCCATATGGGATATACCAATGGGCAC/25 | 501 |

TABLE 38-continued dsRNAs of tomato DND1 and primers used for real-time PCR.

| Target | | Sequence/SEQ ID NO: | Length (nt) |
|---|---|---|---|
| | F primer | CTCACCAAGACGTCCGCTTCT/26 | 21 |
| | R primer | GGTTGAACTGATCTTCGTCGGAAT/27 | 24 |
| | Taqman probe | 6FAM-CTCTCAAAGTGGTTTGGC-MGBNFQ/28 | 18 |
| TIP41 | F primer | AACAGGTGGTGCTCGACTATGACT/29 | 24 |
| | R primer | TGCTTTCGACAGTTTCACTTCCA/30 | 23 |
| | Taqman probe | VIC-ACCTTCACAACACCTTACT-MGBNFQ/31 | 19 |

TABLE 39

Concentration of DND1 mRNA in 15 days old tomato leaves germinated from seeds treated with DND1 dsRNAs.
Means and Std Deviations, Sl.DND1

| Treatment | Number | Mean RQ | Std Dev | Std Err Mean | Lower 95% | Upper 95% | % change from GFP control | fold change | Dunnett's p-value on LOG10 RQ |
|---|---|---|---|---|---|---|---|---|---|
| Formulation_NI | 19 | 1.078 | 0.265 | 0.061 | 0.950 | 1.205 | 23% | 1.2 | 0.0836 |
| T33776_GFP_NI | 19 | 0.879 | 0.303 | 0.070 | 0.733 | 1.025 | 0% | 1.0 | 1 |
| T33781_DND1_NI | 17 | 0.599 | 0.213 | 0.052 | 0.489 | 0.709 | −32% | 0.7 | 0.0018 |
| T33782_DND1_NI | 17 | 0.501 | 0.164 | 0.040 | 0.417 | 0.586 | −43% | 0.6 | <.0001 |

Example 39

Figure 66:
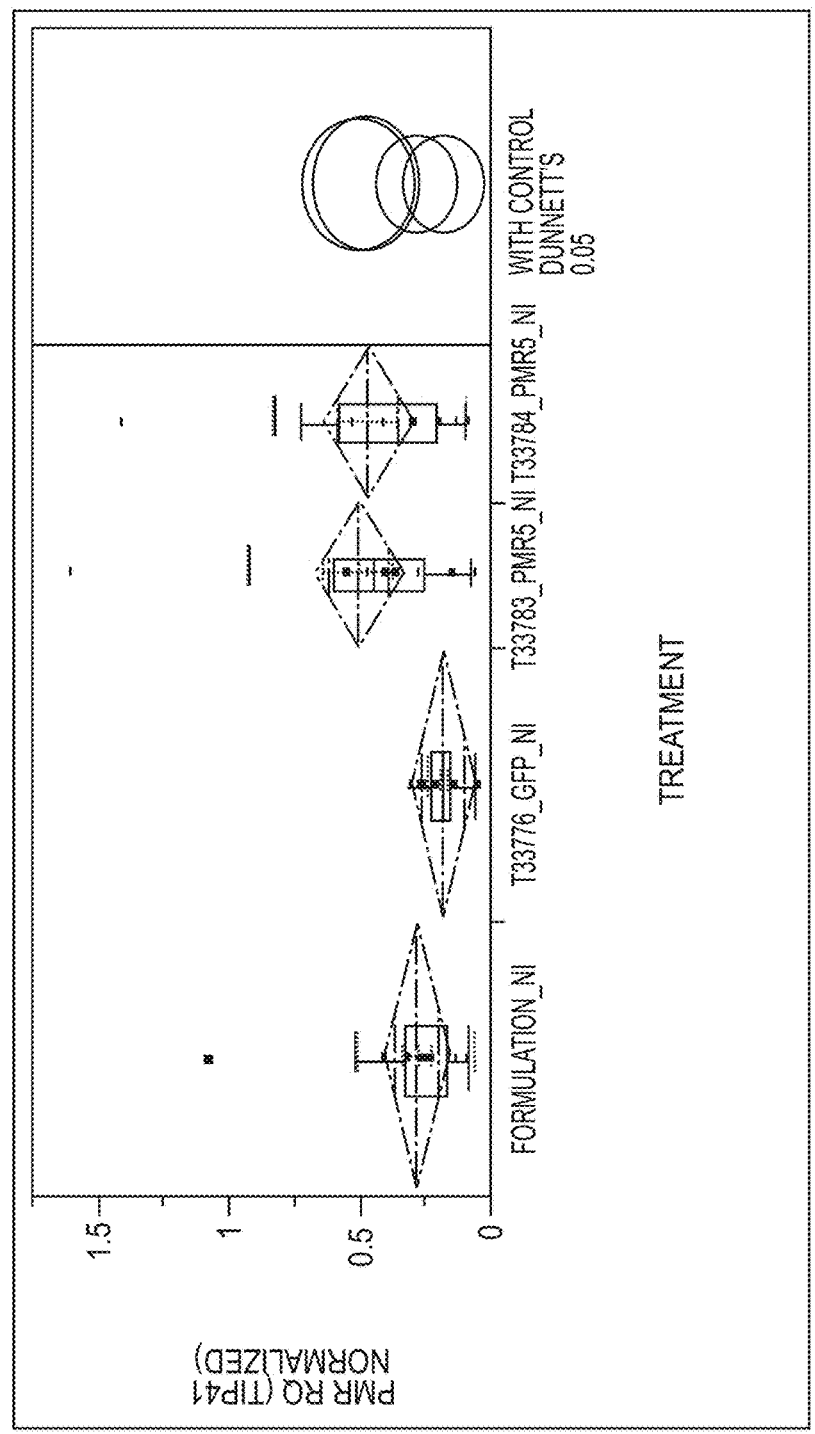
FIG. 66 is a graph showing real-time PCR analysis of PMR5 mRNA expression in 15-days old tomato plants germinated from seeds treated with 100 µg/ml dsRNA (SEQ ID NO: 32) for 24 hours. GFP dsRNA (SEQ ID NO: 176) or 0.1 mM EDTA (formulation) served as controls. Each dot represents one plant.

Altered Expression of PMR5 mRNA in Tomato Following Seed Treatment with PMR5 dsRNAs Tomato seeds were treated with PMR5 dsRNAs (Table 40) as described in Example 35 and 39. Leaves germinated from treated seeds were analyzed as described in Example 38. An altered expression of the PMR5 gene was demonstrated in leaves of treated seeds compared to GFP treated seeds (Table 41 and FIG. 66).

TABLE 40 dsRNAs of tomato PMR5 and primers used for real-time PCR.

| Target | | Sequence/SEQ ID NO: | Length (nt) |
|---|---|---|---|
| PMR5 | dsRNA #1 (T33783) | GTAGCTTTATCTGTTATATTATTAAGGAATCACCATA ATAATAACAATAATTATAATAACCCAAATCACAGAA ACCCAATTCTTCAAGGAAATCAAACTTCATGTTCTCT CTTTATAGGTAGTTGGGTTTACGATGAAACTTACCCA TTTTACCAATCAGCTTCTTGCCCCGCCGTCGATCCAC AGTTCAACTGTCAACTCTACGGCCGACCCGATACGG AATACCTAAAGTATCGATGGAAACCGGCGAACTGTG AGCTACCCAGGTTTAATGGGCTTGAGTTTCTGTTGAA AATGAAAGGGAAAACAGTGATGTTTGTGGGTGATTC ATTAGGCCGGGATCAGTGGGAGTCGTTGATTTGTAT GATTTCAGCTGATGTACCTAAAGCTCAAACGCAGAT GTCGAGGCTTTACCCTATTTCAACTTTCAAGTTCCTG GATTACGGAGTTGCTATTTCATATTACAAAGCACCAT ATCTAGTGGACATAGACACTGTAC/32 | 499 |
| | dsRNA #2 (T33784) | GATGTATTATCTTTTAATACTGGTCATTGGTGGACTC ACAAAGGTCCTCTTCAAGGGTGGGACAACGTAGAAG CAGGAGGGACAATGTATGAAGACATGGATCCACTAA TTGCAATGGAAAAAGGGCTAAGAACGTGGGCAAGAT GGGTTGATACCAATATTGACAGAAGTAGAACCAGAC TCTTCTTTCAGGGCATTTCACCTACGCACTACAATCC GAGTGAATGGAACGCGGGTGCATCAACAGGGAGTTG TTACGGGGAGACAATCCCCGTAACAACCACCCCTAT GACGAGCACGTACCCGGGTCCCGATTTGGATCAATC AAATGTGATCCAAAAAGTTATAAGAGAAATGGACAA TCCACCTTTCTTGCTAGACATAACATTGTTATCAACA ATGAGGAAAGATGCACATCCATCTATTTACAGTGGT | 501 |

TABLE 40-continued dsRNAs of tomato PMR5 and primers used for real-time PCR.

| Target | Sequence/SEQ ID NO: | Length (nt) |
|---|---|---|
|  | GATCTCAATTCTCAACAAAGAATTAACCCTAACAAA CCTGATTGTAGCCATTGGTGTCTGCCTGGC/33 |  |
| F primer | CTCTTTCCTTAACCCTTTTTTAAATTTCTC/34 | 30 |
| R primer | AGAAGAAGACATAATGTAGTTGAAGAACAAG/35 | 31 |
| Taqman probe | 6FAM-CAAATGGAGCTTCTCTC-MGBNFQ/36 | 17 |

TABLE 41

Concentration of PMR5 mRNA in 15 days old tomato leaves germinated from seeds treated with PMR5 dsRNAs.
Means and Std Deviations, Sl.PMR5

| Treatment | Number | Mean RQ | Std Dev | Std Err Mean | Lower 95% | Upper 95% | % change from GFP control | fold change | Dunnett's p-value on LOG10 RQ |
|---|---|---|---|---|---|---|---|---|---|
| Formulation_NI | 19 | 0.295 | 0.223 | 0.051 | 0.188 | 0.402 | 54% | 1.5 | 0.3817 |
| T33776_GFP_NI | 19 | 0.192 | 0.060 | 0.014 | 0.163 | 0.221 | 0% | 1.0 | 1.0000 |
| T33783_PMR5_NI | 10 | 0.512 | 0.427 | 0.135 | 0.206 | 0.817 | 167% | 2.7 | 0.0118 |
| T33784_PMR5_NI | 11 | 0.479 | 0.368 | 0.111 | 0.232 | 0.727 | 150% | 2.5 | 0.0118 |

Example 40

Figure 67:
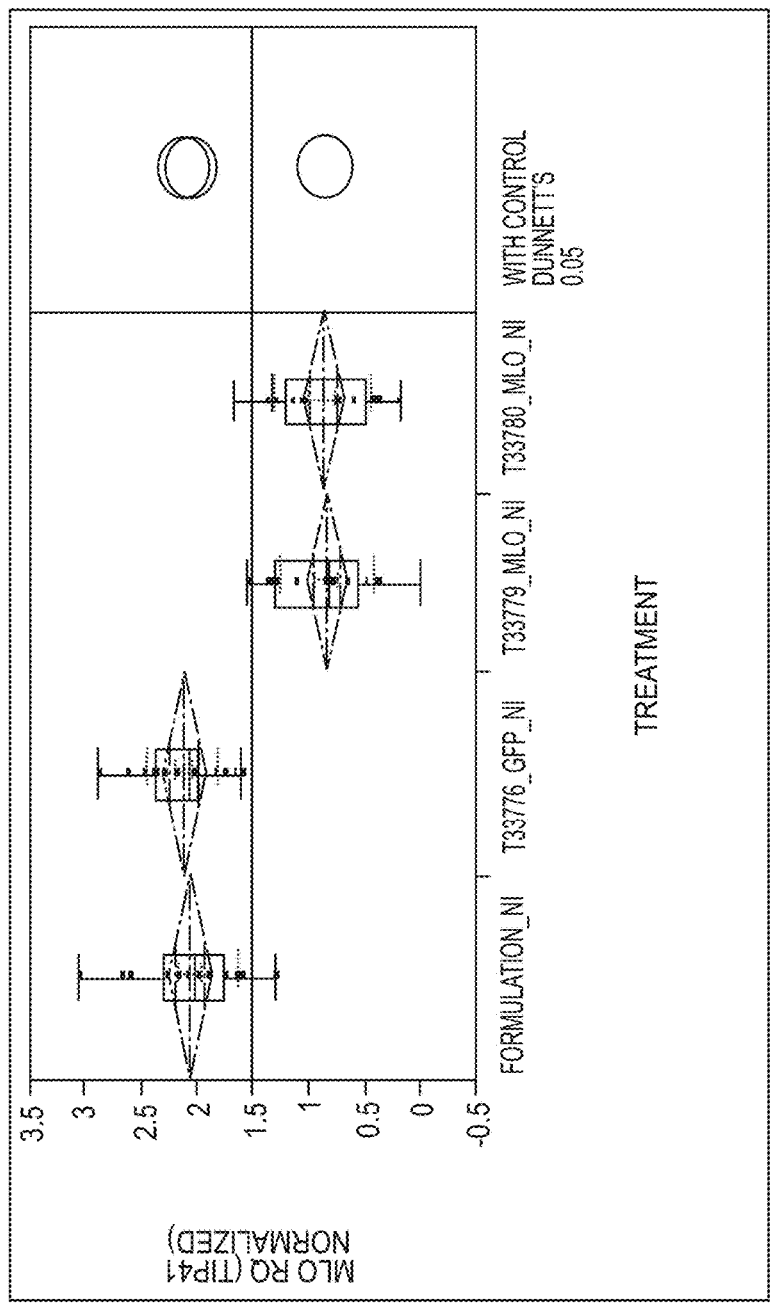
FIG. 67 is a graph showing real-time PCR analysis of MLO mRNA expression in 15-days old tomato plants germinated from seeds treated with 100 µg/ml dsRNA (SEQ ID NOs: 37 and 38) for 24 hours. GFP dsRNA (SEQ ID NO: 176) or 0.1 mM EDTA (formulation) served as controls. Each dot represents one plant.

Altered Expression of MLO mRNA in Tomato Following Seed Treatment with MLO dsRNAs MLO, mildew resistance locus O protein encodes a plant-specific membrane protein and been demonstrated to play a role in powdery mildew resistance in *Arabidopsis*, barley and tomato (Bai et. Al 2007). Tomato seeds were treated with MLO dsRNAs (Table 42) as described in Examples 35 and 38. Leaves germinated from treated seeds were analyzed as described in Example 38. An altered expression of the MLO gene was demonstrated in leaves of treated seeds compared to GFP treated seeds (Table 43 and FIG. 67).

TABLE 42 dsRNAs of tomato MLO and primers used for real-time PCR.

| Target | | Sequence/SEQ ID NO: | Length (nt) |
|---|---|---|---|
| MLO | dsRNA #1 (T33779) | GCACTTGAAAAGATCAAAGCTGAACTTATGCTGTTG GGATTCTTATCACTGTTGTTGACAGTGTTGCAAGATC CAGTTTCTAACTTATGTGTCCCCAAGAGTGTTGGTTA TTCATGGCATCCTTGTATGGCAAAGGAAGATGCCAA GTCTGAGTATGATGACCCTTGTCTACCAAAGGGAAA AGTGCAATTTGCATCTTCATATGCAATACACCAGCTC CATATCTTCATCTTTGTATTGGCAGTTGCTCATGTATT GTACTGTATAGCAACTTTTGCTTTGGGCAGGCTAAAG ATGAGAAAATGGAGGGCATGGGAGGATGAAACAAA AACAATGGAGTACCAATTCTACAACGACCCTGAGAG ATTCAGATTTGCAAGGGAGACCTCGTTTGGACGTAG GCATTTGCATTTCTGGAGCAAGTCCCCCGTGTTGCTC TCGATAGTTTGTTTCTTTCGGCAATTCTTCTCATCAGT TGCAAAAGTTGACTATTTAACCCTTAGAC/37 | 505 |
|  | dsRNA #2 (T33780) | GGCACATTTAACTCCACAAAATCAAAATAATTTTGAT TTTCAATTATACATTAACAGAGCAGTTGACAAAGAC TTCAAAGTTGTTGTTGGAATAAGTCCTGCATTATGGC TCTTCACGGTGCTATATTTTCTGACTACTACCGATCG ATTGTACTCGTATCTTTGGGTGCCATTTATCCCACTT GTAATAATATTGCTAGTTGGCACAAAACTTCAAATG ATCATAACAGAAATGGGAGTAAGGATTTCAGAAAGG GGAGACATAGTAAAAGGTGTACCTGTGGTGGAGACT GGTGACCATCTTTTCTGGTTTAATCGCCCTGCCCTTG TCCTATTCTTGATTAACTTTGTACTCTTTCAGAATGCG TTTCAAGTTGCTTTCTTTTTTTGGAGTTGGTGGAAATT TGGTTTCCCATCTTGCTTTCATAAGAATGCTGCAGAC CTAGCCATAAGGCTAACCATGGGGGTGATCATACAG GTCCATTGCAGCTATGTGACTC/38 | 500 |

TABLE 42-continued dsRNAs of tomato MLO and primers used for real-time PCR.

| Target | Sequence/SEQ ID NO: | Length (nt) |
|---|---|---|
| F primer | GCAATTGCTGTGGTTTGCTTCA/39 | 22 |
| R primer | TTTCCAGTAACCACTCTCCAATGTG/40 | 25 |
| Taqman probe | 6FAM-CTTGCTCGCTATTTCTA-MGBNFQ/41 | 17 |

TABLE 43

Concentration of MLO mRNA in 15 days old tomato leaves germinated from seeds treated with MLO dsRNAs.
Means and Std Deviations, Sl.MLO

| Treatment | Number | Mean RQ | Std Dev | Std Err Mean | Lower 95% | Upper 95% | % change from GFP control | fold change | Dunnett's p-value on LOG10 RQ |
|---|---|---|---|---|---|---|---|---|---|
| Formulation_NI | 19 | 2.098 | 0.441 | 0.101 | 1.885 | 2.311 | −2% | 1.0 | 0.9964 |
| T33776_GFP_NI | 19 | 2.151 | 0.327 | 0.075 | 1.994 | 2.309 | 0% | 1.0 | 1.0000 |
| T33779_MLO_NI | 17 | 0.863 | 0.425 | 0.103 | 0.645 | 1.082 | −60% | 0.4 | <.0001 |
| T33780_MLO_NI | 17 | 0.895 | 0.434 | 0.105 | 0.672 | 1.118 | −58% | 0.4 | <.0001 |

Example 41

Reduction in Tomato Powdery Mildew Disease and Modulation of mRNA Expression Following Seed Treatment with dsRNAs Bi1 is a negative regulator of programmed cell death. Microtom tomato seeds were treated with dsRNAs containing the tomato Bi1 (Table 44, dsRNA #2) and PMR5 (Table 40, dsRNA #1) dsNAs as described Examples 35 and 38.

TABLE 44

Tomato Bi1 dsRNAs.

| Target | | Sequence/SEQ ID NO: | Length (nt) |
|---|---|---|---|
| Bi1 | dsRNA #1 (T33777) | GTGCTTTAGTGGCATCGGCTGCTGGGGCTTACCTTCA CATTCTATGGAATATCGGTGGCCTCCTCACAACAATG GCTTGCATGGGAAGCATGGTGTGGCTTCTCTCAGCTC CTCCTTATCAAGAGCAAAAAGGGTGGCTCTTCTGA TGGCAGCTGCACTTTTTGAAGGCGCCTCTATTGGTCC TCTGATTGAGCTGGGCATTAACTTCGATCCAAGCATT GTGTTTGGCGCTTTTGTAGGTTGTGCTGTGGTTTTTG GTTGCTTCTCAGCTGCTGCCATGTTGGCAAGGCGCAG GGAGTACTTGTACCTCGGGGGCCTTCTTTCATCTGGC GTCTCCCTTCTCTTCTGGTTGCACTTTGCATCCTCCAT TTTTGGTGGTTCCATGGCTGTTTTCAAGTTTGAGTTGT ATTTTGGACTCTTGGTGTTTGTGGGCTACATCGTCTTT GACACCCAAGAAATTATTGAGAAGGCTCACTTGGGT GATATGGATTACGTTAAGC/42 | 501 |
| | dsRNA #2 (T33778) | GCCAGATCTCACCTCTCGTTCAAACTCATCTCAAGCA GGTGTACCTTACGCTATGCTGTGCTTTAGTGGCATCG GCTGCTGGGGCTTACCTTCACATTCTATGGAATATCG GTGGCCTCCTCACAACAATGGCTTGCATGGGAAGCA TGGTGTGGCTTCTCTCAGCTCCTCCTTATCAAGAGCA AAAAGGGTGGCTCTTCTGATGGCAGCTGCACTTTTT GAAGGCGCCTCTATTGGTCCTCTGATTGAGCTGGGCA | 500 |

TABLE 44-continued

Tomato Bi1 dsRNAs.

| Target | Sequence/SEQ ID NO: | Length (nt) |
|---|---|---|
| | TTAACTTCGATCCAAGCATTGTGTTTGGCGCTTTTGT AGGTTGTGCTGTGGTTTTTGGTTGCTTCTCAGCTGCT GCCATGTTGGCAAGGCGCAGGGAGTACTTGTACCTC GGGGGCCTTCTTTCATCTGGCGTCTCCCTTCTCTTCTG GTTGCACTTTGCATCCTCCATTTTTGGTGGTTCCATG GCTGTTTTCAAGTTTGAGTTGTATTTTGGACTCTTGGT GTTTGTGGGCTACATCGTC/43 | |

Seeds treated with dsRNA were planted in M200 soil with fertilizer (Hummerts) and placed in a growth chamber. One tomato seed is planted per pot, approximately 1/4" into the soil and the top of the soil was drenched with water. The growth chamber settings were at 26/24 C, 16 hr light cycle, 50% humidity, light intensity 3 and watered 4×/week by automated subirrigation. Fourteen days after planting pots were organized by similar size. The number of reps was 5 plants/treatment. On day 15 plants were randomized and shifted to the following growth chamber conditions: 22/20 C, 16 hr light cycle, 70%/0 humidity, light intensity 3 and watered M, W, F. Infection with Tomato Powdery Mildew (*Oidium Neolycopersici*) was as follows:

1. 10 μl Tween-20 were mixed in 200 ml of d.i. H2O in a 250 ml flask.
2. About 20-25 leaves from highly infected tomato stock plants were cut and placed into a second flask. Approximately 100-200 ml of Tween 20 solution were added to the leaves until the mildew goes into solution. This was accomplished by shaking the flask. The solution was then transferred into the spray bottle, the nozzle inserted and an even spray on the plants was accomplished. Trays were rotated 4× during spraying.

Eight days post-infection samples were taken for qPCR. PMR5 (Table 40, dsRNA #1) treated plants showed a significant up-regulation of PMR5 expression compare to plants treated with GFP and 0.1 mM EDTA (Formulation) as controls (Table 45).

Figure 68:
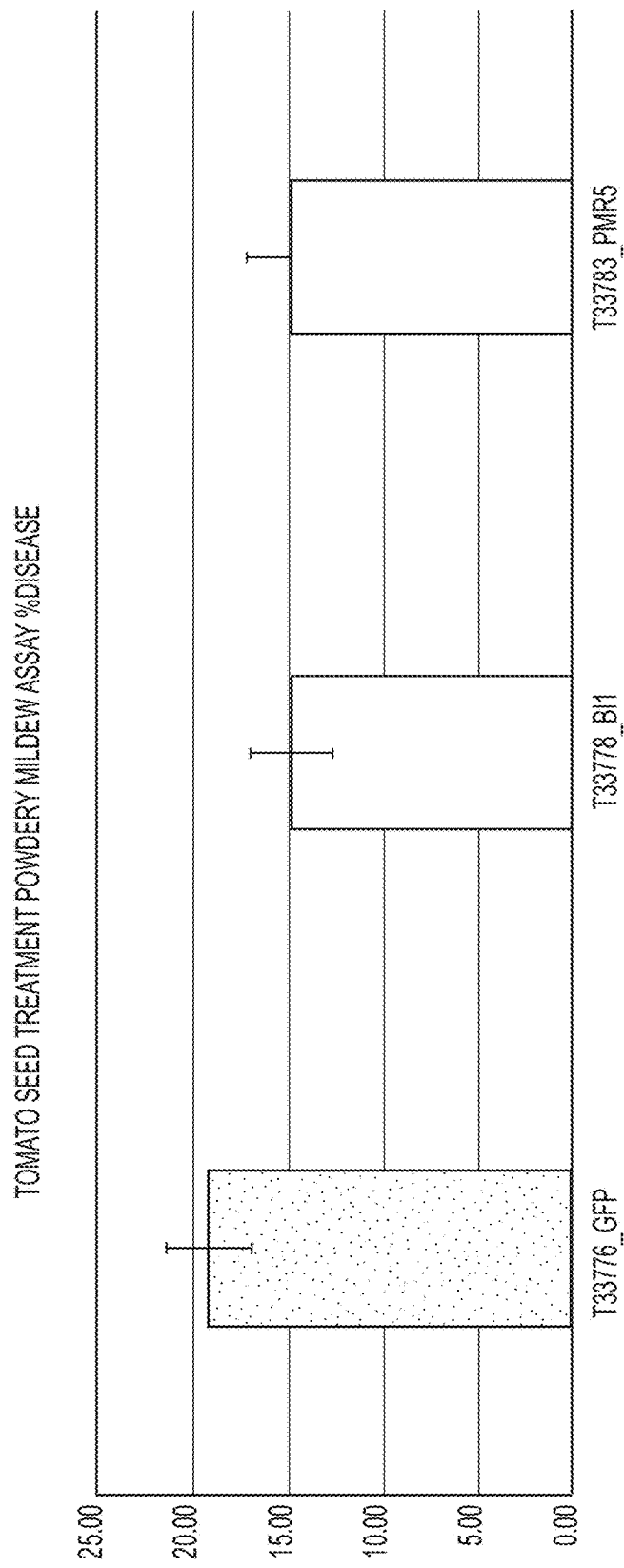
FIG. 68 is a bar graph showing an average percent of Powdery mildew disease in 15-days old tomato plants germinated from seeds treated with Bi1 (SEQ ID NOs: 42 and 43) and PMR5 (SEQ ID NO: 198) dsRNAs. GFP dsRNA served as control.

Fourteen days post-infection disease development was scored for the percentage of leaf area covered with powdery mildew. Ratings were set at 0, 10, 25 and 50% infection. Data was analyzed using Anova Single Factor Analysis (α=0.1). The 1/2 LSD was calculated and custom error bars were created for the graphs. Treatment averages are used to graph a percent disease reduction compared to the GFP control. This analysis demonstrated a 23% reduction in disease compared with GFP treated tomato seeds (p-value <0.1, FIG. 68).

Example 42

Modulation of PHYA mRNA Expression in Soy Following Seed Treatment with dsRNAs Soybean Phytochrome A (PHYA) genes E3 and E4 were targeted by treating seeds with dsRNAs containing sequences from those genes. PHYAE3 and PHYAE4 dsRNA sequences (Table 46) were synthesized in vitro using a convergent T7 RNA polymerase method. dsRNAs for the two genes were combined and brought to a final concentration of 50 μg/ml total nucleic acid in 0.1 mM EDTA. Fifteen soy (Williams 82) seeds were incubated in 7.5 ml of this dsRNA solution or in dsRNA from a GUS control in a 15 ml tube in the dark at 15 C, with gentle oscillation, for 24 hours. After treatment, seeds were transferred to seed germination boxes (15 seed per box) containing moistened filter paper and germinated in a growth chamber set at 25 C in the dark.

Shoot tissues, excluding cotyledons, were harvested from the germinating seeds in the germination boxes 5 days after treatment for RNA analysis. RNA analysis was conducted by Taqman, using the Gm.ref16 gene for normalization of the values to correct for differences in sample concentration (Table 46). RQ values were transformed to log 10 for analysis after outlier removal.

Figure 69:
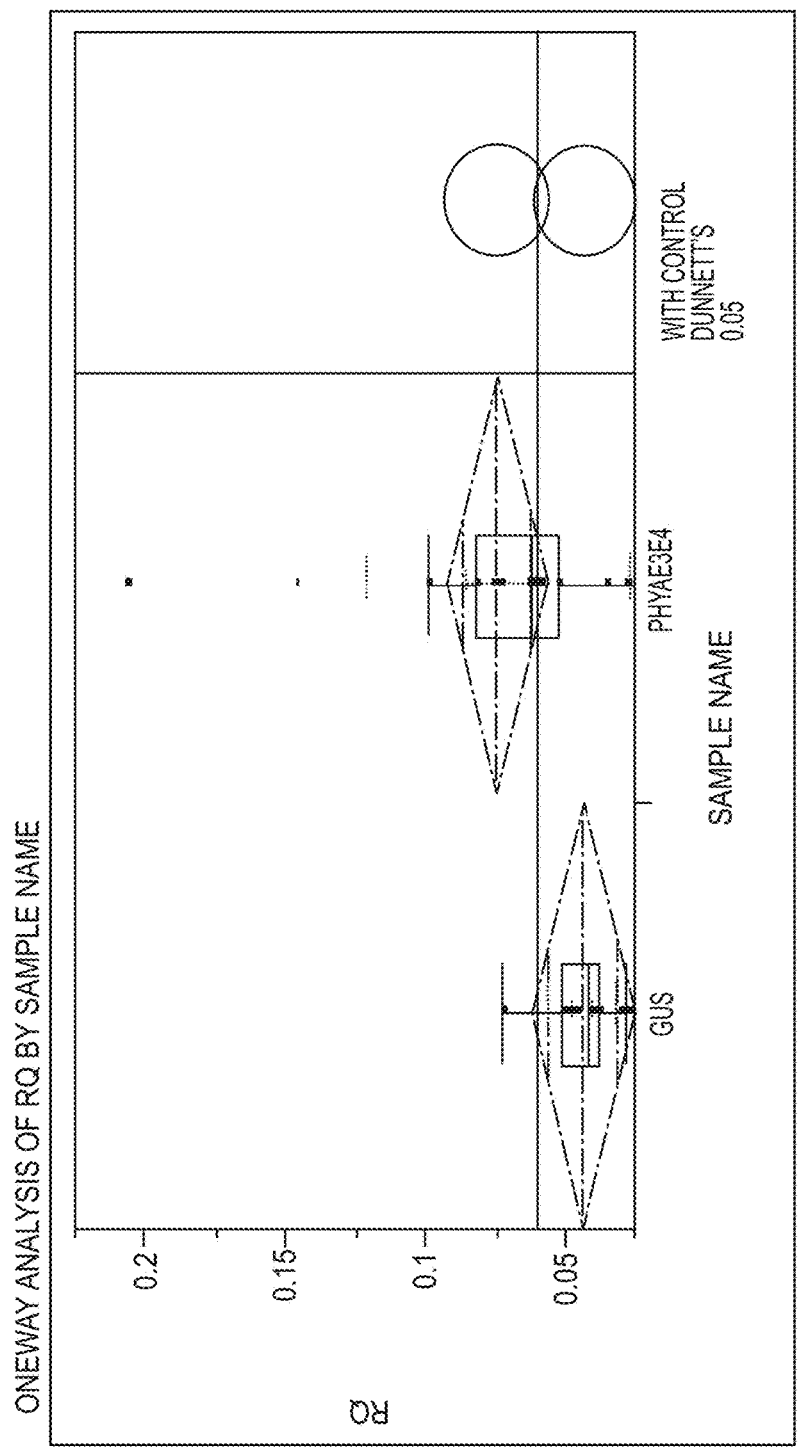
FIG. 69 is a graph showing real-time PCR analysis of PHYAE3 mRNA expression in 1-week old soy plants germinated from seeds treated with 50 µg/ml dsRNAs (SEQ ID NOs: 190 and 194) for 24 hours. GUS dsRNA (SEQ ID NO: 21) served as control. Each dot represents one plant.

Treatment of seeds with PHYAE3 and PHYAE4 dsRNAs resulted in increased PHYAE3 expression in seedling shoots so that PHYAE3 mRNA levels were 1.7 those of GUS control values (Table 47 and FIG. 69).

TABLE 45

Concentration of PMR5 mRNA in 21 days old tomato leaves germinated from seeds treated with PMR5 dsRNA and infected with Powdery Mildew disease.

| Treatment | Number | Mean RQ | Std Dev | Std Err Mean | Lower 95% | Upper 95% | % change from GFP control | fold change | Dunnett's p-value on LOG10 RQ |
|---|---|---|---|---|---|---|---|---|---|
| Formulation_PM | 18 | 0.392 | 0.077 | 0.018 | 0.354 | 0.430 | −7% | 0.9 | 0.9246 |
| T33776_GFP_PM | 18 | 0.421 | 0.105 | 0.025 | 0.369 | 0.474 | 0% | 1.0 | 1.0000 |
| T33783_PMR5_PM | 16 | 0.734 | 0.426 | 0.106 | 0.507 | 0.961 | 74% | 1.7 | 0.0071 |

TABLE 46

Soy PHYAE3 and PHYAE4 dsRNAs and primers used for real-time PCR.

| Target | | Sequence/SEQ ID NO: | Length (nt) |
|---|---|---|---|
| PHYAE3 | dsRNA | TCAAGAAGATGTTGGACATGGCATTGCAGGGTGAGG<br>AAGAGAGAAATGTCCAATTTGAGATCCAAACACATC<br>ATATGAAGATTGATTCTGGTCCCATCAGCTTGGTAGT<br>TAATGCTTGTGCAAGCAGGGATCTTCAAGATAATGTT<br>GTGGGAGTTTGTTTTCTGGCACAAGATATAACTGCTC<br>AGAAAACAATGATGGACAAATTCACCCGAATTGAAG<br>GTGACTACAAGGCAATTGTACAGAACCCAAACCCAT<br>TGATCCCTCCAATATTTGGCACAGATGAATTTGGTTG<br>GTGTTGTGAATGGAATTCAGCTATGGCAAAATTAAC<br>TGGATGGAAGCGAGAGGAGGTAATGGATAAAATGCT<br>TTTAGGAGAGGTTTTCGGGACCCAAATAGCTTGTTGT<br>CGCCTAAGGAATCATGAAGCTGTTGTTAACTTTAGCA<br>TTGTACTTAATACAGCCATGGCTGGTTTGGAAACAG<br>AGAAGGTTCCTTTTGGTTTCTTTGCTCGTGATGGAAA<br>GC/190 | 513 |
| | Forward primer | TCCCTCTTAGGTATGCTTGTCAATT/191 | 25 |
| | Reverse primer | TCTCTAGCTCTTTGCTCACATGAAC/192 | 25 |
| | Taqman probe | 6FAM-CTGGCTCAAGTATTTG-MGBNFQ/193 | 16 |
| PHYAE4 | dsRNA | TCAAGAAGATGCTTAACTTAGCACTGCTAGGTGAAG<br>AAGAGAAGAATGTCCAATTTGAGATCAAAACACATG<br>GGTCTAAGATGGATTCTGGTCCTATTAGTTTAGTAGT<br>AAATGCTTGCGCAAGCAGGGATCTTCGAGATAATGT<br>TGTTGGGGTTTGTTTTGTGGCCCATGATATAACTGCT<br>CAGAAGAATGTCATGGACAAATTTACGCGTATTGAA<br>GGTGATTACAAGGCAATTGTACAGAACCGCAATCCA<br>TTAATCCCTCCTATATTTGGCACAGATGAATTTGGCT<br>GGTGTTGTGAGTGGAATCCAGCTATGACGAAGTTAA<br>CTGGATGGAAGCGAGAGGAGGTGATGGATAAAATG<br>CTTTTGGGAGAGCTTTTTGGCACCCATATGGCTGCTT<br>GTCGCCTAAAGAATCAAGAAGCTTTTGTTAATTTGGG<br>TGTTGTACTTAATAAAGCCATGACTGGTTTGGAAACA<br>GAGAAGGTTCCTTTTGGTTTCTTTGCTCGGAATGGCA<br>AGTATGTGGAATGCC/194 | 525 |
| Gm.ref16 | | CAAGGTTATGAAAATTATGGGTATGC/195 | 26 |
| | | CCCGGATAACTGCCATACATG/196 | 21 |
| | | VIC-CTGCTGCTGGACAGGATCCCA-TAMRA/197 | 21 |

TABLE 47 mRNA concentrations for PHYA genes in 1-week soy seedling shoot tissue.

| Treatment | Assay | Number | Mean RQ | Std Dev | Std Err Mean | Lower 95% | Upper 95% | fold change | Dunnett's p value for RQ log 10 analysis |
|---|---|---|---|---|---|---|---|---|---|
| GUS | PHYAE3 | 15 | 0.045 | 0.012 | 0.003 | 0.038 | 0.052 | | 1 |
| PHYAE3E4 | PHYAE3 | 15 | 0.076 | 0.047 | 0.012 | 0.050 | 0.101 | 1.7 | 0.0141 |

Although the invention has been described in conjunction with specific embodiments thereof, it is evident that many alternatives, modifications and variations are apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application is specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of introducing into a seed naked dsRNA that is capable of down-regulating a target gene, the method comprising shaking the seed in a solution comprising a final concentration of 0.013-100 µg/µL of the naked dsRNA from 1 hour up to 60 hours, thereby introducing the dsRNA into the seed, wherein the naked dsRNA is not associated with a cationic oligopeptide.

2. A method of down-regulating expression of a target gene, the method comprising:
   (a) shaking a seed in a solution comprising a final concentration of 0.013-100 µg/µL of a naked dsRNA from 1 hour up to 60 hours, wherein the naked dsRNA down-regulates expression of the target gene, and wherein the naked dsRNA is not associated with a cationic oligopeptide; and optionally
   (b) generating a plant of the seed.

3. The method of claim 2, wherein said down-regulating expression of the target gene improves tolerance of the plant to abiotic or biotic stress.

4. The method of claim 2, further comprising drying said seed following said shaking.

5. The method of claim 2, wherein said target gene is an endogenous plant gene.

6. The method of claim 2, wherein said target gene is a gene of a viral pathogen.

7. The method of claim 1, wherein said introducing comprises penetration to an endosperm, and alternatively or additionally, an embryo of said seed.

8. The method of claim 2, wherein said naked dsRNA does not integrate into the genome of said seed.

9. The method of claim 1, wherein said introducing results in the presence of said dsRNA in the plant for at least 10 days following germination.

10. The method of claim 6 further comprising observing reduced infectability or replicability of said viral pathogen.

11. The method of claim 1, further comprising priming the seed prior to said shaking.

12. The method of claim 11, wherein said priming is effected by:
   (i) washing the seed prior to said shaking; and
   (ii) drying the seed following step (i).

13. The method of claim 12, wherein said washing is effected for 2-6 hours.

14. The method of claim 12, wherein said drying is effected at 25-30° C. for 10-16 hours.

15. The method of claim 1, wherein said final concentration of the naked dsRNA is 0.013-0.5 µg/µL.

16. The method of claim 1, wherein said shaking is effected prior to breaking of seed dormancy and embryo emergence.

17. The method of claim 1, further comprising coating the seed with an agent selected from the group consisting of a pesticide, a fungicide, an insecticide, a fertilizer, a coating agent, and a coloring agent.

18. The method of claim 2, further comprising coating the seed with an agent selected from the group consisting of a pesticide, a fungicide, an insecticide, a fertilizer, a coating agent, and a coloring agent.

19. The method of claim 1, wherein said final concentration of the naked dsRNA is 0.013-3 µg/µl.

20. The method of claim 2, wherein said final concentration of the naked dsRNA is 0.013-3 µg/µl.

21. The method of claim 1, wherein said shaking is from 1 to 24 hours.

22. The method of claim 2, wherein said shaking is from 1 to 24 hours.

* * * * *

SEQUENCE LISTING

<160> NUMBER OF SEQ ID NOS: 197

<210> SEQ ID NO 1
<211> LENGTH: 20
<212> TYPE: DNA
<213> ORGANISM: Artificial sequence
<220> FEATURE:
<223> OTHER INFORMATION: T7 primer sequence

<400> SEQUENCE: 1
taatacgact cactataggg                                              20

<210> SEQ ID NO 2
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 2
ggtgctctga acgtggatg                                               19

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
catcatcgcc atcctcattc tc                                           22

<210> SEQ ID NO 4
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 4
taatacgact cactataggg gaagaccctc gaaactaagc                        40

<210> SEQ ID NO 5
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 5
taatacgact cactataggg ggtaagcggc attctaaacc                        40

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
actcagcagt cgtaggattg                                              20

<210> SEQ ID NO 7
<211> LENGTH: 20
<212> TYPE: DNA
<213> ORGANISM: Artificial sequence

```
<220> FEATURE:
<223> OTHER INFORMATION: Single strand DNA oligonucleotide

<400> SEQUENCE: 7
cttcttatgt tcccgtcagg                                                 20

<210> SEQ ID NO 8
<211> LENGTH: 616
<212> TYPE: DNA
<213> ORGANISM: Artificial sequence
<220> FEATURE:
<223> OTHER INFORMATION: CGMMV dsRNA product 1

<400> SEQUENCE: 8
taatacgact cactataggg ggtaagcggc attctaaacc tccaaatcgg aggttggact      60
ctgcttctga agagtccagt tctgtttctt ttgaagatgg cttacaatcc gatcacacct    120
agcaaactta ttgcgtttag tgcttcttat gttcccgtca ggactttact taattttcta    180
gttgcttcac aaggtaccgc tttccagact caagcgggaa gagattcttt ccgcgagtcc    240
ctgtctgcgt taccctcgtc tgtcgtagat attaattcta gattcccaga tgcgggtttt    300
tacgctttcc tcaacggtcc tgtgttgagg cctatcttcg tttcgcttct cagctccacg    360
gatacgcgta atagggtcat tgaggttgta gatcctagca atcctacgac tgctgagtcg    420
cttaacgccg taaagcgtac tgatgacgcg tctacggccg ctagggctga gatagataat    480
ttaatagagt ctatttctaa gggttttgat gtttacgata gggcttcatt tgaagccgcg    540
ttttcggtag tctggtcaga ggctaccacc tcgaaagctt agtttcgagg gtcttcccct    600
atagtgagtc gtatta                                                   616

<210> SEQ ID NO 9
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 9
taatacgact cactataggg catcaccatc gaccctaaac                            40

<210> SEQ ID NO 10
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 10
taatacgact cactataggg gctttaccgc cactaagaac                            40

<210> SEQ ID NO 11
<211> LENGTH: 598
<212> TYPE: DNA
<213> ORGANISM: Artificial sequence
<220> FEATURE:
<223> OTHER INFORMATION: CGMMV dsRNA product 2

<400> SEQUENCE: 11
taatacgact cactataggg gctttaccgc cactaagaac tctgtacact cccttgcggg      60
tggtctgagg cttcttgaat tggaatatat gatgatgcaa gtgccctacg gctcaccttg    120
ttatgacatc ggcggtaact atacgcagca cttgttcaaa ggtagatcat atgtgcattg    180
```

```
ctgcaatccg tgcctagatc ttaaagatgt tgcgaggaat gtgatgtaca acgatatgat      240
cacgcaacat gtacagaggc acaagggatc tggcgggtgc agacctcttc caactttcca      300
gatagatgca ttcaggaggt acgatagttc tccctgtgcg gtcacctgtt cagacgtttt      360
ccaagagtgt tcctatgatt ttgggagtgg tagggataat catgcagtct cgttgcattc      420
aatctacgat atcccttatt cttcgatcgg acctgctctt cataggaaaa atgtgcgagt      480
ttgttatgca gcctttcatt tctcggaggc attgctttta ggttcgcctg taggtaattt      540
aaatagtatt ggggctcagt ttagggtcga tggtgatgcc ctatagtgag tcgtatta       598

<210> SEQ ID NO 12
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 12
ggtgctctga acgtggatg                                                    19

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
catcatcgcc atcctcattc tc                                                22

<210> SEQ ID NO 14
<211> LENGTH: 456
<212> TYPE: DNA
<213> ORGANISM: Artificial sequence
<220> FEATURE:
<223> OTHER INFORMATION: SQS dsRNA product 2

<400> SEQUENCE: 14
ctaatacgac tcactatagg gagacgctct gtctcatgct gaagactgcc tccaatacat       60
gtcagcattg aaggatcatg ccatttttccg ttttttgtgca atacctcaga taatggcaat    120
tgggacatgt gctatttgct acaataatgt gaatgtcttt agaggagttg ttaagatgag     180
gcgtgggctc actgcacgag taattgatga dacaaacaca atgtcagatg tctatactgc    240
tttctatgag ttctcttcgc tgatagaatc gaagattgat aataatgatc caaatgcttc    300
cctaacgcgg aaacgtgttg atgcgataaa gagaacctgc aagtcatctt gctcactaaa    360
gagaagggga tacgatttgg agaagtcaaa gtacaactcc atgctgataa tggttgtact    420
tctgttggtg gctctcccta tagtgagtcg tattag                               456

<210> SEQ ID NO 15
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 15
taatacgact cactataggg agcattcccg gcgggatagt ctg                         43

<210> SEQ ID NO 16
<211> LENGTH: 43
```

```
<212> TYPE: DNA
<213> ORGANISM: Artificial sequence
<220> FEATURE:
<223> OTHER INFORMATION: Single strand DNA oligonucleotide

<400> SEQUENCE: 16
taatacgact cactataggg agcattcccg gcgggatagt ctg                    43

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
cagcgcgaag tctttatacc                                              20

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
ctttgccgta atgagtgacc                                              20

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
ccataaccct ggaggttgag                                              20

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
atcagacgct gctggtctgg                                              20

<210> SEQ ID NO 21
<211> LENGTH: 443
<212> TYPE: DNA
<213> ORGANISM: Artificial sequence
<220> FEATURE:
<223> OTHER INFORMATION: GUS dsRNA product

<400> SEQUENCE: 21
taatacgact cactataggg agatcgacgg cctgtgggca ttcagtctgg atcgcgaaaa    60
ctgtggaatt gatcagcgtt ggtgggaaag cgcgttacaa gaaagccggg caattgctgt   120
gccaggcagt tttaacgatc agttcgccga tgcagatatt cgtaattatg cgggcaacgt   180
ctggtatcag cgcgaagtct ttataccgaa aggttgggca ggccagcgta tcgtgctgcg   240
tttcgatgcg gtcactcatt acggcaaagt gtgggtcaat aatcaggaag tgatggagca   300
tcagggcggc tatacgccat ttgaagccga tgtcacgccg tatgttattg ccgggaaaag   360
```

```
tgtacgtatc accgtttgtg tgaacaacga actgaactgg cagactatcc cgccgggaat    420
gctccctata gtgagtcgta tta                                            443

<210> SEQ ID NO 22
<211> LENGTH: 9
<212> TYPE: RNA
<213> ORGANISM: Artificial sequence
<220> FEATURE:
<223> OTHER INFORMATION: Example of an oligonucle-
otide sequence that can     be used to form the shRNA loop

<400> SEQUENCE: 22 uucaagaga                                                              9

<210> SEQ ID NO 23
<211> LENGTH: 9
<212> TYPE: RNA
<213> ORGANISM: Artificial sequence
<220> FEATURE:
<223> OTHER INFORMATION: Example of an oligonucle-
otide sequence that can     be used to form the shRNA loop

<400> SEQUENCE: 23 uuuguguag                                                              9

<210> SEQ ID NO 24
<211> LENGTH: 500
<212> TYPE: DNA
<213> ORGANISM: Artificial sequence
<220> FEATURE:
<223> OTHER INFORMATION: Tomato DND1 dsRNA product #1 (T33781)

<400> SEQUENCE: 24
gatgacgaca tcaatccaat ctcaaattcc attgaatgtt atgcatgtac tcaagttggc     60
gtccctgttt tccactccac cagttgcgat ggagctaacc aaccggagtg ggaagcttca    120
gccggttctt ctctagttcc aattcaaaac cggacggatt caaaaaccgg aaaatcccgg    180
tccagtcgca gccggcacac atcggggccg ttcgggcgtg tattagaccc tcgaagcaag    240
cgcgtgcaga gatggaaccg aatgatttta ttggcacgtg gcatggcttt agccgttgat    300
cctctattct tttacgcctt atccatcggc cgcggtggat cgccgtgttt gtacatggac    360
ggcagcctgg cggctatcgt caccgtgatt cggactagcg tcgacgccgt gcacctcttc    420
catttgtggt tgcagtttcg tttggcttac gtgtcgagag aatcgctggt ggttggttgt    480
gggaaactcg tgtgggatgc                                                500

<210> SEQ ID NO 25
<211> LENGTH: 501
<212> TYPE: DNA
<213> ORGANISM: Artificial sequence
<220> FEATURE:
<223> OTHER INFORMATION: Tomato DND1 dsRNA product #2 (T33782)

<400> SEQUENCE: 25
gattttggtt cgatgctttt gtcatccttc ccgttccaca ggctgtattc tggctggtgg     60
ttccaaaact aataagagaa gagcagataa agcttataat gacgatcctt ttattaatgt    120
tcttgttcca gttccttccc aaagtttatc actgtataag cttaatgaga aggatgcaaa    180
aggttacagg atatattttt ggtaccatct ggtgggg att tggacttaat ctcattgctt    240
attttattgc ttctcatgtt gctgggggat gctggtatgt tcttgcaata caaagagtgg    300
cttcatgtct aaggcagcag tgtgagcgca acccttcgtg taatctatct ttgtcttgct    360
```

```
cagaggaggt gtgttatcag tttctgttgc aacaggaac tgtgggaaat ccatgtgctg    420
ggaactcaac aacagtgacc aggaagccaa tgtgtttgga tgtcaatgga ccatttccat   480
atgggatata ccaatgggca c                                              501
```

<210> SEQ ID NO 26
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 26

```
ctcaccaaga cgtccgcttc t                                              21
```

<210> SEQ ID NO 27
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 27

```
ggttgaactg atcttcgtcg gaat                                           24
```

<210> SEQ ID NO 28
<211> LENGTH: 18
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 28

```
ctctcaaagt ggtttggc                                                  18
```

<210> SEQ ID NO 29
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 29

```
aacaggtggt gctcgactat gact                                           24
```

<210> SEQ ID NO 30
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 30

```
tgctttcgac agtttcactt cca                                            23
```

<210> SEQ ID NO 31
<211> LENGTH: 24
<212> TYPE: DNA
<213> ORGANISM: Artificial sequence
<220> FEATURE:
<223> OTHER INFORMATION: Taqman probe

```
<220> FEATURE:
<221> NAME/KEY: misc_feature
<223> OTHER INFORMATION: 5' conjugated VIC
<220> FEATURE:
<221> NAME/KEY: misc_feature
<223> OTHER INFORMATION: 3' conjugated MGBNFQ

<400> SEQUENCE: 31
ggttgaactg atcttcgtcg gaat                                          24

<210> SEQ ID NO 32
<211> LENGTH: 499
<212> TYPE: DNA
<213> ORGANISM: Artificial sequence
<220> FEATURE:
<223> OTHER INFORMATION: Tomato PMR5 dsRNA product #1 (T33783)

<400> SEQUENCE: 32
gtagctttat ctgttatatt attaaggaat caccataata ataacaataa ttataataac    60
ccaaatcaca gaaacccaat tcttcaagga aatcaaactt catgttctct ctttataggt   120
agttgggttt acgatgaaac ttacccattt taccaatcag cttcttgccc cgccgtcgat   180
ccacagttca actgtcaact ctacggccga cccgatacgg aatacctaaa gtatcgatgg   240
aaaccggcga actgtgagct acccaggttt aatgggcttg agtttctgtt gaaaatgaaa   300
gggaaaacag tgatgtttgt gggtgattca ttaggccggg atcagtggga gtcgttgatt   360
tgtatgattt cagctgatgt acctaaagct caaacgcaga tgtcgaggct ttaccctatt   420
tcaactttca agttcctgga ttacggagtt gctatttcat attacaaagc accatatcta   480
gtggacatag acactgtac                                                499

<210> SEQ ID NO 33
<211> LENGTH: 501
<212> TYPE: DNA
<213> ORGANISM: Artificial sequence
<220> FEATURE:
<223> OTHER INFORMATION: Tomato PMR5 dsRNA product #2 (T33784)

<400> SEQUENCE: 33
gatgtattat ctttttaatac tggtcattgg tggactcaca aaggtcctct tcaagggtgg    60
gacaacgtag aagcaggagg gacaatgtat gaagacatgg atccactaat tgcaatggaa   120
aaagggctaa gaacgtgggc aagatgggtt gataccaata ttgacagaag tagaaccaga   180
ctcttctttc agggcatttc acctacgcac tacaatccga gtgaatggaa cgcgggtgca   240
tcaacaggga gttgttacgg ggagacaatc cccgtaacaa ccaccctat gacgagcacg    300 tacccgggtc ccgatttgga tcaatcaaat gtgatccaaa aagttataag agaaatggac   360
aatccacctt tcttgctaga cataacattg ttatcaacaa tgaggaaaga tgcacatcca   420
tctatttaca gtggtgatct caattctcaa caaagaatta accctaacaa acctgattgt   480
agccattggt gtctgcctgg c                                             501

<210> SEQ ID NO 34
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 34
ctctttcctt aacccttttt taaatttctc                                    30
```

<210> SEQ ID NO 35
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 35
agaagaagac ataatgtagt tgaagaacaa g                              31

<210> SEQ ID NO 36
<211> LENGTH: 17
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 36
caaatggagc ttctctc                                              17

<210> SEQ ID NO 37
<211> LENGTH: 505
<212> TYPE: DNA
<213> ORGANISM: Artificial sequence
<220> FEATURE:
<223> OTHER INFORMATION: Tomato MLO dsRNA product #1 (T33779)

<400> SEQUENCE: 37
gcacttgaaa agatcaaagc tgaacttatg ctgttgggat tcttatcact gttgttgaca      60
gtgttgcaag atccagtttc taacttatgt gtccccaaga gtgttggtta ttcatggcat     120
ccttgtatgg caaggaaga tgccaagtct gagtatgatg acccttgtct accaaaggga      180
aaagtgcaat ttgcatcttc atatgcaata caccagctcc atatcttcat ctttgtattg     240
gcagttgctc atgtattgta ctgtatagca acttttgctt tgggcaggct aaagatgaga     300
aaatggaggg catgggagga tgaaacaaaa acaatggagt accaattcta caacgaccct     360
gagagattca gatttgcaag ggagaccctcg tttggacgta ggcatttgca tttctggagc    420
aagtcccccg tgttgctctc gatagtttgt ttctttcggc aattcttctc atcagttgca    480
aaagttgact atttaaccct tagac                                         505

<210> SEQ ID NO 38
<211> LENGTH: 500
<212> TYPE: DNA
<213> ORGANISM: Artificial sequence
<220> FEATURE:
<223> OTHER INFORMATION: Tomato MLO dsRNA product #2 (T33780)

<400> SEQUENCE: 38
ggcacattta actccacaaa atcaaaataa ttttgatttt caattataca ttaacagagc      60
agttgacaaa gacttcaaag ttgttgttgg aataagtcct gcattatggc tcttcacggt     120
gctatatttt ctgactacta ccgatcgatt gtactcgtat ctttgggtgc catttatccc     180
acttgtaata atattgctag ttggcacaaa acttcaaatg atcataacag aaatgggagt     240
aaggatttca gaaaggggag acatagtaaa aggtgtacct gtggtggaga ctggtgacca     300
tcttttctgg tttaatcgcc ctgccttgt cctattcttg attaactttg tactctttca     360

```
gaatgcgttt caagttgctt tctttttttg gagttggtgg aaatttggtt tcccatcttg      420
ctttcataag aatgctgcag acctagccat aaggctaacc atgggggtga tcatacaggt      480
ccattgcagc tatgtgactc                                                   500

<210> SEQ ID NO 39
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 39
gcaattgctg tggtttgctt ca                                               22

<210> SEQ ID NO 40
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 40
tttccagtaa ccactctcca atgtg                                            25

<210> SEQ ID NO 41
<211> LENGTH: 17
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 41
cttgctcgct atttcta                                                     17

<210> SEQ ID NO 42
<211> LENGTH: 501
<212> TYPE: DNA
<213> ORGANISM: Artificial sequence
<220> FEATURE:
<223> OTHER INFORMATION: Tomato Bi1 dsRNA product #1 (T33777)

<400> SEQUENCE: 42
gtgctttagt ggcatcggct gctggggctt accttcacat tctatggaat atcggtggcc      60
tcctcacaac aatggcttgc atgggaagca tggtgtggct tctctcagct cctccttatc     120
aagagcaaaa aagggtggct cttctgatgg cagctgcact ttttgaaggc gcctctattg     180
gtcctctgat tgagctgggc attaacttcg atccaagcat tgtgtttggc gcttttgtag     240
gttgtgctgt ggttttggt tgcttctcag ctgctgccat gttggcaagg cgcagggagt      300
acttgtacct cgggggcctt cttccatctg gcgtctccct tctcttctgg ttgcactttg     360
catcctccat ttttggtggt tccatggctg ttttcaagtt tgagttgtat tttggactct     420
tggtgtttgt gggctacatc gtctttgaca cccaagaaat tattgagaag gctcacttgg     480
gtgatatgga ttacgttaag c                                                501

<210> SEQ ID NO 43
```

```
<211> LENGTH: 500
<212> TYPE: DNA
<213> ORGANISM: Artificial sequence
<220> FEATURE:
<223> OTHER INFORMATION: Tomato Bi1 dsRNA product #2 (T33778)

<400> SEQUENCE: 43
gccagatctc acctctcgtt caaactcatc tcaagcaggt gtaccttacg ctatgctgtg      60
ctttagtggc atcggctgct ggggcttacc ttcacattct atggaatatc ggtggcctcc     120
tcacaacaat ggcttgcatg ggaagcatgg tgtggcttct ctcagctcct ccttatcaag     180
agcaaaaaag ggtggctctt ctgatggcag ctgcactttt tgaaggcgcc tctattggtc     240
ctctgattga gctgggcatt aacttcgatc caagcattgt gtttggcgct tttgtaggtt     300
gtgctgtggt ttttggttgc ttctcagctg ctgccatgtt ggcaaggcgc agggagtact     360
tgtacctcgg gggccttctt tcatctggcg tctcccttct cttctggttg cactttgcat     420
cctccatttt tggtggttcc atggctgttt caagtttga gttgtatttt ggactcttgg      480
tgtttgtggg ctacatcgtc                                                 500

<210> SEQ ID NO 44
<211> LENGTH: 495
<212> TYPE: DNA
<213> ORGANISM: Zea mays

<400> SEQUENCE: 44
taatacgact cactataggg agattggcga gcttaggatt gaggatcgtt tacagtggaa      60
agaacactct atgatattcg ccatgccaaa caagccagga gaattcagcc ggtttgattt     120
cccagaaact ttgccagcac ctataaatgg gatatgggcc atattgagaa acaatgaaat     180
gcttacctgg cccgagaagg tgaagtttgc aatcggactt ctgccagcaa tggttggtgg     240
tcaaccttat gttgaagctc aagatggctt aaccgtttca gaatggatga aaaagcaggg     300
tgttcctgat cgggtgaacg atgaggtttt tattgcaatg tccaaggcac tcaatttcat     360
aaatcctgat gagctatcta tgcagtgcat tttgattgct ttgaaccgat tcttcagga      420
gaagcatggt tctaaaatgg cattcttgga tggtaatccg cctgaaaggc tatctcccta     480
tagtgagtcg tatta                                                      495

<210> SEQ ID NO 45
<211> LENGTH: 594
<212> TYPE: DNA
<213> ORGANISM: Zea mays

<400> SEQUENCE: 45
taatacgact cactataggg tgatcgggtg aacgatgagg tttttattgc aatgtccaag      60
gcactcaatt tcataaatcc tgatgagcta tctatgcagt gcattttgat tgctttgaac     120
cgatttcttc aggagaagca tggttctaaa atggcattct tggatggtaa tccgcctgaa     180
aggctatgca tgcctattgt tgatcacatt cggtctaggg gtgagaggt ccgcctgaat     240
tctcgtatta aaagatagag ctgaatcct gatggaactg taaaacactt cgcacttagt     300
gatggaactc agataactgg agatgcttat gtttgtgcaa caccagtcga tatcttcaag     360
cttcttgtac ctcaagagtg gagtgaaatt acttatttca agaaactgga gaagttggtg     420
ggagttcctg ttatcaatgt tcatatatgg tttgacagaa aactgaacaa cacatatgac     480
caccttcttt tcagcaggag ttcactttta agtgtctatg cagacatgtc agtaacctgc     540
aaggaatact atgacccaaa ccgttcaatg ctggccctat agtgagtcgt atta            594
```

<210> SEQ ID NO 46
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 46
gattgctgga gcaggattag                                              20

<210> SEQ ID NO 47
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 47
cccttgcctc aagcaatatg                                              20

<210> SEQ ID NO 48
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 48
accacttcga ccgccactac t                                            21

<210> SEQ ID NO 49
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 49
acgcctaagc ctgctggtt                                               19

<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 50
accggcatca gctcagtctc                                              20

<210> SEQ ID NO 51
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 51
tgctgttctc tgggcacagg                                              20

<210> SEQ ID NO 52
<211> LENGTH: 20
<212> TYPE: DNA
<213> ORGANISM: Artificial sequence
<220> FEATURE:

<223> OTHER INFORMATION: Single strand DNA oligonucleotide

<400> SEQUENCE: 52 tccccctcaga tattaacaac                                                    20

<210> SEQ ID NO 53
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 53
aggaggaaag gcagcttctg tg                                                  22

<210> SEQ ID NO 54
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 54
gtgactcgtc accaacaaag                                                     20

<210> SEQ ID NO 55
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 55
tgtgttgtcc gttgagactg                                                     20

<210> SEQ ID NO 56
<211> LENGTH: 547
<212> TYPE: DNA
<213> ORGANISM: Artificial sequence
<220> FEATURE:
<223> OTHER INFORMATION: SQS dsRNA product 1

<400> SEQUENCE: 56
ctaatacgac tcactatagg gagaatatct acaaccgcga ctggcattat tcatgtggaa         60
caaaagacta caaattactg atggataagt ttcgccttgt ctccacggct ttcttggagc        120
ttggtcaagg ttatcaagag gcaattgaag aaatcactag gctaatggga gcaggaatgg        180
caaaatttat ctgcaaggag gttgaaactg ttgatgacta caatgagtac tgtcactatg        240
tagcagggct agtggggtat gggctttcca ggctctttca tgctggtggg acggaagatc        300
tggcttcaga ttcactttca aattcaatgg gcttgtttct gcagaaaatc aatataatta        360
gggattattt ggaggacata aacgagatac aaagtcacg tatgttctgg cctcagaaaa        420
tatggagtaa atatgtcaat aaactcgagg atttgaaata cgaggaaaat tcagaaaagg        480
cagttcagtg tttgaatgat atggtgacta acgctctgtc tcatctccct atagtgagtc        540
gtattag                                                                 547

<210> SEQ ID NO 57
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 57
tcggaagccg taccttcgtg                                               20

<210> SEQ ID NO 58
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 58
cctggagctg ctgctttgtg                                               20

<210> SEQ ID NO 59
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 59
taccaggcgt cgagtggttc                                               20

<210> SEQ ID NO 60
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 60
gaagagggcg tgcaaatggg                                               20

<210> SEQ ID NO 61
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 61
ctattgcgtg tgctccaaac                                               20

<210> SEQ ID NO 62
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 62
acatgaggag gaaccaaagg                                               20

<210> SEQ ID NO 63
<211> LENGTH: 490
<212> TYPE: DNA
<213> ORGANISM: Artificial sequence
<220> FEATURE:
<223> OTHER INFORMATION: Tomato NFY dsRNA product 1

<400> SEQUENCE: 63
ctaatacgac tcactatagg gagaggctca agaaccagtt tatgttaatg ctaagcagta     60
tcgaaggatc ctgcagcgaa gacagtcacg tgctaaagca gaacttgaaa agaagcaaat    120

```
aaagggtaga aagccatatc ttcacgagtc tcgacatcag catgcactga ggagggtaag      180
ggcctcgggt ggacgttttg ccaaaaagac agatgcttct aagggtactg gttctgtgag      240
ttcatcgggt tctgaacctt tgcagttcaa tgctgctgat attcaaaaga ggaatgaaaa      300
tggaaggttg gccgagcttc agcagtctta ttcaaatggt agcagttatg caatcaaag       360 tagctttcaa gaatccaagg atgagtacca gtttgctaaa agcagggaag gaggttttt       420 tgtcaagtaa ttggagatac gttcatgtgt aaactagctc ttgccctctc cctatagtga      480
gtcgtattag                                                             490

<210> SEQ ID NO 64
<211> LENGTH: 497
<212> TYPE: DNA
<213> ORGANISM: Artificial sequence
<220> FEATURE:
<223> OTHER INFORMATION: Tomato NFY dsRNA product 2

<400> SEQUENCE: 64
ctaatacgac tcactatagg gagagcagtt atggcaatca agtagctttt caagaatcca       60
aggatgagta ccagtttgct aaaagcaggg aaggaggttt ttttgtcaag taattggaga     120
tacgttcatg tgtaaactag ctcttgccct gcaacgaggg tagagtatga gcaagaggag     180
tttacaggga ttgtttcatt tcttggcttt tcaagatagg cggcaattca ttcttggctt     240
tttactttag tgttaaaggg agcaacagag gtgacgaggg tatcagtgtt gcagcatttg     300
cttggagatt acatcttccc ttatgtacag agatggatga acttagaact aggattagaa     360 agttttcag taagtttatg tttggccagt tactgtagtt ttagtttagg agaccatgta     420
aaaaggttgt tagttttgca aaaggatctt ttttctttcc ctaattggtg cattctccct      480
atagtgagtc gtattag                                                    497

<210> SEQ ID NO 65
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 65
cgagtcggga tactggaagg                                                  20

<210> SEQ ID NO 66
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 66
cttcttcatg ccgacgaggg                                                  20

<210> SEQ ID NO 67
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 67
acgatgggcg agaaggagtg                                                  20
```

```
<210> SEQ ID NO 68
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 68
tcagtcccgt cgggtacttg                                                   20

<210> SEQ ID NO 69
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 69
agggtcacat cccgaactac                                                   20

<210> SEQ ID NO 70
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 70
acctcgtcag tctccacatc                                                   20

<210> SEQ ID NO 71
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 71
gttggattcg agcttccttc                                                   20

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 72
tgctgctgct cactagctac                                                   20

<210> SEQ ID NO 73
<211> LENGTH: 490
<212> TYPE: DNA
<213> ORGANISM: Artificial sequence
<220> FEATURE:
<223> OTHER INFORMATION: Corn ARF8 dsRNA product

<400> SEQUENCE: 73
ctaatacgac tcactatagg gagacagtcc gttggcctag ttcctattgg agatctgtga       60
aggttggttg ggatgaatca actgcagggg aaagaccacc aagagtttct ttatgggaaa     120
ttgaaccatt gacaaccttt ccaatgtatc catctctgtt cccactgaga gttaagcatc     180
cttggtattc aggagttgct tccctgcatg atgcagcaa tgctttaatg tggctgagag      240
gagttgctgg tgagggaggt tttcagtctc tgaactttca gtcacctggt attggctcct    300
```

```
ggggacaaca gaggctccat ccatccttac tgagcagcga tcacgatcag taccaagcag      360
tagttgctgc tgctgctgct tcccaatctg gtggttactt aaaacagcaa ttcttgcacc      420
ttcagcaacc tatgcagtcc cctcaagaac actgcaacct caaccctctc cctatagtga      480
gtcgtattag                                                             490

<210> SEQ ID NO 74
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 74
ctcagccatg ggatactacc                                                   20

<210> SEQ ID NO 75
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 75
gctggccgtt gacgacattg                                                   20

<210> SEQ ID NO 76
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 76
acctcaggtg gatgtctc                                                     18

<210> SEQ ID NO 77
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 77
tgctggtgct ttgggtag                                                     18

<210> SEQ ID NO 78
<211> LENGTH: 530
<212> TYPE: DNA
<213> ORGANISM: Zea mays

<400> SEQUENCE: 78
taccatgcga tccttaggag gaggcagaca cgtgctaaac tggaggcgca aaacaagatg        60
gtgaaaggtc ggaagccgta ccttcgtgag tctcgacacc gtcatgccat gaagcgggcc      120
cgtggctcag gagggcggtt cctcaacaca aagcagcagc tccaggagca gaaccagcag      180
taccaggcgt cgagtggttc aatgtgctca aagaccattg cgacagcgt aatctcccaa       240 agtggcccca tttgcacgcc ctcttctgac gctgcaggtg cttcagcagc cagccaggac      300
cgcggctgct tgccctcggt tggcttccgc cccacagcca acttcagtga gcaaggtgga      360
ggcggctcga agctggtcgt gaacggcatg cagcagcgtg tttccaccat aaggtgaaga      420
gaagtgggca cgacaccatt cccaggcgcg cactgcctgt ggcaactcat ccttggcttt      480
```

```
tgaaactatg aatatgcaat ggacatgtag ctttgagttc ctcagaataa         530
```

<210> SEQ ID NO 79
<211> LENGTH: 936
<212> TYPE: DNA
<213> ORGANISM: Oryza sativa

<400> SEQUENCE: 79

```
tcagtgtttg tccctcaga tattaacaac aatgatagtt gtggggagcg ggaccatggc    60
actaagtcgg tattgtcttt ggggaacaca gaagctgcct ttcctccttc aaagttcgat  120
tacaaccagc cttttgcatg tgtttcttat ccatatggta ctgatccata ttatggtgga  180
gtatcaacag gatacacttc acatgcattt gttcatcctc aaattactgg tgctgcaaac  240
tctaggatgc cattggctgt tgatccttct gtagaagagc ccatatttgt caatgcaaag  300
caatacaatg cgatccttag aagaaggcaa acgcgtgcaa aattggaggc caaaataag  360
gcggtgaaag gtcggaagcc ttacctccat gaatctcgac atcatcatgc tatgaagcga  420
gcccgtggat caggtggtcg gttccttacc aaaaaggagc tgctggaaca gcagcagcag  480
cagcagcagc agaagccacc accggcatca gctcagtctc caacaggtag agccagaacg  540
agcggcggtg ccgttgtcct tggcaagaac ctgtgcccag agaacagcac atcctgctcg  600
ccatcgacac cgacaggctc cgagatctcc agcatctcat ttggggggcgg catgctggct  660
caccaagagc acatcagctt cgcatccgct gatcgccacc ccacaatgaa ccagaaccac  720
cgtgtccccg tcatgaggtg aaaacctcgg gatcgcggga cacgggcggt tctggtttac  780
cctcactggc gcactccggt gtgcccgtgg caattcatcc ttggcttatg aagtatctac  840
ctgataatag tctgctgtca gtttatatgc aatgcaacct ctgtcagata aactcttata  900
gtttgtttta ttgtaagcta tgactgaacg aactgt                            936
```

<210> SEQ ID NO 80
<211> LENGTH: 512
<212> TYPE: DNA
<213> ORGANISM: Oryza sativa

<400> SEQUENCE: 80

```
catggtggct cagcggctgg ggcaccaatg ctccaccacc cagcctttga gctcacctca    60
ggtggatgtc tcgcgggagt cgccaccgac tccagctgtg ctctctctct tctgtcaact  120
cagccatggg atactaccca aagcaccagc agccacaacc ggtccccgcc aatgtcgtca  180
acggccagcg ccttcggagg cggcaacaac ccggtgtcgc cctcggtcat ggcaagcaac  240
tacatggcgg cgagccccgg ctggaacagc tccagccggg gccatgacgg cgccaggaac  300
gtgcacctgc cgccaccgca cggggttgtg ctgaacgagg tccctccggg ctctgtccac  360
cacggccatt tctccggcga gctcgagctc gcactgcagg gaggtgcccc gtccaaccgg  420
ccggaagcca agcatggctc cggcagcggc gccttcagcc actccaccaa tgccatgaac  480
tggtctctgt agagaccatt gatcatcttc tt                                512
```

<210> SEQ ID NO 81
<211> LENGTH: 840
<212> TYPE: DNA
<213> ORGANISM: Zea Mays

<400> SEQUENCE: 81

```
atggaaggaa acggtggcgc gggcggcggt agcggaagcg cggcaccgcc ctgggatctc    60
```

| | |
|---|---|
| gccatgcact gggcacccgc cgtagtgtcg tcctacccgc cgcagccctt ggagctgcag | 120 |
| cagcaggagc ttacctgcct caagctgggg aagcggcccg cctgctgctg ggcaggggcg | 180 |
| ccgggcaacc aagcggcgca ggtccacggc aatggcggcg ctggtggcgc agctgctgag | 240 |
| ggtaagagga aggacaaggc gcctgccgcg gcggccgtga cgaggtgcca ggtgaggggg | 300 |
| tgccacctgt cgctggcgga cgccaaggag taccaccggc ggcacaaggt gtgcgaggcg | 360 |
| cactccaagt cgcccggggt cgtcgtcctc ggcgccgagc agcgcttctg ccagcagtgc | 420 |
| agccggttcc acgcgatctc ggagttcgac gacgcgaagc ggagctgccg acggcgtctg | 480 |
| gccgggcaca acgagcggcg gcggaagagc aacgccagcg aggccatggc aagaggcgtc | 540 |
| gcgcacccac acggagtgac ggctttcggc cacggcggct cctgccctc gcgcggcctc | 600 |
| gtccccgcag ggtcgtcccc ggcggcggct ggtgctctct ctcttctgtc atcggccaga | 660 |
| ggcagcgtgg cgggcgccag cgggccctgg ctggtcacgg cggcgcggga ggacatcccg | 720 |
| gcgcgctcca gcgcggcgct cgacgacctt atcgccgaga accgcgccgc cgcgctcctc | 780 |
| gcgcggcagt acttcgtctc cgaccgctcg ccggcgccca cgggatttt cgtcgcctct | 840 |

<210> SEQ ID NO 82
<211> LENGTH: 800
<212> TYPE: DNA
<213> ORGANISM: Oryza sativa

<400> SEQUENCE: 82

| | |
|---|---|
| atgagcggga tgaattcgct gagcatggtg gaggcgaggc tgccgccggg gttcaggttc | 60 |
| cacccgcgag acgacgagct cgtgctggac tacctggaaa ggaagctcct cgacggcggc | 120 |
| gtgggcggcg ccgcggcggc ggcggcggcg gtcaccatct acggctgccc ggtgatggtc | 180 |
| gacgtcgatc tcaacaagtg cgagccatgg gaccttcctg agatcgcttg cgttggtggc | 240 |
| aaggagtggt acttctatag ccttagggat aggaagtatg caactggcca acgaacaaat | 300 |
| agagcaaccg aatcgggcta ctggaaggcc acaggaaaag atcgcccaat aagccggaaa | 360 |
| ggattgctcg tcggtatgcg aaaaaccctg gtgttctaca aggtagagc ccctaagggg | 420 |
| aagaagaccg agtgggtcat gcatgaattc cgcaaagaag acaagggga tccgatgaag | 480 |
| ttgcctctca aggaggactg ggtcttgtgt agagtcttct acaagagtag acaaccatt | 540 |
| gccaagctgc caacggaggg tagctacaac aatattgaca gtgtggccac aacttcactg | 600 |
| cctccccctca ctgacaacta cattgcattt gatcagcctg gttcaatgca aaacctagag | 660 |
| ggttatgagc aagtgccctg cttctccaat aatccctctc aacagccatc gtcgtcgatg | 720 |
| aatgttccgt tgacatcggc catggttgat caagagcaaa acaatatggg tagggcgatc | 780 |
| aaggatgtgc tgagccaatt | 800 |

<210> SEQ ID NO 83
<211> LENGTH: 799
<212> TYPE: DNA
<213> ORGANISM: Zea mays

<400> SEQUENCE: 83

| | |
|---|---|
| atggagcacg acgtgcacca ccagcaggcc atggagctgc cgccgggggtt ccgattccac | 60 |
| cccaccgacg aggagctcat cacgcactac ctcgccagga aggccgccga cgcccgcttc | 120 |
| gccccgcgcg ccgtcggcga ggccgacctc aacaagtgcg agccatggga cctgccatcc | 180 |
| cgggcgacga tgggcgagaa ggagtggtac ttcttctgcg tcaaggaccg caagtacccg | 240 |
| acgggactga ggacgaaccg ggccaccgag tcgggatact ggaaggcgac gggcaaggac | 300 |

```
agggagatct tcaggagcaa ggccctcgtc ggcatgaaga agacgctcgt cttctacacg      360
gggagggcgc ccaggggagg caagaccggc tgggtcatgc acgagtaccg cctccacggc      420
aagcacgcca gcagcagccg cctcatgccg tcgtcggtca gagctggcgc gtcaaaggac      480
gagtgggtgc tgtgcagggt gttcaagaag agcatcgagc cgccgccgtc agtgggcaag      540
aggtcgtcgg tcgcgtgtac ggggatgatg ttggtggagg acgtcgtggg accgccgtcc      600
atgtccatgg aggacgacct cgccgcgtgc gcgctgcctc cgctgatgga cgtgtccggc      660
ggtggcggcg ccaacatggc ggcggcgtcc atcgagctgc tggcgccacc ggcaccacac      720
gtgacctgct tctccaacgc gctggagggc cagttcttcc tgaacccacc ctgcctccac      780
ccctccacgt cgccgctcc                                                   799
```

```
<210> SEQ ID NO 84
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 84
taatacgact cactataggg ccgcatgcca ttgtccatcc                             40

<210> SEQ ID NO 85
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 85
taatacgact cactataggg tgcatgccgt tcacgaccag                             40

<210> SEQ ID NO 86
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 86
taatacgact cactataggg caaatagtcc ggttatgttg                             40

<210> SEQ ID NO 87
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 87
taatacgact cactataggg gctacatgtc cattgcatat tc                          42

<210> SEQ ID NO 88
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 88
taatacgact cactataggg ctgcctttcc tccttcaaag ttc                         43
```

<210> SEQ ID NO 89
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 89
taatacgact cactataggg tgctgttctc tgggcacagg                                    40

<210> SEQ ID NO 90
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 90
taatacgact cactataggg cattggctgt tgatccttct g                                  41

<210> SEQ ID NO 91
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 91
taatacgact cactataggg ttcgttcagt catagcttac                                    40

<210> SEQ ID NO 92
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 92
taatacgact cactataggg tcacctcagg tggatgtctc                                    40

<210> SEQ ID NO 93
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 93
taatacgact cactataggg cattggtgga gtggctgaag                                    40

<210> SEQ ID NO 94
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 94
taatacgact cactataggg ccaatgctcc accacccagc cttt                               44

<210> SEQ ID NO 95
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 95
taatacgact cactataggg agttcatggc attggtggag tgg         43

<210> SEQ ID NO 96
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 96
taatacgact cactataggg cgccgtagtg tcgtcctacc         40

<210> SEQ ID NO 97
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 97
taatacgact cactataggg aaagccgtca ctccgtgtgg         40

<210> SEQ ID NO 98
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 98
taatacgact cactataggg cgcaggtcca cggcaatg         38

<210> SEQ ID NO 99
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 99
taatacgact cactataggg cggtcggaga cgaagtactg c         41

<210> SEQ ID NO 100
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 100
taatacgact cactataggg ttcaggttcc acccgcgaga c         41

<210> SEQ ID NO 101
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 101
taatacgact cactataggg ccgttggcag cttggcaatg g         41

<210> SEQ ID NO 102

```
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 102
taatacgact cactataggg cgtgctggac tacctggaaa g                        41

<210> SEQ ID NO 103
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 103
taatacgact cactataggg caaccatggc cgatgtcaac                          40

<210> SEQ ID NO 104
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 104
taatacgact cactataggg ccaccgacga ggagctcatc                          40

<210> SEQ ID NO 105
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 105
taatacgact cactataggg cgacgtcctc caccaacatc                          40

<210> SEQ ID NO 106
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 106
taatacgact cactataggg aggccgacct caacaagtg                           39

<210> SEQ ID NO 107
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 107
taatacgact cactataggg tcaggaagaa ctggccctcc ag                       42

<210> SEQ ID NO 108
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 108
```

```
cctcaacagt cctggatgtc                                                   20
```

<210> SEQ ID NO 109
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 109

```
cccgtaagtt ggaagtgatg                                                   20
```

<210> SEQ ID NO 110
<211> LENGTH: 506
<212> TYPE: DNA
<213> ORGANISM: Artificial sequence
<220> FEATURE:
<223> OTHER INFORMATION: ARF 8 dsRNA product 1

<400> SEQUENCE: 110

```
ctaatacgac tcactatagg gagagcttct cctccctaca actgtgtcta acgtcgctac       60
tacatcaatt gatgctgata tatcctctat gccactaggg acttctggat ttccgaatcc      120
cttgtatagt tatgtgcaag attctactga cttgttgcat aatgtagggc aagctgatgc      180
acaaactgtg ccccgtacat tgtcaaggt ttacaaatca gcgtcccttg ggaggtcatt       240
ggacatcact cggttcaaca gctatcatga gctgcgacag gaattagggc agatgttcgg      300
tatcgaaggg ttgcttgaag accctcaaag atcaggctgg cagcttgtat ttgttgacag      360
ggagaatgat gtccttctcc ttggagacga tccgtgggag gaatttgtca ataatgtttg      420
gtacatcaaa attcttttcac ccgaggatgt gcagaaactg gggaaagagg aggttggatc    480
cctctcccta tagtgagtcg tattag                                           506
```

<210> SEQ ID NO 111
<211> LENGTH: 544
<212> TYPE: DNA
<213> ORGANISM: Artificial sequence
<220> FEATURE:
<223> OTHER INFORMATION: ARF 8 dsRNA product 2

<400> SEQUENCE: 111

```
ctaatacgac tcactatagg gagatgggag attgagcctt tgactacttt tccgatgtat       60
ccatctcttt ttcctctaag gctaaagagg cctttctatc aaggaacctc atcttatcag     120
gatagtaaca atgaagctat taatcgaatg tcatggttaa gagggaatgc tggtgagcta     180
ggacatcatt caatgaatct tcagtctttt ggcatgcttc cttggatgca acagagagtc     240
gattcaacaa ttctcccaaa tgatattaat cagcactatc aagctatgct ggctactggc     300
ttgcaaagtt ttgggagtgg agatttactg aaacagcaat taatgcagtt tcagcagcct     360
gtccaatatc tgcaacatgc aagtactgag aattcaattt tgcatcagca gcagcagcag     420
cagcagcaaa taatgcagca agcagttcat cagcatatgc tgcctgctca aacccaaatg     480
ctgtcagaga accttcaaag gcaatcccag catcaatcca tctccctata gtgagtcgta     540
ttag                                                                  544
```

<210> SEQ ID NO 112
<211> LENGTH: 20
<212> TYPE: DNA
<213> ORGANISM: Artificial sequence
<220> FEATURE:

<223> OTHER INFORMATION: Single strand DNA oligonucleotide

<400> SEQUENCE: 112
gaggcacctt gtgttgattg                                               20

<210> SEQ ID NO 113
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 113
caaagccacg gttcttaagc                                               20

<210> SEQ ID NO 114
<211> LENGTH: 511
<212> TYPE: DNA
<213> ORGANISM: Artificial sequence
<220> FEATURE:
<223> OTHER INFORMATION: FW2.2 dsRNA product

<400> SEQUENCE: 114
ctaatacgac tcactatagg gagatccagg tccaatgaaa caaccttatg ttcctcctca    60
ctatgtatct gcccccggca ccaccacggc gcggtggtcg actggtcttt gtcattgttt   120
tgatgaccct gctaactgtt tagttactag tgtttgccct tgtatcacct ttggacagat   180
ttctgaaata ctaaacaaag gaacaacttc atgtgggagt agaggtgcat tatattgttt   240
gctgggattg acaggattgc ctagcctata ttcctgcttc tacaggtcta aaatgagggg   300
gcaatatgat ctggaagagg caccttgtgt tgattgtctt gtacatgtat tctgtgaacc   360
ttgtgctctt tgccaagaat acagagagct taagaaccgt ggctttgata tgggaatagg   420
gtggcaagct aatatggata dacaaagccg aggagttacc atgccccctt atcatgcagg   480
catgacctct ccctatagtg agtcgtatta g                                  511

<210> SEQ ID NO 115
<211> LENGTH: 513
<212> TYPE: DNA
<213> ORGANISM: Artificial sequence
<220> FEATURE:
<223> OTHER INFORMATION: NRR dsRNA product 1

<400> SEQUENCE: 115
ctaatacgac tcactatagg gagaagctcc tgaacccatc attgaagaac cagtgcttag    60
ccttgatcca gttgcagcag ccatttcgat gatgtctggc agtgagaacg taatggatga   120
aactatagag gttgcagata tcagcgacat tcagaatgac tctcttttaa gcgaagtatt   180
atacgagtgc gagaaggaac tcatggagaa gtccgcaatc gaagagacta tttctgaact   240
gctggacgtc aagattccta tgctgcaagt ggaaagagttc cctagggaaa cccaagtaca   300
actaccggcc atgagaaagg agaagccatc agttcctgaa tgttgttcac tccagaaaag   360
tgtcagttct gggtgcctca actcagctga ttggatcaat ggaccagcca ggccaaactt   420
cctggacttc caaggattgg actttgagac agcgtttggg ttgaggaggg catacagcga   480
aggagacatt ctccctatag tgagtcgtat tag                                513

<210> SEQ ID NO 116
<211> LENGTH: 524
<212> TYPE: DNA
<213> ORGANISM: Artificial sequence

```
<220> FEATURE:
<223> OTHER INFORMATION: NRR dsRNA product 2

<400> SEQUENCE: 116
ctaatacgac tcactatagg gagacatgga gaagtccgca atcgaagaga ctatttctga      60
actgctggac gtcaagattc ctatgctgca agtggaagag ttccctaggg aaacccaagt     120
acaactaccg gccatggaga aggagaagcc atcagttcct gaatgttgtt cactccagaa     180
aagtgtcagt tctgggtgcc tcaactcagc tgattggatc aatggaccag ccaggccaaa     240
cttcctggac ttccaaggat tggactttga dacagcgttt gggttgagga gggcatacag     300
cgaaggagac attcagaatc ttggagctag caccccctcga cccgggaact caggaaacgc     360
tcaattagca tcttgcgaga ggcttgtaac catcagtgac ctgaaatctg aagaaaggaa     420
gcagaagcta tctaggtaca gaagaagaa ggtgaagaga aactttggca gaaagatcaa     480
gtatgcttgc aggaaggctc tctccctata gtgagtcgta ttag                     524

<210> SEQ ID NO 117
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 117
gtgactcgtc accaacaaag                                                 20

<210> SEQ ID NO 118
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 118
tgtgttgtcc gttgagactg                                                 20

<210> SEQ ID NO 119
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 119
cagttcgcgc acaccattcg                                                 20

<210> SEQ ID NO 120
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 120
gcagcatgaa cggctccaag                                                 20

<210> SEQ ID NO 121
<211> LENGTH: 20
<212> TYPE: DNA
<213> ORGANISM: Artificial sequence
<220> FEATURE:
<223> OTHER INFORMATION: Single strand DNA oligonucleotide
```

```
<400> SEQUENCE: 121
tccgcaatgc cgtgtgcatc                                                20

<210> SEQ ID NO 122
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 122
gcggcaggaa tgctagtgtc                                                20

<210> SEQ ID NO 123
<211> LENGTH: 543
<212> TYPE: DNA
<213> ORGANISM: Artificial sequence
<220> FEATURE:
<223> OTHER INFORMATION: Della dsRNA product

<400> SEQUENCE: 123
ctaatacgac tcactatagg gagagcccac ttctacgagt cctgccccta cctcaagttc    60
gcccacttca ccgcaaatca agccatcctc gaggctttcg ccggctgcca ccgcgtccac   120
gtcgtcgact tcggcatcaa gcaggggatg caatggccag ctctcctcca ggccctcgcc   180
cttcgtcccg gcggcccccc atcgttccgc ctcaccggcg tcggccccc gcagccggac    240 gagaccgacg ccttgcagca ggtgggttgg aagcttgccc agttcgcgca caccattcgc   300
gtcgacttcc agtaccgggg actcgtcgcc gccactctcg cggacttgga gccgttcatg   360
ctgcagccgg agggcgaggc ggacgcgaac gaggagcctg aggtgatcgc cgtcaactcg   420
gtgttcgagc tgcaccggct gctcgcgcag cccggcgcgc tggagaaggt cctgggcacg   480
gtgcacgcgg tgcggccaag gatcgtcacc gtggtagagt ctccctatag tgagtcgtat   540
tag                                                                 543

<210> SEQ ID NO 124
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 124
ctaatacgac tcactatagg gagatggccc aataggttct cctca                    45

<210> SEQ ID NO 125
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 125
ctaatacgac tcactatagg gagagctgcc attgatgctg atgc                     44

<210> SEQ ID NO 126
<211> LENGTH: 509
<212> TYPE: DNA
<213> ORGANISM: Artificial sequence
<220> FEATURE:
<223> OTHER INFORMATION: SPL dsRNA product

<400> SEQUENCE: 126
```

```
ctaatacgac tcactatagg gagatggccc aataggttct cctcatatgg atggaaacta    60
acaaatggga agggaagaga agcattactg aagctgaaaa ggaagaggat gaacatggaa   120
gtgttgaaga ggatagcaaa agaaaaaggg tattgactct ctctggtagg aagctagttg   180
gtgaagggtc ggcacatcct tcttgccagg tcgatcagtg cactgcagat atggcagatg   240
ccaagccata ccatcgccgc cacaaggtgt gtgagttcca ttcaaagtct ccaatagtac   300
ttattagtgg actccagaag cgattctgtc agcaatgtag cagatttcat ctgttagcag   360
agtttgatga tgctaagagg agttgccgaa ggcgtttggc aggtcacaat gagcgccgcc   420
gtaaaattac atatgactct catggagaaa atttgggctg aagaagcatc agcatcaatg   480
gcagctctcc ctatagtgag tcgtattag                                     509
```

<210> SEQ ID NO 127
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 127

```
caattcccgg atttctaagc                                                20
```

<210> SEQ ID NO 128
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 128

```
ccctttacac aagggaaatg                                                20
```

<210> SEQ ID NO 129
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 129

```
ttctgaagca acataaacaa gatgtg                                         26
```

<210> SEQ ID NO 130
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 130

```
aatttgctta gaaatccggg aat                                            23
```

<210> SEQ ID NO 131
<211> LENGTH: 19
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 131
ttaagcatgc tctctatct                                              19

<210> SEQ ID NO 132
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 132
gctaagaacg ctggacctaa tg                                          22

<210> SEQ ID NO 133
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 133
agaatagcat ccggtctcag                                             20

<210> SEQ ID NO 134
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 134
ggtggcgcct ttgatgaa                                               18

<210> SEQ ID NO 135
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 135
tccaatagct cgtaaatcag aacaa                                       25

<210> SEQ ID NO 136
<211> LENGTH: 16
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated VIC
<220> FEATURE:
<221> NAME/KEY: misc_feature
<223> OTHER INFORMATION: 3' conjugated MGBNFQ

<400> SEQUENCE: 136
atgccatccg caataa                                                 16

<210> SEQ ID NO 137
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 137
tctctgggct tgtatcatcc                                                  20

<210> SEQ ID NO 138
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 138
gctgctcaag gtgtttgtg                                                   19

<210> SEQ ID NO 139
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 139
ctcgtaatac gactcactat agggcgaaca agaatctgcc ggactac                    47

<210> SEQ ID NO 140
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 140
ctcgtaatac gactcactat agggcgacat ccttccatgc agctaac                    47

<210> SEQ ID NO 141
<211> LENGTH: 517
<212> TYPE: DNA
<213> ORGANISM: Artificial sequence
<220> FEATURE:
<223> OTHER INFORMATION: Wheat PDS dsRNA product #1

<400> SEQUENCE: 141
ctcgtaatac gactcactat agggcgaaca agaatctgcc ggactacttg cttcagtatg       60
gataccagct gcctatcatc tatgaacata gctggagcga agcaagtaag atcttttgct      120
ggacaacttc atacgcagag gtgtttcaca agtagcagcg tccaggcact aaaaactagt      180
catcgtacga cctcccttgg cttaaggaat aaagtaaaag gatcacgtca tggacttcgt      240
gctctgcagg ttgtttgcca agattttcca aggcctccac tagagaacac gattaactat      300
ttggaagctg gccagctttc ttcgtcgttt agaagcagtg aacgcccag taaaccatta       360 caggtcgtga ttgctggtgc aggactggct ggtctatcaa ctgcaaaata cctggcagac      420
gctggccaca aacccatagt gcttgaggca agagatgtgt gggcggaaa gttagctgca       480 tggaaggatg tcgccctata gtgagtcgta ttacgag                               517

<210> SEQ ID NO 142
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 142
ctcgtaatac gactcactat agggcgacgg aacagtgaag cactttg        47

<210> SEQ ID NO 143
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 143
ctcgtaatac gactcactat agggcgattc gggacggtct tgtaaac        47

<210> SEQ ID NO 144
<211> LENGTH: 537
<212> TYPE: DNA
<213> ORGANISM: Artificial sequence
<220> FEATURE:
<223> OTHER INFORMATION: Wheat PDS dsRNA product #2

<400> SEQUENCE: 144
ctcgtaatac gactcactat agggcgacgg aacagtgaag cactttgcac ttactgatgg        60
gactcaaata actggagatg catatgtttt tgcagcacca gttgatatct tcaagcttct       120
tgtaccacaa gagtggagag agatctctta tttcaaaagg ctggataagt tggtgggagt       180
tcctgtcatc aatgttcata tatggtttga cagaaaactg aagaacacgt atgaccacct       240
tcttttcagc aggagttcac ttttaagcgt ttatgcagac atgtctttag cgtgcaagga       300
gtactatgat ccaaaccgtt cgatgctgga gttggttttt gctccagcag aggaatggat       360
cggacggagt gacaccgaaa tcatcgaagc aactatgcta gagctagcca gttgtttcc        420 tgatgaaatc gctgctgacc agagtaaagc aaagattctt aaataccatg ttgtgaagac       480
accgaggtcc gtttacaaga ccgtcccgaa tcgccctata gtgagtcgta ttacgag         537

<210> SEQ ID NO 145
<211> LENGTH: 481
<212> TYPE: DNA
<213> ORGANISM: Artificial sequence
<220> FEATURE:
<223> OTHER INFORMATION: Corn TB1 dsRNA product

<400> SEQUENCE: 145
ctaatacgac tcactatagg gaggtgatca actcgccgga cctgccggtg caggcgctga        60
tggaccacgc gccggcgccg gctacagagc tgggcgcctg cgccagtggt gcagaaggat       120
ccggcgccag cctcgacagg gcggctgccg cggcgaggaa agaccggcac agcaagatat       180
gcaccgccgg cgggatgagg gaccgccgga tgcggctctc ccttgacgtc gcgcgcaaat       240
tcttcgcgct gcaggacatg cttggcttcg acaaggcaag caagacggta cagtggctcc       300
tcaacacgtc caagtccgcc atccaggaga tcatggccga cgacgcgtct tcggagtgcg       360
tggaggacgg ctccagcagc ctctccgtcg acggcaagca caacccggca gagcagctgg       420
gaggaggagg agatcagaag cccaagggta attgccgtct ccctatagtg agtcgtatta       480
g                                                                      481

<210> SEQ ID NO 146
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 146
aatcggtgtc gtcgatttgg                                              20

<210> SEQ ID NO 147
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 147
ggcggatact gtttgatctc                                              20

<210> SEQ ID NO 148
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 148
gctgcgtgtt gtgcgttctg                                              20

<210> SEQ ID NO 149
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 149
tcgtcgcgtg ctgtctgttc                                              20

<210> SEQ ID NO 150
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 150
ctggattgga aactgggatt gt                                           22

<210> SEQ ID NO 151
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 151
ttgccccatt ttgcatatag c                                            21

<210> SEQ ID NO 152
<211> LENGTH: 17
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 152
attgtgccgt tgaatat                                                      17

<210> SEQ ID NO 153
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 153
aggctttcgc tgcgtgtt                                                     18

<210> SEQ ID NO 154
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 154
tggcccatcc aaactcaga                                                    19

<210> SEQ ID NO 155
<211> LENGTH: 16
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated VIC
<220> FEATURE:
<221> NAME/KEY: misc_feature
<223> OTHER INFORMATION: 3' conjugated MGBNFQ

<400> SEQUENCE: 155
tgcgttctgc ttgaat                                                       16

<210> SEQ ID NO 156
<211> LENGTH: 440
<212> TYPE: DNA
<213> ORGANISM: Artificial sequence
<220> FEATURE:
<223> OTHER INFORMATION: Lettuce HY5.5 dsRNA product

<400> SEQUENCE: 156
agagtttcgg ctcaacaagc aagggagagg aagaaggcat acttgaatga attggaagtg        60
cgagtaaaag aaattgaaaa gaagaactcc gagcttgaag agcgactttc aactctccaa       120
aatgagaatc aaatgcttag acatatcttg aaaaacacta cagccggtat gcaagaaaag       180
aagtagacat atgattagaa gaggaaaagc attacatgtg caatccgaat catagcttga       240
aaatcgaagg gtttggttta ggatcgagac ttgttattgt ggttatttct tttcctagca       300
aacataatga gaatccaacc atctttacgt acgattcgat taaagatctt taagtcatgt       360
aggtggtaat gggctgtgtt tctaaatgac caaaaaagat gtaaagtatt gcatatgata       420
tgggttttaa tttgtagcac                                                  440

<210> SEQ ID NO 157
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 157

```
catgtgcaat ccgaatcata gc                                          22
```

<210> SEQ ID NO 158
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 158

```
accacaataa caagtctcga tcctaa                                      26
```

<210> SEQ ID NO 159
<211> LENGTH: 18
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 159

```
tgaaaatcga agggtttg                                               18
```

<210> SEQ ID NO 160
<211> LENGTH: 401
<212> TYPE: DNA
<213> ORGANISM: Artificial sequence
<220> FEATURE:
<223> OTHER INFORMATION: Lettuce HY5.6 dsRNA product

<400> SEQUENCE: 160

```
atgcaggagc aagcagcaac gagttccatg gcggctagtc taccttcaag tagcgagaga    60
tcttcaagct ctgctctaca aattgaaatt aaagaaggaa tggaaagtga tgacgagatc   120
agaagagtgc cggatatggg cggagaagcc gccggagcat caagatccgg cagagaaacc   180
ggttcaaatc aaaataatcc agaccgggtt caacactcag ctgaaggaac aaagaaaaga   240
gggaaaactc ctgctgatag agaaagcaag cgattaaaga gattgttgag aatagagta    300 tcggctcaac aagcaagaga gagaaagaag gcgtacatga ccgagttgga gagccgagtt   360
aaagagttgg agaagaagaa ctcggagctt gaagaacgtt t                       401
```

<210> SEQ ID NO 161
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 161

```
ccacaatgca aaatgaaaac ca                                          22
```

<210> SEQ ID NO 162
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 162

```
gcatcccaga cgttgtgttc t                                              21

<210> SEQ ID NO 163
<211> LENGTH: 17
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 163
tgcttagaca catcttg                                                   17

<210> SEQ ID NO 164
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 164
ttgtcttgaa ttttagcttt gacgtt                                         26

<210> SEQ ID NO 165
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 165
ccttgaccgg aaaaacaatc a                                              21

<210> SEQ ID NO 166
<211> LENGTH: 27
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated VIC
<220> FEATURE:
<221> NAME/KEY: misc_feature
<223> OTHER INFORMATION: 3' conjugated TAMRA

<400> SEQUENCE: 166
tcaatggtgt cggagctttc cacttcc                                        27

<210> SEQ ID NO 167
<211> LENGTH: 524
<212> TYPE: DNA
<213> ORGANISM: Artificial sequence
<220> FEATURE:
<223> OTHER INFORMATION: Lettuce DHFR dsRNA product

<400> SEQUENCE: 167
agaggattct ccgaccaccg tgtgtgtcac tggagctgcc ggattcattg gttcatggct    60
cgttatgaga cttcttgaac gtgggtataa tgttcatgcc actgttcgtg accctgatga   120
cataaagaaa gtgaaacatt tattggaact accaaaagca gcaacaaact tgacgttatg   180
gaaggcagat ttgacacaag aaggaagctt tgatgaagcc attgaaggtt gtcatggagt   240
```

| | |
|---|---|
| ctttcatgtg gctacgccta tggactttca gtccaaggat cctgagaatg agatcataaa | 300 |
| gccaacaata gaaggtgtat taagcatcgt aagatcatgt gtgaaagtca aaacagtcaa | 360 |
| gaaattggtg tttacatcct ctgcggggac agtgaacgtg cacggaaatg atcaacttcc | 420 |
| ggtctatgac gagtctcatt ggagcgattt ggacttcatc tactccaaga aaatgactgc | 480 |
| atggatgtat ttcgtatcaa aaacattggc agaaaaagca gcat | 524 |

```
<210> SEQ ID NO 168
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 168
```

| | |
|---|---|
| ggagatgttc aaaggagcaa ttg | 23 |

```
<210> SEQ ID NO 169
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 169
```

| | |
|---|---|
| ttgattgtgg aatatggaag catt | 24 |

```
<210> SEQ ID NO 170
<211> LENGTH: 17
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 170
```

| | |
|---|---|
| tagttgcaga gagaaag | 17 |

```
<210> SEQ ID NO 171
<211> LENGTH: 498
<212> TYPE: DNA
<213> ORGANISM: Artificial sequence
<220> FEATURE:
<223> OTHER INFORMATION: Cucumber DND1 dsRNA #1

<400> SEQUENCE: 171
```

| | |
|---|---|
| gtcttggaat gctacgcctg tacccaagtg ggcgttccag ccttccactc caccagctgc | 60 |
| gaccacgccc accaacaacc cgaatgggaa gcctccgcgg gctcttccct ggttccaatc | 120 |
| caacccacaa aatcctcacc agcgccccga cattcttcgg cgggttgctt cgggacggtt | 180 |
| ctggacccaa gaaagaaacc ggttcagaga tggaaccggg ttctgttatt ggcccgggga | 240 |
| atgtctcttg cggttgatcc gctttacttc tatgctctgt ctattggaag aggaggatgg | 300 |
| ccttgcctgt acatggatgg tgggttggct gccggagtta cggtggttcg aacgtgtctt | 360 |
| gatatagtgc acttgtggca cgtgtggctt cagttcaggc ttgcttacgt gtcgaaagag | 420 |
| agtatggtga ttgggtgtgg gaaactggtg tgggatgcac gtgatattgc ttctcactat | 480 |

```
gttcgttctt tcaaaggc                                                        498
```

<210> SEQ ID NO 172
<211> LENGTH: 506
<212> TYPE: DNA
<213> ORGANISM: Artificial sequence
<220> FEATURE:
<223> OTHER INFORMATION: Cucumber DND1 dsRNA #2

<400> SEQUENCE: 172

```
gtacggtgct tagtggattg ttgcttttca ctcttttgat tggtaatatt caggtacttt          60
tgcacgctgt catggcaagg aggcgaaaaa tgcagctgag atgtcgagat ttggagtggt         120
ggatgaggag acgacaattg ccatctcgtt tgaaacatcg agttcgacac tatgagcacc         180
agagatgggc agctatggga ggagaagatg agatggaact aatcaatgat ttgccagaag         240
gtcttagaag agatatcaaa cgtcatcttt gtgttgacct aatcagaaag gtgcctctct         300
ttcaaaacct ggaggagctg attctagaca acatatgtga caaagtcaag ccacttgtat         360
tctccaaaga tgaaaagata atcagagaag gagatcctgt tccaaggatg ttattcatag         420
tgtgtggacg agtaaaacgt agccaaagcc tgagcaaggg catgacagcg acaagtttta         480
ttgaaccggg aggatttctt ggtgac                                              506
```

<210> SEQ ID NO 173
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 173

```
cagcgagttg cttcttgtat cca                                                  23
```

<210> SEQ ID NO 174
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 174

```
tcctcagagc aagacaaaga taagttg                                              27
```

<210> SEQ ID NO 175
<211> LENGTH: 20
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 175

```
acattgtgag agaaacaagt                                                      20
```

<210> SEQ ID NO 176
<211> LENGTH: 499
<212> TYPE: DNA
<213> ORGANISM: Artificial sequence
<220> FEATURE:
<223> OTHER INFORMATION: GFP dsRNA product

```
<400> SEQUENCE: 176
ggtgatgcaa catacggaaa acttaccctt aaatttattt gcactactgg aaaactacct      60
gttccatggc caacacttgt cactactttc tcttatggtg ttcaatgctt ttcaagatac     120
ccagatcata tgaagcggca cgacttcttc aagagcgcca tgcctgaggg atacgtgcag     180
gagaggacca tcttcttcaa ggacgacggg aactacaaga cacgtgctga agtcaagttt     240
gagggagaca ccctcgtcaa caggatcgag cttaagggaa tcgatttcaa ggaggacgga     300
aacatcctcg gccacaagtt ggaatacaac tacaactccc acaacgtata catcatggcc     360
gacaagcaaa agaacggcat caaagccaac ttcaagaccc gccacaacat cgaagacggc     420
ggcgtgcaac tcgctgatca ttatcaacaa aatactccaa ttggcgatgg ccctgtcctt     480
ttaccagaca accattacc                                                   499

<210> SEQ ID NO 177
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 177
atggcttgct gcctgatgta tc                                                22

<210> SEQ ID NO 178
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 178
ggtggcaaca gcagcattca                                                   20

<210> SEQ ID NO 179
<211> LENGTH: 17
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated VIC
<220> FEATURE:
<221> NAME/KEY: misc_feature
<223> OTHER INFORMATION: 3' conjugated MGBNFQ

<400> SEQUENCE: 179
atgttgtgcc taaggac                                                      17

<210> SEQ ID NO 180
<211> LENGTH: 509
<212> TYPE: DNA
<213> ORGANISM: Artificial sequence
<220> FEATURE:
<223> OTHER INFORMATION: PMR5 dsRNA product #1 (T33789)

<400> SEQUENCE: 180
gatcctgagt tcaactgcca agcttacggc agacccgatt caaattacct caagtaccgt      60
tggcagccgc tcgattgtga gctcccaagg ttcgatgggg ctgagttttt gatgagaatg     120
agaggaagaa ctgtgatgtt tgttggtgat tcattgggga gaaccaatg ggagtcattg     180
```

```
atttgtttga tcgtgtcatc ttctcctcaa actcctactc aaatgactag aggagaacct     240
ctttcaacct tcagattcct ggaatatgag ttaactgtgt cctattacaa agccccgtat     300
cttgtggaca tagagataga gaatgggaag agagtgttga agctggagga gatatcaatg     360
aatggaaatg cttgggttgg agctgatgtt atttccttca acactggaca ttggtggagc     420
cacactggct ctctacaagg gtgggattac atggaatcag gaggatcata ctatcaagac     480
atggatcggt tgggtgcaat ggaaaaggc                                       509

<210> SEQ ID NO 181
<211> LENGTH: 500
<212> TYPE: DNA
<213> ORGANISM: Artificial sequence
<220> FEATURE:
<223> OTHER INFORMATION: PMR5 dsRNA product #2 (T33790)

<400> SEQUENCE: 181
ggctctctac aagggtggga ttacatggaa tcaggaggat catactatca agacatggat     60
cggttgggtg caatggaaaa ggctttaaga acatgggctg attggttgaa gaagaacatt    120
gatgtctcta gaacaagggt tttcttccaa gctatctccc ccacacatta caatccatct    180
gaatggaaca cggggacagc atcgatgatg acatcaacga aaaattgtta tggggaaacg    240
gcaccaatgg gggggacgac gtacccggga gggtacccta ttcaaatgag ggttgtggat    300
gaagtgataa gggagatgag gaagccagta tacttattgg acataacaat gttatctgag    360
ctaagaaaag atggacaccc ttccattat agtggtgatt tgaatcctca acaaagggct     420
aacccagata gatcagcgga ttgtagccat tggtgtcttc ctggcttacc agatacttgg    480
aaccaattgt tttatactgc                                                500

<210> SEQ ID NO 182
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 182
agcttcctca gctttgattc tcagt                                           25

<210> SEQ ID NO 183
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 183
gcgattatgg tggtcgctgt t                                               21

<210> SEQ ID NO 184
<211> LENGTH: 16
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 184
```

```
tgaagcacca ttaccg                                                          16

<210> SEQ ID NO 185
<211> LENGTH: 512
<212> TYPE: DNA
<213> ORGANISM: Artificial sequence
<220> FEATURE:
<223> OTHER INFORMATION: Cucumber TubG dsRNA product #1 (T33791)

<400> SEQUENCE: 185
gtgggaacca gatcggaatg gagttctgga agcagctttg cctcgagcat ggaatcagca         60
aagacggcat tcttgaagat tttgctactc agggaggtga ccggaaagat gtattcttct        120
atcaagccga tgatcagcac tacataccaa gagctttact tattgacctg gagcccaggg        180
tcattaatgg tatccagaac agtgaatatc gaaatctcta caaccacgag aacatctttg        240
tttcagatca tggaggtggt gctggaaata actgggccag tggatatcat cagggaaagg        300
gcgttgaaga ggatatcatg gacatgattg acagagaagc agatggaagc gatagccttg        360
agggttttgt tctatgccac tcaattgctg gagggacagg atcgggcatg ggttcatatc        420
ttctggagac tctgaatgat cgctacagca aaaaactggt tcagacgtac agtgtttttc        480
ctaatcagat ggaaacaagt gatgttgtag tc                                      512

<210> SEQ ID NO 186
<211> LENGTH: 512
<212> TYPE: DNA
<213> ORGANISM: Artificial sequence
<220> FEATURE:
<223> OTHER INFORMATION: Cucumber TubG dsRNA product #2 (T33792)

<400> SEQUENCE: 186
gccttacaac tcacttttga cttaaagcg actaacactc aatgctgatt gtgttgttgt         60
tcttgataat actgccctaa atagaatagc tgtagaacgc cttcatctat caaatccaac        120
ctttgcacaa acaaactcct tagtgtcgac tgtaatgtca gctagcacaa ccactttgag        180
atacccagga tatatgaaca atgacttggt tggactcttg gcctctctaa ttccaacacc        240
aagatgccat tttctaatga caggatacac accactcacg gttgagcgcc aggctaatgt        300
gataaggaaa accactgttc ttgatgtcat gagaagactt ctccagacaa aaatatttat        360
ggtctcctcg tatgctcgaa caaaagaagc tagtcaagca aaatacatat caatattgaa        420
tatcatacag ggagaagtgg accctacaca ggttcatgaa agtttgcaga gaatacgtga        480
aagaaagctg gtgaatttta ttgagtgggg gc                                      512

<210> SEQ ID NO 187
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 187
gggtcagtgg tcttatgtta gc                                                  22

<210> SEQ ID NO 188
<211> LENGTH: 23
<212> TYPE: DNA
<213> ORGANISM: Artificial sequence
<220> FEATURE:
<223> OTHER INFORMATION: Single strand DNA oligonucleotide
```

<400> SEQUENCE: 188
ttctcaactt ctcatactgg ctc                                            23

<210> SEQ ID NO 189
<211> LENGTH: 27
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated 3IABkFQ

<400> SEQUENCE: 189
agtatccggc atcttttcag caagtgt                                        27

<210> SEQ ID NO 190
<211> LENGTH: 513
<212> TYPE: DNA
<213> ORGANISM: Artificial sequence
<220> FEATURE:
<223> OTHER INFORMATION: Soy PHYAE3 dsRNA product

<400> SEQUENCE: 190
tcaagaagat gttggacatg gcattgcagg gtgaggaaga gagaaatgtc caatttgaga      60
tccaaacaca tcatatgaag attgattctg gtcccatcag cttggtagtt aatgcttgtg     120
caagcaggga tcttcaagat aatgttgtgg gagtttgttt tctggcacaa gatataactg     180
ctcagaaaac aatgatggac aaattcaccc gaattgaagg tgactacaag gcaattgtac     240
agaacccaaa cccattgatc cctccaatat ttggcacaga tgaatttggt tggtgttgtg     300
aatggaattc agctatggca aaattaactg gatggaagcg agaggaggta atggataaaa     360
tgcttttagg agaggttttc gggacccaaa tagcttgttg tcgcctaagg aatcatgaag     420
ctgttgttaa ctttagcatt gtacttaata cagccatggc tggtttggaa acagagaagg     480
ttccttttgg tttctttgct cgtgatggaa agc                                 513

<210> SEQ ID NO 191
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 191
tccctcttag gtatgcttgt caatt                                          25

<210> SEQ ID NO 192
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 192
tctctagctc tttgctcaca tgaac                                          25

<210> SEQ ID NO 193
<211> LENGTH: 16
<212> TYPE: DNA
<213> ORGANISM: Artificial sequence

```
<220> FEATURE:
<223> OTHER INFORMATION: Taqman probe
<220> FEATURE:
<221> NAME/KEY: misc_feature
<223> OTHER INFORMATION: 5' conjugated 6FAM
<220> FEATURE:
<221> NAME/KEY: misc_feature
<223> OTHER INFORMATION: 3' conjugated MGBNFQ

<400> SEQUENCE: 193
ctggctcaag tatttg                                                    16

<210> SEQ ID NO 194
<211> LENGTH: 525
<212> TYPE: DNA
<213> ORGANISM: Artificial sequence
<220> FEATURE:
<223> OTHER INFORMATION: Soy PHYAE4 dsRNA product

<400> SEQUENCE: 194
tcaagaagat gcttaactta gcactgctag gtgaagaaga gaagaatgtc caatttgaga      60
tcaaaacaca tgggtctaag atggattctg gtcctattag tttagtagta aatgcttgcg    120
caagcaggga tcttcgagat aatgttgttg gggtttgttt tgtggcccat gatataactg    180
ctcagaagaa tgtcatggac aaatttacgc gtattgaagg tgattacaag gcaattgtac    240
agaaccgcaa tccattaatc cctcctatat ttggcacaga tgaatttggc tggtgttgtg    300
agtggaatcc agctatgacg aagttaactg gatggaagcg agaggaggtg atggataaaa    360
tgcttttggg agagcttttt ggcacccata tggctgcttg tcgcctaaag aatcaagaag    420
cttttgttaa tttgggtgtt gtacttaata aagccatgac tggtttggaa acagagaagg    480
ttccttttgg tttctttgct cggaatggca agtatgtgga atgcc                    525

<210> SEQ ID NO 195
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 195
caaggttatg aaaattatgg gtatgc                                         26

<210> SEQ ID NO 196
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 196
cccggataac tgccatacat g                                              21

<210> SEQ ID NO 197
<211> LENGTH: 21
<212> TYPE: DNA
<213> ORGANISM: Artificial sequence
<220> FEATURE:
<223> OTHER INFORMATION: Taqman probe
<220> FEATURE:
<221> NAME/KEY: misc_feature
<223> OTHER INFORMATION: 5' conjugated VIC
<220> FEATURE:
<221> NAME/KEY: misc_feature
<223> OTHER INFORMATION: 3' conjugated TAMRA
```

```
<400> SEQUENCE: 197
ctgctgctgg acaggatccc a                                           21
```